United States Patent
Peterson et al.

(10) Patent No.: US 12,049,646 B2
(45) Date of Patent: *Jul. 30, 2024

(54) SC-BETA CELLS AND COMPOSITIONS AND METHODS FOR GENERATING THE SAME

(71) Applicant: President and Fellows of Harvard College, Cambridge, MA (US)

(72) Inventors: Quinn P. Peterson, Cambridge, MA (US); Felicia J. Pagliuca, Cambridge, MA (US); Douglas A. Melton, Cambridge, MA (US); Jeffrey Robert Millman, Cambridge, MA (US); Michael Saris Segel, Cambridge, MA (US); Mads Gurtler, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/395,362

(22) Filed: Dec. 22, 2023

(65) Prior Publication Data

US 2024/0124847 A1    Apr. 18, 2024

Related U.S. Application Data

(63) Continuation of application No. 17/670,124, filed on Feb. 11, 2022, which is a continuation of application No. 17/364,226, filed on Jun. 30, 2021, now abandoned, which is a continuation of application No. 16/042,933, filed on Jul. 23, 2018, now abandoned, which is a continuation of application No. 14/684,101, filed on Apr. 10, 2015, now Pat. No. 10,030,229, which is a continuation of application No. PCT/US2014/041992, filed on Jun. 11, 2014.

(60) Provisional application No. 61/972,212, filed on Mar. 28, 2014, provisional application No. 61/833,898, filed on Jun. 11, 2013.

(51) Int. Cl.
| | |
|---|---|
| *C12N 5/071* | (2010.01) |
| *A61K 35/39* | (2015.01) |
| *A61P 3/10* | (2006.01) |
| *A61P 5/48* | (2006.01) |
| *A61P 5/50* | (2006.01) |
| *C12N 5/0735* | (2010.01) |
| *C12N 5/074* | (2010.01) |

(52) U.S. Cl.
CPC .......... *C12N 5/0678* (2013.01); *A61K 35/39* (2013.01); *A61P 3/10* (2018.01); *A61P 5/48* (2018.01); *A61P 5/50* (2018.01); *C12N 5/0606* (2013.01); *C12N 5/0676* (2013.01); *C12N 5/0696* (2013.01); *C12N 2501/11* (2013.01); *C12N 2501/117* (2013.01); *C12N 2501/15* (2013.01); *C12N 2501/16* (2013.01); *C12N 2501/375* (2013.01); *C12N 2501/385* (2013.01); *C12N 2501/395* (2013.01); *C12N 2501/40* (2013.01); *C12N 2501/41* (2013.01); *C12N 2501/727* (2013.01); *C12N 2501/998* (2013.01); *C12N 2501/999* (2013.01); *C12N 2506/02* (2013.01); *C12N 2506/03* (2013.01); *C12N 2506/22* (2013.01); *C12N 2506/45* (2013.01)

(58) Field of Classification Search
CPC .... C12N 5/0678; C12N 5/0676; A61K 35/39; A61P 3/10; A61P 5/48; A61P 5/50
See application file for complete search history.

(56) References Cited

U.S. PATENT DOCUMENTS

| | | |
|---|---|---|
| 4,378,016 A | 3/1983 | Loeb |
| 4,391,909 A | 7/1983 | Lim |
| 5,674,289 A | 10/1997 | Fournier et al. |
| 6,090,622 A | 7/2000 | Gearhart et al. |
| 6,436,704 B1 | 8/2002 | Roberts et al. |
| 6,667,176 B1 | 12/2003 | Funk et al. |
| 6,800,480 B1 | 10/2004 | Bodnar et al. |
| 7,033,831 B2 | 4/2006 | Fisk et al. |
| 7,157,278 B2 | 1/2007 | Jin |
| 7,297,539 B2 | 11/2007 | Mandalam et al. |
| 7,326,572 B2 | 2/2008 | Fisk et al. |
| 7,410,798 B2 | 8/2008 | Mandalam et al. |
| 7,432,104 B2 | 10/2008 | Mitalipova et al. |
| 7,510,876 B2 | 3/2009 | D'Amour et al. |
| 7,534,608 B2 | 5/2009 | Martinson et al. |
| 7,541,185 B2 | 6/2009 | D'Amour et al. |
| 7,625,753 B2 | 12/2009 | Kelly et al. |
| 7,695,963 B2 | 4/2010 | Agulnick et al. |

(Continued)

FOREIGN PATENT DOCUMENTS

| | | |
|---|---|---|
| EP | 1456356 A2 | 9/2004 |
| EP | 1676574 A2 | 7/2006 |

(Continued)

OTHER PUBLICATIONS

Rezania et al., (2012) Maturation of human embryonic stem cell-derived pancreatic progenitors into functional islets capable of treating pre-existing diabetes in mice. Diabetes, 61(8):2016-2029 (Year: 2012).*

(Continued)

*Primary Examiner* — Kara D Johnson
(74) *Attorney, Agent, or Firm* — Morse, Barnes-Brown & Pendleton, P.C.; Lisa M. Warren, Esq.; Erin E. Bryan, Esq.

(57) ABSTRACT

Disclosed herein are methods, compositions, kits, and agents useful for inducing β cell maturation, and isolated populations of SC-β cells for use in various applications, such as cell therapy.

30 Claims, 21 Drawing Sheets

(56) References Cited

U.S. PATENT DOCUMENTS

| | | |
|---|---|---|
| 7,695,965 B2 | 4/2010 | Martinson et al. |
| 7,704,738 B2 | 4/2010 | D'Amour et al. |
| 7,964,402 B2 | 6/2011 | Terskikh et al. |
| 7,985,585 B2 | 7/2011 | D'Amour et al. |
| 7,993,916 B2 | 8/2011 | Agulnick et al. |
| 7,993,920 B2 | 8/2011 | Martinson et al. |
| 8,008,075 B2 | 8/2011 | Green et al. |
| 8,129,182 B2 | 3/2012 | D'Amour et al. |
| 8,153,429 B2 | 4/2012 | Robins et al. |
| 8,187,878 B2 | 5/2012 | Dalton et al. |
| 8,211,699 B2 | 7/2012 | Robins et al. |
| 8,216,836 B2 | 7/2012 | D'Amour et al. |
| 8,278,106 B2 | 10/2012 | Martinson et al. |
| 8,334,138 B2 | 12/2012 | Robins et al. |
| 8,338,170 B2 | 12/2012 | Kelly et al. |
| 8,361,489 B2 | 1/2013 | Kennedy et al. |
| 8,415,153 B2 | 4/2013 | Majumdar et al. |
| 8,445,273 B2 | 5/2013 | Green et al. |
| 8,603,811 B2 | 12/2013 | D'Amour et al. |
| 8,623,645 B2 | 1/2014 | D'Amour et al. |
| 8,647,873 B2 | 2/2014 | D'Amour et al. |
| 8,658,151 B2 | 2/2014 | Kelly et al. |
| 8,785,184 B2 | 7/2014 | Xu |
| 8,785,185 B2 | 7/2014 | Xu et al. |
| 8,859,286 B2 | 10/2014 | Agulnick |
| 9,062,290 B2 | 6/2015 | Rezania |
| 9,096,832 B2 | 8/2015 | Xu |
| 9,109,245 B2 | 8/2015 | Agulnick et al. |
| 9,186,381 B2 | 11/2015 | Zender et al. |
| 9,650,610 B2 | 5/2017 | Agulnick |
| 9,744,195 B2 | 8/2017 | Xu |
| 9,974,784 B2 | 5/2018 | Groppe |
| 10,030,229 B2 | 7/2018 | Peterson et al. |
| 10,138,465 B2 | 11/2018 | Rezania |
| 10,190,096 B2 | 1/2019 | Melton et al. |
| 10,253,298 B2 | 4/2019 | Melton et al. |
| 10,443,042 B2 | 10/2019 | Melton et al. |
| 10,655,106 B2 | 5/2020 | Peterson et al. |
| 10,927,350 B2 | 2/2021 | Melton et al. |
| 11,078,463 B2 | 8/2021 | Peterson et al. |
| 11,085,025 B2 | 8/2021 | Melton et al. |
| 11,085,026 B2 | 8/2021 | Melton et al. |
| 11,085,027 B2 | 8/2021 | Melton et al. |
| 11,104,883 B2 | 8/2021 | Peterson et al. |
| 11,155,787 B2 | 10/2021 | Melton et al. |
| 11,162,078 B2 | 11/2021 | Peterson et al. |
| 2001/0049130 A1 | 12/2001 | Spielberg |
| 2002/0094569 A1 | 7/2002 | Yu et al. |
| 2003/0138948 A1 | 7/2003 | Fisk et al. |
| 2004/0121460 A1 | 6/2004 | Lumelsky et al. |
| 2004/0191901 A1 | 9/2004 | Assady et al. |
| 2004/0259244 A1 | 12/2004 | Scharp et al. |
| 2005/0053588 A1 | 3/2005 | Yin |
| 2006/0040385 A1 | 2/2006 | Itskovitz-Eldor et al. |
| 2006/0040387 A1 | 2/2006 | Fisk et al. |
| 2006/0194321 A1 | 8/2006 | Colman et al. |
| 2007/0259421 A1 | 11/2007 | D'Amour et al. |
| 2008/0145889 A1 | 6/2008 | Fisk et al. |
| 2008/0267926 A1 | 10/2008 | Martinson et al. |
| 2008/0299582 A1 | 12/2008 | Mandalam et al. |
| 2009/0004152 A1 | 1/2009 | Martinson et al. |
| 2009/0170198 A1 | 7/2009 | Rezania |
| 2009/0263896 A1 | 10/2009 | Kelly et al. |
| 2009/0298169 A1 | 12/2009 | Dalton et al. |
| 2009/0298178 A1 | 12/2009 | D'Amour |
| 2009/0325180 A1 | 12/2009 | Fisk et al. |
| 2010/0015100 A1 | 1/2010 | Xu |
| 2010/0015711 A1 | 1/2010 | Davis et al. |
| 2010/0112693 A1 | 5/2010 | Rezania et al. |
| 2010/0144033 A1 | 6/2010 | Mandalam et al. |
| 2010/0240130 A1 | 9/2010 | Majumdar et al. |
| 2010/0255580 A1 | 10/2010 | Rezania |
| 2010/0260728 A1 | 10/2010 | Martinson et al. |
| 2010/0272695 A1 | 10/2010 | Agulnick et al. |
| 2010/0311166 A1 | 12/2010 | Florio et al. |
| 2011/0008819 A1 | 1/2011 | Chipperfield et al. |
| 2011/0014702 A1 | 1/2011 | Xu |
| 2011/0053930 A1 | 3/2011 | Yu et al. |
| 2011/0151560 A1 | 6/2011 | Xu |
| 2011/0280842 A1* | 11/2011 | Melton ............... A61P 3/10 514/6.9 |
| 2011/0281355 A1 | 11/2011 | Xu |
| 2012/0009675 A1 | 1/2012 | Martinson et al. |
| 2012/0052571 A1 | 3/2012 | Fryer |
| 2012/0052575 A1 | 3/2012 | Rezania |
| 2012/0052576 A1 | 3/2012 | Rezania |
| 2012/0135015 A1 | 5/2012 | Noguchi et al. |
| 2012/0141436 A1 | 6/2012 | Bonner-Weir et al. |
| 2013/0034526 A1 | 2/2013 | Itskovitz-Eldor et al. |
| 2013/0071931 A1 | 3/2013 | Ishikawa |
| 2013/0189777 A1 | 7/2013 | Rezania |
| 2013/0316357 A1 | 11/2013 | D'Amour et al. |
| 2013/0330823 A1 | 12/2013 | Rezania |
| 2013/0337564 A1 | 12/2013 | Davis et al. |
| 2014/0080210 A1 | 3/2014 | Davis et al. |
| 2014/0134726 A1 | 5/2014 | D'Amour et al. |
| 2014/0154801 A1 | 6/2014 | D'Amour et al. |
| 2014/0154802 A1 | 6/2014 | Robins et al. |
| 2014/0162359 A1 | 6/2014 | Rezania |
| 2014/0186305 A1 | 7/2014 | Rezina |
| 2014/0186948 A1 | 7/2014 | Schulz et al. |
| 2014/0186953 A1 | 7/2014 | Rezania |
| 2014/0193902 A1 | 7/2014 | D'Amour et al. |
| 2014/0193904 A1 | 7/2014 | D'Amour et al. |
| 2014/0242693 A1 | 8/2014 | Fryer et al. |
| 2014/0287944 A1 | 9/2014 | Hrvatin et al. |
| 2014/0329704 A1 | 11/2014 | Melton et al. |
| 2014/0335611 A1 | 11/2014 | Chen et al. |
| 2015/0218522 A1 | 8/2015 | Peterson et al. |
| 2015/0240212 A1 | 8/2015 | Peterson et al. |
| 2015/0247123 A1 | 9/2015 | Ekberg et al. |
| 2015/0329828 A1 | 11/2015 | Rezania |
| 2015/0376574 A1 | 12/2015 | Talavera-Adame et al. |
| 2016/0022742 A1 | 1/2016 | Zender et al. |
| 2016/0175363 A1 | 6/2016 | Melton et al. |
| 2016/0177267 A1 | 6/2016 | Melton et al. |
| 2016/0177268 A1 | 6/2016 | Melton et al. |
| 2016/0177269 A1 | 6/2016 | Melton et al. |
| 2016/0186143 A1 | 6/2016 | Melton et al. |
| 2016/0208215 A1 | 7/2016 | Doehn et al. |
| 2017/0029778 A1 | 2/2017 | Peterson et al. |
| 2017/0233700 A1 | 8/2017 | Kunisada |
| 2017/0240866 A1 | 8/2017 | Wells et al. |
| 2018/0153941 A1 | 6/2018 | Melton et al. |
| 2019/0040362 A1 | 2/2019 | Peterson et al. |
| 2019/0119649 A1 | 4/2019 | Melton et al. |
| 2019/0169575 A1 | 6/2019 | Peterson et al. |
| 2019/0185817 A1 | 6/2019 | Melton et al. |
| 2019/0338250 A1 | 11/2019 | Melton et al. |
| 2020/0199539 A1 | 6/2020 | Melton et al. |
| 2020/0347355 A1 | 11/2020 | Melton et al. |
| 2020/0347356 A1 | 11/2020 | Melton et al. |
| 2020/0347357 A1 | 11/2020 | Melton et al. |
| 2020/0347358 A1 | 11/2020 | Peterson et al. |
| 2020/0385681 A1 | 12/2020 | Peterson et al. |
| 2021/0060083 A1 | 3/2021 | Melton et al. |
| 2021/0079355 A1 | 3/2021 | Peterson et al. |
| 2022/0396775 A1 | 12/2022 | Peterson et al. |
| 2023/0076529 A1 | 3/2023 | Peterson et al. |
| 2024/0101963 A1 | 3/2024 | Peterson et al. |

FOREIGN PATENT DOCUMENTS

| | | |
|---|---|---|
| EP | 2267116 A1 | 12/2010 |
| EP | 2283117 A1 | 2/2011 |
| EP | 2292734 A1 | 3/2011 |
| EP | 2341147 A2 | 7/2011 |
| EP | 2377922 A2 | 10/2011 |
| EP | 2505639 A1 | 10/2012 |
| EP | 2569419 A2 | 3/2013 |
| EP | 2650359 A1 | 10/2013 |
| EP | 2650360 A2 | 10/2013 |
| EP | 2664669 A1 | 11/2013 |
| EP | 2674485 A1 | 12/2013 |

(56) References Cited

FOREIGN PATENT DOCUMENTS

| | | |
|---|---|---|
| JP | HEI-11-505411 | 5/1999 |
| JP | 2006-506047 A | 2/2006 |
| JP | 2011-504753 A | 2/2011 |
| JP | 2012-509086 A | 4/2012 |
| JP | 2016503654 A | 2/2016 |
| JP | 2016-506246 A | 3/2016 |
| RU | 2011121843 A | 12/2012 |
| WO | WO-1996/031242 A1 | 10/1996 |
| WO | WO-1999/020740 A2 | 4/1999 |
| WO | WO-2001/088104 A2 | 11/2001 |
| WO | WO-2002/042445 A2 | 5/2002 |
| WO | WO-2003/050249 A2 | 6/2003 |
| WO | WO-2003/100026 A2 | 12/2003 |
| WO | WO-2004/058764 A1 | 7/2004 |
| WO | WO-2007/002136 A2 | 1/2007 |
| WO | WO-2007/075807 A2 | 7/2007 |
| WO | WO-2007/103282 A2 | 9/2007 |
| WO | WO-2007/127927 A2 | 11/2007 |
| WO | WO-2008/083331 A2 | 7/2008 |
| WO | WO-2008/102000 A1 | 8/2008 |
| WO | WO-2009/012428 A2 | 1/2009 |
| WO | WO-2009/018453 A1 | 2/2009 |
| WO | WO-2009/070592 A2 | 6/2009 |
| WO | WO-2010/051223 A1 | 5/2010 |
| WO | WO-2010/057039 A2 | 5/2010 |
| WO | WO-2010/059778 A1 | 5/2010 |
| WO | WO-2011/011302 A2 | 1/2011 |
| WO | WO-2011/059725 A2 | 5/2011 |
| WO | WO-2011/079017 A2 | 6/2011 |
| WO | WO-2011/109279 A2 | 9/2011 |
| WO | WO-2011/123572 A1 | 10/2011 |
| WO | WO-2011/139628 A1 | 11/2011 |
| WO | WO-2012/020845 A1 | 2/2012 |
| WO | WO-2012/021698 A2 | 2/2012 |
| WO | WO-2012/025725 A1 | 3/2012 |
| WO | WO-2012/030540 A1 | 3/2012 |
| WO | WO-2012/168930 A2 | 12/2012 |
| WO | WO-2013/057164 A1 | 4/2013 |
| WO | WO-2013/095953 A1 | 6/2013 |
| WO | WO-2014/033322 A1 | 3/2014 |
| WO | WO-2014/105543 A1 | 7/2014 |
| WO | WO-2014/105546 A1 | 7/2014 |
| WO | WO-2014/151871 A2 | 9/2014 |
| WO | WO-2014/160413 A1 | 10/2014 |
| WO | WO-2014/201167 A1 | 12/2014 |
| WO | WO-2015/002724 A2 | 1/2015 |
| WO | WO-2015/028614 A1 | 3/2015 |
| WO | WO-2015/175307 A1 | 11/2015 |
| WO | WO-2016/100898 A1 | 6/2016 |
| WO | WO-2016/100909 A1 | 6/2016 |
| WO | WO-2016/100921 A1 | 6/2016 |
| WO | WO-2016/100925 A1 | 6/2016 |
| WO | WO-2016/100930 A1 | 6/2016 |
| WO | WO-2017/144695 A1 | 8/2017 |

OTHER PUBLICATIONS

Yang et al., (2002) Survival of pancreatic islet xenografts in NOD mice with the theracyte device. Transplantation Proceedings, 34(8), 3349-3350 (Year: 2002).*
Advisory Action Before the Filing of an Appeal Brief for U.S. Appl. 14/684,101, dated Sep. 1, 2016.
Advisory Action Before the Filing of an Appeal Brief for U.S. Appl. 14/684,129, dated Nov. 9, 2016.
Aguayo-Mazzucato, et al., "Mafa Expression Enhances Glucose-Responsible Insulin Secretion in Neonatal Rat Beta Cells," *Diabetologia*, 54(3):583-593, (Mar. 2011).
Aguayo-Mazzucato, et al., "Thyroid Hormone Promotes Postnatal Rat Pancreatic β-Cell Development and Glucose-Responsive Insulin Secretion Through MAFA," *Diabetes*, 62:1569-1580, (2013).
Amariglio, et al., "Donor-Derived Brain Tumor Following Neural Stem Cell Transplantation in an Ataxia Telangiectasia Patient," *PLOS Medicine*, 6(2): 1-3, (2009). (2 pages of translation of relevance).
Apelqvist, et al., "Notch Signaling Controls Pancreatic Cell Differentiation," *Nature*, 400:877-881, (1999).
Ashery-Padan et al., "Conditional Inactivation of Pax6 in the Pancreas Causes Early Onset of Diabetes," *Developmental Biology*, 269:479-488, (2004).
Assady, et al., "Insulin Production by Human Embryonic Stem Cells," *Diabetes*, 50:1691-1697, (Aug. 2001).
Axxora.com Product Search Results for "Alk5 Inhibitor." Retrieved from URL: https://www.axxora.com/product-listing/ on Oct. 21, 2020 (Year: 2020).
Baetge, et al., "Production of β-Cells From Human Embryonic Stem Cells," *Diabetes, Obesity and Metabolism*, 10:186-194, (2008).
Banerjee, et al., "A Simple Two-Step Protocol for the Purification of Human Pancreatic Beta Cells," *Diabetologia*, 52:621-625, (2009).
Basford, et al., "The Functional and Molecular Characterisation of Human Embryonic Stem Cell-Derived Insulin-Positive Cells Compared With Adult Pancreatic Beta Cells," *Diabetologia*, 55:358-371, (2012).
Beattie, et al., "Sustained Proliferation of PDX-1+ Cells Derived From Human Islets," *Diabetes*, 48: 1013-1019, (May 1999).
Bellin, et al., "Potent Induction Immunotherapy Promotes Long-Term Insulin Independence After Islet Transplantation in Type 1 Diabetes," *Am. J. Transplant.*, 12:1576-1583, (2012).
Bennett, et al., "SP600125, An Anthrapyrazolone Inhibitor of Jun N-Terminal Kinase," *PNAS*, 98(24):13681-13686, (Nov. 20, 2001).
Bhandari, et al., "The Simplest Method for in vitro B-Cell Production From Human Adult Stem Cells," *Differentiation*, 82(3): 144-152, (Jul. 22, 2011).
Blazhevich, et al., "Cell Culturing: Lecture Course," 6 pages (1 page of translation of relevance) (2004).
Boretti, et al., "Induced Cell Clustering Enhances Islet Beta Cell Formation From Human Cultures Enriched for Pancreatic Ductal Epithelial Cells," *2003 Summer Bioengineering Conference*, Jun. 25-29, Sonesta Beach Report in Key Biscayne, Florida, 2 pages.
Boretti, et al., "Induced Cell Clustering Enhances Islet Beta Cell Formation From Human Cultures Enriched for Pancreatic Ductal Epithelial Cells," *Tissue Eng.*, 12(4):939-948, (2006).
Bose, et al., "Human Embryonic Stem Cell Differentiation Into Insulin Secreting Beta-Cells for Diabetes," *Cell Biol Int.*, 36(11):1013-1020, (2012).
Brolen, et al., "Signals From the Embryonic Mouse Pancreas Induce Differentiation of Human Embryonic Stem Cells Into Insulin-Producing β-cell-like Cells," *Diabetes*, 54:2867-2874, (2005).
Cai, et al., "Generation of Homogeneous PDX1+ Pancreatic Progenitors from Human ES Cell-Derived Endoderm Cells," *Journal of Molecular Cell Biology*, 2:50-60, (2010).
Campbell-Thompson, et al., "Collection Protocol for Human Pancreas," *Journal of Visualized Experiments*, 63:1-5, (May 2012).
Cerf, "Transcription Factors Regulating β-cell Function," *European Journal of Endocrinology*, 155:671-679, (2006).
Chakrabarti, et al., "Transcription Factors Direct the Development and Function of Pancreatic Beta Cells," *Trends Endocrinol Metab.*, 14(2):78-84, (Mar. 2003).
Chen, et al., "Scalable GMP Compliant Suspension Culture System for Human ES Cells," *Stem Cell Research*, 8:388-402, (2012).
Cheng, et al., "Self-Renewing Endodermal Progenitor Lines Generated From Human Pluripotent Stem Cells," *Cell Stem Cell*, 10:371-384, (2012).
Chiang, et al., "Single-Cell Transcript Analysis of Pancreas Development," *Dev. Cell.*, 4(3):383-393, (Mar. 2003).
Cho, et al. "Inhibition of Activin/Nodal Signalling is Necessary for Pancreatic Differentiation of Human Pluripotent Stem Cells," *Diabetologia*, 55:3284-3295, (2012).
Choi, et al., "A Comparison of Genetically Matched Cell Lines Reveals the Equivalence of Human iPSCs and ESCs," *Nat. Biotechnol.*, Oct. 26, 2015. doi: 10.1038/nbt.3388. [Epub ahead of print].
CMRL-1066 Data Sheet. Retrieved online Sep. 30, 2017. https://www.sigmaaldrich.com/content/dam/sigma-aldrich/docs/sigma/datasheet/c0422dat.pdf (1998).
Cohen, et al., "Antibiotics Reduce the Growth Rate and Differentiation of Embryonic Stem Cell Cultures," *Tissue Eng.*, 12(7):2025-2030, (2006).

(56) References Cited

OTHER PUBLICATIONS

Corkey, et al., "A Role for Malonyl-CoA in Glucose-Stimulated Insulin Secretion from Clonal Pancreatic β-Cells," *J. Biol. Chem.*, 254(36):21608-21612, (Dec. 1989).
D'Amour, et al., "Efficient Differentiation of Human Embryonic Stem Cells to Definitive Endoderm," *Nat. Biotechnol.*, 23(12):1534-1541, (2005).
D'Amour, et al., "Production of Pancreatic Hormone-Expressing Endocrine Cells From Human Embryonic Stem Cells," *Nat. Biotechnol.*, 24(11):1392-1401, (2006).
Declaration of Maria Cristina Nostro, Ph.D. dated Jul. 22, 2021 in Toronto, Canada.
Docherty, "Pancreatic Stellate Cells Can Form New β-Like Cells," *Biochem, J.*, 421:e1-e4, (2009).
Dror, et al., "Notch Signaling Suppresses Apoptosis in Adult Human and Mouse Pancreatic Islet Cells," *Diabetlogia* 50:2504-2515, (2007).
Eberhardt, et al., "Multipotential Nestin and Isl-1 Positive Mesenchymal Stem Cells Isolated From Human Pancreatic Islets," *Biochem. Biophys. Res. Commun.*, 345(3):1167-1176, (2006).
Extended European Search Report for European Application EP 14819763.5, dated May 23, 2017.
Falzacappa, et al., "3,5,3'-Triiodothyronine (T3) is a Survival Factor for Pancreatic Beta-Cells Undergoing Apoptosis," *J. Cell Physiol.*, 206(2):309-321, (Feb. 2006).
Feng, et al., "Differentiation of Mouse Embryonic Stem Cells into Insulin Producing Cells Induced by Various Growth Factors," *Chinese Journal of Tissue Engineering Research*, 53:4167-4171, (2008).
Final Office Action for U.S. Appl. No. 14/684,101, dated Jan. 16, 2018.
Final Office Action for U.S. Appl. No. 14/684,101, dated Jan. 28, 2016.
Final Office Action for U.S. Appl. No. 14/684,129, dated Jan. 31, 2020.
Final Office Action for U.S. Appl. No. 14/684,129, dated Mar. 8, 2016.
Final Office Action for U.S. Appl. No. 14/684,129, dated Mar. 9, 2018.
Final Office Action for U.S. Appl. No. 14/898,015, dated Aug. 10, 2018.
Final Office Action for U.S. Appl. No. 14/975,457, dated Apr. 19, 2018.
Final Office Action for U.S. Appl. No. 14/975,457, dated May 23, 2018.
Final Office Action for U.S. Appl. No. 15/666,555, dated Oct. 9, 2019.
Final Office Action for U.S. Appl. No. 16/273,076, dated Feb. 6, 2023.
Final Office Action for U.S. Appl. No. 16/573,985, dated May 19, 2023.
Final Office Action for U.S. Appl. No. 16/934,848, dated Mar. 17, 2021.
Final Office Action for U.S. Appl. No. 16/934,885, dated Mar. 17, 2021.
Final Office Action for U.S. Appl. No. 14/975,158, dated Jun. 28, 2018.
Fraker, et al. "Enhanced Oxygenation Promotes B-Cell Differentiation in Vitro," *Stem Cells*, 25:3155-3164, (2007).
Greggio, et al., "Artificial Three-Dimensional Niches Deconstruct Pancreas Development in vitro," *Development*, 140:4452-4462, (2013).
Guillemain, et al., "Glucose Is Necessary For Embryonic Pancreatic Endocrine Cell Differentiation," *The Journal of Biological Chemistry*, 282(20):15228-15237, (May 18, 2007).
Habener, et al., "Minireview: Transcriptional Regulation in Pancreatic Development," *Endocrinology*, 146(3):1025-1034, (2004).
Hanley, "Closing in on Pancreatic Beta Cells," *Nature Biotechnology*, 32(11):1100-1102, (Nov. 2014).

Haycock, "3D Cell Culture: A Review of Current Approaches and Techniques," *Molecular Biology*, 695:1-15, (2011).
Heinis, et al., "Oxygen Tension Regulates Pancreatic Beta-Cell Differentiation Through Hypoxia-Inducible Factor 1x," *Diabetes*, 59:662-669, (Mar. 2010).
Heremans, et al., "Recapitulation of Embryonic Neuroendocrine Differentiation in Adult Human Pancreatic Duct Cells Expressing Neurogenin 3," *The Journal of Cell Biology*, 159(2):303-311, (Oct. 2002).
Hering et al. "Phase 3 trial of transplantation of human islets in type 1 diabetes complicated by severe hypoglycemia." Diabetes care 39.7 (2016): 1230-1240.
Hernandez, et al., "Microcapsules and Microcarriers for in Situ Cell Delivery," *Advanced Drug Delivery Reviews*, 62:711-730, (2010).
Hrvatin et al., "Differentiated Human Stem Cells Resemble Fetal, Not Adult, β-cells," *PNAS*, 111(8):3038-3043, (2014).
Hrvatin, Ph.D. Dissertation, Harvard University, Dec. 2012. Accessible at http://nrs.harvard.edu/urn-3:HUL.InstRepos:10433470 (Year: 2012).
Huynh, et al., "Screening and Identification of a Novel Class of TGF-β Type 1 Receptor Kinase Inhibitor," *Society for Laboratory Automation and Screening*, 16(7):724-733, (2011).
International Search Report for International Application PCT/US2014/041988, dated Dec. 24, 2014.
International Search Report for International Application PCT/US2014/041992, dated Oct. 24, 2014.
International Search Report for International Application PCT/US2015/066840, dated Mar. 31, 2016.
International Search Report for International Application PCT/US2015/066858, dated Mar. 11, 2016.
International Search Report for International Application PCT/US2015/066881, dated Mar. 3, 2016.
International Search Report for International Application PCT/US2015/066888, dated Feb. 26, 2016.
International Search Report for International Application PCT/US2015/066900, dated Mar. 3, 2016.
Isayeva, et al., "Characterization and Performance of Membranes Designed for Macroencapsulation/Implantation of Pancreatic Islet Cells," *Biomaterials*, 24(20):3483-3491, (2003).
Iype, et al. "The Transcriptional Repressor Nkx6.1 Also Functions as Deoxyribonucleic Acid Context-Dependent Transcriptional Activator During Pancreatic B-cell Differentiation: Evidence for Feedback Activation of the nkx6.1 Gene by Nkx6.1," *Molecular Endocrinology*, 18(6): 1363-1375, Jun. 2004.
Jahansouz, et al., "Evolution of β-Cell Replacement Therapy in Diabetes Mellitus: Islet Cell Transplantation," *Journal of Transplantation*, pp. 1-21, (2011).
Jeon, et al., "Differentiation and Transplantation of Functional Pancreatic Beta Cells Generated from Induced Pluripotent Stem Cells Derived from a Type 1 Diabetes Mouse Model," *Stem Cells Dev.*, 21(14):2642-2655, (2012).
Jiang, et al., "Generation of Insulin-Producing Islet-Like Clusters from Human Embryonic Stem Cells," *Stem Cells*, 25:1940-1953, (2007).
Jiang, et al., "In vitro Derivation of Functional Insulin-Producing Cells from Human Embryonic Stem Cells," *Cell Research*, 17(4):333-344, (2007).
Korytnikov, et al., "Generation of Polyhormonal and Multipotent Pancreatic Progenitor Lineages form Human Pluripotent Stem Cells," *Methods*, 101:56-64, (2015).
Kozhucharova, et al., "Novel Human Embryonic Stem Cell Lines C612 and C910," *Cytology*, 51(7):551-558, (2009). (2 pages of translation of relevance).
Kroon, et al., "Pancreatic Endoderm Derived From Human Embryonic Stem Cell Generates Glucose-Responsive Insulin-Secreting Cells In Vivo," *Nat. Biotechnol.*, 26(4):443-452, (Apr. 2008).
Kumar, et al., "Recent Developments in β-Cell Differentiation of Pluripotent Stem Cells Induced by Small and Large Molecules," *Int. J. Mol. Sci.*, 15(12):23418-23447, (2014).
Kumar, et al., "Signals From Lateral Plate Mesoderm Instruct Endoderm Toward A Pancreatic Fate," *Dev. Biol.*, 259(1):109-122, (Jul. 2003).

(56) References Cited

OTHER PUBLICATIONS

Kunisada, et al., "Small Molecules Induce Efficient Differentiation Into Insulin-Producing Cells From Human Induced Pluripotent Stem Cells," *Stem Cell Research*, 8:274-284, (2012).

Lee, et al., "All-Trans-Retinoic Acid as a Novel Therapeutic Strategy for Alzheimer's Disease," *Expert Rev. Neurother*, 9(11):1615-1621, (2009).

Lim, et al., Microencapsulated Islets as Bioartificial Endocrine Pancreas, *Science*, 210(4472):908-910, (Nov. 21, 1980).

Lin, et al., "Transforming Growth Factor-β/Smad3 Signaling Regulates Insulin Gene Transcription and Pancreatic Islet β-Cell Function," *The Journal of Biological Chemistry*, 284(18):12246-12257, (May 1, 2009).

Lumelsky, et al., "Differentiation of Embryonic Stem Cells to Insulin-Secreting Structures Similar to Pancreatic Islets," *Science*, 292:1389-1394, (2001).

Madsen, et al., "Towards Cell Therapy For Diabetes," *Nat. Biotechnol.*, 24(12):1481-1483, (Dec. 2006).

Maehr, et al., "Generation of Pluripotent Stem Cells From Patients With Type 1 Diabetes," *PNAS*, 106(37):15768-15773, (2009).

Manning, et al., "The Protein Kinase Complement of the Human Genome," *Science*, 298:1912-1934, (Dec. 6, 2002).

Marzorati, et al., "Culture Medium Modulates Proinflammatory Conditions of Human Pancreatic Islets Before Transplantation," *Am. J. Transplant*, 6(11):2791-2795, (2006).

Matschinsky, "Assessing the Potential of Glucokinase Activators in Diabetes Therapy," *Nature Reviews Drug Discovery*, 8:399-416, (2009).

McLean, et al., "Activin A Efficiently Specifies Definitive Endoderm From Human Embryonic Stem Cells Only When Phosphatidylinositol 3-Kinase Signaling is Suppressed," *Stem Cells*, 25(1):29-38, (Jan. 2007).

McQuilling, et al., "New Alginate Microcapsule System for Angiogenic Protein Delivery and Immunoisolation of Islets for Transplantation in the Rat Omentum Pouch," *Transplantation Proceedings*, 43(9):3262-3264, (Nov. 2011).

Micallef, et al. "INSGFP/W Human Embryonic Stem Cells Facilitate Isolation of in vitro Derived Insulin-Producing Cells," *Diabetologia*, 55:694-706, (2012).

Michael, et al., "Pancreatic β-cells Secrete Insulin in Fast- and Slow-Release Forms," *Diabetes*, 55: 600-607, (2006).

Moens, et al., "Dual Glucagon Recognition by Pancreatic Beta-Cells Via Glucagon and Glucagon-Like Peptide 1 Receptors," *Diabetes*, 47:66-72, (1998).

Mollard, et al., "Design, Synthesis, and Biological Evaluation of a Series of Novel AXL Kinase Inhibitors," *ACS Medicinal Chemistry Letters*, 2:907-912, (2011).

Motté, et al., "Composition and Function of Macroencapsulated Human Embryonic Stem Cell-Derived Implants: Comparison With Clinical Human Islet Cell Grafts," *American Journal of Physiology-Endocrinology and Metabolism*, 307(9):E838-E846, (2004).

Mudduluru, et al., "Regulation of Axl Receptor Tyrosine Kinase Expression by miR-34a and miR-199a/b in Solid Cancer," *Oncogene*, 30(25):2889-2899, (2011).

Murua, et al., "Cell Microencapsulation Technology: Towards Clinical Application," *Journal of Controlled Release*, 132(2):76-83, (2008).

Narayanan, et al., "Extracellular Matrix-Mediated Differentiation of Human Embryonic Stem Cells: Differentiation to Insulin-Secreting Beta Cells," *Tissue Engineering: Part A*, 20(1-2):424-433, (2013).

Natalicchio, et al., "Exendin-4 Protects Pancreatic Beta Cells from Palmitate-Induced Apoptosis by Interfering with GPR40 and the MKK4/7 Stress Kinase Signalling Pathway," *Diabetologia*, 56:2456-2466, (2013).

Nelson, et al., "The Transcription Factors Nkx6.1 and Nkx6.2 Possess Equivalent Activities in Promoting Beta-Cell Fate Specification in Pdx1+ Pancreatic Progenitor Cells," *Development*, 134:2491-2500, (2007).

Nishimura, et al., "A Switch from MafB to MafA Expression Accompanies Differentiation to Pancreatic β-Cells," *Developmental Biology*, 293:526-539, (2006).

Non-Final Office Action for U.S. Appl. No. 14/684,101, dated Aug. 25, 2015.

Non-Final Office Action for U.S. Appl. No. 14/684,101, dated Jun. 1, 2017.

Non-Final Office Action for U.S. Appl. No. 14/684,129, dated Apr. 16, 2019.

Non-Final Office Action for U.S. Appl. No. 14/684,129, dated May 8, 2017.

Non-Final Office Action for U.S. Appl. No. 14/684,129, dated Sep. 4, 2015.

Non-Final Office Action for U.S. Appl. No. 14/898,015, dated Oct. 13, 2017.

Non-Final Office Action for U.S. Appl. No. 14/975,158, dated Sep. 13, 2017.

Non-Final Office Action for U.S. Appl. No. 14/975,255, dated Apr. 12, 2018.

Non-Final Office Action for U.S. Appl. No. 14/975,255, dated Jul. 17, 2017.

Non-Final Office Action for U.S. Appl. No. 14/975,383, dated Feb. 1, 2017.

Non-Final Office Action for U.S. Appl. No. 14/975,421, dated Mar. 1, 2017.

Non-Final Office Action for U.S. Appl. No. 14/975,457, dated Aug. 10, 2017.

Non-Final Office Action for U.S. Appl. No. 14/975,457, dated Aug. 7, 2018.

Non-Final Office Action for U.S. Appl. No. 15/666,555, dated Feb. 4, 2019.

Non-Final Office Action for U.S. Appl. No. 16/042,917, dated Dec. 3, 2018.

Non-Final Office Action for U.S. Appl. No. 16/042,933, dated Dec. 30, 2020.

Non-Final Office Action for U.S. Appl. No. 16/273,076, dated Jul. 6, 2022.

Non-Final Office Action for U.S. Appl. No. 16/292,231, dated Mar. 26, 2021.

Non-Final Office Action for U.S. Appl. No. 16/573,985, dated Mar. 2, 2022.

Non-Final Office Action for U.S. Appl. No. 16/925,276, dated Mar. 3, 2023.

Non-Final Office Action for U.S. Appl. No. 16/934,333, dated Oct. 26, 2020.

Non-Final Office Action for U.S. Appl. No. 16/934,412, dated Mar. 30, 2021.

Non-Final Office Action for U.S. Appl. No. 16/934,503, dated Jan. 19, 2021.

Non-Final Office Action for U.S. Appl. No. 16/934,764, dated Nov. 13, 2020.

Non-Final Office Action for U.S. Appl. No. 16/934,848, dated Nov. 13, 2020.

Non-Final Office Action for U.S. Appl. No. 16/934,885, dated Nov. 13, 2020.

Non-Final Office Action for U.S. Appl. No. 17/670,124, dated Dec. 19, 2023.

Non-Final Office Action for U.S. Appl. No. 17/978,936, dated Feb. 3, 2023.

Non-Final Office Action for U.S. Appl. No. 16/573,985, dated Sep. 13, 2022.

Non-Final Office Action for U.S. Appl. No. 14/975,421, dated Sep. 15, 2016.

Nostro, et al., "Generation of Beta Cells From Human Pluripotent Stem Cells: Potential for Regenerative Medicine," *Seminars in Cell & Developmental Biology*, 23:701-710, (2012).

Nostro, et al., "Stage-Specific Signaling Through TGFβ Family Members and WNT Regulates Patterning and Pancreatic Specification of Human Pluripotent Stem Cells," *Development*, 138:861-871, (2011).

Notice of Allowance for U.S. Appl. No. 14/975,158, dated Jun. 3, 2019.

(56) References Cited

OTHER PUBLICATIONS

Notice of Allowance for U.S. Appl. No. 16/042,917, dated Aug. 26, 2019.
Notice of Allowance for U.S. Appl. No. 16/042,917, dated Dec. 18, 2019.
Notice of Allowance for U.S. Appl. No. 16/042,917, dated Dec. 31, 2019.
Notice of Allowance for U.S. Appl. No. 16/042,917, dated Jul. 17, 2019.
Notice of Allowance for U.S. Appl. No. 16/042,917, dated Sep. 20, 2019.
Notice of Allowance for U.S. Appl. No. 14/684,101, dated May 4, 2018.
Notice of Allowance for U.S. Appl. No. 14/975,255, dated Sep. 6, 2018.
Notice of Allowance for U.S. Appl. No. 14/975,457, dated Nov. 23, 2018.
Notice of Allowance for U.S. Appl. No. 16/213,950 dated, Oct. 23, 2020.
Notice of Allowance for U.S. Appl. No. 16/292,231, dated Jul. 7, 2021.
Notice of Allowance for U.S. Appl. No. 16/934,333, dated Feb. 9, 2021.
Notice of Allowance for U.S. Appl. No. 16/934,412, dated Jul. 13, 2021.
Notice of Allowance for U.S. Appl. No. 16/934,503 dated May 5, 2021.
Notice of Allowance for U.S. Appl. No. 16/934,764, dated Apr. 15, 2021.
Notice of Allowance for U.S. Appl. No. 16/934,848, dated Apr. 23, 2021.
Notice of Allowance for U.S. Appl. No. 16/934,885 dated Apr. 26, 2021.
Notice of Allowance for U.S. Appl. No. 17/978,936, dated May 23, 2023.
O'Brien, et al., "Suspended in Culture—Human Pluripotent Cells for Scalable Technologies," *Stem Cell Research*, 9:167-170, (2012).
Okazaki, et al., "Staurosporine, a Novel Protein Kinase Inhibitor, Enhances HL-60-Cell Differentiation Induced by Various Compounds," *Exp. Hemtaol.*, 16:42-48, (1988).
Orive, et al., "Application of Cell Encapsulation for Controlled Delivery of Biological Therapeutics," *Advanced Drug Delivery Reviews*, pp. 1-12, (2013).
Pagliuca, et al., "How to Make a Functional β-cell," *Development*, 140:2472-2483, (2013).
Pagliuca, et al., "Generation of Functional Human Pancreatic β Cells In Vitro," *Cell*, 159(2):428-439, (Oct. 2014).
Parsons, et al., "Notch-Responsive Cells Initiate the Secondary Transition in Larval Zebrafish Pancreas," *Mechanisms of Development*, 126(10):898-912, (2009).
Patent Assignment from U.S. Appl. No. 14/684,101, from Douglas A. Melton to Howard Hughes Medical Institute dated Mar. 22, 2016.
Patent Assignment from U.S. Appl. No. 16/042,917, from Howard Hughes Medical Institute to President and Fellows of Harvard College, dated Feb. 28, 2019.
Phillips, et al., "Directed Differentiation of Human Embryonic Stem Cells into the Pancreatic Endocrine Lineage," *Stem Cells and Dev.*, 16:561-578, (2007).
Piran, et al., "Pharmacological Induction of Pancreatic Islet Cell Transdifferentiation; Relevance to Type I Diabetes," *Cell Death and Disease*, 5(e1357):1-36, (2014).
Qi, et al., "PVA Hydrogel Sheet Macroencapsulation of the Bioartificial Pancreas," *Biomaterials*, 24(27):5885-5892, (2004).
Ratanasavanh, et al., "Immunocytochemical Evidence for the Maintenance of Cytochrome P-450 Isozymes, NADPH Cytochrome C Reductase, and Epoxide Hydrolase in Pure and Mixed Primary Cultures of Adult Human Hepatocytes," *J. Histochem. Cytochem.*, 34(4):527-533, (Apr. 1986).
Rathaore, et al., "Microencapsulation of Microbial Cells," *Journal of Food Engineering*, 116:369-381, (2013).
Ravassard, et al., "A Genetically Engineered Human Pancreatic β Cell Line Exhibiting Glucose-Inducible Insulin Secretion," *The Journal of Clinical Investigation*, 121(9):3589-3597, (2011).
Rezania, et al., "Enrichment of Human Embryonic Stem Cell-Derived NKX6.1-Expressing Pancreatic Progenitor Cells Accelerates the Maturation of Insulin-Secreting Cells In Vivo," *Stem Cells*, 31:2432-2442, (2013).
Rezania, et al., "Maturation of Human Embryonic Stem Cell-Derived Pancreatic Progenitors Into Functional Islets Capable of Treating Pre-Existing Diabetes in Mice," *Diabetes*, 61:2016-2029, (2012).
Rezania, et al., "Production of Functional Glucagon-Secreting α-cells From Human Embryonic Stem Cells," *Diabetes*, 60:239-247, (Jan. 2011).
Rezania, et al., "Reversal of Diabetes With Insulin-Producing Cells Derived In Vitro from Human Pluripotent Stem Cells," *Nat. Biotechnol.*, 21(11):1121-1133, (Nov. 2014).
Roche, "Protocols to Differentiate Embryonic Stem Cells Into Insulin Producing Cells," *Av. Diabetol.*, 24(2):128-137, (2008).
Ropiquet, et al., "FGF7/KGF Triggers Cell Transformation and Invasion on Immortalised Human Prostatic Epithelial PNT1A Cells," *Int. J. Cancer*, 82:237-243 (1999).
Roskoski, "A Historical Overview of Protein Kinases and Their Targeted Small Molecule Inhibitors," Pharmalogical Res., 100:1-23, (2015).
Rovira, et al., "Chemical Screen Identifies FDA-Approved Drugs and Target Pathways That Induce Precocious Pancreatic Endocrine Differentiation," *Proc. Natl. Acad. Sci. U.S.A.*, 108(48):19264-19269, (2011).
Sander, et al., "Homeobox Gene Nkx6.1 Lies Downstream of Nkx2.2 in the Major Pathway of β-cell Formation in the Pancreas," *Development*, 127:5533-5540, (2000).
Sander, et al., "The β-cell Transcription Factors and Development of the Pancreas," *J. Mol. Med.*, 75:327-340, (1997).
Schuldiner, et al., "Effects of Eight Growth Factors on the Differentiation of Cells Derived From Human Embryonic Stem Cells," *Proc. Natl. Acad. Sci. U.S.A.*, 97(21):11307-11312, (Oct. 2000).
Schulz, et al., "A Scalabe System for Production of Functional Pancreatic Progenitors From Human Embryonic Stem Cells," *PLoS One*, 7(5):1-17, (May 2012).
Schumacher, et al., "Staurosporine is a Potent Activator of Neuronal, Glial, and "CNS Stem Cell-Like" Neurosphere Differentiation in Murine Embryonic Stem Cells," *Molecular and Cellular Neuroscience*, 23:669-680, (2003).
Segerstolpe et al. "Single-cell transcriptome profiling of human pancreatic islets in health and type 2 diabetes." Cell metabolism 24.4 (2016): 593-607.
Segrev, et al., "Differentiation of Human Embryonic Stem Cells into Insulin-Producing Clusters," *Stem Cells*, 22:265-274, (2004).
Shaer, et al., "Differentiation of Human-Induced Pluripotent Stem Cells Into Insulin-Producing Clusters," *Exp. Clin. Transplant*, 13(1):68-75, (2014).
Shahjalal, et al., "Generation of Insulin-Producing β-Like Cells from Human iPS Cells in a Defined and Completely Xeno-Free Culture System," *Journal of Molecular Cell Biology*, 6(5):394-408, (2014).
Shapiro, et al., "International Trial of the Edmonton Protocol for Islet Transplantation," *N. Engl. J. Med.*, 355:1318-1330, (2006).
Shi, et al., "Inducing Embryonic Stem Cells to Differentiate into Pancreatic β-cells by a Novel Three-Step Approach with Activin A and All-Trans Retinoic Acid," *Stem Cells 23*:656-662, (2005).
Shim, et al., "Directed Differentiation of Human Embryonic Stem Cells Towards a Pancreatic Cell Fate," *Diabetologia*, 50:1128-1238, (2007).
Skurikhin, et al., "Differentiation of Pancreatic Stem and Progenitor Beta-Cells into Insulin Secreting Cells in Mice with Diabetes Mellitus," *Experimental Biology and Medicine*, 156(6):726-730, (Apr. 2014).
Sneddon, et al., "Self-Renewal of Embryonic-Stem-Cell-Derived Progenitors by Organ-Matched Mesenchyme," *Nature*, 491:765-768, (2012).
SoRelle, et al., "Beta Cell Replacement Therapy," *Type 1 Diabetes—Pathogenesis, Genetics and Immunotherapy*, 22:503-526, (2011).

(56) References Cited

OTHER PUBLICATIONS

Soria, "In-vitro Differentiation of Pancreatic β-cells," *Differentiation*, 68:205-219, (2001).
Spence, et al., "Sox17 Regulates Organ Lineage Segregation of Ventral Foregut Progenitor Cells," *Dev. Cell.*, 17(1):62-74, (Jul. 2009).
Street et al. "Islet graft assessment in the Edmonton Protocol: implications for predicting long-term clinical outcome." Diabetes 53.12 (2004): 3107-3114.
Street et al. "Stem cell-based approaches to solving the problem of tissue supply for islet transplantation in type 1 diabetes." The international journal of biochemistry & cell biology 36.4 (2004): 667-683.
Sui, et al., "Stem Cell Therapy for Diabetes: A Call for Efficient Differentiation of Pancreatic Progenitors," *J. Regen. Med.* 2(1):1-4, (2013).
Supplementary European Search Report for European Application EP 14 81 0778, dated Sep. 28, 2016.
Supplementary European Search Report for European Application EP 14819763.5, dated Jan. 26, 2017.
Talchai et al. "Pancreatic β cell dedifferentiation as a mechanism of diabetic β cell failure." Cell 150.6 (2012): 1223-1234.
Taylor, et al., "NKX6-I Is Essential for Maintaining the Functional State of Pancreatic Beta Cells," *Cell Rep*, 4:1262-1275, (2013).
Thatava, et al., "Indolactam V/GLP-1-Mediated Differentiation of Human iPS Cells into Glucose-Responsive Insulin-Secreting Progeny," *Gene Ther.*, 18(3):283-293, (2011).
ThermoFisher Scientific, "B-27 Serum-Free Supplement (50X) liquid," ThermoFisher Scientific Website, Retrieved from the Internet: URL:https://www.thermofisher.com/nl/en/home/technical-resources/media-formulation.250.html, on Jun. 13, 2016.
Third Party Submission from U.S. Appl. No. 16/042,933, dated Jul. 19, 2019.
Thowfeequ, et al., "Betacellulin Inhibits Amylase and Glucagon Production and Promotes Beta Cell Differentiation in Mouse Embryonic Pancreas," *Diabetologia*, 50:1688-1697, (2007).
Tian, et al., "Protein Kinase C and Calcium Regulation of Adenylyl Cyclase in Isolated Rat Pancreatic Islets," *Diabetes*, 50:2505-2513, (2001).
Treff, et al., "Differentiation of Embryonic Stem Cells Conditionally Expressing Neurogenin 3," *Stem Cells*, 24(11):2529-2537, (1999).
Tsaniras, et al., "Generating Pancreatic β-Cells from Embryonic Stem Cells by Manipulating Signaling Pathways," *Journal of Endocrinology*, 206:13-26, (2010).
Tsuchida, et al., "Activin Signaling as an Emerging Target for Therapeutic Interventions," *Cell Communication & Signaling*, 7(15):1-11, (2009).

Verkhovskaya, et al., "The Effect of Alkoxy-Substituted Derivatives of Glycerol on Morphological and Functional Properties of Continuous Cell Culture," *Cryobiology*, 1:30-34, (1990).
Vogt, et al., "The Specificities of Small Molecule Inhibitors of the TGFβ and BMP Pathways," *Cellular Signaling*, 23:1831-1842, (2011).
Wachs, et al., "High Efficacy of Clonal Growth and Expansion of Adult Neural Stem Cells," Laboratory Investigation, 83(7):949-962, (Jul. 2003).
Xie, et al., "Dynamic Chromatin Remodeling Mediated by Polycomb Proteins Orchestrates Pancreatic Differentiation of Human Embryonic Stem Cells," *Cell Stem Cell*, 12:224-237, (2013).
Xu, et al., "Revealing a Core Signaling Regulatory Mechanism for Pluripotent Stem Cell Survival and Self-Renewal by Small Molecules," PNAS, 107(18):8129-8134, (May 4, 2010).
Zanin, et al., "The Development of Encapsulated Cell Technologies as Therapies for Neurological and Sensory NIHDiseases," *Journal of Controlled Release*, 160:3-13, (2012).
Zhang, et al., "Highly Efficient Differentiation of Human ES Cells and iPS Cells Into Mature Pancreatic Insulin-Producing Cells," Cell Research, 19:429-438, (2009).
Zhdanov, et al., "The Secrets of the Third Kingdom," *Publishing House "Znanie" Moscow*.pp. 124-125, (1975). (2 pages of translation).
Zhu, et al., "Generation of Pancreatic Insulin-Producing Cells from Rhesus Monkey Induced Pluripotent Stem Cells," *Diabetologia*, 54:2325-2336, (2011).
Zhu, et al., "Preventive Effect of Notch Signaling Inhibition by a γ-Secretase Inhibitor on Peritoneal Dialysis Fluid-Induced Peritoneal Fibrosis In Rats," *American Journal of Pathology*, 176(2):650-659, (2010).
Zulewski, "Stem Cells with Potential to Generate Insulin-Producing Cells in Man," *Swiss Med. Wkly*, 136:647-654, (2006).
Zweigerdt, et al., "Scalable Expansion of Human Pluripotent Stem Cells in Suspension Culture," *Nature Protocols*, 6(5):689-700, (2011).
Kajabadi, et al., "Computational predictions of intracellular Thiazovivin interactions as one of the best hESCs apoptosis inhibitors," Research in Pharmaceutical Sciences; 7(5), 2012, 1 page abstract.
Non-Final Office Action for U.S. Appl. No. 17/503,143, dated Feb. 28, 2024.
Xin et al., "Pseudotime Ordering of Single Human b-Cells Reveals States of Insulin Production and Unfolded Protein Response," Diabetes, 67(9): 1783-94 (including single-cell sequencing data stored in the Gene Expression Omnibus database under accession No. GSE114297); <https://www.ncbi.nlm.nih.gov/geo/query/acc.cgi?acc=GSE114297>, 2018.

\* cited by examiner

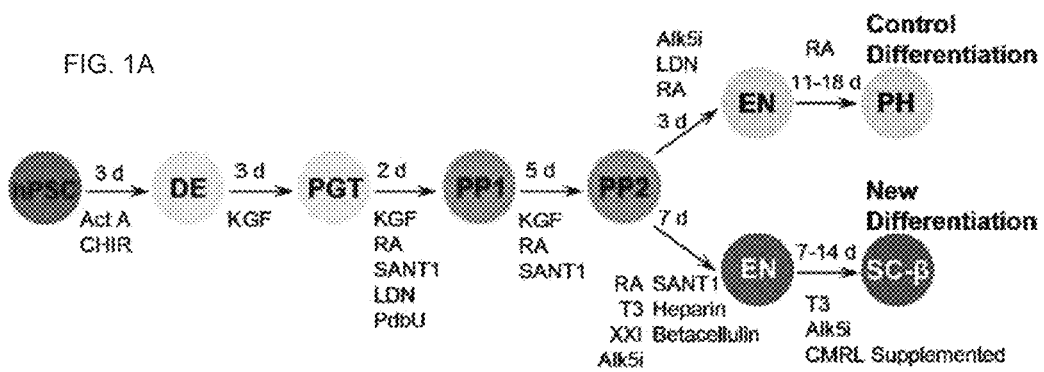
FIG. 1A
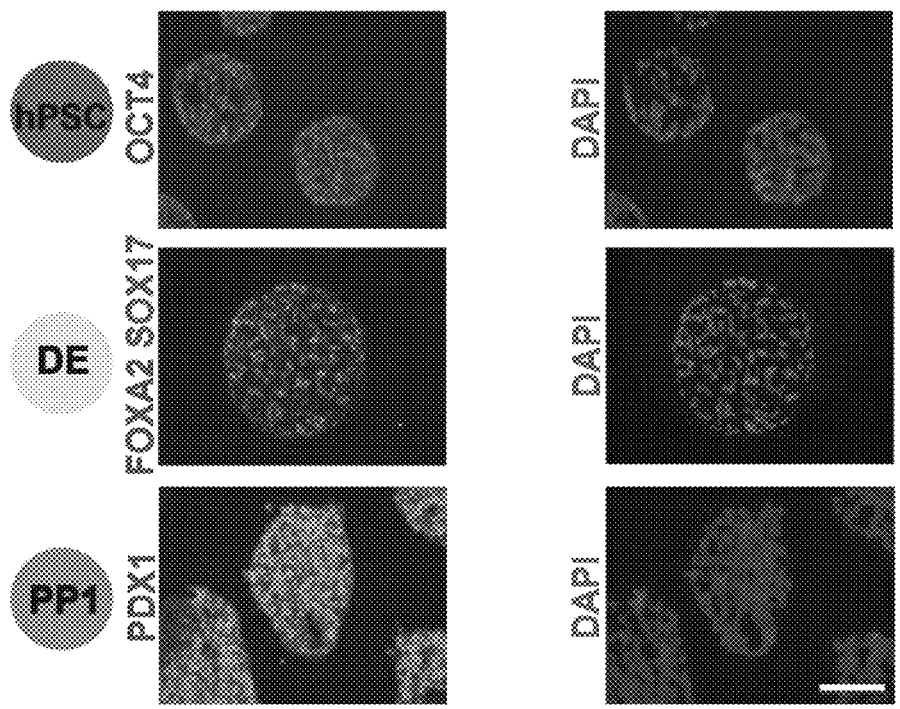
FIG. 1B
FIGS. 1A-1B

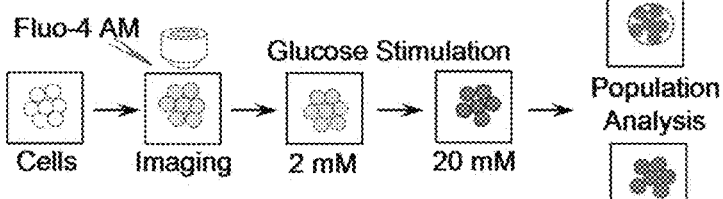
FIG. 4A
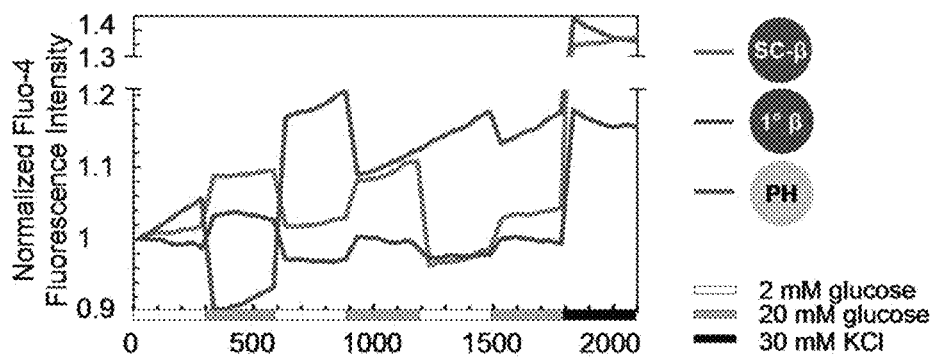
Population Analysis
FIG. 4B
Single Cell Analysis
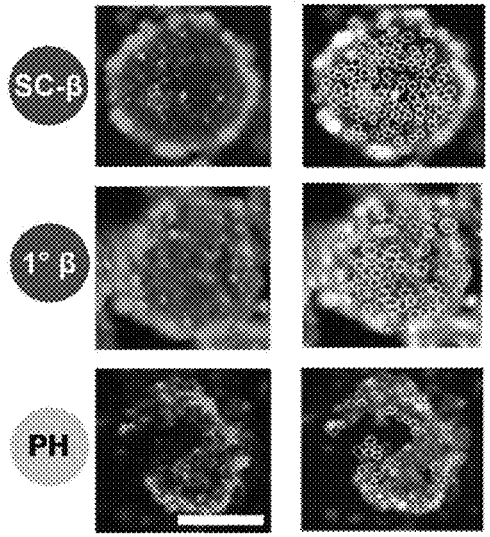
FIG. 4C  FIG. 4D
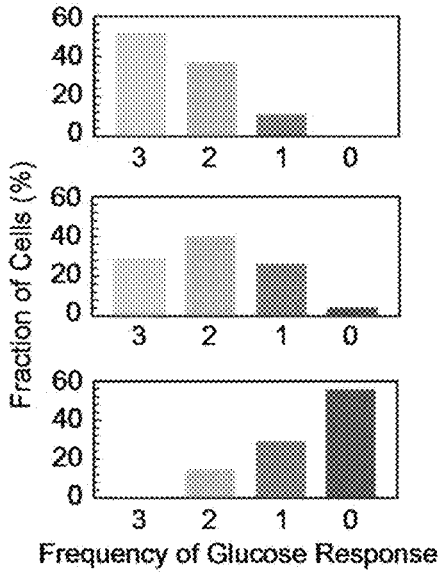
FIG. 4E
FIGS. 4A-4E

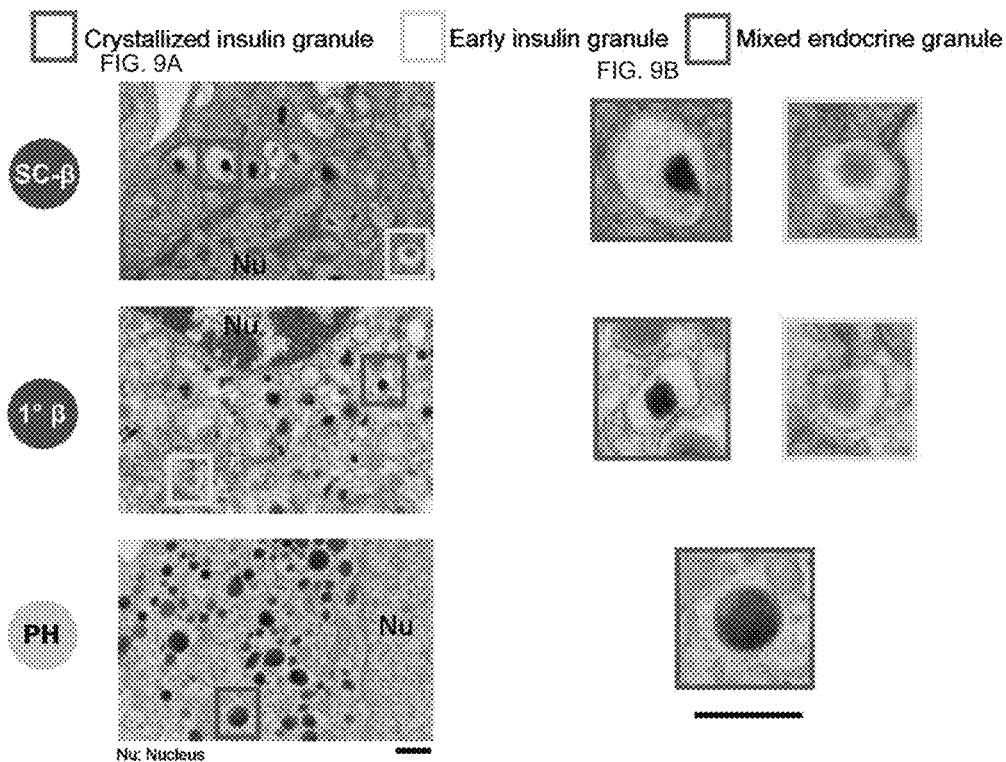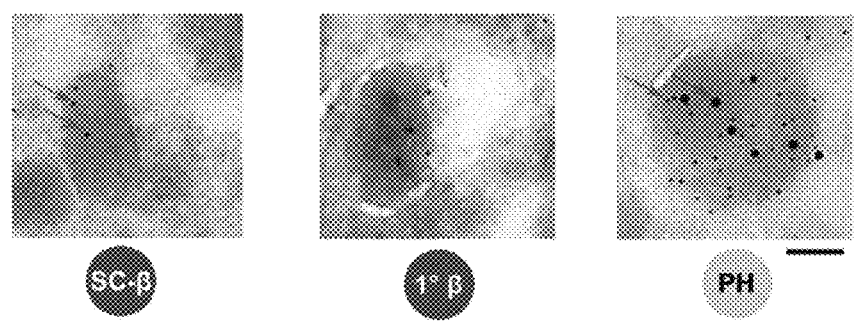
FIGS. 9A-9C

FIG. 11A
FIG. 11B
FIG. 11C
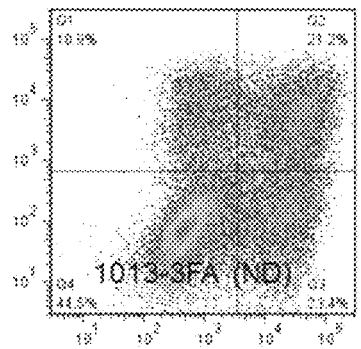
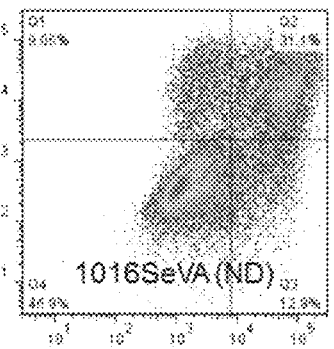
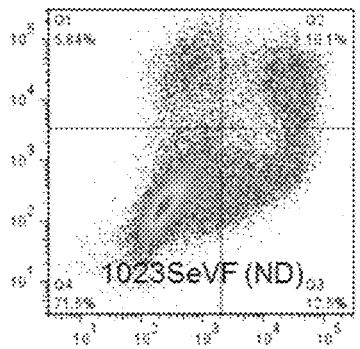
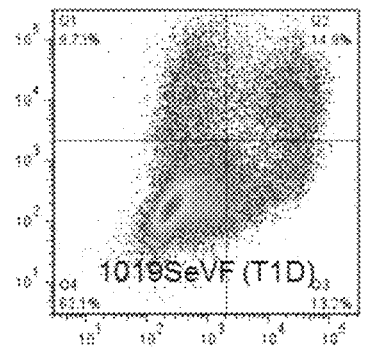
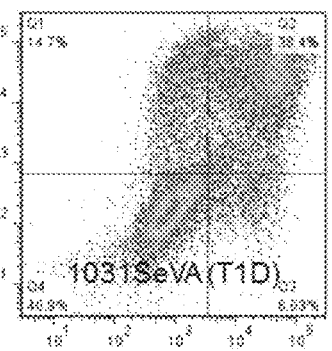
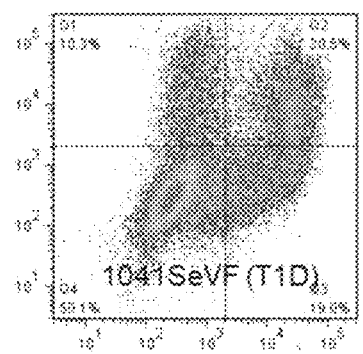
FIG. 11D
FIG. 11E
FIG. 11F
FIGS. 11A-11F

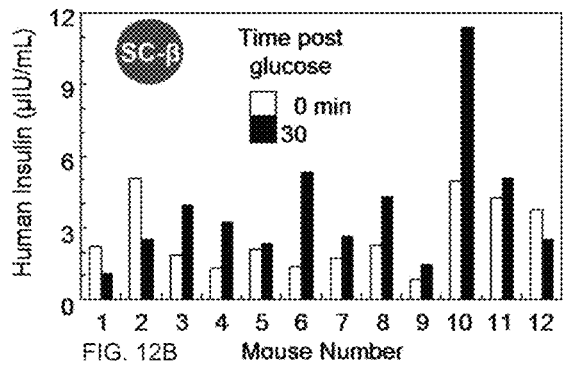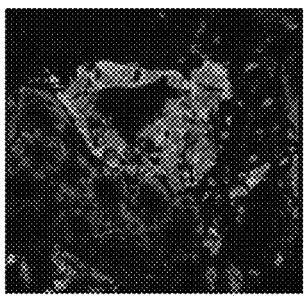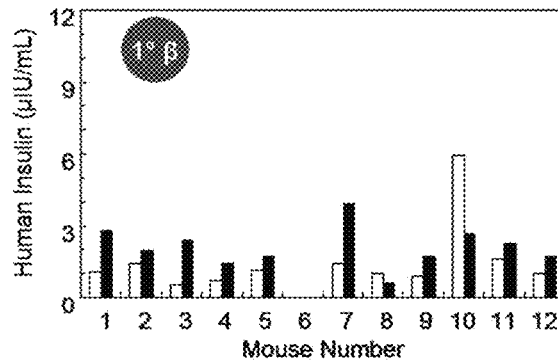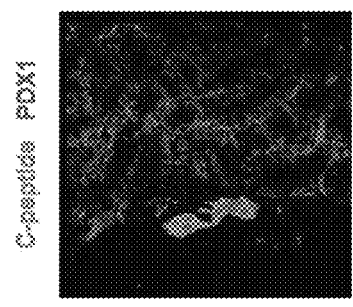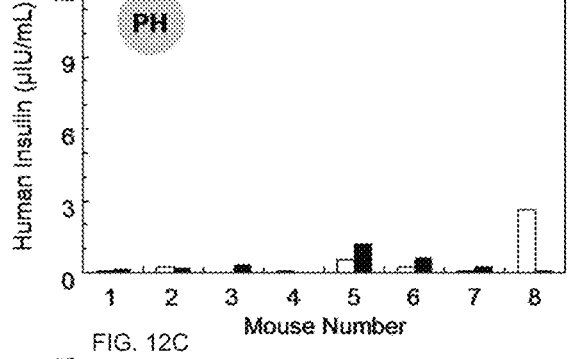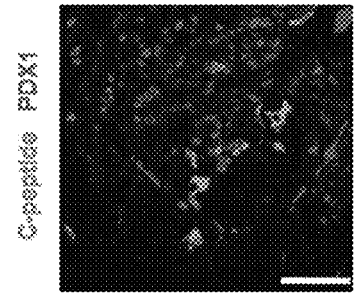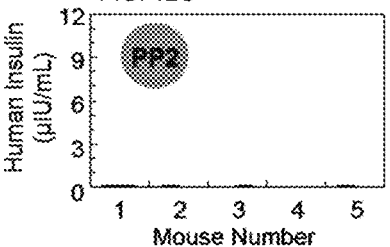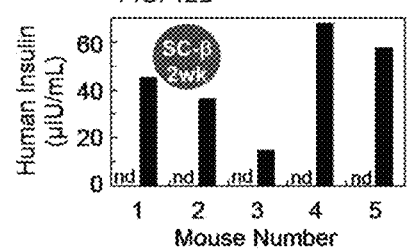
FIGS. 12A-12D FIG. 13A
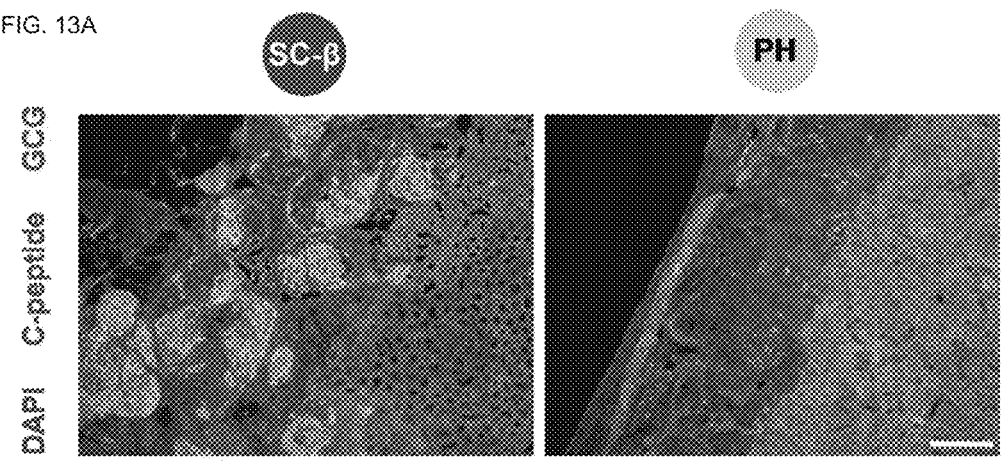
FIG. 13B
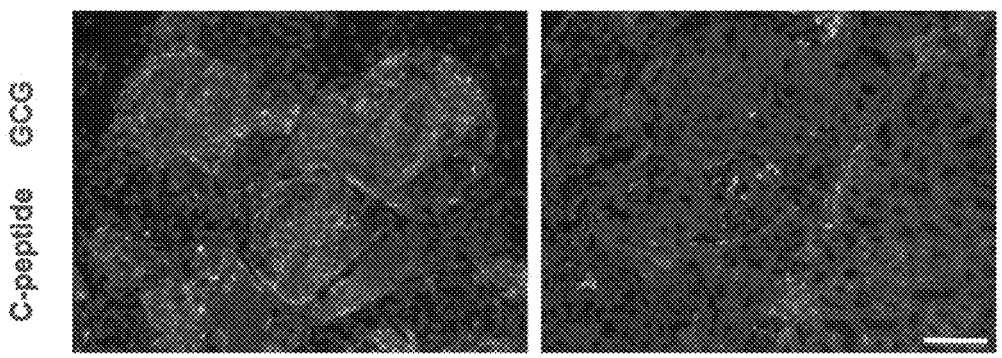
FIGS. 13A-13B

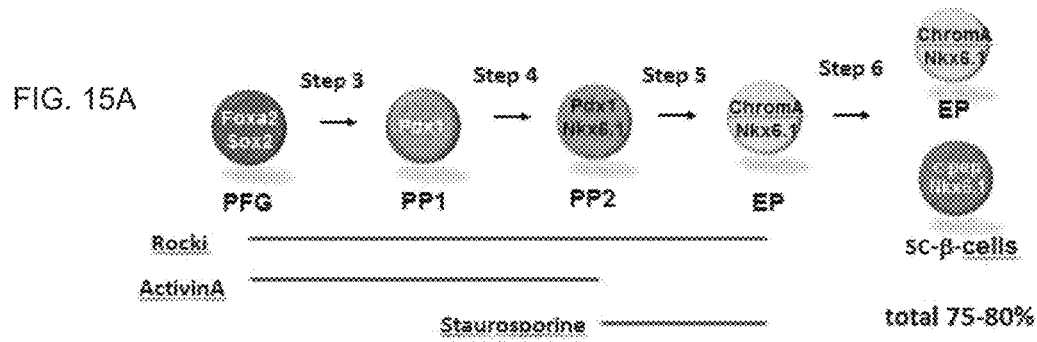
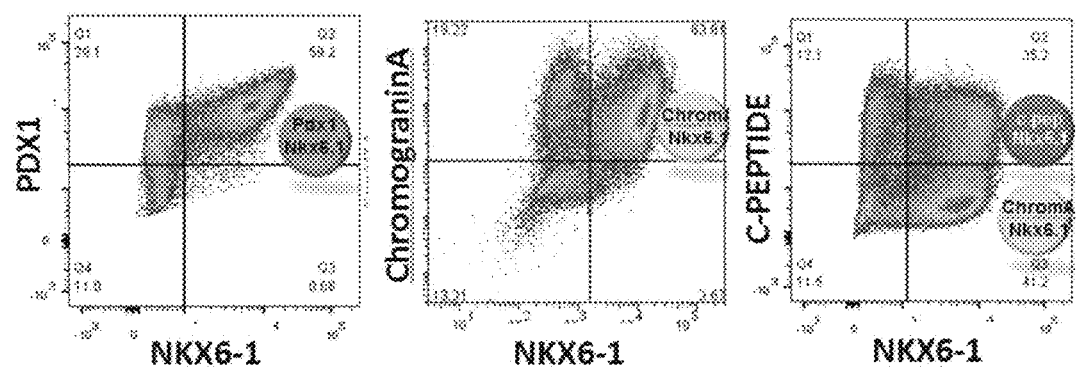
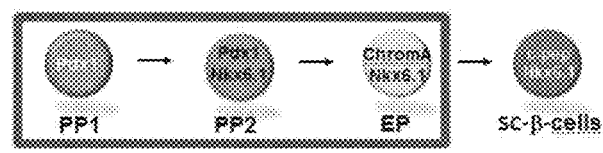
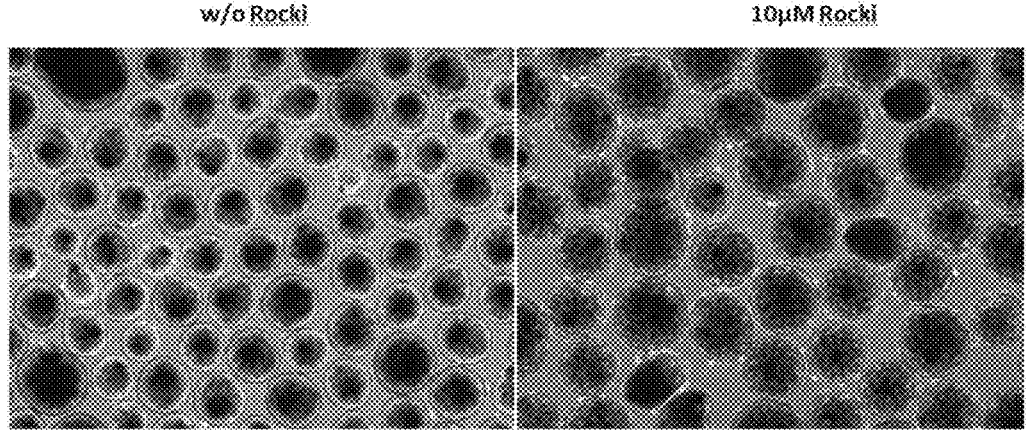
FIGS. 15A-15C

FIG. 15F
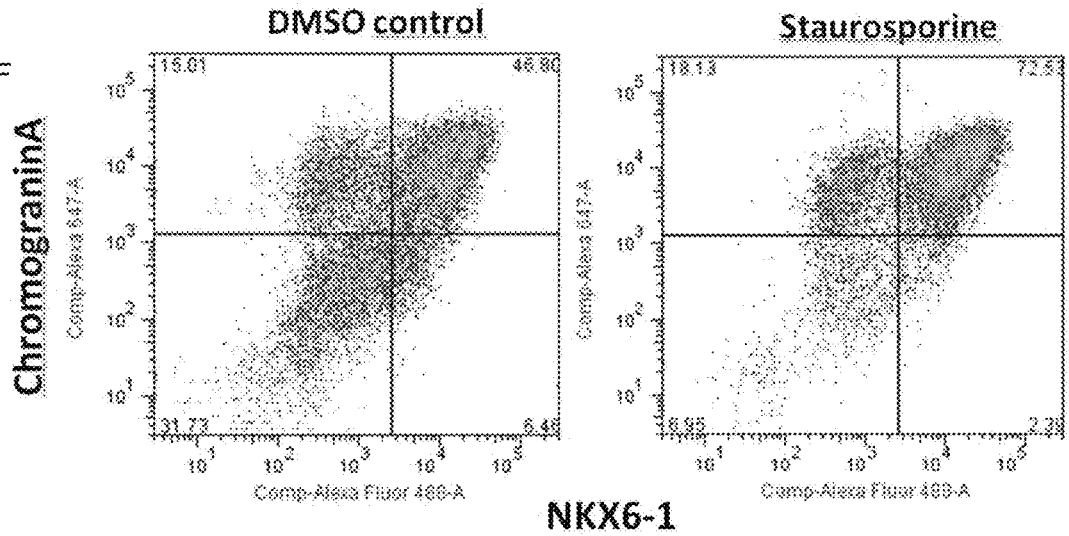
FIG. 15G
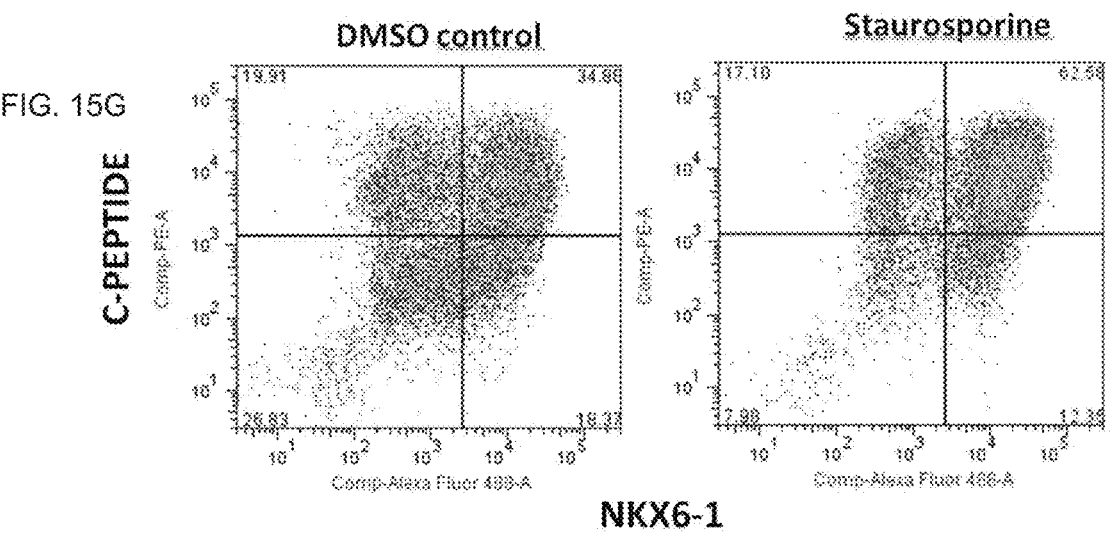
FIGS. 15F-15G

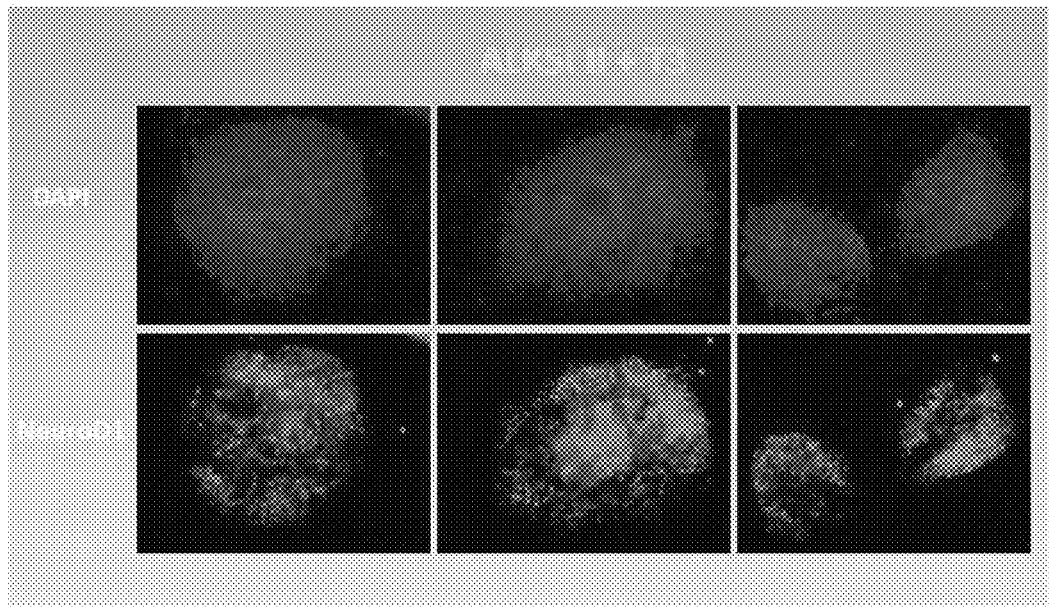
FIG. 15H
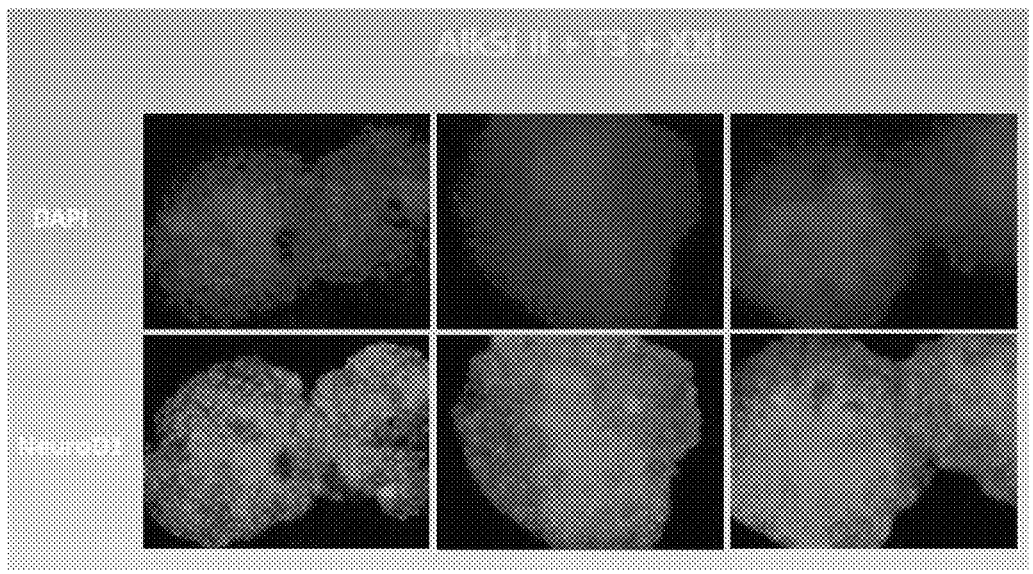
FIG. 15I
FIGS. 15H-15I

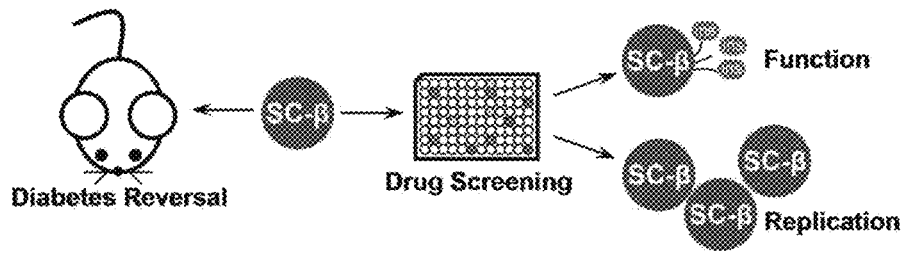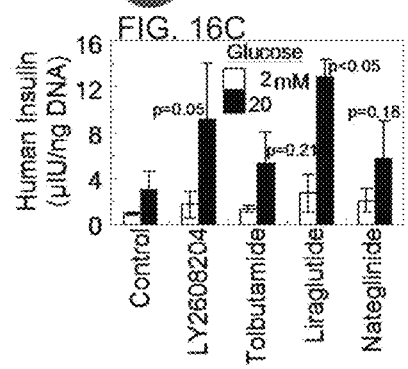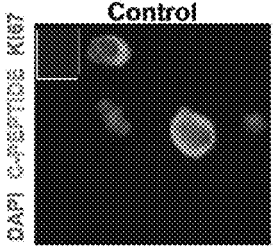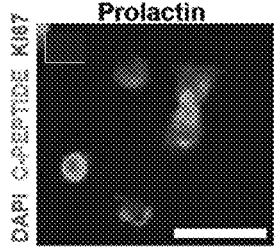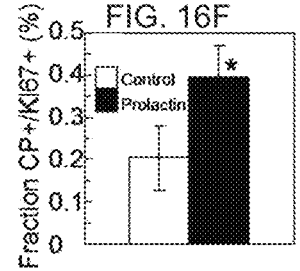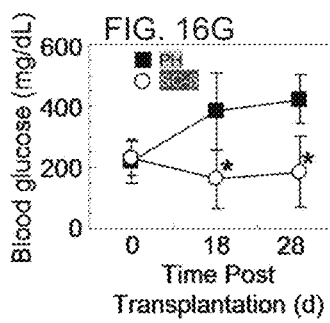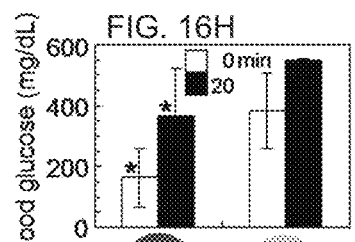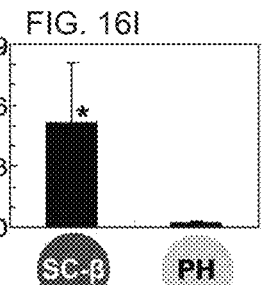
FIGS. 16A-16I

SC-BETA CELLS AND COMPOSITIONS AND METHODS FOR GENERATING THE SAME

CROSS-REFERENCE TO RELATED APPLICATIONS

This application is a continuation application of U.S. application Ser. No. 17/670,124, filed Feb. 11, 2022, which is a continuation application of U.S. application Ser. No. 17/364,226, filed Jun. 30, 2021, which is a continuation application of U.S. application Ser. No. 16/042,933, filed Jul. 23, 2018, which is a continuation application of U.S. application Ser. No. 14/684,101, filed on Apr. 10, 2015 (now U.S. Pat. No. 10,030,229), which is a continuation of PCT Application No. PCT/US2014/041992, filed Jun. 11, 2014, which claims the benefit of U.S. Provisional Application No. 61/833,898, filed on Jun. 11, 2013, and U.S. Provisional Application No. 61/972,212, filed on Mar. 28, 2014, the contents of which are hereby incorporated by reference in their entirety.

BACKGROUND OF THE INVENTION

Research to-date has generated only abnormally functioning insulin-expressing cells, which do not secrete appropriate amounts of insulin in response to sequentially varied glucose levels, or pancreatic progenitor cells that can only mature into functioning insulin-expressing cells after 3 months of transplantation into a mouse host (Cheng et. al., 2012; D'Amour et al., 2005; D'Amour et al., 2006; Kroon et al., 2008; Nostro et al., 2011; Rezania et al., 2012; Schulz et al., 2012; Xie et al., 2013). In contrast to normal islets or dispersed adult β cells, which release high levels of insulin in response to high levels of glucose in the "glucose stimulated insulin secretion" (GSIS) assay and can do so repeatedly, hPSC-derived insulin-expressing cells generated by existing methods fail to secrete insulin appropriately in response to the addition of various concentrations of glucose. Accordingly, there exists a need for a method of deriving cells from hPSCs which exhibit a phenotype of normal islets or mature adult β cells.

SUMMARY OF THE INVENTION

In some aspects, the disclosure provides a stem cell-derived β cell (SC-β).

In some embodiments, the cell is mature. In some embodiments, the cell exhibits an in vitro glucose stimulated insulin secretion (GSIS) response. In some embodiments, the cell exhibits an iv vivo GSIS response. In some embodiments, the cell exhibits in vitro and in vivo glucose stimulated insulin secretion (GSIS) responses. In some embodiments, the cell exhibits a GSIS response to at least one glucose challenge. In some embodiments, the cell exhibits a GSIS response to at least two sequential glucose challenges. In some embodiments, the cell exhibits a GSIS response to at least three sequential glucose challenges. In some embodiments, the GSIS response is observed immediately upon transplanting the cell into a human or animal. In some embodiments, the GSIS response is observed within approximately 24 hours of transplanting the cell into a human or animal. In some embodiments, the GSIS response is observed within approximately two weeks of transplanting the cell into a human or animal. In some embodiments, the stimulation index of the cell as characterized by the ratio of insulin secreted in response to high glucose concentrations compared to low glucose concentrations is similar to the stimulation index of an endogenous mature pancreatic β cell. In some embodiments, the stimulation index is greater than or equal to 1, or greater than or equal to 1.1, or greater than or equal to 1.3, or greater than or equal to 2, or greater than or equal to 2.3, or greater than or equal to 2.6. In some embodiments, the cell exhibits cytokine-induced apoptosis in response to a cytokine. In some embodiments, the cytokine is selected from the group consisting of interleukin-1β (IL-β), interferon-γ (INF-γ), tumor necrosis factor-α (TNF-α), and combinations thereof. In some embodiments, insulin secretion from the cell is enhanced in response to an anti-diabetic agent. In some embodiments, the anti-diabetic agent comprises a secretagogue selected from the group consisting of an incretin mimetic, a sulfonylurea, a meglitinide, and combinations thereof. In some embodiments, the cell is monohormonal. In some embodiments, the cell exhibits a morphology that resembles the morphology of an endogenous mature pancreatic β cell. In some embodiments, the cell exhibits encapsulated crystalline insulin granules under electron microscopy that resemble insulin granules of an endogenous mature pancreatic β cell. In some embodiments, the cell exhibits a low rate of replication. In some embodiments, the cell exhibits a glucose stimulated $Ca^{2+}$ flux (GSCF) that resembles the GSCF of an endogenous mature pancreatic β cell. In some embodiments, the cell exhibits a GSCF response to at least one glucose challenge. In some embodiments, the cell exhibits a GSCF response to at least two glucose challenges. In some embodiments, the cell exhibits a GSCF response to at least three glucose challenges. In some embodiments, the cell exhibits an increased calcium flux. In some embodiments, the increased calcium flux comprises an increased amount of influx or a ratio of influx at low relative to high glucose concentrations. In some embodiments, the cell expresses at least one marker characteristic of an endogenous mature pancreatic β cell selected from the group consisting of insulin, C-peptide, PDX1, MAFA, NKX6-1, PAX6, NEUROD1, glucokinase (GCK), SLC2A1, PCSK1, KCNJ11, ABCC8, SLC30A8, SNAP25, RAB3A, GAD2, PTPRN, NKX2-2, Pax4. In some embodiments, the cell does not express at least one marker selected from the group consisting of a) a hormone selected from the group consisting of i) glucagon (GCG), and ii) somatostatin (SST); or b) an acinar cell marker selected from the group consisting of i) amylase, and ii) carboxypeptidase A (CPA1); c) an α cell marker selected from the group consisting of i) GCG, ii) Arx, iii) Irx1, and Irx2; and d) a ductal cell marker selected from the group consisting of i) CFTR, and ii) Sox9. In some embodiments, the cell is differentiated in vitro from an insulin-positive endocrine cell or a precursor thereof selected from the group consisting of a Nkx6-1-positive pancreatic progenitor cell, a Pdx1-positive pancreatic progenitor cell, and a pluripotent stem cell. In some embodiments, the pluripotent stem cell is selected from the group consisting of an embryonic stem cell and induced pluripotent stem cell. In some embodiments, the cell is human. In some embodiments, the cell is not genetically modified. In some embodiments, the cell is genetically modified. In some embodiments, the insulin produced per cell is between 0.5 and 10 μIU per 1000 cells per 30 minute incubation at a high glucose concentration. In some embodiments, the insulin produced per cell is approximately 2.5 μIU per 1000 cells per 30 minute incubation at a high glucose concentration. In some embodiments, the incubation occurs ex vivo.

In some aspects, the disclosure provides a cell line comprising a SC-β cell. In some embodiments, the cell line stably expresses insulin. In some embodiments, the cells can be frozen, thawed, and amplified with a doubling time of between about 24 and 44 hours without significant morphological changes until at least 30 passages.

In some aspects, the disclosure provides a method of generating a SC-β cell from insulin-positive endocrine cells, the method comprising contacting a population of cells comprising insulin-positive endocrine cells under conditions that promote cell clustering with at least two β cell-maturation factors comprising a) a transforming growth factor β (TGF-β) signaling pathway inhibitor and b) a thyroid hormone signaling pathway activator, to induce the in vitro maturation of at least one insulin-positive endocrine cell in the population into a SC-β cell.

In some embodiments, the SC-β cell exhibits a response to at least one glucose challenge. In some embodiments, the SC-β cell exhibits a response to at least two sequential glucose challenges. In some embodiments, the SC-β cell exhibits a response to at least three sequential glucose challenges. In some embodiments, the morphology of the SC-β cell resembles the morphology of an endogenous mature β cell. In some embodiments, the SC-β cell exhibits in vitro and/or in vivo glucose stimulated insulin secretion (GSIS) responses. In some embodiments, the GSIS response is observed immediately upon transplantation of the SC-β cell into a subject. In some embodiments, the GSIS response is observed within approximately 24 hours upon transplantation of the SC-β cell into a subject. In some embodiments, the GSIS response is observed within approximately two weeks of transplantation of the SC-β cell into a subject. In some embodiments, the population of cells is contacted with the TGF-β signaling pathway inhibitor at a concentration of between 100 nM-100 μM. In some embodiments, the population of cells is contacted with the TGF-β signaling pathway inhibitor at a concentration of 10 μM. In some embodiments, the TGF-β signaling pathway comprises TGF-β receptor type I kinase signaling. In some embodiments, the TGF-β signaling pathway inhibitor comprises Alk5 inhibitor II. In some embodiments, the TGF-β signaling pathway inhibitor comprises an analog or derivative of Alk5 inhibitor II. In some embodiments, the population of cells is contacted with the thyroid hormone signaling pathway activator at a concentration of between 0.1 μM-10 μM. In some embodiments, the population of cells is contacted with the thyroid hormone signaling pathway activator at a concentration of 1 μM. In some embodiments, the thyroid hormone signaling pathway activator comprises triiodothyronine (T3). In some embodiments, the population of cells is optionally contacted with a protein kinase inhibitor. In some embodiments, the population of cells is not contacted with the protein kinase inhibitor. In some embodiments, the population of cells is contacted with the protein kinase inhibitor. In some embodiments, the population of cells is contacted with the protein kinase inhibitor at a concentration of between 10 nM-1 μM. In some embodiments, the population of cells is contacted with the protein kinase inhibitor at a concentration of 100 nM. In some embodiments, the protein kinase inhibitor comprises staurosporine. In some embodiments, the method includes contacting the population of cells with at least one additional β cell-maturation factor. In some embodiments, the at least one additional β cell-maturation factor comprises a cystic fibrosis transmembrane conductance regulator (CFTR) inhibitor. In some embodiments, the population of cells is contacted with the CFTR inhibitor at a concentration of between 100 nM-100 μM. In some embodiments, the population of cells is contacted with the CFTR inhibitor at a concentration of between 10 nM-10 μM. In some embodiments, the CFTR inhibitor comprises Gly-H101. In some embodiments, the at least one additional β cell-maturation factor comprises a O-GlcNAcase inhibitor. In some embodiments, the population of cells is contacted with the O-GlcNAcase inhibitor at a concentration of between 100 nM-100 μM. In some embodiments, the population of cells is contacted with the O-GlcNAcase inhibitor at a concentration of 10 nM-10 μM. In some embodiments, the inhibitor of O-GlcNAcase comprises Thiamet G. In some embodiments, the population of cells is cultured in a suitable culture medium. In some embodiments, the suitable culture medium comprises Connought Medical Research Laboratories 1066 supplemented islet media (CMRLS) or a component of CMRLS. In some embodiments, the CMRLS is supplemented with serum. In some embodiments, the CMRLS is supplemented with 10% fetal bovine serum. In some embodiments, the conditions that promote cell clustering comprise a suspension culture. In some embodiments, the population of cells is maintained in a suspension culture for a period of time sufficient to induce the in vitro maturation of at least one of the insulin-positive endocrine cells in the population of cells into at least one SC-β cell. In some embodiments, the period of time comprises at least 7 days. In some embodiments, the period of time comprises between 7 days and 21 days. In some embodiments, the period of time comprises between 7 and 14 days. In some embodiments, the period of time comprises between 10 and 14 days. In some embodiments, the period of time comprises 14 days. In some embodiments, the β cell-maturation factors are replenished every other day. In some embodiments, at least 1% of the insulin-positive endocrine cells in the population of cells are induced to mature into SC-β cells. In some embodiments, at least 99% of the insulin-positive endocrine cells in the population are induced to mature into SC-β cells. In some embodiments, at least 30% of the resulting cells in the population comprise SC-β cells. In some embodiments, the SC-β cells express C-peptide, insulin, NKX6-1, Pdx1, and co-express NKX6-1 and C-peptide. In some embodiments, the insulin-positive endocrine cells also express Pdx1 and NKX6-1. In some embodiments, the insulin-positive endocrine cells are produced from a population of pluripotent stem cells selected from the group consisting of embryonic stem cells and induced pluripotent stem cells. In some embodiments, the SC-β cells comprise human cells. In some embodiments, the generation of SC-β cells in vitro is scalable.

In some aspects, the disclosure provides an isolated population of SC-β cells produced according to the methods described herein.

In some aspects, the disclosure provides a microcapsule comprising an isolated population of SC-β cells encapsulated therein.

In some aspects, the disclosure provides a composition comprising a population of SC-β cells produced according to a method described herein.

In some aspects, the disclosure provides an assay comprising an isolated population of SC-β cells produced according to a method described herein.

In some embodiments, the assay is for use in identifying one or more candidate agents which promote or inhibit a β cell fate selected from the group consisting of β cell proliferation, β cell replication, β cell death, β cell function, β cell susceptibility to immune attack, or β cell susceptibility to dedifferentiation or differentiation. In some embodiments, the assay is for use in identifying one or more candidate agents which promote the differentiation of at least one insulin-positive endocrine cell or a precursor thereof into at least one SC-β cell.

In some aspects, the disclosure provides a method for the treatment of a subject in need thereof, the method comprising administering to a subject a composition comprising an isolated population of SC-β cells produced according a method described herein. In some embodiments, the SC-β cells are encapsulated in a microcapsule. In some embodiments, the SC-β cells are produced from a population of pluripotent stem cells obtained from the same subject that the SC-β cells are administered to. In some embodiments, the SC-β cells are produced from a population of iPS cells, wherein the iPS cells are derived from a cell obtained from the same subject that the SC-β cells are administered to. In some embodiments, the subject has, or has an increased risk of developing, diabetes. In some embodiments, the diabetes is selected from the group of Type I diabetes, Type II diabetes, Type 1.5 diabetes and pre-diabetes. In some embodiments, the subject has, or has an increased risk of developing a metabolic disorder.

In some aspects, the disclosure relates to the use of an isolated population of SC-β cells produced by the methods described herein for administering to a subject in need thereof.

In some embodiments, the isolated population of SC-β cells is administered to the subject encapsulated in microcapsules. In some embodiments, the subject has, or has an increased risk of developing diabetes. In some embodiments, the diabetes is selected from the group of Type I diabetes, Type II diabetes, Type 1.5 diabetes and pre-diabetes. In some embodiments, the subject has, or has an increased risk of developing a metabolic disorder.

In some aspects, the disclosure provides a culture medium comprising a) Alk5 inhibitor, b) triiodothyronine (T3), optionally c) staurosporine, and optionally d) CMRLS or a component of CMRLS.

In some aspects, the disclosure involves the use of the culture medium of to induce the in vitro maturation of insulin-positive endocrine cells into SC-β cells, wherein the SC-β cells exhibit both an in vitro and/or in vivo GSIS response.

In some aspects, the disclosure provides a method of producing a NKX6-1-positive pancreatic progenitor cell from a Pdx1-positive pancreatic progenitor cell comprising contacting a population of cells comprising Pdx1-positive pancreatic progenitor cells under conditions that promote cell clustering with at least two β cell-maturation factors comprising a) at least one growth factor from the fibroblast growth factor (FGF) family, b) a sonic hedgehog pathway inhibitor, and optionally c) a low concentration of a retinoic acid (RA) signaling pathway activator, for a period of at least five days to induce the differentiation of at least one Pdx1-positive pancreatic progenitor cell in the population into NKX6-1-positive pancreatic progenitor cells, wherein the NKX6-1-positive pancreatic progenitor cells express NKX6-1.

In some embodiments, the population of cells is contacted with the at least one growth factor from the FGF family at a concentration of between 1 ng/mL-100 ng/mL. In some embodiments, the population of cells is contacted with the at least one growth factor from the FGF family at a concentration of 50 ng/mL. In some embodiments, the at least one growth factor from the FGF family comprises keratinocyte growth factor (KGF). In some embodiments, the at least one growth factor from the FGF family is selected from the group consisting of FGF2, FGF8B, FGF10, and FGF21. In some embodiments, the population of cells is not contacted with the RA signaling pathway activator. In some embodiments, the population of cells is contacted with the RA signaling pathway activator at a concentration of between 0.01 μM-1.0 μM. In some embodiments, the population of cells is contacted with the RA signaling pathway activator at a concentration of 0.1 μM. In some embodiments, the RA signaling pathway activator comprises RA. In some embodiments, the population of cells is contacted with the SHH pathway inhibitor at a concentration of between 0.1 μM and 0.5 μM. In some embodiments, the population of cells is contacted with the SHH pathway inhibitor at a concentration of 0.25 μM. In some embodiments, the SHH pathway inhibitor comprises Sant1. In some embodiments, the method includes exposing the population of cells to at least one additional β cell-maturation factor. In some embodiments, the at least one additional β cell-maturation factor comprises at least one growth factor from the EGF family. In some embodiments, the population of cells is exposed to the at least one growth factor from the EGF family at a concentration of between 2 ng/mL-200 ng/mL. In some embodiments, the population of cells is exposed to the at least one growth factor from the EGF family at a concentration of 20 ng/mL. In some embodiments, at least one growth factor from the EGF family is selected from the group consisting of betacellulin and EGF. In some embodiments, the population of cells is cultured in a suitable culture medium. In some embodiments, the conditions that promote cell clustering comprise a suspension culture. In some embodiments, the β cell-maturation factors are replenished every other day. In some embodiments, an activator of protein kinase C is not added to the suspension culture during the 5 days. In some embodiments, an activator of protein kinase C is removed from the suspension culture prior to the 5 days. In some embodiments, the activator of protein kinase C comprises PdbU. In some embodiments, a BMP signaling pathway inhibitor is not added to the suspension culture during the 5 days. In some embodiments, a BMP signaling pathway inhibitor is removed from the suspension culture prior to the 5 days. In some embodiments, the BMP signaling pathway inhibitor comprises LDN193189. In some embodiments, at least 10% of the Pdx1-positive pancreatic progenitor cells in the population are induced to differentiate into NKX6-1-positive pancreatic progenitor cells. In some embodiments, at least 95% of the Pdx1-positive pancreatic progenitor cells in the population are induced to differentiate into NKX6-1-positive pancreatic progenitor cells. In some embodiments, the NKX6-1-positive pancreatic progenitor cells express Pdx1, NKX6-1, and FoxA2. In some embodiments, the Pdx1-positive pancreatic progenitor cells are produced from a population of pluripotent stem cells selected from the group consisting of embryonic stem cells and induced pluripotent stem cells.

In some aspects, the disclosure provides an isolated population of NKX6-1-positive pancreatic progenitor cells obtained by a method described herein.

In some aspects, the disclosure provides a microcapsule comprising the isolated population of NKX6-1-positive pancreatic progenitor cells encapsulated therein.

In some aspects, the disclosure provides a composition comprising an isolated population of NKX6-1-positive pancreatic progenitor cells produced according to a method described herein.

In some aspects, the disclosure provides an assay comprising an isolated population of NKX6-1-positive pancreatic progenitor cells produced according to a method described herein.

In some embodiments, the assay is for use in identifying one or more candidate agents which promote the differentiation of at least one Pdx1-positive pancreatic progenitor cell or precursor thereof into NKX6-1-positive pancreatic progenitor cells.

In some aspects, the disclosure provides a method for the treatment of a subject in need thereof, the method comprising administering to a subject a composition comprising an isolated population of NKX6-1-positive pancreatic progenitor cells produced according to a method described herein.

In some embodiments, the NKX6-1-positive pancreatic progenitor cells are produced from a population of pluripotent stem cells obtained from the same subject as the NKX6-1-positive pancreatic progenitor cells are administered to. In some embodiments, the NKX6-1-positive pancreatic progenitor cells are encapsulated in a microcapsule. In some embodiments, the subject has, or has an increased risk of developing diabetes. In some embodiments, the diabetes is selected from the group of Type I diabetes, Type II diabetes, Type 1.5 diabetes and pre-diabetes. In some embodiments, the subject has, or has an increased risk of developing a metabolic disorder.

In some aspects, the disclosure relates to the use of an isolated population of NKX6-1-positive pancreatic progenitor cells produced by the methods described herein for differentiating into SC-β cells.

In some aspects, the disclosure involves the use of an isolated population of NKX6-1-positive pancreatic progenitor cells produced by a method described herein for administering to a subject in need thereof.

In some embodiments, the isolated population of NKX6-1-positive pancreatic progenitor cells is administered to the subject encapsulated in microcapsules. In some embodiments, the subject has, or has an increased risk of developing diabetes. In some embodiments, the diabetes is selected from the group of Type I diabetes, Type II diabetes, Type 1.5 diabetes and pre-diabetes. In some embodiments, the subject has, or has an increased risk of developing a metabolic disorder.

In some aspects, the disclosure provides a culture medium comprising a) KGF, b) SANT1), and optionally c) RA, wherein the culture medium is substantially free of PdbU and LDN 193189. In some embodiments, the disclosure involves the use of the culture medium described herein to induce the in vitro differentiation of Pdx1-positive pancreatic progenitor cells into NKX6-1-positive pancreatic progenitor cells.

In some aspects, the disclosure provides a method of producing an insulin-positive endocrine cell from an NKX6-1-positive pancreatic progenitor cell comprising contacting a population of cells comprising NKX6-1-positive pancreatic progenitor cells under conditions that promote cell clustering with at least two β cell-maturation factors comprising a) a TGF-β signaling pathway inhibitor, and b) thyroid hormone signaling pathway activator, to induce the differentiation of at least one NKX6-1-positive pancreatic progenitor cell in the population into at least one insulin-positive endocrine cell, wherein the insulin-positive pancreatic progenitor cell expresses insulin. In some embodiments, the population of cells is contacted with the TGF-β signaling pathway inhibitor at a concentration of between 100 nM-100 µM. In some embodiments, the population of cells is contacted with the TGF-β signaling pathway inhibitor at a concentration of 10 µM. In some embodiments, the TGF-β signaling pathway comprises TGF-β receptor type I kinase signaling. In some embodiments, the TGF-β signaling pathway inhibitor comprises Alk5 inhibitor II. In some embodiments, the population of cells is contacted with the thyroid hormone signaling pathway activator at a concentration of between 0.1 µM-10 µM. In some embodiments, the population of cells is contacted with the thyroid hormone signaling pathway activator at a concentration of 1 µM. In some embodiments, the thyroid hormone signaling pathway activator comprises triiodothyronine (T3). In some embodiments, the method includes contacting the population of cells with at least one additional β cell-maturation factor. In some embodiments, the at least one additional β cell-maturation factor comprises a γ-secretase inhibitor. In some embodiments, the population of cells is contacted with the γ-secretase inhibitor at a concentration of between 0.1 µM-10 µM. In some embodiments, the population of cells is contacted with the γ-secretase inhibitor at a concentration of 1 µM. In some embodiments, the γ-secretase inhibitor comprises XXI. In some embodiments, the γ-secretase inhibitor comprises DAPT. In some embodiments, the at least one additional β cell-maturation factor comprises at least one growth factor from the EGF family. In some embodiments, the population of cells is contacted with the at least one growth factor from the EGF family at a concentration of between 2 ng/mL-200 ng/mL. In some embodiments, the population of cells is contacted with at least one growth factor from the EGF family at a concentration of 20 ng/mL. In some embodiments, the at least one growth factor from the EGF family comprises betacellulin. In some embodiments, the at least one growth factor from the EGF family comprises EGF. In some embodiments, the at least one additional β cell-maturation factor comprises a low concentration of a retinoic acid (RA) signaling pathway activator. In some embodiments, the population of cells is contacted with the RA signaling pathway activator at a concentration of between 0.01 µM-1.0 µM. In some embodiments, the population of cells is contacted with the RA signaling pathway activator at a concentration of 0.1 µM. In some embodiments, the RA signaling pathway activator comprises RA. In some embodiments, the at least one additional β cell-maturation factor comprises a sonic hedgehog (SHH) pathway inhibitor. In some embodiments, the population of cells is contacted with the SHH pathway inhibitor at a concentration of between 0.1 µM and 0.5 µM. In some embodiments, the population of cells is contacted with the SHH pathway inhibitor at a concentration of 0.25 µM. In some embodiments, the SHH pathway inhibitor comprises Sant1. In some embodiments, the population of cells is optionally contacted with a protein kinase inhibitor. In some embodiments, the population of cells is not contacted with the protein kinase inhibitor. In some embodiments, the population of cells is contacted with the protein kinase inhibitor. In some embodiments, the population of cells is contacted with the protein kinase inhibitor at a concentration of between 10 nM-1 µM. In some embodiments, the population of cells is contacted with the protein kinase inhibitor at a concentration of 100 nM. In some embodiments, the protein kinase inhibitor comprises staurosporine. In some embodiments, the method includes exposing the population of cells to glucose. In some embodiments, the population of cells is exposed to glucose at a concentration of between 1 mM-50 mM. In some embodiments, the population of cells is exposed to glucose at a concentration of 25 mM. In some embodiments, the conditions that promote cell clustering comprise a suspension culture. In some embodiments, the population of cells is maintained in suspension culture for a period of time sufficient to induce the differentiation of at least one of the NKX6-1-positive pancreatic progenitor cells in the population into an insulin-positive endocrine cell. In some embodiments, the period of time is at least 7 days. In some embodiments, the β cell-maturation factors are replenished in the suspension culture every other day. In some embodiments, at least 15% of the NKX6-1-positive pancreatic progenitor cells in the population are induced to differentiate into insulin-positive endocrine cells. In some embodiments, at least 99% of the NKX6-1-positive pancreatic progenitor cells in the population are induced to differentiate into insulin-positive endocrine cells. In some embodiments, the insulin-positive endocrine cells express Pdx1, NKX6-1, NKX2-2, Mafb, glis3, Sur1, Kir6.2, Znt8, SLC2A1, SLC2A3 and/or insulin. In some embodiments, the NKX6-1-positive pancreatic progenitor cells are produced from a population of pluripotent stem cells selected from the group consisting of embryonic stem cells and induced pluripotent stem cells.

In some aspects, the disclosure provides an isolated population of insulin-positive endocrine cells produced according to a method described herein.

In some aspects, the disclosure provides a microcapsule comprising the isolated population of insulin-positive endocrine cells encapsulated therein. In some embodiments, the disclosure provides a composition comprising a population of insulin-positive endocrine cells produced according to a method described herein.

In some aspects, the disclosure provides a method for the treatment of a subject in need thereof, the method comprising administering to a subject a composition comprising an isolated population of insulin-positive endocrine cells produced according to a method described herein.

In some embodiments, the insulin-positive endocrine cells are produced from a population of pluripotent stem cells obtained from the same subject as the insulin-positive endocrine cells are administered to. In some embodiments, the insulin-positive endocrine cells are encapsulated in a microcapsule. In some embodiments, the subject has, or has an increased risk of developing diabetes. In some embodiments, the diabetes is selected from the group of Type I diabetes, Type II diabetes, Type 1.5 diabetes and pre-diabetes. In some embodiments, the subject has, or has an increased risk of developing a metabolic disorder.

In some aspects, the disclosure involves the use of an isolated population of insulin-positive endocrine cells produced by a method described herein for differentiating into SC-β cells.

In some aspects, the disclosure involves the use of an isolated population of insulin-positive endocrine cells produced by a method described herein for administering to a subject in need thereof.

In some embodiments, the isolated population of insulin-positive endocrine cells is administered to the subject encapsulated in microcapsules. In some embodiments, the subject has, or has an increased risk of developing diabetes. In some embodiments, the diabetes is selected from the group of Type I diabetes, Type II diabetes, Type 1.5 diabetes and pre-diabetes. In some embodiments, the subject has, or has an increased risk of developing a metabolic disorder.

In some aspects, the disclosure provides a culture medium comprising a) TGF-β signaling pathway inhibitor, b) a TH pathway activator, and at least one additional β cell-maturation factor selected from the group consisting of i) XXI, ii) Betacellulin, iii) a low concentration of a RA signaling pathway activator, and iv) a SHH pathway inhibitor.

In some aspects, the disclosure involves the use of the culture medium described herein to induce the in vitro differentiation of NKX6-1-positive pancreatic progenitor cells into insulin-positive endocrine cells.

In some aspects, the disclosure provides a method of generating SC-β cells, the method comprising: contacting Pdx1-positive, NKX6-1-positive, insulin-positive endocrine cells under conditions that promote cell clustering with i) a transforming growth factor β (TGF-β) signaling pathway inhibitor, ii) a thyroid hormone signaling pathway activator, and optionally iii) a protein kinase inhibitor, to induce the in vitro maturation of at least some of the Pdx1-positive, NKX6-1-positive, insulin-positive endocrine cells into SC-β cells, wherein the SC-β cells exhibit a GSIS response in vitro and/or in vivo.

In some embodiments, the GSIS response is observed (i) immediately upon transplantation of the SC-β cell into a subject; (ii) within approximately 24 hours of transplantation into a subject; or (iii) within approximately two weeks of transplantation into a subject. In some embodiments, the SC-β cells exhibit a response to (i) at least one glucose challenge; (ii) at least two sequential glucose challenges; or (iii) at least three sequential glucose challenges. In some embodiments, the morphology of the SC-β cells resembles the morphology of endogenous β cells. In some embodiments, the Pdx1-positive, NKX6-1-positive, insulin-positive endocrine cells are contacted with the TGF-β signaling pathway inhibitor at a concentration of between 100 nM-100 μM. In some embodiments, the Pdx1-positive, NKX6-1-positive, insulin-positive endocrine cells are contacted with the TGF-β signaling pathway inhibitor at a concentration of 10 μM. In some embodiments, the TGF-β signaling pathway comprises TGF-β receptor type I kinase signaling. In some embodiments, the TGF-β signaling pathway inhibitor comprises Alk5 inhibitor II. In some embodiments, the Pdx1-positive, NKX6-1-positive, insulin-positive endocrine cells are contacted with the thyroid hormone signaling pathway activator at a concentration of between 0.1 μM-10 μM. In some embodiments, the Pdx1-positive, NKX6-1-positive, insulin-positive endocrine cells are contacted with the thyroid hormone signaling pathway activator at a concentration of 1 μM. In some embodiments, the thyroid hormone signaling pathway activator comprises triiodothyronine (T3). In some embodiments, the Pdx1-positive, NKX6-1-positive, insulin-positive endocrine cells are not contacted with the protein kinase inhibitor. In some embodiments, the Pdx1-positive, NKX6-1-positive, insulin-positive endocrine cells are contacted with the protein kinase inhibitor. In some embodiments, the Pdx1-positive, NKX6-1-positive, insulin-positive endocrine cells are contacted with the protein kinase inhibitor at a concentration of between 10 nM-1 μM. In some embodiments, the Pdx1-positive, NKX6-1-positive, insulin-positive endocrine cells are contacted with the protein kinase inhibitor at a concentration of 100 nM. In some embodiments, the protein kinase inhibitor comprises staurosporine. In some embodiments, the method includes contacting the Pdx1-positive, NKX6-1-positive, insulin-positive endocrine cells with a cystic fibrosis transmembrane conductance regulator (CFTR) inhibitor. In some embodiments, the Pdx1-positive, NKX6-1-positive, insulin-positive endocrine cells are contacted with the CFTR inhibitor at a concentration of between 100 nM and 100 μM. In some embodiments, the Pdx1-positive, NKX6-1-positive, insulin-positive endocrine cells are contacted with the CFTR inhibitor at a concentration of 10 nM and 10 uM. In some embodiments, the CFTR inhibitor comprises Gly-H101. In some embodiments, the method includes contacting the Pdx1-positive, NKX6-1-positive, insulin-positive endocrine cells with a O-GlcNAcase inhibitor. In some embodiments, the Pdx1-positive, NKX6-1-positive, insulin-positive endocrine cells are contacted with the O-GlcNAcase inhibitor at a concentration of between 100 nM and 100 μM. In some embodiments, the Pdx1-positive, NKX6-1-positive, insulin-positive endocrine cells are contacted with the O-GlcNAcase inhibitor at a concentration of between 10 nM and 10 uM. In some embodiments, the inhibitor of O-GlcNAcase comprises Thiamet G. In some embodiments, the Pdx1-positive, NKX6-1-positive, insulin-positive endocrine cells are cultured in a suitable culture medium. In some embodiments, the suitable culture medium comprises Connought Medical Research Laboratories 1066 supplemented islet media (CMRLS) or a component of CMRLS. In some embodiments, the CMRLS is supplemented with serum. In some embodiments, the CMRLS is supplemented with 10% fetal bovine serum. In some embodiments, the conditions that promote cell clustering comprise suspension culture. In some embodiments, the Pdx1-positive, NKX6-1-positive, insulin-positive endocrine cells are maintained in a suspension culture for a period of time sufficient to induce the in vitro maturation of at least some of the Pdx1-positive, NKX6-1-positive, insulin-positive endocrine cells into SC-β cells. In some embodiments, the period of time comprises at least 7 days. In some embodiments, the period of time comprises between 7 days and 21 days. In some embodiments, the period of time comprises between 7 and 14 days. In some embodiments, the period of time comprises 14 days. In some embodiments, the suspension culture is replenished every other day. In some embodiments, at least 30% of the cells generated comprise SC-β cells. In some embodiments, the SC-β cells express C-peptide, insulin, NKX6-1, Pdx1, and co-express NKX6-1 and C-peptide. In some embodiments, the SC-β cells comprise human cells. In some embodiments, the generation of the SC-β cells in vitro is scalable.

In some embodiments, the insulin-positive, endocrine cells are obtained by contacting Pdx1-positive, NKX6-1-positive pancreatic progenitor cells under conditions that promote cell clustering with i) a TGF-β signaling pathway inhibitor, and ii) a thyroid hormone signaling pathway activator, to induce the differentiation of at least some of the Pdx1-positive, NKX6-1-positive pancreatic progenitor cells into Pdx1-positive, NKX6-1-positive, insulin-positive endocrine cells, wherein the Pdx1-positive, NKX6-1-positive, insulin-positive endocrine cells express Pdx1, NKX6-1, NKX2-2, Math, glis3, Sur1, Kir6.2, Znt8, SLC2A1, SLC2A3 and/or insulin.

In some embodiments, the Pdx1-positive, NKX6-1-positive pancreatic progenitor cells are contacted with the TGF-β signaling pathway inhibitor at a concentration of between 100 nM-100 μM. In some embodiments, the Pdx1-positive, NKX6-1-positive pancreatic progenitor cells are contacted with the TGF-β signaling pathway inhibitor at a concentration of 10 μM. In some embodiments, the TGF-β signaling pathway comprises TGF-β receptor type I kinase signaling. In some embodiments, the TGF-β signaling pathway inhibitor comprises Alk5 inhibitor II. In some embodiments, the Pdx1-positive, NKX6-1-positive pancreatic progenitor cells are contacted with the thyroid hormone signaling pathway activator at a concentration of between 0.1 μM-10 μM. In some embodiments, the Pdx1-positive, NKX6-1-positive pancreatic progenitor cells are contacted with the thyroid hormone signaling pathway activator at a concentration of 1 μM. In some embodiments, the thyroid hormone signaling pathway activator comprises triiodothyronine (T3). In some embodiments, the method includes contacting the Pdx1-positive NKX6-1-positive pancreatic progenitor cells with at least one of i) a SHH pathway inhibitor, ii) a RA signaling pathway activator, iii) a γ-secretase inhibitor, iv) at least one growth factor from the epidermal growth factor (EGF) family, and optionally v) a protein kinase inhibitor. In some embodiments, the Pdx1-positive, NKX6-1-positive pancreatic progenitor cells are contacted with the SHH pathway inhibitor at a concentration of between 0.1 μM and 0.5 μM. In some embodiments, the Pdx1-positive, NKX6-1-positive pancreatic progenitor cells are contacted with a SHH pathway inhibitor at a concentration of 0.25 μM. In some embodiments, the SHH pathway inhibitor comprises Sant1. In some embodiments, the Pdx1-positive, NKX6-1-positive pancreatic progenitor cells are contacted with the RA signaling pathway activator at a concentration of between 0.01 μM-1.0 μM. In some embodiments, the Pdx1-positive, NKX6-1-positive pancreatic progenitor cells are contacted with the RA signaling pathway activator at a concentration of 0.1 μM. In some embodiments, the RA signaling pathway activator comprises RA. In some embodiments, the Pdx1-positive, NKX6-1-positive pancreatic progenitor cells are contacted with the γ-secretase inhibitor at a concentration of between 0.1 μM-10 μM. In some embodiments, the Pdx1-positive, NKX6-1-positive pancreatic progenitor cells are contacted with the γ-secretase inhibitor at a concentration of 1 μM. In some embodiments, the γ-secretase inhibitor comprises XXI. In some embodiments, the γ-secretase inhibitor comprises DAPT. In some embodiments, the Pdx1-positive, NKX6-1-positive pancreatic progenitor cells are contacted with the at least one growth factor from the EGF family at a concentration of between 2 ng/mL-200 ng/mL. In some embodiments, the Pdx1-positive, NKX6-1-positive pancreatic progenitor cells are contacted with the at least one growth factor from the EGF family at a concentration of 20 ng/mL. In some embodiments, the at least one growth factor from the EGF family comprises betacellulin. In some embodiments, the at least one growth factor from the EGF family comprises EGF. In some embodiments, the Pdx1-positive, NKX6-1-positive pancreatic progenitor cells are not contacted with the protein kinase inhibitor. In some embodiments, the Pdx1-positive, NKX6-1-positive pancreatic progenitor cells are contacted with the protein kinase inhibitor. In some embodiments, the Pdx1-positive, NKX6-1-positive pancreatic progenitor cells are contacted with the protein kinase inhibitor at a concentration of between 10 nM-1 μM. In some embodiments, the Pdx1-positive, NKX6-1-positive pancreatic progenitor cells are contacted with the protein kinase inhibitor at a concentration of 100 nM. In some embodiments, the protein kinase inhibitor comprises staurosporine. In some embodiments, the method includes exposing the population of cells to glucose. In some embodiments, the population of cells is exposed to glucose at a concentration of between 1 mM-50 mM. In some embodiments, the population of cells is exposed to glucose at a concentration of 25 mM. In some embodiments, the conditions that promote cell clustering comprise suspension culture. In some embodiments, the Pdx1-positive, NKX6-1-positive pancreatic progenitor cells are maintained in suspension culture for a period of time sufficient to induce the differentiation of at least some of the Pdx1-positive, NKX6-1-positive pancreatic progenitor cells into Pdx1-positive, NKX6-1-positive, insulin-positive endocrine cells. In some embodiments, the period of time is at least 7 days. In some embodiments, the suspension culture is replenished every other day. In some embodiments, at least 15% of the Pdx1-positive, NKX6-1-positive pancreatic progenitor cells are induced to differentiate into Pdx1-positive, NKX6-1-positive, insulin-positive endocrine cells. In some embodiments, at least 99% of the Pdx1-positive, NKX6-1-positive pancreatic progenitor cells are induced to differentiate into Pdx1-positive, NKX6-1-positive, insulin-positive endocrine cells.

In some embodiments, the Pdx1-positive, NKX6-1-positive pancreatic progenitor cells are obtained by contacting Pdx1-positive pancreatic progenitor cells under conditions that promote cell clustering with i) at least one growth factor from the FGF family, ii) at least one SHH pathway inhibitor, and optionally iii) low concentrations of a RA signaling pathway activator, for a period of five days to induce the differentiation of at least some of the Pdx1-positive pancreatic progenitor cells into Pdx1-positive, NKX6-1-positive pancreatic progenitor cells, wherein the Pdx1-positive, NKX6-1-positive pancreatic progenitor cells expresses Pdx1 and NKX6-1.

In some embodiments, the Pdx1-positive pancreatic progenitor cells are contacted with the at least one growth factor from the FGF family at a concentration of between 1 ng/mL-100 ng/mL. In some embodiments, the Pdx1-positive pancreatic progenitor cells are contacted with the at least one growth factor from the FGF family at a concentration of 50 ng/mL. In some embodiments, the at least one growth factor from the FGF family comprises keratinocyte growth factor (KGF). In some embodiments, the at least one growth factor from the FGF family is selected from the group consisting of FGF2, FGF8B, FGF10, and FGF21. In some embodiments, the Pdx1-positive pancreatic progenitor cells are contacted with the at least one SHH pathway inhibitor at a concentration of between 0.1 µM and 0.5 µM. In some embodiments, the Pdx1-positive pancreatic progenitor cells are contacted with the at least one SHH pathway inhibitor at a concentration of 0.25 µM. In some embodiments, the at least one SHH pathway inhibitor comprises Sant1. In some embodiments, the Pdx1-positive pancreatic progenitor cells are contacted with the RA signaling pathway activator at a concentration of between 0.01 µM-1.0 µM. In some embodiments, the Pdx1-positive pancreatic progenitor cells are contacted with the RA signaling pathway activator at a concentration of 0.1 µM. In some embodiments, the RA signaling pathway activator comprises RA. In some embodiments, the method includes contacting the Pdx1-positive pancreatic progenitor cells with at least one growth factor from the EGF family. In some embodiments, the Pdx1-positive pancreatic progenitor cells are contacted with the at least one growth factor from the EGF family at a concentration of between 2 ng/mL-200 ng/mL. In some embodiments, the Pdx1-positive pancreatic progenitor cells are contacted with the at least one growth factor from the EGF family at a concentration of 20 ng/mL. In some embodiments, the at least one growth factor from the EGF family comprises betacellulin. In some embodiments, the at least one growth factor from the EGF family comprises EGF. In some embodiments, the Pdx1-positive pancreatic progenitor cells are cultured in a suitable culture medium. In some embodiments, the conditions that promote cell clustering comprise suspension culture. In some embodiments, the suspension culture is replenished every other day. In some embodiments, an activator of protein kinase C is not added to the suspension culture during the 5 days. In some embodiments, an activator of protein kinase C is removed from the suspension culture prior to the 5 days. In some embodiments, the activator of protein kinase C comprises PdbU. In some embodiments, a BMP signaling pathway inhibitor is not added to the suspension culture during the 5 days. In some embodiments, a BMP signaling pathway inhibitor is removed from the suspension culture prior to the 5 days. In some embodiments, the BMP signaling pathway inhibitor comprises LDN193189. In some embodiments, at least 10% of the Pdx1-positive pancreatic progenitor cells in the population are induced to differentiate into Pdx1-positive, NKX6-1-positive pancreatic progenitor cells. In some embodiments, at least 95% of the Pdx1-positive pancreatic progenitor cells are induced to differentiate into Pdx1-positive, NKX6-1-positive pancreatic progenitor cells.

In some aspects, the disclosure provides a method of generating SC-β cells from pluripotent cells, the method comprising: a) differentiating pluripotent stem cells in a population into Pdx1-positive pancreatic progenitor cells; b) differentiating at least some of the Pdx1-positive pancreatic progenitor cells into Pdx1-positive, NKX6-1-positive pancreatic progenitor cells by a process of contacting the Pdx1-positive pancreatic progenitor cells under conditions that promote cell clustering with i) at least one growth factor from the FGF family, ii) at least one SHH pathway inhibitor, and optionally iii) a RA signaling pathway activator, every other day for a period of five days to induce the differentiation of at least some of the Pdx1-positive pancreatic progenitor cells in the population into NKX6-1-positive pancreatic progenitor cells, wherein the NKX6-1-positive pancreatic progenitor cells expresses Pdx1 and NKX6-1; c) differentiating at least some of the Pdx1-positive, NKX6-1-positive pancreatic progenitor cells into Pdx1-positive, NKX6-1-positive, insulin-positive endocrine cells by a process of contacting the Pdx1-positive, NKX6-1-positive pancreatic progenitor cells under conditions that promote cell clustering with i) a TGF-β signaling pathway inhibitor, b) a TH signaling pathway activator, and optionally c) at least one SHH pathway inhibitor, ii) a RA signaling pathway activator, iii) a γ-secretase inhibitor, and vi) at least one growth factor from the epidermal growth factor (EGF) family, every other day for a period of between five and seven days to induce the differentiation of at least some of the Pdx1-positive, NKX6-1-positive pancreatic progenitor cells into Pdx1-positive, NKX6-1, insulin-positive endocrine cells, wherein the Pdx1-positive, NKX6-1, insulin-positive endocrine cells express Pdx1, NKX6-1, NKX2-2, Math, glis3, Sur1, Kir6.2, Znt8, SLC2A1, SLC2A3 and/or insulin; and d) differentiating at least some of the Pdx1-positive, NKX6-1-positive, insulin-positive endocrine cells into SC-β cells by a process of contacting the Pdx1-positive, NKX6-1-positive, insulin-positive endocrine cells under conditions that promote cell clustering with i) a transforming growth factor β (TGF-β) signaling pathway inhibitor, ii) a thyroid hormone signaling pathway activator, and optionally iii) a protein kinase inhibitor, every other day for a period of between seven and 14 days to induce the in vitro maturation of at least some of the Pdx1-positive, NKX6-1-positive, insulin-positive endocrine cells into SC-β cells, wherein the SC-β cells exhibit a GSIS response in vitro and/or in vivo.

In some embodiments, the disclosure provides a method of generating SC-β cells from pluripotent cells, the method comprising: a) differentiating at least some pluripotent cells in a population into Pdx1-positive pancreatic progenitor cells; b) differentiating at least some of the Pdx1-positive pancreatic progenitor cells into Pdx1-positive, NKX6-1-positive pancreatic progenitor cells by a process of contacting the Pdx1-positive pancreatic progenitor cells under conditions that promote cell clustering with i) KGF, ii) Sant1, and optionally iii) low concentrations of RA, every other day for a period of five days to induce the differentiation of at least one Pdx1-positive pancreatic progenitor cell in the population into NKX6-1-positive pancreatic progenitor cells, wherein the NKX6-1-positive pancreatic progenitor cells expresses Pdx1 and NKX6-1; c) differentiating at least some of the Pdx1-positive, NKX6-1-positive pancreatic progenitor cells into Pdx1-positive, NKX6-1-positive, insulin-positive endocrine cells by a process of contacting the Pdx1-positive, NKX6-1-positive pancreatic progenitor cells with i) Alk5 Inhibitor II, ii) T3, and optionally iii) Sant1, iv) RA, v) XXI, and vi) betacellulin, every other day for a period of between five and seven days to induce the differentiation of at least some of the Pdx1-positive, NKX6-1-positive pancreatic progenitor cells into Pdx1-positive, NKX6-1, insulin-positive endocrine cells, wherein the Pdx1-positive, NKX6-1, insulin-positive endocrine cells express Pdx1, NKX6-1, NKX2-2, Math, glis3, Sur1, Kir6.2, Znt8, SLC2A1, SLC2A3 and/or insulin; and d) differentiating at least some of the Pdx1-positive, NKX6-1-positive, insulin-positive endocrine cells into SC-β cells by a process of contacting the Pdx1-positive, NKX6-1-positive, insulin-positive endocrine cells under conditions that promote cell clustering with i) Alk5 inhibitor II, ii) T3, and optionally iii) staurosporine, every other day for a period of between seven and 14 days to induce the in vitro maturation of at least some of the Pdx1-positive, NKX6-1-positive, insulin-producing endocrine cells into SC-β cells, wherein the SC-β cells exhibit a GSIS response in vitro and/or in vivo.

In some aspects, the disclosure provides an artificial islet comprising SC-β cells differentiated in vitro from pluripotent stem cells.

In some aspects, the disclosure provides an artificial pancreas comprising SC-β cells differentiated in vitro from pluripotent stem cells.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), Current Protocols in Molecular Biology, Current Protocols in Immunology, Current Protocols in Protein Science, and Current Protocols in Cell Biology, all John Wiley & Sons, N.Y., edition as of December 2008; Sambrook, Russell, and Sambrook, Molecular Cloning: A Laboratory Manual, 3rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N J, 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, MD) and National Center for Biotechnology Information, National Library of Medicine (Bethesda, MD), as of May 1, 2010, available on the worldwide web at subdomain ncbi.nlm.nih.gov/omim/ and in Online Mendelian Inheritance in Animals (OMIA), a database of genes, inherited disorders and traits in animal species (other than human and mouse), on the worldwide web at subdomain omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A and 1B show comparisons between a previously published control differentiation method and a new directed differentiation method. FIG. 1A shows a schematic comparing an exemplary directed differentiation method of the disclosure for generating INS+ cells from hPSC compared to a previously published control differentiation method. FIG. 1B illustrates histological sections of HUES8 undifferentiated (top), differentiated to DE (middle), and differentiated to PP1 (bottom) and stained with OCT4, SOX17, and PDX1, respectively using a previously published control differentiation method. Scale bar=100 μM.

FIGS. 2A, 2B, and 2C are graphs showing ELISA measurements of secreted human insulin from SC-β (FIG. 2A), primary β cells (FIG. 2B), and PH cells (FIG. 2C) challenged sequentially with 2, 20, 2, 20, 2, and 20 mM glucose. After sequential low/high glucose challenges, cells were depolarized with 30 mM KCl.

FIG. 3A), primary β cells (1° β; FIG. 3B), and PH cells (FIG. 3C) were challenged sequentially with 2, 20, 2, 20, 2, and 20 mM glucose and 30 mM KCl and human insulin measured with ELISA.

FIGS. 4A, 4B, 4C, 4D and 4E demonstrate that SC-β cells flux cytosolic $Ca^{2+}$ in response to multiple sequential high glucose challenges like primary β cells. FIG. 4A is a schematic representation of population level and single cell level detection of cytosolic $Ca^{2+}$ using Fluo-4 AM staining. Population level measurements were taken on individual whole clusters (marked by large red circle in schematic), and individual cells within intact clusters (marked by small red circles) were analyzed for single cell analysis. FIG. 4B is a graph showing population measurements of dynamic normalized Fluo-4 fluorescence intensity for SC-β cells, primary β cells, and PH cells challenged sequentially with 2, 20, 2, 20, 2, and 20 mM glucose and 30 mM KCl. FIG. 4C shows fluorescence images of Fluo-4 AM staining used in single cell analysis. FIG. 4D shows representative images indicating location of single cells that responded to 3 (yellow), 2 (orange), 1 (blue), and 0 (red) glucose challenges. FIG. 4E shows graphical quantification of the frequency of SC-β cells (n=156), primary β cells (n=114), and PH cells (n=138) that responded to 20 mM glucose. Scale bar=100 μm.

FIG. 5A shows immunohistochemistry images of cells stained for C-peptide (green), NKX6-1 (red), and somatostatin (grey). FIG. 5B shows immunohistochemistry images of cells stained for C-peptide (green) and PDX1 (red). FIG. 5C shows immunohistochemistry images of cells stained for C-peptide (green) and glucagon (red) with the corresponding DAPI stain (blue). FIG. 5D shows representative flow cytometry dot plots and population percentages of cells stained for C-peptide and NKX6-1. FIG. 5E shows hierarchal clustering analysis based on all genes measured by microarray of undifferentiated HUES8, PH cells, fetal β cells, and adult primary β cells sorted for INS (data from Hrvatin et al. (Hrvatin et al., 2014)), and SC-β cells (SC-β) sorted for INS and NKX6-1. FIG. 5F shows a heat map of the 100 genes with the most variance across all samples. CP=C-peptide, SST=somatostatin, GCG=glucagon. Scale bar=100 μm.

FIG. 7A illustrates staining for C-peptide (green) and ISL1 (red). FIG. 7B illustrates staining for C-peptide (green) and MAFA (red). FIG. 7C illustrates staining for C-peptide (green) and MAFB (red). Scale bar=100 μm.

FIGS. 9A, 9B and 9C demonstrate that SC-β cell granules are structurally similar to primary human β cell granules. FIG. 9A shows electron microscopy images of granules highlighting representative crystallized insulin granules (red), early insulin granules (yellow), and mixed endocrine granules (blue). Scale bar=500 nm. FIG. 9B shows higher magnification images of granules highlighted in (FIG. 9A). Scale bar=500 nm. FIG. 9C shows electron microscopy images of cells labeled with immunogold staining showing granules that contain insulin (smaller 5 nm black dots) and/or glucagon (larger 15 nm black dots). Representative immunogold particles are highlighted with red arrows (insulin) and blue arrows (glucagon). Scale bar=100 nm.

FIGS. 10A and 10B are graphs showing ELISA measurements of secreted human insulin from SC-β generated from non-diabetic cells (FIG. 10A) and type 1 diabetic cells (FIG. 10B) challenged sequentially with 2, 20, 2, 20, 2, and 20 mM glucose.

FIGS. 11A, 11B, 11C, 11D, 11E, and 11F show representative flow cytometry dot plots and population percentages of cells stained for C-peptide and NKX6-1 from multiple hiPSC lines. FIGS. 11A, 11B, and 11C show representative flow cytometry dot plots and population percentages of cells stained for C-peptide and NKX6-1 from non-diabetic hiPSC lines. FIGS. 11D, 11E, and 11F show representative flow cytometry dot plots and population percentages of cells stained for C-peptide and NKX6-1 from type 1 diabetic hiPSC lines.

FIGS. 12A, 12B, 12C and 12D demonstrate that transplanted SC-β cells function rapidly in vivo. FIG. 12A is a graph showing ELISA measurements of human insulin from the serum of individual mice transplanted with SC-β cells (cultured for 1 week in the final in vitro step), primary human β cells (1° β), or PH cells. Measurements were taken before (white bars) and 30 min after (black bars) a glucose injection of mice two weeks post-transplantation. FIG. 12B shows immunohistochemistry images of cells transplanted in (FIG. 12A) stained with C-peptide (green) and PDX1 (red) to confirm presence of graft. FIG. 12C is a graph showing ELISA measurements of human insulin from the serum of individual mice transplanted with pancreatic progenitors. Measurements were taken before (white bars) and 30 min after (black bars) a glucose injection of mice two weeks post-transplantation. FIG. 12D is a graph showing ELISA measurements of human insulin from the serum of individual mice transplanted with SC-β cells cultured for 2 weeks during the final in vitro step. Measurements were taken 30 min after (black bars) a glucose injection of mice two weeks post-transplantation. nd=not determined. scale bar=100 μm.

FIGS. 13A and 13B illustrate additional histological sections of SC-β cells and PH cells transplanted into mice 2 wk prior. FIG. 13A shows low magnification images of grafts stained for DAPI (blue), C-peptide (green), and GCG (red). Scale bar=200 uM. FIG. 13B shows higher magnification images of grafts stained for C-peptide (green) and GCG (red). Scale bar=100 uM.

FIG. 14A shows a schematic showing the use of various media in the various steps of the differentiation process. FIG. 14B shows that adding additional factors, such as Sant1, XXI, and SSP, to the CMRL media at the last step of differentiation generates a better glucose stimulated insulin secretion (GSIS) response by SC-β cells as measured by stimulation index between high and low glucose challenges. FIG. 14C shows that adding additional factors, such as Sant1, XXI, and SSP, to the CMRL media at the last step of differentiation generates a better glucose stimulated insulin secretion (GSIS) response by SC-β cells as measured by the amount of insulin released.

FIGS. 15A, 15B, 15C, 15D, 15E, 15F, 15G, 15H and 15I demonstrate modifications to the protocol that can enhance survival and quality of SC-β cells generated. FIG. 15A is a schematic illustration of the protocol. FIG. 15B shows how more pure NKX6.1+ endocrine clusters can be generated (FIG. 15B) using the modified protocol. FIG. 15C demonstrates how the use of a Rock inhibitor at Steps 3-5 can improve cell survival. FIG. 15D demonstrates how the use of Activin A together with Nicotinamide can downregulate SOX2 and improve cell survival. FIG. 15E shows that SOX2 and NKX6-1 are mutually exclusive. FIG. 15F demonstrates how the use of staurospaurine at Step 6 generates a near pure endocrine population and FIG. 15G demonstrates how the use of staurospaurine at Step 6 generates a higher percentage of NKX6-1/C-peptide+ cells. FIG. 15I demonstrates how the use of XXI in combination with Alk5i and T3 at Steps 5-6 increases the NeuroD+ population when compared to the use of only Alk5i and T3 (FIG. 15H).

FIGS. 16A, 16B, 16C, 16D, 16E, 16F, 16G, 16H and 16I demonstrate clinical utility of SC-β cells as a diabetes therapy or drug discovery platform. FIG. 16A is a schematic illustration of the utility of SC-β cells for treating diabetes or screening drugs to improve function or replication. FIG. 16B is a table listing diabetic drugs investigated and their general therapeutic category. FIG. 16C is a graph showing ELISA measurements of secreted human insulin from plated SC-β cells treated with the indicated drugs in 2 and 20 mM glucose. Indicated p values compare the insulin value in 20 mM glucose between the drug and the control. FIG. 16D is an immunofluorescence image of dispersed and plated SC-β cells stained with DAPI (blue), C-peptide (green), and Ki67 (red) without treatment. FIG. 16E is an immunofluorescence image of dispersed and plated SC-β cells stained with DAPI (blue), C-peptide (green), and Ki67 (red) treated with prolactin for 48 hours. FIG. 16F shows a graphical quantification of the fraction of cells that co-express C-peptide and Ki67. *$p<0.05$. FIG. 16G is a graph illustrating fasting blood glucose measurements of Akita mice transplanted with SC-β cells (n=6) or PH cells (n=6). *$p<0.05$ comparing the two cell groups on the same day. FIG. 16H is a graph illustrating blood glucose measurements from progressively diabetic Akita mice transplanted with SC-β cells or PH cells. Measurements were taken before (white bars) and 20 min after (black bars) a glucose injection of mice transplanted 2 weeks prior. Glucose measurements were saturated at 550 mg/dL. *$p<0.05$ comparing the two cell groups at the same time post glucose injection. FIG. 16I is a graph showing ELISA measurements of human insulin from the serum of Akita mice 20 min after a glucose injection. Mice were challenged with glucose 2 weeks post transplantation. *$p<0.05$ comparing the two cell groups. Scale bar=50 μm.

DETAILED DESCRIPTION OF THE INVENTION

Figure 2A:
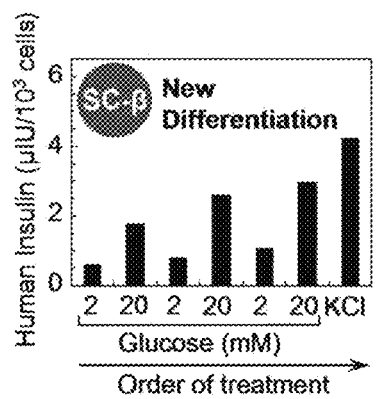
FIGS. 2A, 2B and 2C demonstrate that stem cell-derived β (SC-β) cells generated in vitro secrete insulin in response to multiple sequential high glucose challenges like primary human β cells.
Figure 2B:
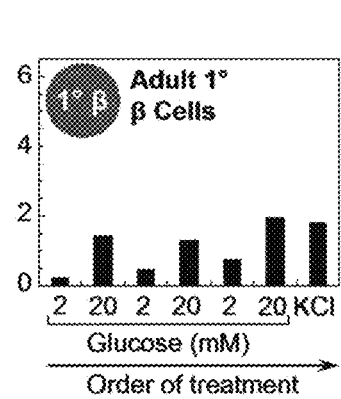
Figure 2C:
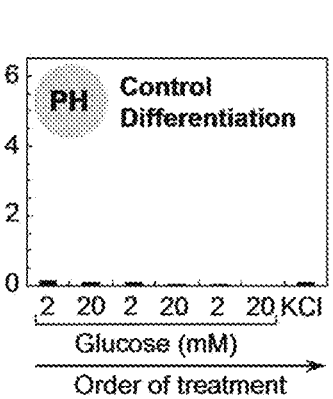
Figures 3A, 3B, 3C:
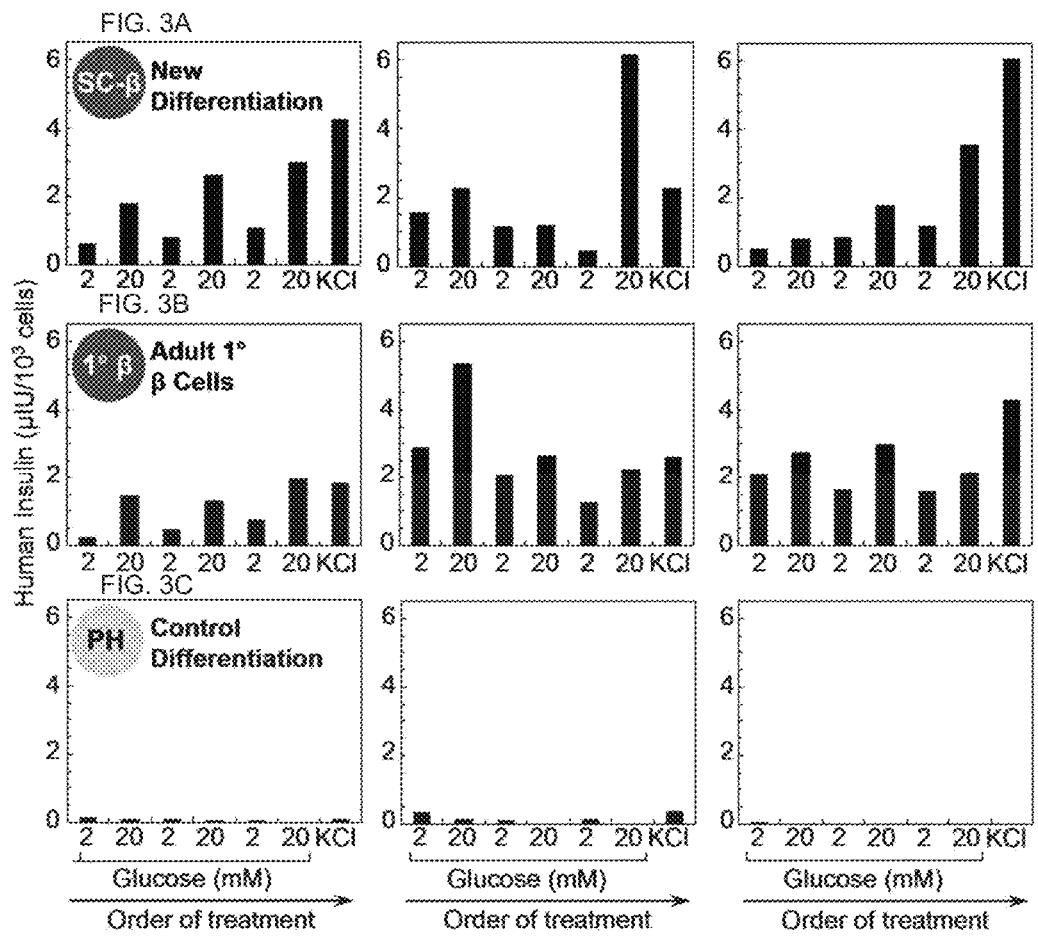
FIGS. 3A, 3B, and 3C demonstrate additional biological replicates of in vitro-derived SC-β cells that secrete insulin in response to multiple sequential high glucose challenges like primary β cells. The left panels are the same as in FIG. 2. Cells SC-β cells (SC-β.

Aspects of the disclosure relate to compositions, methods, kits, and agents for generating stem cell-derived β (SC-β) cells (e.g., mature pancreatic β cells) from at least one insulin-positive endocrine cell or a precursor thereof (e.g., iPS cells, hESCs, definitive endoderm cells, primitive gut tube cells, Pdx1-positive pancreatic progenitor cells, Pdx1-positive, NKX6-1-positive pancreatic progenitor cells, Ngn3-positive endocrine progenitor cells, etc.), and SC-β cells produced by those compositions, methods, kits, and agents for use in cell therapies, assays (e.g., drug screening), and various methods of treatment.

In addition, aspects of the disclosure relate to methods of identification of the SC-β cells that are detectable based on morphological criteria, without the need to employ a selectable marker, as well as functional characteristics, such as ability to express insulin, secrete insulin in response to one or more glucose challenges, exhibit a mature GSIS response, and organize in islets in pancreas in vivo, and typically have small spindle like cells of about 9-15 μm diameter.

In addition, aspects of the disclosure relate to methods of identifying β cell maturation factors. One of skill in the art will be aware of, or will readily be able to ascertain, whether a particular β cell maturation factor is functional using assays known in the art. For example, the ability of a β cell maturation factor to convert at least one insulin-positive endocrine cell or a precursor thereof to a SC-β cell can be assessed using the assays as disclosed herein in. Other convenient assays include measuring the ability to activate transcription of a reporter construct containing a β cell marker binding site operably linked to a nucleic acid sequence encoding a detectable marker such as luciferase. One assay involves determining whether the candidate β cell maturation factor induces at least one insulin-positive endocrine cell to become a SC-β cell or express markers of a β cell or exhibit functional characteristics of a mature β cell as disclosed herein. Determination of such expression of β cell markers can be determined using any suitable method, e.g., immunoblotting. Such assays may readily be adapted to identify or confirm activity of agents that directly convert at least one insulin-positive endocrine cell or a precursor thereof to a SC-β cell.

The in vitro-matured, SC-β cells (i.e., pancreatic β cells) generated according to the inventive methods described herein demonstrate many advantages, for example, they perform glucose stimulated insulin secretion in vitro, resemble human islet β cells by gene expression and ultrastructure, secrete human insulin and ameliorate hyperglycemia when transplanted into mice, provide a new platform for cell therapy (e.g., transplantation into a subject in need of additional and/or functional β cells), drug screening (e.g., for insulin production/secretion, survival, dedifferentiation, etc.), research (e.g., determining the differences in function between normal and diabetic β cells), and tissue engineering (e.g., using the SC-β cells as the first cell type in reconstructing an islet).

Definitions

For convenience, certain terms employed herein, in the specification, examples and appended claims are collected here. Unless otherwise defined, all technical and scientific terms used herein have the same meaning as commonly understood by one of ordinary skill in the art to which this invention belongs.

The term "differentiated cell" is meant any primary cell that is not, in its native form, pluripotent as that term is defined herein. Stated another way, the term "differentiated cell" refers to a cell of a more specialized cell type derived from a cell of a less specialized cell type (e.g., a stem cell such as an induced pluripotent stem cell) in a cellular differentiation process. Without wishing to be limited to theory, a pluripotent stem cell in the course of normal ontogeny can differentiate first to an endoderm cell that is capable of forming pancreas cells and other endoderm cell types. Further differentiation of an endoderm cell leads to the pancreatic pathway, where ~98% of the cells become exocrine, ductular, or matrix cells, and ~2% become endocrine cells. Early endocrine cells are islet progenitors, which can then differentiate further into insulin-producing cells (e.g. functional endocrine cells) which secrete insulin, glucagon, somatostatin, or pancreatic polypeptide. Endoderm cells can also be differentiate into other cells of endodermal origin, e.g. lung, liver, intestine, thymus etc.

As used herein, the term "somatic cell" refers to any cells forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro. Unless otherwise indicated the methods for converting at least one insulin-positive endocrine cell or precursor thereof to an insulin-producing, glucose responsive cell can be performed both in vivo and in vitro (where in vivo is practiced when at least one insulin-positive endocrine cell or precursor thereof are present within a subject, and where in vitro is practiced using an isolated at least one insulin-positive endocrine cell or precursor thereof maintained in culture).

As used herein, the term "adult cell" refers to a cell found throughout the body after embryonic development.

The term "endoderm cell" as used herein refers to a cell which is from one of the three primary germ cell layers in the very early embryo (the other two germ cell layers are the mesoderm and ectoderm). The endoderm is the innermost of the three layers. An endoderm cell differentiates to give rise first to the embryonic gut and then to the linings of the respiratory and digestive tracts (e.g. the intestine), the liver and the pancreas.

The term "a cell of endoderm origin" as used herein refers to any cell which has developed or differentiated from an endoderm cell. For example, a cell of endoderm origin includes cells of the liver, lung, pancreas, thymus, intestine, stomach and thyroid. Without wishing to be bound by theory, liver and pancreas progenitors (also referred to as pancreatic progenitors) are develop from endoderm cells in the embryonic foregut. Shortly after their specification, liver and pancreas progenitors rapidly acquire markedly different cellular functions and regenerative capacities. These changes are elicited by inductive signals and genetic regulatory factors that are highly conserved among vertebrates. Interest in the development and regeneration of the organs has been fueled by the intense need for hepatocytes and pancreatic β cells in the therapeutic treatment of liver failure and type I diabetes. Studies in diverse model organisms and humans have revealed evolutionarily conserved inductive signals and transcription factor networks that elicit the differentiation of liver and pancreatic cells and provide guidance for how to promote hepatocyte and β cell differentiation from diverse stem and progenitor cell types.

The term "definitive endoderm" as used herein refers to a cell differentiated from an endoderm cell and which can be differentiated into a SC-β cell (e.g., a pancreatic β cell). A definitive endoderm cell expresses the marker Sox17. Other markers characteristic of definitive endoderm cells include, but are not limited to MIXL2, GATA4, HNF3b, GSC, FGF17, VWF, CALCR, FOXQ1, CXCR4, Cerberus, OTX2, goosecoid, C-Kit, CD99, CMKOR1 and CRIP1. In particular, definitive endoderm cells herein express Sox17 and in some embodiments Sox17 and HNF3B, and do not express significant levels of GATA4, SPARC, APF or DAB. Definitive endoderm cells are not positive for the marker Pdx1 (e.g. they are Pdx1-negative). Definitive endoderm cells have the capacity to differentiate into cells including those of the liver, lung, pancreas, thymus, intestine, stomach and thyroid. The expression of Sox17 and other markers of definitive endoderm may be assessed by any method known by the skilled person such as immunochemistry, e.g., using an anti-Sox17 antibody, or quantitative RT-PCR.

The term "pancreatic endoderm" refers to a cell of endoderm origin which is capable of differentiating into multiple pancreatic lineages, including pancreatic β cells, but no longer has the capacity to differentiate into non-pancreatic lineages.

The term "primitive gut tube cell" or "gut tube cell" as used herein refers to a cell differentiated from an endoderm cell and which can be differentiated into a SC-β cell (e.g., a pancreatic β cell). A primitive gut tube cell expresses at least one of the following markers: HNF1-β, HNF3-β or HNF4-α. Primitive gut tube cells have the capacity to differentiate into cells including those of the lung, liver, pancreas, stomach, and intestine. The expression of HNF1-β and other markers of primitive gut tube may be assessed by any method known by the skilled person such as immunochemistry, e.g., using an anti-HNF1-β antibody.

The term "pancreatic progenitor", "pancreatic endocrine progenitor", "pancreatic precursor" or "pancreatic endocrine precursor" are used interchangeably herein and refer to a stem cell which is capable of becoming a pancreatic hormone expressing cell capable of forming pancreatic endocrine cells, pancreatic exocrine cells or pancreatic duct cells. These cells are committed to differentiating towards at least one type of pancreatic cell, e.g. beta cells that produce insulin; alpha cells that produce glucagon; delta cells (or D cells) that produce somatostatin; and/or F cells that produce pancreatic polypeptide. Such cells can express at least one of the following markers: NGN3, NKX2.2, NeuroD, ISL-1, Pax4, Pax6, or ARX.

The term "pdx1-positive pancreatic progenitor" as used herein refers to a cell which is a pancreatic endoderm (PE) cell which has the capacity to differentiate into SC-β cells, such as pancreatic β cells. A Pdx1-positive pancreatic progenitor expresses the marker Pdx1. Other markers include, but are not limited to Cdcp1, or Ptf1a, or HNF6 or NRx2.2. The expression of Pdx1 may be assessed by any method known by the skilled person such as immunochemistry using an anti-Pdx1 antibody or quantitative RT-PCR.

The term "pdx1-positive, NKX6-1-positive pancreatic progenitor" as used herein refers to a cell which is a pancreatic endoderm (PE) cell which has the capacity to differentiate into insulin-producing cells, such as pancreatic β cells. A pdx1-positive, NKX6-1-positive pancreatic progenitor expresses the markers Pdx1 and NKX6-1. Other markers include, but are not limited to Cdcp1, or Ptf1a, or HNF6 or NRx2.2. The expression of NKX6-1 may be assessed by any method known by the skilled person such as immunochemistry using an anti-NKX6-1 antibody or quantitative RT-PCR.

The term "Ngn3-positive endocrine progenitor" as used herein refers to precursors of pancreatic endocrine cells expressing the transcription factor Neurogenin-3 (Ngn3). Progenitor cells are more differentiated than multipotent stem cells and can differentiate into only few cell types. In particular, Ngn3-positive endocrine progenitor cells have the ability to differentiate into the five pancreatic endocrine cell types (α, β, δ, ε and PP). The expression of Ngn3 may be assessed by any method known by the skilled person such as immunochemistry using an anti-Ngn3 antibody or quantitative RT-PCR.

The terms "NeuroD" and "NeuroD1" are used interchangeably and identify a protein expressed in pancreatic endocrine progenitor cells and the gene encoding it.

The terms "insulin-positive β-like cell" and "insulin-positive endocrine cell" refer to cells (e.g., pancreatic endocrine cells) that displays at least one marker indicative of a pancreatic β cell and also expresses insulin but lack a GSIS response characteristic of an endogenous β cell.

A "precursor thereof" as the term relates to an insulin-positive endocrine cell refers to any cell that is capable of differentiating into an insulin-positive endocrine cell, including for example, a pluripotent stem cell, a definitive endoderm cell, a primitive gut tube cell, a pancreatic progenitor cell, or endocrine progenitor cell, when cultured under conditions suitable for differentiating the precursor cell into the insulin-positive endocrine cell.

The terms "stem cell-derived β cell", "SC-β cell", "functional β cell", "functional pancreatic β cell" and "mature SC-β cell" refer to cells (e.g., pancreatic β cells) that display at least one marker indicative of a pancreatic β cell (e.g., PDX-1 or NKX6-1), expresses insulin, and display a GSIS response characteristic of an endogenous mature β cell. In some embodiments, the "SC-β cell" comprises a mature pancreatic β cells. It is to be understood that the SC-β cells need not be derived (e.g., directly) from stem cells, as the methods of the disclosure are capable of deriving SC-β cells from any insulin-positive endocrine cell or precursor thereof using any cell as a starting point (e.g., one can use embryonic stem cells, induced-pluripotent stem cells, progenitor cells, partially reprogrammed somatic cells (e.g., a somatic cell which has been partially reprogrammed to an intermediate state between an induced pluripotent stem cell and the somatic cell from which it was derived), multipotent cells, totipotent cells, a transdifferentiated version of any of the foregoing cells, etc, as the invention is not intended to be limited in this manner). In some embodiments, the SC-β cells exhibit a response to multiple glucose challenges (e.g., at least one, at least two, or at least three or more sequential glucose challenges). In some embodiments, the response resembles the response of endogenous islets (e.g., human islets) to multiple glucose challenges. In some embodiments, the morphology of the SC-β cell resembles the morphology of an endogenous β cell. In some embodiments, the SC-β cell exhibits an in vitro GSIS response that resembles the GSIS response of an endogenous β cell. In some embodiments, the SC-β cell exhibits an in vivo GSIS response that resembles the GSIS response of an endogenous β cell. In some embodiments, the SC-β cell exhibits both an in vitro and in vivo GSIS response that resembles the GSIS response of an endogenous β cell. The GSIS response of the SC-β cell can be observed within two weeks of transplantation of the SC-β cell into a host (e.g., a human or animal). In some embodiments, the SC-β cells package insulin into secretory granules. In some embodiments, the SC-β cells exhibit encapsulated crystalline insulin granules. In some embodiments, the SC-β cells exhibit a stimulation index of greater than 1. In some embodiments, the SC-β cells exhibit a stimulation index of greater than 1.1. In some embodiments, the SC-β cells exhibit a stimulation index of greater than 2. In some embodiments, the SC-β cells exhibit cytokine-induced apoptosis in response to cytokines. In some embodiments, insulin secretion from the SC-β cells is enhanced in response to known antidiabetic drugs (e.g., secretagogues). In some embodiments, the SC-β cells are monohormonal. In some embodiments, the SC-β cells do not abnormally co-express other hormones, such as glucagon, somatostatin or pancreatic polypeptide. In some embodiments, the SC-β cells exhibit a low rate of replication. In some embodiments, the SC-β cells increase intracellular $Ca^{2+}$ in response to glucose. The term "exocrine cell" as used herein refers to a cell of an exocrine gland, i.e. a gland that discharges its secretion via a duct. In particular embodiments, an exocrine cells refers to a pancreatic exocrine cell, which is a pancreatic cell that produces enzymes that are secreted into the small intestine. These enzymes help digest food as it passes through the gastrointestinal tract. Pancreatic exocrine cells are also known as islets of Langerhans, that secrete two hormones, insulin and glucagon. A pancreatic exocrine cell can be one of several cell types: alpha-2 cells (which produce the hormone glucagon); or β cells (which manufacture the hormone insulin); and alpha-1 cells (which produce the regulatory agent somatostatin). Non-insulin-producing exocrine cells as used herein refers to alpha-2 cells or alpha-1 cells. Note, the term pancreatic exocrine cells encompasses "pancreatic endocrine cells" which refer to a pancreatic cell that produces hormones (e.g., insulin (produced from β cells), glucagon (produced by alpha-2 cells), somatostatin (produced by delta cells) and pancreatic polypeptide (produced by F cells) that are secreted into the bloodstream.

As used herein, the term "insulin-producing cell" refers to a cell differentiated from a pancreatic progenitor, or precursor thereof, which secretes insulin. An insulin-producing cell includes pancreatic β cells as that term is described herein, as well as pancreatic β-like cells (i.e., insulin-positive, endocrine cells) that synthesize (i.e., transcribe the insulin gene, translate the proinsulin mRNA, and modify the proinsulin mRNA into the insulin protein), express (i.e., manifest the phenotypic trait carried by the insulin gene), or secrete (release insulin into the extracellular space) insulin in a constitutive or inducible manner A population of insulin-producing cells e.g. produced by differentiating insulin-positive, endocrine cells or a precursor thereof into SC-β cells according to the methods of the present invention can be pancreatic β cells or β-like cells (e.g., cells that have at least one, or at least two least two) characteristic of an endogenous β cell and exhibit a GSIS response that resembles an endogenous adult β cell. The novelty of the present composition and methods is not negated by the presence of cells in the population that produce insulin naturally (e.g., β cells). It is also contemplated that the population of insulin-producing cells, e.g. produced by the methods as disclosed herein can comprise mature pancreatic β cells or SC-β cells, and can also contain non-insulin-producing cells (i.e. cells of β cell like phenotype with the exception they do not produce or secrete insulin).

As used herein, the terms "endogenous β cell", "endogenous mature pancreatic β cell" or "endogenous pancreatic β cell" refer to an insulin-producing cell of the pancreas or a cell of a pancreatic β cell (β cell) phenotype. The phenotype of a pancreatic β cell is well known by persons of ordinary skill in the art, and include, for example, secretion of insulin in response to an increase in glucose level, expression of markers such as c-peptide, Pdx1 polypeptide and Glut 2, as well as distinct morphological characteristics such as organized in islets in pancreas in vivo, and typically have small spindle like cells of about 9-15 μm diameter.

The term "SC-β cell", "pancreatic β-like cell", and "mature pancreatic β-like" as used herein refer to cells produced by the methods as disclosed herein which expresses at least 15% of the amount of insulin expressed by an endogenous pancreatic β cell, or at least about 20% or at least about 30%, or at least about 40%, or at least about 50%, or at least about 60%, or at least about 70%, or at least about 80%, or at least about 90%, or at least about 100% or greater than 100%, such as at least about 1.5-fold, or at least about 2-fold, or at least about 2.5-fold, or at least about 3-fold, or at least about 4-fold or at least about 5-fold or more than about 5-fold the amount of the insulin secreted by an endogenous pancreatic β cell, or alternatively exhibits at least one, or at least two characteristics of an endogenous pancreatic β cell, for example, but not limited to, secretion of insulin in response to glucose, and expression of β cell markers, such as for example, c-peptide, Pdx1 and glut-2. In one embodiment, the SC-β cell is not an immortalized cell (e.g. proliferate indefinitely in culture). In one embodiment, the SC-β cell is not a transformed cell, e.g., a cell that exhibits a transformation property, such as growth in soft agar, or absence of contact inhibition.

The term "β cell marker" refers to, without limitation, proteins, peptides, nucleic acids, polymorphism of proteins and nucleic acids, splice variants, fragments of proteins or nucleic acids, elements, and other analytes which are specifically expressed or present in pancreatic β cells. Exemplary β cell markers include, but are not limited to, pancreatic and duodenal homeobox 1 (Pdx1) polypeptide, insulin, c-peptide, amylin, E-cadherin, Hnf3β, PCI/3, B2, Nkx2.2, NKX6-1, GLUT2, PC2, ZnT-8, Isll, Pax6, Pax4, NeuroD, Hnflb, Hnf-6, Hnf-3beta, and MafA, and those described in Zhang et al., Diabetes. 50(10):2231-6 (2001). In some embodiment, the β cell marker is a nuclear 3-cell marker. In some embodiments, the β cell marker is Pdx1 or PH3.

The term "pancreatic endocrine marker" refers to without limitation, proteins, peptides, nucleic acids, polymorphism of proteins and nucleic acids, splice variants, fragments of proteins or nucleic acids, elements, and other analytes which are specifically expressed or present in pancreatic endocrine cells. Exemplary pancreatic endocrine cell markers include, but are not limited to, Ngn-3, NeuroD and Islet-1.

The term "non-insulin-producing cell" as used herein is meant any cell of endoderm origin that does not naturally synthesize, express, or secrete insulin constitutively or by induction. Thus, the term "non-insulin-producing cells" as used herein excludes pancreatic β cells. Examples of non-insulin-producing cells that can be used in the methods of the present invention include pancreatic non-β cells, such as amylase producing cells, acinar cells, cells of ductal adenocarcinoma cell lines (e.g., CD18, CD11, and Capan-I cells (see Busik et al., 1997; Schaffert et al. 1997). Non-pancreatic cells of endoderm origin could also be used, for example, non-pancreatic stem cells and cells of other endocrine or exocrine organs, including, for example, liver cells, tymus cells, thyroid cells, intestine cells, lung cells and pituitary cells. In some embodiments, the non-insulin-producing endodermal cells can be mammalian cells or, even more specifically, human cells. Examples of the present method using mammalian pancreatic non-islet, pancreatic amylase producing cells, pancreatic acinar cells are provided herein.

The term "phenotype" refers to one or a number of total biological characteristics that define the cell or organism under a particular set of environmental conditions and factors, regardless of the actual genotype.

The term "pluripotent" as used herein refers to a cell with the capacity, under different conditions, to differentiate to more than one differentiated cell type, and preferably to differentiate to cell types characteristic of all three germ cell layers. Pluripotent cells are characterized primarily by their ability to differentiate to more than one cell type, preferably to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. It should be noted that simply culturing such cells does not, on its own, render them pluripotent. Reprogrammed pluripotent cells (e.g. iPS cells as that term is defined herein) also have the characteristic of the capacity of extended passaging without loss of growth potential, relative to primary cell parents, which generally have capacity for only a limited number of divisions in culture.

As used herein, the terms "iPS cell" and "induced pluripotent stem cell" are used interchangeably and refers to a pluripotent stem cell artificially derived (e.g., induced or by complete reversal) from a non-pluripotent cell, typically an adult somatic cell, for example, by inducing a forced expression of one or more genes.

The term "progenitor" or "precursor" cell are used interchangeably herein and refer to cells that have a cellular phenotype that is more primitive (i.e., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "stem cell" as used herein, refers to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retrodifferentiation" by persons of ordinary skill in the art. As used herein, the term "pluripotent stem cell" includes embryonic stem cells, induced pluripotent stem cells, placental stem cells, etc.

In the context of cell ontogeny, the adjective "differentiated", or "differentiating" is a relative term meaning a "differentiated cell" is a cell that has progressed further down the developmental pathway than the cell it is being compared with. Thus, stem cells can differentiate to lineage-restricted precursor cells (such as a mesodermal stem cell), which in turn can differentiate into other types of precursor cells further down the pathway (such as an cardiomyocyte precursor), and then to an end-stage differentiated cell, which plays a characteristic role in a certain tissue type, and may or may not retain the capacity to proliferate further.

The term "embryonic stem cell" is used to refer to the pluripotent stem cells of the inner cell mass of the embryonic blastocyst (see U.S. Pat. Nos. 5,843,780, 6,200,806). Such cells can similarly be obtained from the inner cell mass of blastocysts derived from somatic cell nuclear transfer (see, for example, U.S. Pat. Nos. 5,945,577, 5,994,619, 6,235, 970). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture. Exemplary adult stem cells include neural stem cells, neural crest stem cells, mesenchymal stem cells, hematopoietic stem cells, and pancreatic stem cells. As indicated above, stem cells have been found resident in virtually every tissue. Accordingly, the present invention appreciates that stem cell populations can be isolated from virtually any animal tissue.

The term "pancreas" refers to a glandular organ that secretes digestive enzymes and hormones. In humans, the pancreas is a yellowish organ about 7 in. (17.8 cm) long and 1.5 in. (3.8 cm) wide. It lies beneath the stomach and is connected to the small intestine, muscular hoselike portion of the gastrointestinal tract extending from the lower end of the stomach (pylorus) to the anal opening. Most of the pancreatic tissue consists of grapelike clusters of cells that produce a clear fluid (pancreatic juice) that flows into the duodenum through a common duct along with bile from the liver. Pancreatic juice contains three digestive enzymes: tryptase, amylase, and lipase, that, along with intestinal enzymes, complete the digestion of proteins, carbohydrates, and fats, respectively. Scattered among the enzyme-producing cells of the pancreas are small groups of endocrine cells, called the islets of Langerhans, that secrete two hormones, insulin and glucagon. The pancreatic islets contain several types of cells: alpha-2 cells, which produce the hormone glucagon; β cells (also referred to herein as "pancreatic β cells"), which manufacture the hormone insulin; and alpha-1 cells, which produce the regulatory agent somatostatin. These hormones are secreted directly into the bloodstream, and together, they regulate the level of glucose in the blood. Insulin lowers the blood sugar level and increases the amount of glycogen (stored carbohydrate) in the liver; glucagon has the opposite action. Failure of the insulin-secreting cells to function properly results in diabetes or diabetes mellitus.

The term "reprogramming" as used herein refers to the process that alters or reverses the differentiation state of a somatic cell. The cell can either be partially or terminally differentiated prior to the reprogramming. Reprogramming encompasses complete reversion of the differentiation state of a somatic cell to a pluripotent cell. Such complete reversal of differentiation produces an induced pluripotent (iPS) cell. Reprogramming as used herein also encompasses partial reversion of a cells differentiation state, for example to a multipotent state or to a somatic cell that is neither pluripotent or multipotent, but is a cell that has lost one or more specific characteristics of the differentiated cell from which it arises, e.g. direct reprogramming of a differentiated cell to a different somatic cell type. Reprogramming generally involves alteration, e.g., reversal, of at least some of the heritable patterns of nucleic acid modification (e.g., methylation), chromatin condensation, epigenetic changes, genomic imprinting, etc., that occur during cellular differentiation as a zygote develops into an adult.

The term "agent" as used herein means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

As used herein, the term "contacting" (i.e., contacting at least one insulin-positive endocrine cell or a precursor thereof with a β cell maturation factor, or combination of β cell maturation factors) is intended to include incubating the β cell maturation factor and the cell together in vitro (e.g., adding the β cell maturation factors to cells in culture). In some embodiments, the term "contacting" is not intended to include the in vivo exposure of cells to the compounds as disclosed herein that may occur naturally in a subject (i.e., exposure that may occur as a result of a natural physiological process). The step of contacting at least one insulin-positive endocrine cell or a precursor thereof with a β cell maturation factor as in the embodiments related to the production of SC-β cells can be conducted in any suitable manner. For example, the cells may be treated in adherent culture, or in suspension culture. In some embodiments, the cells are treated in conditions that promote cell clustering. The disclosure contemplates any conditions which promote cell clustering. Examples of conditions that promote cell clustering include, without limitation, suspension culture in low attachment tissue culture plates, spinner flasks, aggrewell plates. In some embodiments, the inventors have observed that clusters have remained stable in media containing 10% serum. In some embodiments, the conditions that promote clustering include a low serum medium.

It is understood that the cells contacted with a β cell maturation factor can also be simultaneously or subsequently contacted with another agent, such as a growth factor or other differentiation agent or environments to stabilize the cells, or to differentiate the cells further.

Similarly, at least one insulin-positive endocrine cell or a precursor thereof can be contacted with at least one β cell maturation factor and then contacted with at least another β cell maturation factor. In some embodiments, the cell is contacted with at least one β cell maturation factor, and the contact is temporally separated, and in some embodiments, a cell is contacted with at least one β cell maturation factor substantially simultaneously. In some embodiments, the cell is contacted with at least two, at least three, at least four, at least five, at least six, at least seven, at least eight, at least nine, or at least 10 β cell maturation factors.

The term "cell culture medium" (also referred to herein as a "culture medium" or "medium") as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art.

The term "cell line" refers to a population of largely or substantially identical cells that has typically been derived from a single ancestor cell or from a defined and/or substantially identical population of ancestor cells. The cell line may have been or may be capable of being maintained in culture for an extended period (e.g., months, years, for an unlimited period of time). It may have undergone a spontaneous or induced process of transformation conferring an unlimited culture lifespan on the cells. Cell lines include all those cell lines recognized in the art as such. It will be appreciated that cells acquire mutations and possibly epigenetic changes over time such that at least some properties of individual cells of a cell line may differ with respect to each other. In some embodiments, a cell line comprises a SC-β cell described herein.

The term "exogenous" refers to a substance present in a cell or organism other than its native source. For example, the terms "exogenous nucleic acid" or "exogenous protein" refer to a nucleic acid or protein that has been introduced by a process involving the hand of man into a biological system such as a cell or organism in which it is not normally found or in which it is found in lower amounts. A substance will be considered exogenous if it is introduced into a cell or an ancestor of the cell that inherits the substance. In contrast, the term "endogenous" refers to a substance that is native to the biological system.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene and polypeptides obtained by translation of mRNA transcribed from a gene.

The terms "genetically modified" or "engineered" cell as used herein refers to a cell into which an exogenous nucleic acid has been introduced by a process involving the hand of man (or a descendant of such a cell that has inherited at least a portion of the nucleic acid). The nucleic acid may for example contain a sequence that is exogenous to the cell, it may contain native sequences (i.e., sequences naturally found in the cells) but in a non-naturally occurring arrangement (e.g., a coding region linked to a promoter from a different gene), or altered versions of native sequences, etc. The process of transferring the nucleic into the cell can be achieved by any suitable technique. Suitable techniques include calcium phosphate or lipid-mediated transfection, electroporation, and transduction or infection using a viral vector. In some embodiments the polynucleotide or a portion thereof is integrated into the genome of the cell. The nucleic acid may have subsequently been removed or excised from the genome, provided that such removal or excision results in a detectable alteration in the cell relative to an unmodified but otherwise equivalent cell. It should be appreciated that the term genetically modified is intended to include the introduction of a modified RNA directly into a cell (e.g., a synthetic, modified RNA). Such synthetic modified RNAs include modifications to prevent rapid degradation by endo- and exo-nucleases and to avoid or reduce the cell's innate immune or interferon response to the RNA. Modifications include, but are not limited to, for example, (a) end modifications, e.g., 5' end modifications (phosphorylation dephosphorylation, conjugation, inverted linkages, etc.), 3' end modifications (conjugation, DNA nucleotides, inverted linkages, etc.), (b) base modifications, e.g., replacement with modified bases, stabilizing bases, destabilizing bases, or bases that base pair with an expanded repertoire of partners, or conjugated bases, (c) sugar modifications (e.g., at the 2' position or 4' position) or replacement of the sugar, as well as (d) internucleoside linkage modifications, including modification or replacement of the phosphodiester linkages. To the extent that such modifications interfere with translation (i.e., results in a reduction of 50% or more in translation relative to the lack of the modification—e.g., in a rabbit reticulocyte in vitro translation assay), the modification is not suitable for the methods and compositions described herein. In some embodiments, the SC-β cell is genetically modified to express neurogenin 3. In some embodiments, genetic modification of the SC-β cell comprise introducing a synthetic, modified mRNA encoding neurogenin 3. It is believed that genetic modification of SC-β cells with synthetic, modified RNA encoding neurogenin 3 increases production of insulin form the cells. It is expected that such genetic modification of any insulin producing cell is expected to increased insulin production in that cell.

In some aspects, the disclosure provides a SC-β cell genetically modified to include a detectable marker at the insulin locus. In some embodiments, the SC-β cell is modified to replace both alleles of the insulin locus with a detectable marker. In some embodiments, the SC-β cell is genetically modified to insert the detectable marker into the insulin locus so that it is expressed with insulin in the SC-β cell in response to a glucose challenge. In some embodiments, the SC-β cell is genetically modified to insert the detectable marker into the insulin locus in place of insulin so that it is expressed instead of insulin in the SC-β cell in response to a glucose challenge. It is contemplated that any detectable marker can be inserted into the insulin locus, including for example, a nucleic acid encoding a fluorescent protein (e.g., GFP). Those skilled in the art will appreciate that such genetically modified SC-β cells can be used in various screening methods, e.g., to identify agents which stimulate insulin expression and/or secretion from β cells by assaying for the detectable marker in response to the agent. For example, an SC-β cell genetically modified to replace the insulin gene at both alleles (e.g., with GFP) can be contacted with a test agent and those agents which cause the SC-β cells to fluoresce due to expression of the GFP are considered to be candidate agents which are capable of activating insulin gene expression in β cells. In other words, the detectable marker may be used as a surrogate marker for insulin expression in such genetically modified SC-β cells.

The term "identity" as used herein refers to the extent to which the sequence of two or more nucleic acids or polypeptides is the same. The percent identity between a sequence of interest and a second sequence over a window of evaluation, e.g., over the length of the sequence of interest, may be computed by aligning the sequences, determining the number of residues (nucleotides or amino acids) within the window of evaluation that are opposite an identical residue allowing the introduction of gaps to maximize identity, dividing by the total number of residues of the sequence of interest or the second sequence (whichever is greater) that fall within the window, and multiplying by 100. When computing the number of identical residues needed to achieve a particular percent identity, fractions are to be rounded to the nearest whole number. Percent identity can be calculated with the use of a variety of computer programs known in the art. For example, computer programs such as BLAST2, BLASTN, BLASTP, Gapped BLAST, etc., generate alignments and provide percent identity between sequences of interest. The algorithm of Karlin and Altschul (Karlin and Altschul, Proc. Natl. Acad. Sci. USA 87:22264-2268, 1990) modified as in Karlin and Altschul, Proc. Natl. Acad. Sci USA 90:5873-5877, 1993 is incorporated into the NBLAST and XBLAST programs of Altschul et al. (Altschul, et al., J. Mol. Biol. 215:403-410, 1990). To obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. A PAM250 or BLOSUM62 matrix may be used. Software for performing BLAST analyses is publicly available through the National Center for Biotechnology Information (NCBI). See the Web site having URL world-wide web address of: "ncbi.nlm nih.gov" for these programs. In a specific embodiment, percent identity is calculated using BLAST2 with default parameters as provided by the NCBI.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated".

The term "isolated cell" as used herein refers to a cell that has been removed from an organism in which it was originally found or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched from.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a population of SC-β cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not SC-β cells as defined by the terms herein. In some embodiments, the present invention encompasses methods to expand a population of SC-β cells, wherein the expanded population of SC-β cells is a substantially pure population of SC-β cells.

Similarly, with regard to a "substantially pure" or "essentially purified" population of insulin-positive endocrine cells refers to a population of cells that contain fewer than about 20%, more preferably fewer than about 15%, 10%, 8%, 7%, most preferably fewer than about 5%, 4%, 3%, 2%, 1%, or less than 1%, of cells that are not insulin-positive endocrine cells as defined by the terms herein. In some embodiments, the present invention encompasses methods to expand a population of insulin-positive endocrine cells, wherein the expanded population of insulin-positive endocrine cells is a substantially pure population of insulin-positive endocrine cells.

Similarly, with regard to a "substantially pure" or "essentially purified" population of Ngn3-positive endocrine progenitors, refers to a population of cells that contain fewer than about 20%, more preferably fewer than about 15%, 10%, 8%, 7%, most preferably fewer than about 5%, 4%, 3%, 2%, 1%, or less than 1%, of cells that are not Ngn3-positive endocrine progenitors or their progeny as defined by the terms herein. In some embodiments, the present invention encompasses methods to expand a population of Ngn3-positive endocrine progenitors, wherein the expanded population of Ngn3-positive endocrine progenitors is a substantially pure population of Ngn3-positive endocrine progenitors.

Similarly, with regard to a "substantially pure" or "essentially purified" population of Pdx1-positive, NKX6-1-positive pancreatic progenitors, refers to a population of cells that contain fewer than about 20%, more preferably fewer than about 15%, 10%, 8%, 7%, most preferably fewer than about 5%, 4%, 3%, 2%, 1%, or less than 1%, of cells that are not Pdx1-positive, NKX6-1-positive pancreatic progenitors or their progeny as defined by the terms herein. In some embodiments, the present invention encompasses methods to expand a population of Pdx1-positive, NKX6-1-positive pancreatic progenitors, wherein the expanded population of Pdx1-positive, NKX6-1-positive pancreatic progenitors is a substantially pure population of Pdx1-positive, NKX6-1-positive pancreatic progenitors.

Similarly, with regard to a "substantially pure" or "essentially purified" population of Pdx1-positive pancreatic progenitors, refers to a population of cells that contain fewer than about 20%, more preferably fewer than about 15%, 10%, 8%, 7%, most preferably fewer than about 5%, 4%, 3%, 2%, 1%, or less than 1%, of cells that are not Pdx1-positive pancreatic progenitors or their progeny as defined by the terms herein. In some embodiments, the present invention encompasses methods to expand a population of Pdx1-positive pancreatic progenitors, wherein the expanded population of Pdx1-positive pancreatic progenitors is a substantially pure population of Pdx1-positive pancreatic progenitors.

Similarly, with regard to a "substantially pure" or "essentially purified" population of primitive gut tube cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not primitive gut tube cells or their progeny as defined by the terms herein. In some embodiments, the present invention encompasses methods to expand a population of primitive gut tube cells, wherein the expanded population of primitive gut tube cells is a substantially pure population of primitive gut tube cells.

Similarly, with regard to a "substantially pure" or "essentially purified" population of definitive endoderm cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not definitive endoderm cells or their progeny as defined by the terms herein. In some embodiments, the present invention encompasses methods to expand a population of definitive endoderm cells, wherein the expanded population of definitive endoderm cells is a substantially pure population of definitive endoderm cells.

Similarly, with regard to a "substantially pure" or "essentially purified" population of pluripotent cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not pluripotent cells or their progeny as defined by the terms herein. In some embodiments, the present invention encompasses methods to expand a population of pluripotent cells, wherein the expanded population of pluripotent cells is a substantially pure population of pluripotent cells.

The terms "enriching" or "enriched" are used interchangeably herein and mean that the yield (fraction) of cells of one type is increased by at least 10% over the fraction of cells of that type in the starting culture or preparation.

The terms "renewal" or "self-renewal" or "proliferation" are used interchangeably herein, are used to refer to the ability of stem cells to renew themselves by dividing into the same non-specialized cell type over long periods, and/or many months to years. In some instances, proliferation refers to the expansion of cells by the repeated division of single cells into two identical daughter cells.

The term "lineages" as used herein describes a cell with a common ancestry or cells with a common developmental fate. For example, in the context of a cell that is of endoderm origin or is "endodermal linage" this means the cell was derived from an endoderm cell and can differentiate along the endoderm lineage restricted pathways, such as one or more developmental lineage pathways which give rise to definitive endoderm cells, which in turn can differentiate into liver cells, thymus, pancreas, lung and intestine.

As used herein, the term "xenogeneic" refers to cells that are derived from different species.

A "marker" as used herein is used to describe the characteristics and/or phenotype of a cell. Markers can be used for selection of cells comprising characteristics of interests. Markers will vary with specific cells. Markers are characteristics, whether morphological, functional or biochemical (enzymatic) characteristics of the cell of a particular cell type, or molecules expressed by the cell type. Preferably, such markers are proteins, and more preferably, possess an epitope for antibodies or other binding molecules available in the art. However, a marker may consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers may be detected by any method available to one of skill in the art. Markers can also be the absence of a morphological characteristic or absence of proteins, lipids etc. Markers can be a combination of a panel of unique characteristics of the presence and absence of polypeptides and other morphological characteristics.

The term "modulate" is used consistently with its use in the art, i.e., meaning to cause or facilitate a qualitative or quantitative change, alteration, or modification in a process, pathway, or phenomenon of interest. Without limitation, such change may be an increase, decrease, or change in relative strength or activity of different components or branches of the process, pathway, or phenomenon. A "modulator" is an agent that causes or facilitates a qualitative or quantitative change, alteration, or modification in a process, pathway, or phenomenon of interest.

As used herein, the term "DNA" is defined as deoxyribonucleic acid.

The term "polynucleotide" is used herein interchangeably with "nucleic acid" to indicate a polymer of nucleosides. Typically a polynucleotide of this invention is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e. the succession of letters used as abbreviations for bases) that biochemically characterizes a specific nucleic acid. A polynucleotide sequence presented herein is presented in a 5' to 3' direction unless otherwise indicated.

The terms "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a non-polypeptide moiety covalently or non-covalently associated therewith is still considered a "polypeptide". Exemplary modifications include glycosylation and palmitoylation. Polypeptides may be purified from natural sources, produced using recombinant DNA technology, synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

The term a "variant" in referring to a polypeptide could be, e.g., a polypeptide at least 80%, 85%, 90%, 95%, 98%, or 99% identical to full length polypeptide. The variant could be a fragment of full length polypeptide. The variant could be a naturally occurring splice variant. The variant could be a polypeptide at least 80%, 85%, 90%, 95%, 98%, or 99% identical to a fragment of the polypeptide, wherein the fragment is at least 50%, 60%, 70%, 80%, 85%, 90%, 95%, 98%, or 99% as long as the full length wild type polypeptide or a domain thereof having an activity of interest, such as the ability to detect the presence of a SC-β cell, or an insulin-positive endocrine cell or precursor thereof from which the SC-β cell is derived. In some embodiments the domain is at least 100, 200, 300, or 400 amino acids in length, beginning at any amino acid position in the sequence and extending toward the C-terminus. Variations known in the art to eliminate or substantially reduce the activity of the protein are preferably avoided. In some embodiments, the variant lacks an N- and/or C-terminal portion of the full length polypeptide, e.g., up to 10, 20, or 50 amino acids from either terminus is lacking. In some embodiments the polypeptide has the sequence of a mature (full length) polypeptide, by which is meant a polypeptide that has had one or more portions such as a signal peptide removed during normal intracellular proteolytic processing (e.g., during co-translational or post-translational processing). In some embodiments wherein the protein is produced other than by purifying it from cells that naturally express it, the protein is a chimeric polypeptide, by which is meant that it contains portions from two or more different species. In some embodiments wherein a protein is produced other than by purifying it from cells that naturally express it, the protein is a derivative, by which is meant that the protein comprises additional sequences not related to the protein so long as those sequences do not substantially reduce the biological activity of the protein.

The term "functional fragments" as used herein is a polypeptide having amino acid sequence which is smaller in size than, but substantially homologous to the polypeptide it is a fragment of, and where the functional fragment polypeptide sequence is about at least 50%, or 60% or 70% or at 80% or 90% or 100% or greater than 100%, for example 1.5-fold, 2-fold, 3-fold, 4-fold or greater than 4-fold effective biological action as the polypeptide from which it is a fragment of. Functional fragment polypeptides may have additional functions that can include decreased antigenicity, increased DNA binding (as in transcription factors), or altered RNA binding (as in regulating RNA stability or degradation).

The term "vector" refers to a carrier DNA molecule into which a DNA sequence can be inserted for introduction into a host cell. Preferred vectors are those capable of autonomous replication and/or expression of nucleic acids to which they are linked. Vectors capable of directing the expression of genes to which they are operatively linked are referred to herein as "expression vectors". Thus, an "expression vector" is a specialized vector that contains the necessary regulatory regions needed for expression of a gene of interest in a host cell. In some embodiments the gene of interest is operably linked to another sequence in the vector. Vectors can be viral vectors or non-viral vectors. Should viral vectors be used, it is preferred the viral vectors are replication defective, which can be achieved for example by removing all viral nucleic acids that encode for replication. A replication defective viral vector will still retain its infective properties and enters the cells in a similar manner as a replicating adenoviral vector, however once admitted to the cell a replication defective viral vector does not reproduce or multiply. Vectors also encompass liposomes and nanoparticles and other means to deliver DNA molecule to a cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

The term "viral vectors" refers to the use of viruses, or virus-associated vectors as carriers of a nucleic acid construct into a cell. Constructs may be integrated and packaged into non-replicating, defective viral genomes like Adenovirus, Adeno-associated virus (AAV), or Herpes simplex virus (HSV) or others, including retroviral and lentiviral vectors, for infection or transduction into cells. The vector may or may not be incorporated into the cell's genome. The constructs may include viral sequences for transfection, if desired. Alternatively, the construct may be incorporated into vectors capable of episomal replication, e.g EPV and EBV vectors.

The terms "regulatory sequence" and "promoter" are used interchangeably herein, and refer to nucleic acid sequences, such as initiation signals, enhancers, and promoters, which induce or control transcription of protein coding sequences with which they are operatively linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of a protein. In some instances the promoter sequence is recognized by the synthetic machinery of the cell, or introduced synthetic machinery, required for initiating transcription of a specific gene.

As used herein, the term "transcription factor" refers to a protein that binds to specific parts of DNA using DNA binding domains and is part of the system that controls the transfer (or transcription) of genetic information from DNA to RNA. As used herein, "proliferating" and "proliferation" refer to an increase in the number of cells in a population (growth) by means of cell division. Cell proliferation is generally understood to result from the coordinated activation of multiple signal transduction pathways in response to the environment, including growth factors and other mitogens. Cell proliferation may also be promoted by release from the actions of intra- or extracellular signals and mechanisms that block or negatively affect cell proliferation.

The term "selectable marker" refers to a gene, RNA, or protein that when expressed, confers upon cells a selectable phenotype, such as resistance to a cytotoxic or cytostatic agent (e.g., antibiotic resistance), nutritional prototrophy, or expression of a particular protein that can be used as a basis to distinguish cells that express the protein from cells that do not. Proteins whose expression can be readily detected such as a fluorescent or luminescent protein or an enzyme that acts on a substrate to produce a colored, fluorescent, or luminescent substance ("detectable markers") constitute a subset of selectable markers. The presence of a selectable marker linked to expression control elements native to a gene that is normally expressed selectively or exclusively in pluripotent cells makes it possible to identify and select somatic cells that have been reprogrammed to a pluripotent state. A variety of selectable marker genes can be used, such as neomycin resistance gene (neo), puromycin resistance gene (puro), guanine phosphoribosyl transferase (gpt), dihydrofolate reductase (DHFR), adenosine deaminase (ada), puromycin-N-acetyltransferase (PAC), hygromycin resistance gene (hyg), multidrug resistance gene (mdr), thymidine kinase (TK), hypoxanthine-guanine phosphoribosyltransferase (HPRT), and hisD gene. Detectable markers include green fluorescent protein (GFP) blue, sapphire, yellow, red, orange, and cyan fluorescent proteins and variants of any of these. Luminescent proteins such as luciferase (e.g., firefly or *Renilla* luciferase) are also of use. As will be evident to one of skill in the art, the term "selectable marker" as used herein can refer to a gene or to an expression product of the gene, e.g., an encoded protein.

In some embodiments the selectable marker confers a proliferation and/or survival advantage on cells that express it relative to cells that do not express it or that express it at significantly lower levels. Such proliferation and/or survival advantage typically occurs when the cells are maintained under certain conditions, i.e., "selective conditions." To ensure an effective selection, a population of cells can be maintained for a under conditions and for a sufficient period of time such that cells that do not express the marker do not proliferate and/or do not survive and are eliminated from the population or their number is reduced to only a very small fraction of the population. The process of selecting cells that express a marker that confers a proliferation and/or survival advantage by maintaining a population of cells under selective conditions so as to largely or completely eliminate cells that do not express the marker is referred to herein as "positive selection", and the marker is said to be "useful for positive selection". Negative selection and markers useful for negative selection are also of interest in certain of the methods described herein. Expression of such markers confers a proliferation and/or survival disadvantage on cells that express the marker relative to cells that do not express the marker or express it at significantly lower levels (or, considered another way, cells that do not express the marker have a proliferation and/or survival advantage relative to cells that express the marker). Cells that express the marker can therefore be largely or completely eliminated from a population of cells when maintained in selective conditions for a sufficient period of time.

A "reporter gene" as used herein encompasses any gene that is genetically introduced into a cell that adds to the phenotype of the stem cell. Reporter genes as disclosed in this invention are intended to encompass fluorescent, luminescent, enzymatic and resistance genes, but also other genes which can easily be detected by persons of ordinary skill in the art. In some embodiments of the invention, reporter genes are used as markers for the identification of particular stem cells, cardiovascular stem cells and their differentiated progeny. A reporter gene is generally operatively linked to sequences that regulate its expression in a manner dependent upon one or more conditions which are monitored by measuring expression of the reporter gene. In some cases, expression of the reporter gene may be determined in live cells. Where live cell reporter gene assays are used, reporter gene expression may be monitored at multiple time points, e.g., 2, 3, 4, 5, 6, 8, or 10 or more time points. In some cases, where a live cell reporter assay is used, reporter gene expression is monitored with a frequency of at least about 10 minutes to about 24 hours, e.g., 20 minutes, 1 hour, 2 hours, 3 hours, 4 hours, 5 hours, 6 hours, 7 hours, 8 hours, 9 hours, 10 hours, 12 hours, 18 hours, or another frequency from any integer between about 10 minutes to about 24 hours.

The terms "subject" and "individual" are used interchangeably herein, and refer to an animal, for example, a human from whom cells can be obtained and/or to whom treatment, including prophylactic treatment, with the cells as described herein, is provided. For treatment of those infections, conditions or disease states which are specific for a specific animal such as a human subject, the term subject refers to that specific animal. The "non-human animals" and "non-human mammals" as used interchangeably herein, includes mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like, or production mammal, e.g. cow, sheep, pig, and the like.

The terms "diabetes" and "diabetes mellitus" are used interchangeably herein. The World Health Organization defines the diagnostic value of fasting plasma glucose concentration to 7.0 mmol/l (126 mg/dl) and above for Diabetes Mellitus (whole blood 6.1 mmol/l or 110 mg/dl), or 2-hour glucose level 11.1 mmol/L or higher (200 mg/dL or higher). Other values suggestive of or indicating high risk for Diabetes Mellitus include elevated arterial pressure 140/90 mm Hg or higher; elevated plasma triglycerides (1.7 mmol/L; 150 mg/dL) and/or low HDL-cholesterol (less than 0.9 mmol/L, 35 mg/dl for men; less than 1.0 mmol/L, 39 mg/dL women); central obesity (males: waist to hip ratio higher than 0.90; females: waist to hip ratio higher than 0.85) and/or body mass index exceeding 30 kg/m$^2$; microalbuminuria, where the urinary albumin excretion rate 20 µg/min or higher, or albumin:creatinine ratio 30 mg/g or higher). The term diabetes encompasses all forms of diabetes, e.g. Type I, Type II and Type 1.5.

The terms "treat", "treating", "treatment", etc., as applied to an isolated cell, include subjecting the cell to any kind of process or condition or performing any kind of manipulation or procedure on the cell. As applied to a subject, the terms refer to providing medical or surgical attention, care, or management to an individual. The individual is usually ill or injured, or at increased risk of becoming ill relative to an average member of the population and in need of such attention, care, or management.

As used herein, the term "treating" and "treatment" refers to administering to a subject an effective amount of a composition so that the subject as a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Thus, one of skill in the art realizes that a treatment may improve the disease condition, but may not be a complete cure for the disease. As used herein, the term "treatment" includes prophylaxis. Alternatively, treatment is "effective" if the progression of a disease is reduced or halted. "Treatment" can also mean prolonging survival as compared to expected survival if not receiving treatment.

Those in need of treatment include those already diagnosed with a cardiac condition, as well as those likely to develop a cardiac condition due to genetic susceptibility or other factors such as weight, diet and health.

As used herein, the terms "administering," "introducing" and "transplanting" are used interchangeably in the context of the placement of cells, e.g., SC-β cells) of the invention into a subject, by a method or route which results in at least partial localization of the introduced cells at a desired site. The cells e.g. SC-β cells (e.g., pancreatic β cells or pancreatic β-like cells) can be implanted directly to the pancreas, or alternatively be administered by any appropriate route which results in delivery to a desired location in the subject where at least a portion of the implanted cells or components of the cells remain viable. The period of viability of the cells after administration to a subject can be as short as a few hours, e.g. twenty-four hours, to a few days, to as long as several years. In some instances, the cells can also be administered at a non-pancreatic location, such as in the liver or subcutaneously, for example, in a capsule (e.g., microcapsule) to maintain the implanted cells at the implant location and avoid migration of the implanted cells.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein mean the administration of cardiovascular stem cells and/or their progeny and/or compound and/or other material other than directly into the central nervous system, such that it enters the animal's system and, thus, is subject to metabolism and other like processes, for example, subcutaneous administration.

The term "tissue" refers to a group or layer of specialized cells which together perform certain special functions. The term "tissue-specific" refers to a source of cells from a specific tissue.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Stem Cells

Stem cells are cells that retain the ability to renew themselves through mitotic cell division and can differentiate into a diverse range of specialized cell types. The two broad types of mammalian stem cells are: embryonic stem (ES) cells that are found in blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin or intestinal tissues. Pluripotent stem cells can differentiate into cells derived from any of the three germ layers.

While certain embodiments are described below in reference to the use of stem cells for producing SC-β cells (e.g., mature pancreatic β cells or β-like cells) or precursors thereof, germ cells may be used in place of, or with, the stem cells to provide at least one SC-β cell, using similar protocols as the illustrative protocols described herein. Suitable germ cells can be prepared, for example, from primordial germ cells present in human fetal material taken about 8-11 weeks after the last menstrual period. Illustrative germ cell preparation methods are described, for example, in Shamblott et al., Proc. Natl. Acad. Sci. USA 95:13726, 1998 and U.S. Pat. No. 6,090,622.

ES cells, e.g., human embryonic stem cells (hESCs) or mouse embryonic stem cells (mESCs), with a virtually endless replication capacity and the potential to differentiate into most cell types, present, in principle, an unlimited starting material to generate the differentiated cells for clinical therapy (worldwide web at subdomain stemcells.nih.gov/info/scireport/2006report.htm). One possible application of ES cells is to generate new pancreatic β cells for the cell replacement therapy of type I diabetics, by first producing endoderm, e.g., definitive endoderm, from, e.g., hESCs, and then further differentiating the definitive endoderm into at least one insulin-positive endocrine cell or precursor thereof, and then further differentiating the at least one insulin-positive endocrine cell or precursor thereof into a SC-β cell.

hESC cells, are described, for example, by Cowan et al. (N Engl. J. Med. 350:1353, 2004) and Thomson et al. (Science 282:1145, 1998); embryonic stem cells from other primates, Rhesus stem cells (Thomson et al., Proc. Natl. Acad. Sci. USA 92:7844, 1995), marmoset stem cells (Thomson et al., Biol. Reprod. 55:254, 1996) and human embryonic germ (hEG) cells (Shamblott et al., Proc. Natl. Acad. Sci. USA 95:13726, 1998) may also be used in the methods disclosed herein. mESCs, are described, for example, by Tremml et al. (Curr Protoc Stem Cell Biol. Chapter 1: Unit 1C.4, 2008). The stem cells may be, for example, unipotent, totipotent, multipotent, or pluripotent. In some examples, any cells of primate origin that are capable of producing progeny that are derivatives of at least one germinal layer, or all three germinal layers, may be used in the methods disclosed herein.

In certain examples, ES cells may be isolated, for example, as described in Cowan et al. (N Engl. J. Med. 350:1353, 2004) and U.S. Pat. No. 5,843,780 and Thomson et al., Proc. Natl. Acad. Sci. USA 92:7844, 1995. For example, hESCs cells can be prepared from human blastocyst cells using the techniques described by Thomson et al. (U.S. Pat. No. 6,200,806; Science 282:1145, 1998; Curr. Top. Dev. Biol. 38:133 ff., 1998) and Reubinoff et al, Nature Biotech. 18:399, 2000. Equivalent cell types to hESCs include their pluripotent derivatives, such as primitive ectoderm-like (EPL) cells, as outlined, for example, in WO 01/51610 (Bresagen). hESCs can also be obtained from human pre-implantation embryos. Alternatively, in vitro fertilized (IVF) embryos can be used, or one-cell human embryos can be expanded to the blastocyst stage (Bongso et al., Hum Reprod 4: 706, 1989). Embryos are cultured to the blastocyst stage in G1.2 and G2.2 medium (Gardner et al., Feral. Steril. 69:84, 1998). The zona pellucida is removed from developed blastocysts by brief exposure to pronase (Sigma). The inner cell masses can be isolated by immunosurgery, in which blastocysts are exposed to a 1:50 dilution of rabbit anti-human spleen cell antiserum for 30 min, then washed for 5 min three times in DMEM, and exposed to a 1:5 dilution of Guinea pig complement (Gibco) for 3 min (Solter et al., Proc. Natl. Acad. Sci. USA 72:5099, 1975). After two further washes in DMEM, lysed trophectoderm cells are removed from the intact inner cell mass (ICM) by gentle pipetting, and the ICM plated on mEF feeder layers. After 9 to 15 days, inner cell mass-derived outgrowths can be dissociated into clumps, either by exposure to calcium and magnesium-free phosphate-buffered saline (PBS) with 1 mM EDTA, by exposure to dispase or trypsin, or by mechanical dissociation with a micropipette; and then replated on mEF in fresh medium. Growing colonies having undifferentiated morphology can be individually selected by micropipette, mechanically dissociated into clumps, and replated. ES-like morphology is characterized as compact colonies with apparently high nucleus to cytoplasm ratio and prominent nucleoli. Resulting hESCs can then be routinely split every 1-2 weeks, for example, by brief trypsinization, exposure to Dulbecco's PBS (containing 2 mM EDTA), exposure to type IV collagenase (about 200 U/mL; Gibco) or by selection of individual colonies by micropipette. In some examples, clump sizes of about 50 to 100 cells are optimal.

mESCs cells can be prepared from using the techniques described by e.g., Conner et al. (Curr. Prot. in Mol. Biol. Unit 23.4, 2003).

Embryonic stem cells can be isolated from blastocysts of members of the primate species (U.S. Pat. No. 5,843,780; Thomson et al., Proc. Natl. Acad. Sci. USA 92:7844, 1995). Human embryonic stem (hES) cells can be prepared from human blastocyst cells using the techniques described by Thomson et al. (U.S. Pat. No. 6,200,806; Science 282:1145, 1998; Curr. Top. Dev. Biol. 38:133 ff., 1998) and Reubinoff et al, Nature Biotech. 18:399, 2000. Equivalent cell types to hES cells include their pluripotent derivatives, such as primitive ectoderm-like (EPL) cells, as outlined in WO 01/51610 (Bresagen).

Alternatively, in some embodiments, hES cells can be obtained from human preimplantation embryos. Alternatively, in vitro fertilized (IVF) embryos can be used, or one-cell human embryos can be expanded to the blastocyst stage (Bongso et al., Hum Reprod 4: 706, 1989). Embryos are cultured to the blastocyst stage in G1.2 and G2.2 medium (Gardner et al., Feral. Steril. 69:84, 1998). The zona pellucida is removed from developed blastocysts by brief exposure to pronase (Sigma). The inner cell masses are isolated by immunosurgery, in which blastocysts are exposed to a 1:50 dilution of rabbit anti-human spleen cell antiserum for 30 min, then washed for 5 min three times in DMEM, and exposed to a 1:5 dilution of Guinea pig complement (Gibco) for 3 min (Solter et al., Proc. Natl. Acad. Sci. USA 72:5099, 1975). After two further washes in DMEM, lysed trophectoderm cells are removed from the intact inner cell mass (ICM) by gentle pipetting, and the ICM plated on mEF feeder layers.

After 9 to 15 days, inner cell mass-derived outgrowths are dissociated into clumps, either by exposure to calcium and magnesium-free phosphate-buffered saline (PBS) with 1 mM EDTA, by exposure to dispase or trypsin, or by mechanical dissociation with a micropipette; and then replated on mEF in fresh medium. Growing colonies having undifferentiated morphology are individually selected by micropipette, mechanically dissociated into clumps, and replated. ES-like morphology is characterized as compact colonies with apparently high nucleus to cytoplasm ratio and prominent nucleoli. Resulting ES cells are then routinely split every 1-2 weeks by brief trypsinization, exposure to Dulbecco's PBS (containing 2 mM EDTA), exposure to type IV collagenase (~200 U/mL; Gibco) or by selection of individual colonies by micropipette. Clump sizes of about 50 to 100 cells are optimal.

In some embodiments, human Embryonic Germ (hEG) cells are pluripotent stem cells which can be used in the methods as disclosed herein to differentiate into primitive endoderm cells. hEG cells can be used be prepared from primordial germ cells present in human fetal material taken about 8-11 weeks after the last menstrual period. Suitable preparation methods are described in Shamblott et al., Proc. Natl. Acad. Sci. USA 95:13726, 1998 and U.S. Pat. No. 6,090,622, which is incorporated herein in its entirety by reference.

Briefly, genital ridges processed to form disaggregated cells. EG growth medium is DMEM, 4500 mg/L D-glucose, 2200 mg/L mM NaHCO$_3$; 15% ES qualified fetal calf serum (BRL); 2 mM glutamine (BRL); 1 mM sodium pyruvate (BRL); 1000-2000 U/mL human recombinant leukemia inhibitory factor (LIF, Genzyme); 1-2 ng/mL human recombinant bFGF (Genzyme); and 10 μM forskolin (in 10% DMSO). Ninety-six well tissue culture plates are prepared with a sub-confluent layer of feeder cells (e.g., STO cells, ATCC No. CRL 1503) cultured for 3 days in modified EG growth medium free of LIF, bFGF or forskolin, inactivated with 5000 rad γ-irradiation ~0.2 mL of primary germ cell (PGC) suspension is added to each of the wells. The first passage is done after 7-10 days in EG growth medium, transferring each well to one well of a 24-well culture dish previously prepared with irradiated STO mouse fibroblasts. The cells are cultured with daily replacement of medium until cell morphology consistent with EG cells is observed, typically after 7-30 days or 1-4 passages.

In certain examples, the stem cells can be undifferentiated (e.g. a cell not committed to a specific linage) prior to exposure to at least one β cell maturation factor according to the methods as disclosed herein, whereas in other examples it may be desirable to differentiate the stem cells to one or more intermediate cell types prior to exposure of the at least one β cell maturation factor (s) described herein. For example, the stems cells may display morphological, biological or physical characteristics of undifferentiated cells that can be used to distinguish them from differentiated cells of embryo or adult origin. In some examples, undifferentiated cells may appear in the two dimensions of a microscopic view in colonies of cells with high nuclear/cytoplasmic ratios and prominent nucleoli. The stem cells may be themselves (for example, without substantially any undifferentiated cells being present) or may be used in the presence of differentiated cells. In certain examples, the stem cells may be cultured in the presence of suitable nutrients and optionally other cells such that the stem cells can grow and optionally differentiate. For example, embryonic fibroblasts or fibroblast-like cells may be present in the culture to assist in the growth of the stem cells. The fibroblast may be present during one stage of stem cell growth but not necessarily at all stages. For example, the fibroblast may be added to stem cell cultures in a first culturing stage and not added to the stem cell cultures in one or more subsequent culturing stages.

Stem cells used in all aspects of the present invention can be any cells derived from any kind of tissue (for example embryonic tissue such as fetal or pre-fetal tissue, or adult tissue), which stem cells have the characteristic of being capable under appropriate conditions of producing progeny of different cell types, e.g. derivatives of all of at least one of the 3 germinal layers (endoderm, mesoderm, and ectoderm). These cell types may be provided in the form of an established cell line, or they may be obtained directly from primary embryonic tissue and used immediately for differentiation. Included are cells listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). In some embodiments, the source of human stem cells or pluripotent stem cells used for chemically-induced differentiation into mature, insulin positive cells did not involve destroying a human embryo.

In another embodiment, the stem cells can be isolated from tissue including solid tissue. In some embodiments, the tissue is skin, fat tissue (e.g. adipose tissue), muscle tissue, heart or cardiac tissue. In other embodiments, the tissue is for example but not limited to, umbilical cord blood, placenta, bone marrow, or chondral.

Stem cells of interest also include embryonic cells of various types, exemplified by human embryonic stem (hES) cells, described by Thomson et al. (1998) Science 282:1145; embryonic stem cells from other primates, such as Rhesus stem cells (Thomson et al. (1995) Proc. Natl. Acad. Sci. USA 92:7844); marmoset stem cells (Thomson et al. (1996) Biol. Reprod. 55:254); and human embryonic germ (hEG) cells (Shambloft et al., Proc. Natl. Acad. Sci. USA 95:13726, 1998). Also of interest are lineage committed stem cells, such as mesodermal stem cells and other early cardiogenic cells (see Reyes et al. (2001) Blood 98:2615-2625; Eisenberg & Bader (1996) Circ Res. 78(2):205-16; etc.) The stem cells may be obtained from any mammalian species, e.g. human, equine, bovine, porcine, canine, feline, rodent, e.g. mice, rats, hamster, primate, etc. In some embodiments, a human embryo was not destroyed for the source of pluripotent cell used on the methods and compositions as disclosed herein.

ES cells are considered to be undifferentiated when they have not committed to a specific differentiation lineage. Such cells display morphological characteristics that distinguish them from differentiated cells of embryo or adult origin. Undifferentiated ES cells are easily recognized by those skilled in the art, and typically appear in the two dimensions of a microscopic view in colonies of cells with high nuclear/cytoplasmic ratios and prominent nucleoli. Undifferentiated ES cells express genes that may be used as markers to detect the presence of undifferentiated cells, and whose polypeptide products may be used as markers for negative selection. For example, see U.S. application Ser. No. 2003/0224411 A1; Bhattacharya (2004) Blood 103(8): 2956-64; and Thomson (1998), supra., each herein incorporated by reference. Human ES cell lines express cell surface markers that characterize undifferentiated nonhuman primate ES and human EC cells, including stage-specific embryonic antigen (SSEA)-3, SSEA-4, TRA-1-60, TRA-1-81, and alkaline phosphatase. The globo-series glycolipid GL7, which carries the SSEA-4 epitope, is formed by the addition of sialic acid to the globo-series glycolipid GbS, which carries the SSEA-3 epitope. Thus, GL7 reacts with antibodies to both SSEA-3 and SSEA-4. The undifferentiated human ES cell lines did not stain for SSEA-1, but differentiated cells stained strongly for SSEA-I. Methods for proliferating hES cells in the undifferentiated form are described in WO 99/20741, WO 01/51616, and WO 03/020920.

A mixture of cells from a suitable source of endothelial, muscle, and/or neural stem cells can be harvested from a mammalian donor by methods known in the art. A suitable source is the hematopoietic microenvironment. For example, circulating peripheral blood, preferably mobilized (i.e., recruited), may be removed from a subject. Alternatively, bone marrow may be obtained from a mammal, such as a human patient, undergoing an autologous transplant. In some embodiments, stem cells can be obtained from the subjects adipose tissue, for example using the CELUTION™ SYSTEM from Cytori, as disclosed in U.S. Pat. Nos. 7,390,484 and 7,429,488 which is incorporated herein in its entirety by reference.

In some embodiments, human umbilical cord blood cells (HUCBC) are useful in the methods as disclosed herein. Human UBC cells are recognized as a rich source of hematopoietic and mesenchymal progenitor cells (Broxmeyer et al., 1992 Proc. Natl. Acad. Sci. USA 89:4109-4113). Previously, umbilical cord and placental blood were considered a waste product normally discarded at the birth of an infant. Cord blood cells are used as a source of transplantable stem and progenitor cells and as a source of marrow repopulating cells for the treatment of malignant diseases (i.e. acute lymphoid leukemia, acute myeloid leukemia, chronic myeloid leukemia, myelodysplastic syndrome, and neuroblastoma) and non-malignant diseases such as Fanconi's anemia and aplastic anemia (Kohli-Kumar et al., 1993 Br. J. Haematol. 85:419-422; Wagner et al., 1992 Blood 79; 1874-1881; Lu et al., 1996 Crit. Rev. Oncol. Hematol 22:61-78; Lu et al., 1995 Cell Transplantation 4:493-503). A distinct advantage of HUCBC is the immature immunity of these cells that is very similar to fetal cells, which significantly reduces the risk for rejection by the host (Taylor & Bryson, 1985 J. Immunol. 134:1493-1497). Human umbilical cord blood contains mesenchymal and hematopoietic progenitor cells, and endothelial cell precursors that can be expanded in tissue culture (Broxmeyer et al., 1992 Proc. Natl. Acad. Sci. USA 89:4109-4113; Kohli-Kumar et al., 1993 Br. J. Haematol. 85:419-422; Wagner et al., 1992 Blood 79; 1874-1881; Lu et al., 1996 Crit. Rev. Oncol. Hematol 22:61-78; Lu et al., 1995 Cell Transplantation 4:493-503; Taylor & Bryson, 1985 J. Immunol. 134: 1493-1497 Broxmeyer, 1995 Transfusion 35:694-702; Chen et al., 2001 Stroke 32:2682-2688; Nieda et al., 1997 Br. J. Haematology 98:775-777; Erices et al., 2000 Br. J. Haematology 109:235-242). The total content of hematopoietic progenitor cells in umbilical cord blood equals or exceeds bone marrow, and in addition, the highly proliferative hematopoietic cells are eightfold higher in HUCBC than in bone marrow and express hematopoietic markers such as CD14, CD34, and CD45 (Sanchez-Ramos et al., 2001 Exp. Neur. 171:109-115; Bicknese et al., 2002 Cell Transplantation 11:261-264; Lu et al., 1993 J. Exp Med. 178:2089-2096).

In another embodiment, pluripotent cells are cells in the hematopoietic micro-environment, such as the circulating peripheral blood, preferably from the mononuclear fraction of peripheral blood, umbilical cord blood, bone marrow, fetal liver, or yolk sac of a mammal. The stem cells, especially neural stem cells, may also be derived from the central nervous system, including the meninges.

In another embodiment, pluripotent cells are present in embryoid bodies are formed by harvesting ES cells with brief protease digestion, and allowing small clumps of undifferentiated human ESCs to grow in suspension culture. Differentiation is induced by withdrawal of conditioned medium. The resulting embryoid bodies are plated onto semi-solid substrates. Formation of differentiated cells may be observed after around about 7 days to around about 4 weeks. Viable differentiating cells from in vitro cultures of stem cells are selected for by partially dissociating embryoid bodies or similar structures to provide cell aggregates. Aggregates comprising cells of interest are selected for phenotypic features using methods that substantially maintain the cell to cell contacts in the aggregate.

In an alternative embodiment, the stem cells can be reprogrammed stem cells, such as stem cells derived from somatic or differentiated cells. In such an embodiment, the de-differentiated stem cells can be for example, but not limited to, neoplastic cells, tumor cells and cancer cells or alternatively induced reprogrammed cells such as induced pluripotent stem cells or iPS cells.

Cloning and Cell Culture

Illustrative methods for molecular genetics and genetic engineering that may be used in the technology described herein may be found, for example, in current editions of Molecular Cloning: A Laboratory Manual, (Sambrook et al., Cold Spring Harbor); Gene Transfer Vectors for Mammalian Cells (Miller & Calos eds.); and Current Protocols in Molecular Biology (F. M. Ausubel et al. eds., Wiley & Sons). Cell biology, protein chemistry, and antibody techniques can be found, for example, in Current Protocols in Protein Science (J. E. Colligan et al. eds., Wiley & Sons); Current Protocols in Cell Biology (J. S. Bonifacino et al., Wiley & Sons) and Current protocols in Immunology (J. E. Colligan et al. eds., Wiley & Sons.). Illustrative reagents, cloning vectors, and kits for genetic manipulation may be commercially obtained, for example, from BioRad, Stratagene, Invitrogen, ClonTech, and Sigma-Aldrich Co.

Suitable cell culture methods may be found, for example, in Cell culture methods are described generally in the current edition of Culture of Animal Cells: A Manual of Basic Technique (R. I. Freshney ed., Wiley & Sons); General Techniques of Cell Culture (M. A. Harrison & I. F. Rae, Cambridge Univ. Press), and Embryonic Stem Cells: Methods and Protocols (K. Turksen ed., Humana Press). Suitable tissue culture supplies and reagents are commercially available, for example, from Gibco/BRL, Nalgene-Nunc International, Sigma Chemical Co., and ICN Biomedicals.

Pluripotent stem cells can be propagated by one of ordinary skill in the art and continuously in culture, using culture conditions that promote proliferation without promoting differentiation. Exemplary serum-containing ES medium is made with 80% DMEM (such as Knock-Out DMEM, Gibco), 20% of either defined fetal bovine serum (FBS, Hyclone) or serum replacement (WO 98/30679), 1% non-essential amino acids, 1 mM L-glutamine, and 0.1 mM β-mercaptoethanol. Just before use, human bFGF is added to 4 ng/mL (WO 99/20741, Geron Corp.). Traditionally, ES cells are cultured on a layer of feeder cells, typically fibroblasts derived from embryonic or fetal tissue.

Scientists at Geron have discovered that pluripotent SCs can be maintained in an undifferentiated state even without feeder cells. The environment for feeder-free cultures includes a suitable culture substrate, particularly an extracellular matrix such as MATRIGEL™ or laminin Typically, enzymatic digestion is halted before cells become completely dispersed (about 0.5 min with collagenase IV). Clumps of ~10 to 2,000 cells are then plated directly onto the substrate without further dispersal.

Feeder-free cultures are supported by a nutrient medium containing factors that support proliferation of the cells without differentiation. Such factors may be introduced into the medium by culturing the medium with cells secreting such factors, such as irradiated (~4,000 rad) primary mouse embryonic fibroblasts, telomerized mouse fibroblasts, or fibroblast-like cells derived from pPS cells. Medium can be conditioned by plating the feeders at a density of ~5-6×10$^4$ cm$^{-2}$ in a serum free medium such as KO DMEM supplemented with 20% serum replacement and 4 ng/mL bFGF. Medium that has been conditioned for 1-2 days is supplemented with further bFGF, and used to support pluripotent SC culture for 1-2 days. Features of the feeder-free culture method are further discussed in International Patent Publication WO 01/51616; and Xu et al., Nat. Biotechnol. 19:971, 2001.

Under the microscope, ES cells appear with high nuclear/cytoplasmic ratios, prominent nucleoli, and compact colony formation with poorly discernable cell junctions. Primate ES cells express stage-specific embryonic antigens (SSEA) 3 and 4, and markers detectable using antibodies designated Tra-1-60 and Tra-1-81 (Thomson et al., Science 282:1145, 1998). Mouse ES cells can be used as a positive control for SSEA-1, and as a negative control for SSEA-4, Tra-1-60, and Tra-1-81. SSEA-4 is consistently present human embryonal carcinoma (hEC) cells. Differentiation of pluripotent SCs in vitro results in the loss of SSEA-4, Tra-1-60, and Tra-1-81 expression, and increased expression of SSEA-1, which is also found on undifferentiated hEG cells.

Stem Cell-Derived β Cell (SC-β)

In some aspects, the disclosure provides a stem cell-derived β cell (SC-β). The SC-β cells disclosed herein share many distinguishing features of native β cells, but are different in certain aspects (e.g., gene expression profiles). In some embodiments, the SC-β cell is non-native. As used herein, "non-native" means that the SC-β cells are markedly different in certain aspects from β cells which exist in nature, i.e., native β cells. It should be appreciated, however, that these marked differences typically pertain to structural features which may result in the SC-β cells exhibiting certain functional differences, e.g., although the gene expression patterns of SC-β cells differs from native β cells, the SC-β cells behave in a similar manner to native β cells but certain functions may be altered (e.g., improved) compared to native β cells. For example, as is shown in FIG. 2E, a higher frequency of SC-β cells respond to 20 mM glucose compared to the frequency of native β cells. Other differences between SC-β cells and native β cells would be apparent to the skilled artisan based on the data disclosed herein.

The SC-β cells of the disclosure share many characteristic features of β cells which are important for normal β cell function. In some embodiments, the SC-β cell exhibits a glucose stimulated insulin secretion (GSIS) response in vitro. In some embodiments, the SC-β cell exhibits a GSIS response in vivo. In some embodiments, the SC-β cell exhibits in vitro and in vivo GSIS responses. In some embodiments, the GSIS responses resemble the GSIS responses of an endogenous mature pancreatic β cell. In some embodiments, the SC-β cell exhibits a GSIS response to at least one glucose challenge. In some embodiments, the SC-β cell exhibits a GSIS response to at least two sequential glucose challenges. In some embodiments, the SC-β cell exhibits a GSIS response to at least three sequential glucose challenges. In some embodiments, the GSIS responses resemble the GSIS response of endogenous human islets to multiple glucose challenges. In some embodiments, the GSIS response is observed immediately upon transplanting the cell into a human or animal. In some embodiments, the GSIS response is observed within approximately 24 hours of transplanting the cell into a human or animal. In some embodiments, the GSIS response is observed within approximately one week of transplanting the cell into a human or animal. In some embodiments, the GSIS response is observed within approximately two weeks of transplanting the cell into a human or animal. In some embodiments, the stimulation index of the cell as characterized by the ratio of insulin secreted in response to high glucose concentrations compared to low glucose concentrations is similar to the stimulation index of an endogenous mature pancreatic β cell. In some embodiments, the SC-β cell exhibits a stimulation index of greater than 1. In some embodiments, the SC-β cell exhibits a stimulation index of greater than or equal to 1. In some embodiments, the SC-β cell exhibits a stimulation index of greater than 1.1. In some embodiments, the SC-β cell exhibits a stimulation index of greater than or equal to 1.1. In some embodiments, the SC-β cell exhibits a stimulation index of greater than 2. In some embodiments, the SC-β cell exhibits a stimulation index of greater than or equal to 2. In some embodiments, the SC-β cell exhibits a stimulation index of at least 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 or greater.

In some embodiments, the SC-β cell exhibits cytokine-induced apoptosis in response to cytokines. In some embodiments, the SC-β cell exhibits cytokine-induced apoptosis in response to a cytokine selected from the group consisting of interleukin-1β (IL-β), interferon-γ (INF-γ), tumor necrosis factor-α (TNF-α), and combinations thereof.

In some embodiments, insulin secretion from the SC-β cell is enhanced in response to known anti-diabetic drugs (e.g., anti-diabetic drugs which act on β cells ex vivo or in vitro, and/or anti-diabetic drugs generally in vivo). The disclosure contemplates any known anti-diabetic drug. In some embodiments, insulin secretion from the SC-β cell is enhanced in response to a secretagogue. In some embodiments, the secretagogue is selected from the group consisting of an incretin mimetic, a sulfonylurea, a meglitinide, and combinations thereof.

In some embodiments, the SC-β cell is monohormonal. In some embodiments, the SC-β cell exhibits a morphology that resembles the morphology of an endogenous mature pancreatic β cell. In some embodiments, the SC-β cell encapsulates crystalline insulin granules. In some embodiments, the SC-β cell exhibits encapsulated crystalline insulin granules under electron microscopy that resemble insulin granules of an endogenous mature pancreatic β cell. In some embodiments, the SC-β cell exhibits a low rate of replication. In some embodiments, the SC-β cell exhibits a low rate of replication. In some embodiments, the SC-β cell exhibits a low, but increased rate of replication as measured by staining for C-peptide and Ki67 in response to treatment with prolactin.

In some embodiments, the SC-β cell increases intracellular $Ca^{2+}$ in response to glucose. In some embodiments, the SC-β cell exhibits a glucose stimulated $Ca^{2+}$ flux (GSCF) that resembles the GSCF of an endogenous mature pancreatic β cell. In some embodiments, the SC-β cell exhibits a GSCF response to at least three sequential glucose challenges in a manner that resembles the GSCF response of an endogenous mature pancreatic β cell to multiple glucose challenges.

In some embodiments, the SC-β cell expresses at least one marker characteristic of an endogenous mature pancreatic β cell selected from the group consisting of insulin, C-peptide, PDX1, MAFA, NKX6-1, PAX6, NEUROD1, glucokinase (GCK), SLC2A1, PCSK1, KCNJ11, ABCC8, SLC30A8, SNAP25, RAB3A, GAD2, and PTPRN.

In some embodiments, the SC-β cell does not express at least one marker (e.g., a marker not expressed by endogenous mature pancreatic β cells) selected from the group consisting of a) a hormone selected from the group consisting of i) glucagon (GCG), and ii) somatostatin (SST); b) an acinar cell marker selected from the group consisting of i) amylase, and ii) carboxypeptidase A (CPA1), c) an α cell marker selected from the group consisting of i) GCG, Arx, Irx1, and Irx2, d) a ductal cell marker selected from the group consisting of i) CFTR, and ii) Sox9.

The SC-β cells are differentiated in vitro from any starting cell as the invention is not intended to be limited by the starting cell from which the SC-β cells are derived. Exemplary starting cells include, without limitation, insulin-positive endocrine cells or any precursor thereof such as a Nkx6-1-positive pancreatic progenitor cell, a Pdx1-positive pancreatic progenitor cell, and a pluripotent stem cell, an embryonic stem cell, and induced pluripotent stem cell. In some embodiments, the SC-β cells are differentiated in vitro from a reprogrammed cell, a partially reprogrammed cell (i.e., a somatic cell, e.g., a fibroblast which has been partially reprogrammed such that it exists in an intermediate state between an induced pluripotency cell and the somatic cell from which it has been derived), a transdifferentiated cell. In some embodiments, the SC-β cells disclosed herein can be differentiated in vitro from an insulin-positive endocrine cell or a precursor thereof. In some embodiments, the SC-β cell is differentiated in vitro from a precursor selected from the group consisting of a Nkx6-1-positive pancreatic progenitor cell, a Pdx1-positive pancreatic progenitor cell, and a pluripotent stem cell. In some embodiments, the pluripotent stem cell is selected from the group consisting of an embryonic stem cell and induced pluripotent stem cell. In some embodiments, the SC-β cell or the pluripotent stem cell from which the SC-β cell is derived is human. In some embodiments, the SC-β cell is human.

In some embodiments, the SC-β cell is not genetically modified. In some embodiments, the SC-β cell obtains the features it shares in common with native β cells in the absence of a genetic modification of cells. In some embodiments, the SC-β cell is genetically modified.

In some embodiments, the insulin produced per SC-β cell is at least 0.5 μIU per 1000 cells per 30 minute incubation (e.g., ex vivo) at a high glucose concentration.

In some embodiments, the insulin produced per SC-β cell is at least 1, at least 2, at least 3, at least 4 at least 5 at least 6, at least 7 at least 8 or at least 9 μIU per 1000 cells per 30 minute incubation at a high glucose concentration. In some embodiments, the insulin produced per SC-β cell is between 0.5 and 100 U per 1000 cells per 30 minute incubation at a high glucose concentration. In some embodiments, the insulin produced per SC-β cell is approximately 2.50 U per 1000 cells per 30 minute incubation at a high glucose concentration.

In some aspects, the disclosure provides a cell line comprising a SC-β cell described herein. In some embodiments, the SC-β cells stably express insulin. In some embodiments, the SC-β cell can be frozen, thawed, and amplified with a doubling time of 24 to 44 hours without significant morphological changes until at least 30 passages.

Generating SC-β Cells

Aspects of the disclosure relate to generating SC-β cells (e.g., pancreatic β cells). Generally, the at least one SC-β cell or precursor thereof, e.g., pancreatic progenitors produced according to the methods disclosed herein can comprise a mixture or combination of different cells, e.g., for example a mixture of cells such as a Pdx1-positive pancreatic progenitors, pancreatic progenitors co-expressing Pdx1 and NKX6-1, a Ngn3-positive endocrine progenitor cell, an insulin-positive endocrine cell (e.g., a β-like cell), and an insulin-positive endocrine cell, and/or other pluripotent or stem cells.

The at least one SC-β cell or precursor thereof can be produced according to any suitable culturing protocol to differentiate a stem cell or pluripotent cell to a desired stage of differentiation. In some embodiments, the at least one SC-β cell or the precursor thereof are produced by culturing at least one pluripotent cell for a period of time and under conditions suitable for the at least one pluripotent cell to differentiate into the at least one SC-β cell or the precursor thereof.

In some embodiments, the at least one SC-β cell or precursor thereof is a substantially pure population of SC-β cells or precursors thereof. In some embodiments, a population of SC-β cells or precursors thereof comprises a mixture of pluripotent cells or differentiated cells. In some embodiments, a population SC-β cells or precursors thereof are substantially free or devoid of embryonic stem cells or pluripotent cells or iPS cells.

In some embodiments, a somatic cell, e.g., fibroblast can be isolated from a subject, for example as a tissue biopsy, such as, for example, a skin biopsy, and reprogrammed into an induced pluripotent stem cell for further differentiation to produce the at least one SC-β cell or precursor thereof for use in the compositions and methods described herein. In some embodiments, a somatic cell, e.g., fibroblast is maintained in culture by methods known by one of ordinary skill in the art, and in some embodiments, propagated prior to being converted into SC-β cells by the methods as disclosed herein.

In some embodiments, the at least one SC-β cell or precursor thereof are maintained in culture by methods known by one of ordinary skill in the art, and in some embodiments, propagated prior to being converted into SC-β cells by the methods as disclosed herein.

Further, at least one SC-β cell or precursor thereof, e.g., pancreatic progenitor can be from any mammalian species, with non-limiting examples including a murine, bovine, simian, porcine, equine, ovine, or human cell. For clarity and simplicity, the description of the methods herein refers to a mammalian at least one SC-β cell or precursor thereof but it should be understood that all of the methods described herein can be readily applied to other cell types of at least one SC-β cell or precursor thereof. In some embodiments, the at least one SC-β cell or precursor thereof is derived from a human individual.

Inducing the Differentiation of Pluripotent Stem Cells to Definitive Endoderm Cells Aspects of the disclosure involve definitive endoderm cells. Definitive endoderm cells of use herein can be derived from any source or generated in accordance with any suitable protocol. In some aspects, pluripotent stem cells, e.g., iPSCs or hESCs, are differentiated to endoderm cells. In some aspects, the endoderm cells are further differentiated, e.g., to primitive gut tube cells, Pdx1-positive pancreatic progenitor cells, NKX6-1-positive pancreatic progenitor cells, Ngn3-positive endocrine progenitor cells, or insulin-positive endocrine cells, followed by induction or maturation to SC-β cells.

In some embodiments, the stem cells may be plated onto a new substrate or the medium may be exchanged to remove extracellular matrix or soluble factors that inhibit differentiation. This is sometimes referred to as the "direct differentiation method", and is described in general terms in International patent publication WO 01/51616, and U.S. Patent Publication 2002/0019046, which is incorporated herein in its entirety by reference. It is usually preferable in the direct differentiation method to begin with a feeder-free culture of stem cells, so as to avoid potential complications in the differentiation process caused by residual feeder cells. Another approach is to put undifferentiated stem cells in suspension culture, which will frequently cause them to form aggregates of differentiated and undifferentiated cells. For example, stem cells can be harvested by brief collagenase digestion, dissociated into clusters, and passaged in non-adherent cell culture plates. The aggregates can be fed every few days, and then harvested after a suitable period, typically 4-8 days. Depending on the conditions, aggregates generally start by forming a heterogeneous population of cell types, including a substantial frequency of endoderm cells. The aggregates can then be dispersed and replated for the next stage in the differentiation process, on substrates such as laminin or fibronectin; or passaged in suspension culture using, for example, non-adherent plates and a suitable medium.

Direct differentiation or differentiation in aggregates can be monitored for the presence of endoderm cells using suitable markers such as those listed in U.S. Pat. No. 7,326,572. In some preferred embodiments, differentiation can be monitored for the presence of endoderm cells using markers such as Sox17. Once a sufficient proportion of endoderm is obtained, cells can be replated or otherwise manipulated to begin another stage of differentiation. In certain circumstances, differentiation or maintenance of cells may be enhanced if the cells are kept in micromass clusters (for example, 50 to 5,000 cells). Additional stages of differentiation contemplated by the disclosure are shown in FIG. 1.

In some embodiments, definitive endoderm cells are produced by contacting (e.g., culturing) a pluripotent stem cell with a compound of Formula (I) as described in U.S. Pat. No. 8,507,274 ("the '274 patent"), incorporated by reference herein. Compound with Formula (I) as described in the '274 patent are cell permeable small molecules, and can control cellular processes by modulating signal transduction pathways, gene expression or metabolism and have been effectively used in stem cell differentiation protocols. Small molecules can be synthesized in high quantity and purity as well as conveniently supplied or removed, giving them great potential to be useful for therapeutic applications. High throughput screens have been performed to identify novel small molecules that can support the self renewal of ES cells (Chen et al., 2006; Desbordes et al., 2008), cardiogenic specification of mouse ES cells (Wu et al., 2004) or neural progenitor cells (Diamandis et al., 2007) as well as inducing specific cell types, notably neuronal and muscle cells (reviewed by (Ding and Schultz, 2004). It is expected that compounds of Formula (I) from the '274 patent can be used to differentiate a pluripotent stem cell to a definitive endoderm cell.

In some embodiments, the compound of Formula (I) from the '274 patent comprises:

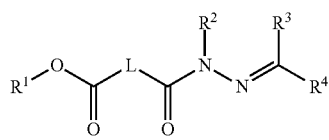

Formula (I)

wherein:

$R^1$ and $R^2$ are independently H, alkyl, alkenyl, alkynyl, aryl, heteroaryl, cyclyl, or cyclyl, each of which can be optionally substituted and/or can be interrupted in the backbone with one or more of O, N, S, S(O), and C(O);

$R^3$ and $R^4$ are independently H, halogen, alkyl, alkenyl, alkynyl, alkoxy, aryl, heteroaryl, cyclyl, or cyclyl, each of which can be optionally substituted, or $R^3$ and $R^4$ together with the carbon to which they are attached from an optionally substituted cyclyl of heterocycyl; and L is $C_1$-$C_{10}$ alkylenyl, $C_2$-$C_{10}$ alkenylenyl, or $C_2$-$C_{10}$ alkynylenyl, each of which can be optionally substituted and/or can be interrupted in the backbone with one or more of O, N, S, S(O), and C(O).

In some embodiments, the compound of Formula (I) from the '274 patent comprises IDE1 below:

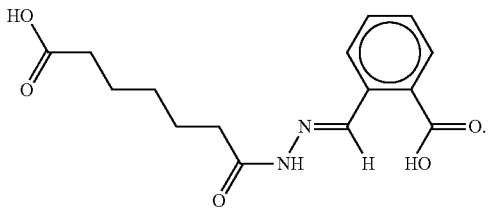

In some embodiments, the compound of Formula (I) from the '274 patent comprises IDE2 below:

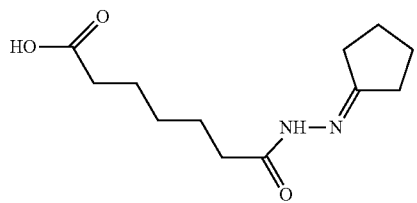

The '274 patent describes methods for confirming the identity of the definitive endoderm cell thus derived, as well as methods for isolating, storing, expanding, and further differentiating definitive endoderm, which can all be used with the compositions and methods described herein, as will be appreciated by the skilled artisan.

In some embodiments, definitive endoderm cells can be obtained by differentiating at least some pluripotent cells in a population into definitive endoderm cells, e.g., by contacting a population of pluripotent cells with i) at least one growth factor from the TGF-β superfamily, and ii) a WNT signaling pathway activator, to induce the differentiation of at least some of the pluripotent cells into definitive endoderm cells, wherein the definitive endoderm cells express at least one marker characteristic of definitive endoderm.

The disclosure contemplates the use of any growth factor from the TGF-β superfamily that induces the pluripotent stem cell to differentiate into definitive endoderm cells (e.g., alone, or in combination with a WNT signaling pathway activator). In some embodiments, the at least one growth factor from the TGF-β superfamily comprises Activin A. In some embodiments, the at least one growth factor from the TGF-β superfamily comprises growth differentiating factor 8 (GDF8).

The disclosure contemplates the use of any WNT signaling pathway activator that induces the pluripotent stem cells to differentiate into definitive endoderm cells (e.g., alone, or in combination with a growth factor from the TGF-β superfamily) In some embodiments, the WNT signaling pathway activator comprises CHIR99021. In some embodiments, the WNT signaling pathway activator comprises Wnt3a recombinant protein.

The skilled artisan will appreciate that the concentrations of agents (e.g., growth factors) employed may vary. In some embodiments, the pluripotent cells are contacted with the at least one growth factor from the TGF-β superfamily at a concentration of between 10 ng/mL-1000 ng/mL. In some embodiments, the pluripotent cells are contacted with the at least one growth factor from the TGF-β superfamily at a concentration of 100 ng/mL. In some embodiments, the pluripotent cells are contacted with the at least one growth factor from the TGF-β superfamily at a concentration of 20 ng/mL, 30 ng/mL, 40 ng/mL, 50 ng/mL, 60 ng/mL, 70 ng/mL, 80 ng/mL, or 90 ng/mL. In some embodiments, the pluripotent cells are contacted with the at least one growth factor from the TGF-β superfamily at a concentration of 91 ng/mL, 92 ng/mL, 93 ng/mL, 94 ng/mL, 95 ng/mL, 96 ng/mL, 97 ng/mL, 98 ng/mL or 99 ng/mL. In some embodiments, the pluripotent cells are contacted with the at least one growth factor from the TGF-β superfamily at a concentration of 110 ng/mL, 120 ng/mL, 130 ng/mL, 140 ng/mL, 150 ng/mL, 160 ng/mL, 170 ng/mL, 180 ng/mL, or 190 ng/mL. In some embodiments, the pluripotent cells are contacted with the at least one growth factor from the TGF-β superfamily at a concentration of 101 ng/mL, 102 ng/mL, 103 ng/mL, 104 ng/mL, 105 ng/mL, 106 ng/mL, 107 ng/mL, 108 ng/mL or 109 ng/mL.

In some embodiments, the pluripotent cells are contacted with the WNT signaling pathway activator at a concentration of between 1.4 µg/mL-140 µg/mL. In some embodiments, the pluripotent cells are contacted with the WNT signaling pathway activator at a concentration of 14 µg/mL. In some embodiments, the pluripotent cells are contacted with the WNT signaling pathway activator at a concentration of 2 µg/mL, 3 µg/mL, 4 µg/mL, 5 µg/mL, 6 µg/mL, 7 µg/mL, 8 µg/mL, 9 µg/mL, 10 µg/mL, 11 µg/mL, 12 µg/mL or 13 µg/mL. In some embodiments, the pluripotent cells are contacted with the WNT signaling pathway activator at a concentration of 15 µg/mL, 16 µg/mL, 17 µg/mL, 18 µg/mL, 19 µg/mL, 20 µg/mL, 21 µg/mL, 22 µg/mL, 23 µg/mL, 24 µg/mL, 25 µg/mL, 26 µg/mL, 27 µg/mL, 28 µg/mL, 29 µg/mL, or 30 µg/mL. In some embodiments, the pluripotent cells are contacted with the WNT signaling pathway activator at a concentration of 13.1 µg/mL, 13.2 µg/mL, 13.3 µg/mL, 13.4 µg/mL, 13.5 µg/mL, 13.6 µg/mL, 13.7 µg/mL, 13.8 µg/mL, or 13.9 µg/mL. In some embodiments, the pluripotent cells are contacted with the WNT signaling pathway activator at a concentration of 14.1 µg/mL, 14.2 µg/mL, 14.3 µg/mL, 14.4 µg/mL, 14.5 µg/mL, 14.6 µg/mL, 14.7 µg/mL, 14.8 µg/mL, or 14.9 µg/mL.

Generally, the pluripotent cells are maintained in suitable culture medium (e.g., suspension culture) for a period of time sufficient to induce the differentiation of at least some of the pluripotent cells into definitive endoderm cells. An exemplary suitable culture medium is shown in Table 1 below.

TABLE 1

| Agent | Amount |
|---|---|
| MCDB131 | 1 L |
| Glucose | 0.44 |
| NaHCO3 | 2.46 g |
| FAF-BSA | 20 g |
| ITS-X | 20 uL |
| GlutaMAX ™ | 10 mL |
| Vitamin C | 0.044 g |
| Heparin | 0 g |
| P/S | 10 mL |

In some embodiments, a suitable culture medium for differentiating pluripotent cells into definitive endoderm cells comprises S1 media.

In some embodiments, contacting the pluripotent cells is effected in suspension culture. In some embodiments, the suspension culture is maintained in a spinner flask. In some embodiments, the period of time is 3 days. In some embodiments, the at least one growth factor from the TGF-β superfamily, and WNT signaling pathway activator are added to the suspension culture on the first day. In some embodiments, the at least one growth factor from the TGF-β superfamily is replenished in the suspension culture on the second day. In some embodiments, the WNT signaling pathway activator is not replenished in the suspension culture on the second day. In some embodiments, the WNT signaling pathway activator is removed from the suspension culture on the second day. In some embodiments, the at least one growth factor from the TGF-β superfamily is replenished in the suspension culture on the second day, and the WNT signaling pathway activator is removed from the suspension culture or not replenished in the suspension culture on the second day. In some embodiments, neither the at least one growth factor from the TGF-β superfamily or the WNT signaling pathway activator are replenished in the suspension culture on the third day. In some embodiments, both the at least one growth factor from the TGF-β superfamily and the WNT signaling pathway activator are removed from the suspension culture on the third day.

The methods are capable of inducing the differentiation of at least one pluripotent cell in a population of cells into a definitive endoderm cell. Generally, any pluripotent cell can be differentiated into a definitive endoderm cell using a method described herein. In some embodiments, the pluripotent cells comprise induced pluripotent stem cells. In some embodiments, the pluripotent cells comprise embryonic stem cells. In some embodiments, the pluripotent cells comprise human cells.

In some embodiments, differentiating at least some pluripotent cells in a population into definitive endoderm cells is achieved by a process of contacting a population of pluripotent cells with i) Activin A, and ii) CHIR99021, to induce the differentiation of at least some of the pluripotent cells in the population into definitive endoderm cells, wherein the definitive endoderm cells express at least one marker characteristic of definitive endoderm.

Other methods for producing definitive endoderm cells are known in the art, including, for example the methods which are set forth in United States application publication US2006/0003446 to G. Keller, et al.; US2006/0003313 to K. D'Amour, et al., US2005/0158853 to K. D'Amour, et al., and US2005/0260749 of Jon Odorico, et al., relevant portions of which are incorporated by reference herein.

In some embodiments, a definitive endoderm cell produced by the methods as disclosed herein expresses at least one marker selected from the group consisting of: Nodal, Tmprss2, Tmem30b, St14, Spink3, Sh3gl2, Ripk4, Rab15, Npnt, Clic6, Cldn8, Cacna1b, Bnipl, Anxa4, Emb, FoxA1, Sox17, and Rbm35a, wherein the expression of at least one marker is upregulated to by a statistically significant amount in the definitive endoderm cell relative to the pluripotent stem cell from which it was derived. In some embodiments, a definitive endoderm cell produced by the methods as disclosed herein does not express by a statistically significant amount at least one marker selected the group consisting of: Gata4, SPARC, AFP and Dab2 relative to the pluripotent stem cell from which it was derived. In some embodiments, a definitive endoderm cell produced by the methods as disclosed herein does not express by a statistically significant amount at least one marker selected the group consisting of: Zic1, Pax6, Flk1 and CD31 relative to the pluripotent stem cell from which it was derived.

In some embodiments, a definitive endoderm cell produced by the methods as disclosed herein has a higher level of phosphorylation of Smad2 by a statistically significant amount relative to the pluripotent stem cell from which it was derived. In some embodiments, a definitive endoderm cell produced by the methods as disclosed herein has the capacity to form gut tube in vivo. In some embodiments, a definitive endoderm cell produced by the methods as disclosed herein can differentiate into a cell with morphology characteristic of a gut cell, and wherein a cell with morphology characteristic of a gut cell expresses FoxA2 and/or Claudin6. In some embodiments, a definitive endoderm cell produced by the methods as disclosed herein can be further differentiated into a cell of endoderm origin.

In some embodiments, a population of pluripotent stem cells are cultured in the presence of at least one β cell maturation factor prior to any differentiation or during the first stage of differentiation. One can use any pluripotent stem cell, such as a human pluripotent stem cell, or a human iPS cell or any of pluripotent stem cell as discussed herein or other suitable pluripotent stem cells. In some embodiments, a β cell maturation factor as described herein can be present in the culture medium of a population of pluripotent stem cells or may be added in bolus or periodically during growth (e.g. replication or propagation) of the population of pluripotent stem cells. In certain examples, a population of pluripotent stem cells can be exposed to at least one β cell maturation factor prior to any differentiation. In other examples, a population of pluripotent stem cells may be exposed to at least one β cell maturation factor during the first stage of differentiation.

Inducing the Differentiation of Definitive Endoderm Cells to Primitive Gut Tube Cells Aspects of the disclosure involve primitive gut tube cells. Primitive gut tube cells of use herein can be derived from any source or generated in accordance with any suitable protocol. In some aspects, definitive endoderm cells are differentiated to primitive gut tube cells. In some aspects, the primitive gut tube cells are further differentiated, e.g., to Pdx1-positive pancreatic progenitor cells, NKX6-1-positive pancreatic progenitor cells, Ngn3-positive endocrine progenitor cells, insulin-positive endocrine cells, followed by induction or maturation to SC-β cells.

In some embodiments, primitive gut tube cells can be obtained by differentiating at least some definitive endoderm cells in a population into primitive gut tube cells, e.g., by contacting definitive endoderm cells with at least one growth factor from the fibroblast growth factor (FGF) family, to induce the differentiation of at least some of the definitive endoderm cells into primitive gut tube cells, wherein the primitive gut tube cells express at least one marker characteristic of primitive gut tube cells.

The disclosure contemplates the use of any growth factor from the FGF family that induces definitive endoderm cells to differentiate into primitive gut tube cells (e.g., alone, or in combination with other factors). In some embodiments, the at least one growth factor from the FGF family comprises keratinocyte growth factor (KGF). In some embodiments, the at least one growth factor from the FGF family comprises FGF2. In some embodiments, the at least one growth factor from the FGF family comprises FGF8B. In some embodiments, the at least one growth factor from the FGF family comprises FGF10. In some embodiments, the at least one growth factor from the FGF family comprises FGF21.

The skilled artisan will appreciate that the concentrations of growth factor employed may vary. In some embodiments, the definitive endoderm cells are contacted with the at least one growth factor from the FGF family at a concentration of between 5 ng/mL-500 ng/mL. In some embodiments, the definitive endoderm cells are contacted with the at least one growth factor from the FGF family at a concentration of 10 ng/mL, 15 ng/mL, 20 ng/mL, 25 ng/mL, 30 ng/mL, 35 ng/mL, or 40 ng/mL. In some embodiments, the definitive endoderm cells are contacted with the at least one growth factor from the FGF family at a concentration of 60 ng/mL, 65 ng/mL, 70 ng/mL, 75 ng/mL, 80 ng/mL, 85 ng/mL, 90 ng/mL, 95 ng/mL or 100 ng/mL. In some embodiments, the definitive endoderm cells are contacted with the at least one growth factor from the FGF family at a concentration of 41 ng/mL, 42 ng/mL, 43 ng/mL, 44 ng/mL, 45 ng/mL, 46 ng/mL, 47 ng/mL, 48 ng/mL or 49 ng/mL. In some embodiments, the definitive endoderm cells are contacted with the at least one growth factor from the FGF family at a concentration of 51 ng/mL, 52 ng/mL, 53 ng/mL, 54 ng/mL, 55 ng/mL, 56 ng/mL, 57 ng/mL, 58 ng/mL or 59 ng/mL. In some embodiments, the definitive endoderm cells are contacted with the at least one growth factor from the FGF family at a concentration of 50 ng/mL.

In some embodiments, the definitive endoderm cells are cultured in a suitable culture medium.

Generally, the definitive endoderm cells are maintained in a suitable culture medium (e.g., suspension culture) for a period of time sufficient to induce the differentiation of at least some of the definitive endoderm cells into primitive gut tube cells. An exemplary suitable culture medium is shown in Table 2 below.

TABLE 2

| Agent | Amount |
| --- | --- |
| MCDB131 | 1 L |
| Glucose | 0.44 g |
| NaHCO3 | 1.23 g |
| FAF-BSA | 20 g |
| ITS-X | 20 uL |
| GlutaMAX ™ | 10 mL |
| Vitamin C | 0.044 g |
| Heparin | 0 g |
| P/S | 10 mL |

In some embodiments, a suitable culture medium for differentiating definitive endoderm cells into primitive gut tube cells comprises S2 media.

In some embodiments, contacting the definitive endoderm cells is effected in suspension culture. In some embodiments, the suspension culture is maintained in a spinner flask. In some embodiments, the period of time is between 2 days and 5 days. In some embodiments, the period of time is 3 days. In some embodiments, the suspension culture is replenished every other day.

In some embodiments, definitive endoderm cells can be obtained by differentiating at least some of the definitive endoderm cells in a population into primitive gut tube cells, e.g., by contacting the definitive endoderm cells with KGF, to induce the differentiation of at least some of the definitive endoderm cells into primitive gut tube cells, wherein the primitive gut tube cells express at least one marker characteristic of definitive endoderm.

Inducing the Differentiation of Primitive Gut Tube Cells to Pdx1-Positive Pancreatic Progenitor Cells Aspects of the disclosure involve Pdx1-positive pancreatic progenitor cells. Pdx1-positive pancreatic progenitor cells of use herein can be derived from any source or generated in accordance with any suitable protocol. In some aspects, primitive gut tube cells are differentiated to Pdx1-positive pancreatic progenitor cells. In some aspects, the Pdx1-positive pancreatic progenitor cells are further differentiated, e.g., NKX6-1-positive pancreatic progenitor cells, Ngn3-positive endocrine progenitor cells, insulin-positive endocrine cells, followed by induction or maturation to SC-β cells.

In some aspects, Pdx1-positive pancreatic progenitor cells can be obtained by differentiating at least some primitive gut tube cells in a population into Pdx1-positive pancreatic progenitor cells, e.g., by contacting primitive gut tube cells with i) at least one bone morphogenic protein (BMP) signaling pathway inhibitor, ii) at least one growth factor from the FGF family, iii) at least one SHH pathway inhibitor, iv) at least one retinoic acid (RA) signaling pathway activator; and v) at least one protein kinase C activator, to induce the differentiation of at least some of the primitive gut tube cells into Pdx1-positive pancreatic progenitor cells, wherein the Pdx1-positive pancreatic progenitor cells express Pdx1.

The disclosure contemplates the use of any BMP signaling pathway inhibitor that induces primitive gut tube cells to differentiate into Pdx1-positive pancreatic progenitor cells (e.g., alone, or with any combination of at least one growth factor from the FGF family, at least one SHH pathway inhibitor, at least one retinoic acid signaling pathway activator, and at least one protein kinase C activator). In some embodiments, the BMP signaling pathway inhibitor comprises LDN193189.

The disclosure contemplates the use of any growth factor from the FGF family that induces primitive gut tube cells to differentiate into Pdx1-positive pancreatic progenitor cells (e.g., alone, or with any combination of at least one BMP signaling pathway inhibitor, at least one SHH pathway inhibitor, at least one retinoic acid signaling pathway activator, and at least one protein kinase C activator). In some embodiments, the at least one growth factor from the FGF family comprises keratinocyte growth factor (KGF). In some embodiments, the at least one growth factor from the FGF family is selected from the group consisting of FGF2, FGF8B, FGF10, and FGF21.

The disclosure contemplates the use of any SHH pathway inhibitor that induces primitive gut tube cells to differentiate into Pdx1-positive pancreatic progenitor cells (e.g., alone, or with any combination of at least one BMP signaling pathway inhibitor, at least one growth factor from the FGF family, at least one retinoic acid signaling pathway activator, and at least one protein kinase C activator). In some embodiments, the SHH pathway inhibitor comprises Sant1.

The disclosure contemplates the use of any RA signaling pathway activator that induces primitive gut tube cells to differentiate into Pdx1-positive pancreatic progenitor cells (e.g., alone, or with any combination of at least one BMP signaling pathway inhibitor, at least one growth factor from the FGF family, at least one SHH pathway inhibitor, and at least one protein kinase C activator). In some embodiments, the RA signaling pathway activator comprises retinoic acid.

The disclosure contemplates the use of any PKC activator that induces primitive gut tube cells to differentiate into Pdx1-positive pancreatic progenitor cells (e.g., alone, or with any combination of at least one BMP signaling pathway inhibitor, at least one growth factor from the FGF family, at least one SHH pathway inhibitor, and at least one RA signaling pathway activator). In some embodiments, the PKC activator comprises PdbU. In some embodiments, the PKC activator comprises TPB.

The skilled artisan will appreciate that the concentrations of agents (e.g., growth factors) employed may vary. In some embodiments, the primitive gut tube cells are contacted with the BMP signaling pathway inhibitor at a concentration of between 20 nM-2000 nM. In some embodiments, the primitive gut tube cells are contacted with the BMP signaling pathway inhibitor at a concentration of 30 40 nM, 50 nM, 60 nM, 70 nM, 80 nM, 90 nM, 100 nM, 110 nM, 120 nM, 130 nM, 140 nM, 150 nM, 160 nM, 170 nM, 180 nM, or 190 nM. In some embodiments, the primitive gut tube cells are contacted with the BMP signaling pathway inhibitor at a concentration of 191 nM, 192 nM, 193 nM, 194 nM, 195 nM, 196 nM, 197 nM, 198 nM, or 199 nM. In some embodiments, the primitive gut tube cells are contacted with the BMP signaling pathway inhibitor at a concentration of 300 nM, 400 nM, 500 nM, 600 nM, 700 nM, 800 nM, 900 nM, 1000 nM, 1100 nM, 1200 nM, 1300 nM, 1400 nM, 1500 nM, 1600 nM, 1700 nM, 1800 nM, or 1900 nM. In some embodiments, the primitive gut tube cells are contacted with the BMP signaling pathway inhibitor at a concentration of 210 nM, 220 nM, 230 nM, 240 nM, 250 nM, 260 nM, 270 nM, 280 nM, or 290 nM. In some embodiments, the primitive gut tube cells are contacted with the BMP signaling pathway inhibitor at a concentration of 200 nM.

In some embodiments, the primitive gut tube cells are contacted with the at least one growth factor from the FGF family at a concentration of between 5 ng/mL-500 ng/mL. In some embodiments, the primitive gut tube cells are contacted with the at least one growth factor from the FGF family at a concentration of 10 ng/mL, 15 ng/mL, 20 ng/mL, 25 ng/mL, 30 ng/mL, 35 ng/mL, or 40 ng/mL. In some embodiments, the primitive gut tube cells are contacted with the at least one growth factor from the FGF family at a concentration of 60 ng/mL, 65 ng/mL, 70 ng/mL, 75 ng/mL, 80 ng/mL, 85 ng/mL, 90 ng/mL, 95 ng/mL or 100 ng/mL. In some embodiments, the primitive gut tube cells are contacted with the at least one growth factor from the FGF family at a concentration of 41 ng/mL, 42 ng/mL, 43 ng/mL, 44 ng/mL, 45 ng/mL, 46 ng/mL, 47 ng/mL, 48 ng/mL or 49 ng/mL. In some embodiments, the primitive gut tube cells are contacted with the at least one growth factor from the FGF family at a concentration of 51 ng/mL, 52 ng/mL, 53 ng/mL, 54 ng/mL, 55 ng/mL, 56 ng/mL, 57 ng/mL, 58 ng/mL or 59 ng/mL. In some embodiments, the primitive gut tube cells are contacted with the at least one growth factor from the FGF family at a concentration of 50 ng/mL.

In some embodiments, the primitive gut tube cells are contacted with the at least one SHH pathway inhibitor at a concentration of between 0.1 μM and 0.5 μM. In some embodiments, the primitive gut tube cells are contacted with the at least one SHH pathway inhibitor at a concentration of 0.11 μM, 0.12 μM, 0.13 μM, 0.14 μM, 0.15 μM, 0.16 μM, 0.17 μM, 0.18 μM, 0.19 μM, 0.2 μM, 0.21 μM, 0.22 μM, 0.23 μM, or 0.24 μM. In some embodiments, the primitive gut tube cells are contacted with the at least one SHH pathway inhibitor at a concentration of 0.26 μM, 0.27 μM, 0.28 μM, 0.29 μM, 0.30 μM, 0.31 μM, 0.32 μM, 0.33 μM, 0.34 μM, 0.35 μM, 0.36 μM, 0.37 μM, 0.38 μM, 0.39 μM, 0.40 μM, 0.41 μM, 0.42 μM, 0.43 μM, 0.44 μM, 0.45 μM, 0.46 μM, 0.47 μM, 0.48 μM, 0.49 μM. In some embodiments, the primitive gut tube cells are contacted with the at least one SHH pathway inhibitor at a concentration of 0.25 μM.

In some embodiments, the primitive gut tube cells are contacted with the RA signaling pathway activator at a concentration of between 0.01 μM-1.0 μM. In some embodiments, the primitive gut tube cells are contacted with the RA signaling pathway activator at a concentration of 0.02 μM, 0.03 μM, 0.04 μM, 0.05 μM, 0.06 μM, 0.07 μM, 0.08 μM, or 0.09 μM. In some embodiments, the primitive gut tube cells are contacted with the RA signaling pathway activator at a concentration of 0.20 μM, 0.30 μM, 0.40 μM, 0.05 μM, 0.60 μM, 0.70 μM, 0.80 μM, or 0.90 μM. In some embodiments, the primitive gut tube cells are contacted with the RA signaling pathway activator at a concentration of 0.1 µM.

In some embodiments, the primitive gut tube cells are contacted with PKC activator at a concentration of between 50 nM-5000 nM. In some embodiments, the primitive gut tube cells are contacted with the PKC activator at a concentration of 100 nM, 150 nM, 200 nM, 250 nM, 300 nM, 350 nM, 400 nM, 450 nM, 460 nM, 470 nM, 480 nM, or 490 nM. In some embodiments, the primitive gut tube cells are contacted with the PKC activator at a concentration of 491 nM, 492 nM, 493 nM, 494 nM, 495 nM, 496 nM, 497 nM, 498 nM, or 499 nM. In some embodiments, the primitive gut tube cells are contacted with the PKC activator at a concentration of 600 nM, 700 nM, 800 nM, 900 nM, 1000 nM, 1100 nM, 1200 nM, 1300 nM, 1400 nM, 1500 nM, 1600 nM, 1700 nM, 1800 nM, 1900 nM, or 2000 nM. In some embodiments, the primitive gut tube cells are contacted with the PKC activator at a concentration of 501 nM, 502 nM, 503 nM, 504 nM, 505 nM, 506 nM, 507 nM, 508 nM, or 509 nM, 510 nM, 520 nM, 530 nM, 540 nM, 550 nM, 560 nM, 570 nM, 580 nM, or 590 nM. In some embodiments, the primitive gut tube cells are contacted with the PKC activator at a concentration of 500 nM.

Generally, the primitive gut tube cells are maintained in a suitable culture medium (e.g., suspension culture) for a period of time sufficient to induce the differentiation of at least some of the primitive gut tube cells into Pdx1-positive pancreatic progenitor cells. An exemplary suitable culture medium is shown in Table 3 below.

TABLE 3

| Agent | Amount |
| --- | --- |
| MCDB131 | 1 L |
| Glucose | 0.44 g |
| NaHCO3 | 1.23 |
| FAF-BSA | 20 g |
| ITS-X | 5 mL |
| GlutaMAX ™ | 10 mL |
| Vitamin C | 0.044 g |
| Heparin | 0 g |
| P/S | 10 mL |

In some embodiments, S3 media can be used as a suitable culture medium for differentiating primitive gut tube cells into pancreatic progenitor cells.

In some embodiments, contacting the primitive gut tube cells is effected in suspension culture. In some embodiments, the suspension culture is maintained in a spinner flask. In some embodiments, the period of time is at least 2 days. In some embodiments, the suspension culture is replenished every day.

In some embodiments, primitive gut tube cells can be obtained by differentiating at least some of the primitive gut tube cells in a population into Pdx1-positive pancreatic progenitor cells, e.g., by contacting the primitive gut tube cells with i) LDN193189, ii) KGF, iii) Sant1; iv) RA; and iv) PdbU, to induce the differentiation of at least some of the primitive gut tube cells into Pdx1-positive pancreatic progenitor cells, wherein the Pdx1-positive pancreatic progenitor cells express Pdx1.

Inducing the Differentiation of Pdx1-Positive Pancreatic Progenitor Cells to NKX6-1+ Pancreatic Progenitor Cells Aspects of the disclosure involve NKX6-1-positive pancreatic progenitor cells. NKX6-1-positive pancreatic progenitor cells of use herein can be derived from any source or generated in accordance with any suitable protocol. In some aspects, Pdx1-positive pancreatic progenitor cells are differentiated to NKX6-1-positive pancreatic progenitor cells. In some aspects, the NKX6-1-positive pancreatic progenitor cells are further differentiated, e.g., to Ngn3-positive endocrine progenitor cells, or insulin-positive endocrine cells, followed by induction or maturation to SC-β cells.

In some aspects, a method of producing a NKX6-1-positive pancreatic progenitor cell from a Pdx1-positive pancreatic progenitor cell comprises contacting a population of cells (e.g., under conditions that promote cell clustering) comprising Pdx1-positive pancreatic progenitor cells with at least two β cell-maturation factors comprising a) at least one growth factor from the fibroblast growth factor (FGF) family, b) a sonic hedgehog pathway inhibitor, and optionally c) a low concentration of a retinoic acid (RA) signaling pathway activator, for a period of at least five days to induce the differentiation of at least one Pdx1-positive pancreatic progenitor cell in the population into NKX6-1-positive pancreatic progenitor cells, wherein the NKX6-1-positive pancreatic progenitor cells expresses NKX6-1.

In some embodiments, the Pdx1-positive, NKX6-1-positive pancreatic progenitor cells are obtained by contacting Pdx1-positive pancreatic progenitor cells under conditions that promote cell clustering with i) at least one growth factor from the FGF family, ii) at least one SHH pathway inhibitor, and optionally iii) low concentrations of a RA signaling pathway activator, for a period of five days to induce the differentiation of at least some of the Pdx1-positive pancreatic progenitor cells into Pdx1-positive, NKX6-1-positive pancreatic progenitor cells, wherein the Pdx1-positive, NKX6-1-positive pancreatic progenitor cells expresses Pdx1 and NKX6-1.

In some embodiments, the Pdx1-positive, NKX6-1-positive pancreatic progenitor cells are obtained by contacting Pdx1-positive pancreatic progenitor cells with i) at least one growth factor from the FGF family, ii) at least one SHH pathway inhibitor, and iii) a RA signaling pathway activator, to induce the differentiation of at least some of the Pdx1-positive pancreatic progenitor cells into Pdx1-positive, NKX6-1-positive pancreatic progenitor cells, wherein the Pdx1-positive, NKX6-1-positive pancreatic progenitor cells expresses Pdx1 and NKX6-1.

In some embodiments, the Pdx1-positive pancreatic progenitor cells are produced from a population of pluripotent cells. In some embodiments, the Pdx1-positive pancreatic progenitor cells are produced from a population of iPS cells. In some embodiments, the Pdx1-positive pancreatic progenitor cells are produced from a population of ESC cells. In some embodiments, the Pdx1-positive pancreatic progenitor cells are produced from a population of definitive endoderm cells. In some embodiments, the Pdx1-positive pancreatic progenitor cells are produced from a population of primitive gut tube cells.

The disclosure contemplates the use of any growth factor from the FGF family that induces Pdx1-positive pancreatic progenitor cells to differentiate into NKX6-1-positive pancreatic progenitor cells (e.g., alone, or with any combination of at least one SHH pathway inhibitor, or optionally at least one retinoic acid signaling pathway activator). In some embodiments, the at least one growth factor from the FGF family comprises keratinocyte growth factor (KGF). In some embodiments, the at least one growth factor from the FGF family is selected from the group consisting of FGF2, FGF8B, FGF10, and FGF21.

The disclosure contemplates the use of any SHH pathway inhibitor that induces Pdx1-positive pancreatic progenitor cells to differentiate into NKX6-1-positive pancreatic progenitor cells (e.g., alone, or with any combination of at least one growth factor from the FGF family, or at least one retinoic acid signaling pathway activator). In some embodiments, the SHH pathway inhibitor comprises Sant1.

The disclosure contemplates the use of any RA signaling pathway activator that induces Pdx1-positive pancreatic progenitor cells to differentiate into NKX6-1-positive pancreatic progenitor cells (e.g., alone, or with any combination of at least one growth factor from the FGF family, and at least one SHH pathway inhibitor). In some embodiments, the RA signaling pathway activator comprises retinoic acid.

In some embodiments, the method comprises contacting the population of cells (e.g., Pdx1-positive pancreatic progenitor cells) with at least one additional β cell-maturation factor. In some embodiments, the at least one additional β cell-maturation factor comprises at least one growth factor from the EGF family. In some embodiments, the method comprises contacting the Pdx1-positive pancreatic progenitor cells with at least one growth factor from the EGF family. The disclosure contemplates the use of any growth factor from the EGF family that facilitates the differentiation of Pdx1-positive pancreatic progenitor cells into NKX6-1-positive pancreatic progenitor cells (e.g., together with any combination of at least one growth factor from the FGF family, at least one SHH pathway inhibitor, and optionally at least one RA signaling pathway activator). In some embodiments, the at least one growth factor from the EGF family comprises betacellulin. In some embodiments, the at least one growth factor from the EGF family comprises EGF.

The skilled artisan will appreciate that the concentrations of agents (e.g., growth factors) employed may vary. In some embodiments, the Pdx1-positive pancreatic progenitor cells are contacted with the at least one growth factor from the FGF family at a concentration of between 1 ng/mL-100 ng/mL. In some embodiments, the Pdx1-positive pancreatic progenitor cells are contacted with the at least one growth factor from the FGF family at a concentration of 5 ng/mL, 10 ng/mL, 15 ng/mL, 20 ng/mL, 25 ng/mL, 30 ng/mL, 35 ng/mL, or 40 ng/mL. In some embodiments, the Pdx1-positive pancreatic progenitor cells are contacted with the at least one growth factor from the FGF family at a concentration of 60 ng/mL, 65 ng/mL, 70 ng/mL, 75 ng/mL, 80 ng/mL, 85 ng/mL, 90 ng/mL, 95 ng/mL or 100 ng/mL. In some embodiments, the Pdx1-positive pancreatic progenitor cells are contacted with the at least one growth factor from the FGF family at a concentration of 41 ng/mL, 42 ng/mL, 43 ng/mL, 44 ng/mL, 45 ng/mL, 46 ng/mL, 47 ng/mL, 48 ng/mL or 49 ng/mL. In some embodiments, the Pdx1-positive pancreatic progenitor cells are contacted with the at least one growth factor from the FGF family at a concentration of 51 ng/mL, 52 ng/mL, 53 ng/mL, 54 ng/mL, 55 ng/mL, 56 ng/mL, 57 ng/mL, 58 ng/mL or 59 ng/mL. In some embodiments, the Pdx1-positive pancreatic progenitor cells are contacted with the at least one growth factor from the FGF family at a concentration of 50 ng/mL.

In some embodiments, the p Pdx1-positive pancreatic progenitor cells are contacted with the at least one SHH pathway inhibitor at a concentration of between 0.1 μM and 0.5 μM. In some embodiments, the Pdx1-positive pancreatic progenitor cells are contacted with the at least one SHH pathway inhibitor at a concentration of 0.11 μM, 0.12 μM, 0.13 μM, 0.14 μM, 0.15 μM, 0.16 μM, 0.17 μM, 0.18 μM, 0.19 μM, 0.2 μM, 0.21 μM, 0.22 μM, 0.23 μM, or 0.24 μM. In some embodiments, the Pdx1-positive pancreatic progenitor cells are contacted with the at least one SHH pathway inhibitor at a concentration of 0.26 μM, 0.27 μM, 0.28 μM, 0.29 μM, 0.30 μM, 0.31 μM, 0.32 μM, 0.33 μM, 0.34 μM, 0.35 μM, 0.36 μM, 0.37 μM, 0.38 μM, 0.39 μM, 0.40 μM, 0.41 μM, 0.42 μM, 0.43 μM, 0.44 μM, 0.45 μM, 0.46 μM, 0.47 μM, 0.48 μM, 0.49 μM. In some embodiments, the Pdx1-positive pancreatic progenitor cells are contacted with the at least one SHH pathway inhibitor at a concentration of 0.25 μM.

In some embodiments, the Pdx1-positive pancreatic progenitor cells are contacted with the RA signaling pathway activator at a concentration of between 0.01 μM-1.0 μM. In some embodiments, the Pdx1-positive pancreatic progenitor cells are contacted with the RA signaling pathway activator at a concentration of 0.02 μM, 0.03 μM, 0.04 μM, 0.05 μM, 0.06 μM, 0.07 μM, 0.08 μM, or 0.09 μM. In some embodiments, the Pdx1-positive pancreatic progenitor cells are contacted with the RA signaling pathway activator at a concentration of 0.20 μM, 0.30 μM, 0.40 μM, 0.05 μM, 0.60 μM, 0.70 μM, 0.80 μM, or 0.90 μM. In some embodiments, the Pdx1-positive pancreatic progenitor cells are contacted with the RA signaling pathway activator at a concentration of 0.1 μM.

In some embodiments, the Pdx1-positive pancreatic progenitor cells are contacted with the at least one growth factor from the EGF family at a concentration of between 2 ng/mL-200 ng/mL. In some embodiments, the Pdx1-positive pancreatic progenitor cells are contacted with the at least one growth factor from the EGF family at a concentration of 3 ng/mL, 4 ng/mL, 5 ng/mL, 6 ng/mL, 7 ng/mL, 8 ng/mL, 9 ng/mL, 10 ng/mL, 11 ng/mL, 12 ng/mL, 13 ng/mL, 14 ng/mL, 16 ng/mL, 17 ng/mL, 18 ng/mL, or 19 ng/mL. In some embodiments, the Pdx1-positive pancreatic progenitor cells are contacted with the at least one growth factor from the EGF family at a concentration of 30 ng/mL, 35 ng/mL, 40 ng/mL, 45 ng/mL, 50 ng/mL, 55 ng/mL, 60 ng/mL, 65 ng/mL, 70 ng/mL, 75 ng/mL, 80 ng/mL, 85 ng/mL, 90 ng/mL, 95 ng/mL, or 100 ng/mL. In some embodiments, the Pdx1-positive pancreatic progenitor cells are contacted with the at least one growth factor from the EGF family at a concentration of 21 ng/mL, 22 ng/mL, 23 ng/mL, 24 ng/mL, 25 ng/mL, 26 ng/mL, 27 ng/mL, 28 ng/mL or 29 ng/mL. In some embodiments, the Pdx1-positive pancreatic progenitor cells are contacted with the at least one growth factor from the EGF family at a concentration of 20 ng/mL.

Generally, the Pdx1-positive pancreatic progenitor cells are maintained in a suitable culture medium for a period of time sufficient to induce the differentiation of at least some of the Pdx1-positive pancreatic progenitor cells in the population into Pdx1-positive, NKX6-1-positive pancreatic progenitor cells. An exemplary suitable culture medium is shown in Table 3 above. In some embodiments, conditions that promote cell clustering comprise a suspension culture. In some embodiments, the suspension culture is maintained in a spinner flask. In some embodiments, the period of time is at least 5 days. In some embodiments, the suspension culture is replenished every other day. In some embodiments, the β cell-maturation factors are replenished every other day.

In some embodiments, an activator of protein kinase C is not added to the suspension culture during the 5 days. In some embodiments, an activator of protein kinase C is removed from the suspension culture prior to the 5 days. In some embodiments, the activator of protein kinase C comprises PdbU. In some embodiments, a BMP signaling pathway inhibitor is not added to the suspension culture during the 5 days. In some embodiments, a BMP signaling pathway inhibitor is removed from the suspension culture prior to the 5 days. In some embodiments, the BMP signaling pathway inhibitor comprises LDN193189.

In some embodiments, at least 10% of the Pdx1-positive pancreatic progenitor cells in the population are induced to differentiate into Pdx1-positive, NKX6-1-positive pancreatic progenitor cells. In some embodiments, at least 95% of the Pdx1-positive pancreatic progenitor cells are induced to differentiate into Pdx1-positive, NKX6-1-positive pancreatic progenitor cells.

Generally, any Pdx1-positive pancreatic progenitor cell can be differentiated into a Pdx1-positive, NKX6-1-positive pancreatic progenitor cell. In some embodiments, the NKX6-1-positive pancreatic progenitor cells express Pdx1, NKX6-1 and/or FoxA2.

In some embodiments, the Pdx1-positive, NKX6-1-positive pancreatic progenitor cells are obtained by contacting Pdx1-positive pancreatic progenitor cells under conditions that promote cell clustering with i) at least one growth factor from the FGF family, ii) at least one SHH pathway inhibitor, and optionally iii) low concentrations of a RA signaling pathway activator, for a period of five days to induce the differentiation of at least some of the Pdx1-positive pancreatic progenitor cells into Pdx1-positive, NKX6-1-positive pancreatic progenitor cells, wherein the Pdx1-positive, NKX6-1-positive pancreatic progenitor cells expresses Pdx1 and NKX6-1.

In some embodiments, NKX6-1-positive pancreatic progenitor cells can be obtained by differentiating at least some of the Pdx1-positive pancreatic progenitor cells into Pdx1-positive, NKX6-1-positive pancreatic progenitor cells by a process of contacting the Pdx1-positive pancreatic progenitor cells under conditions that promote cell clustering with i) at least one growth factor from the FGF family, ii) at least one SHH pathway inhibitor, and optionally iii) a RA signaling pathway activator, every other day for a period of five days to induce the differentiation of at least some of the Pdx1-positive pancreatic progenitor cells in the population into NKX6-1-positive pancreatic progenitor cells, wherein the NKX6-1-positive pancreatic progenitor cells expresses Pdx1 and NKX6-1.

In some embodiments, NKX6-1-positive pancreatic progenitor cells can be obtained by differentiating at least some of the Pdx1-positive pancreatic progenitor cells in a population into Pdx1-positive, NKX6-1-positive pancreatic progenitor cells, e.g., by contacting the Pdx1-positive pancreatic progenitor cells with i) at least one growth factor from the FGF family, ii) at least one SHH pathway inhibitor, and optionally iii) a RA signaling pathway activator, to induce the differentiation of at least some of the Pdx1-positive pancreatic progenitor cells in the population into NKX6-1-positive pancreatic progenitor cells, wherein the NKX6-1-positive pancreatic progenitor cells expresses Pdx1 and NKX6-1.

Inducing the Differentiation of NKX6-1+ Pancreatic Progenitor Cells to Insulin+ Endocrine Cells Aspects of the disclosure involve insulin-positive endocrine cells. Insulin-positive endocrine cells of use herein can be derived from any source or generated in accordance with any suitable protocol. In some aspects, NKX6-1-positive pancreatic progenitor cells are differentiated to insulin-positive endocrine cells. In some aspects, the insulin-positive endocrine cells are further differentiated, e.g., by induction or maturation to SC-β cells.

In some aspects, a method of producing an insulin-positive endocrine cell from an NKX6-1-positive pancreatic progenitor cell comprises contacting a population of cells (e.g., under conditions that promote cell clustering) comprising NKX6-1-positive pancreatic progenitor cells with at least two β cell-maturation factors comprising a) a TGF-β signaling pathway inhibitor, and b) a thyroid hormone signaling pathway activator, to induce the differentiation of at least one NKX6-1-positive pancreatic progenitor cell in the population into an insulin-positive endocrine cell, wherein the insulin-positive pancreatic progenitor cell expresses insulin.

The disclosure contemplates the use of any TGF-β signaling pathway inhibitor that induces the differentiation of NKX6-1-positive pancreatic progenitor cells to differentiate into insulin-positive endocrine cells (e.g., alone, or in combination with other β cell-maturation factors, e.g., a thyroid hormone signaling pathway activator). In some embodiments, the TGF-β signaling pathway comprises TGF-β receptor type I kinase signaling. In some embodiments, the TGF-β signaling pathway inhibitor comprises Alk5 inhibitor II.

The disclosure contemplates the use of any thyroid hormone signaling pathway activator that induces the differentiation of NKX6-1-positive pancreatic progenitor cells to differentiate into insulin-positive endocrine cells (e.g., alone, or in combination with other β cell-maturation factors, e.g., a TGF-β signaling pathway inhibitor). In some embodiments, the thyroid hormone signaling pathway activator comprises triiodothyronine (T3).

In some embodiments, the method comprises contacting the population of cells (e.g., NKX6-1-positive pancreatic progenitor cells) with at least one additional β cell-maturation factor. IN some embodiments, the method comprises contacting the Pdx1-positive NKX6-1-positive pancreatic progenitor cells with at least one of i) a SHH pathway inhibitor, ii) a RA signaling pathway activator, iii) a γ-secretase inhibitor, iv) at least one growth factor from the epidermal growth factor (EGF) family, and optionally v) a protein kinase inhibitor.

In some embodiments, the at least one additional β cell-maturation factor comprises a γ-secretase inhibitor. The disclosure contemplates the use of any γ-secretase inhibitor that is capable of inducing the differentiation of NKX6-1-positive pancreatic progenitor cells in a population into insulin-positive endocrine cells (e.g., alone, or in combination with any of a TGF-β signaling pathway inhibitor and/or a thyroid hormone signaling pathway activator). In some embodiments, the γ-secretase inhibitor comprises XXI. In some embodiments, the γ-secretase inhibitor comprises DAPT.

In some embodiments, the at least one additional β cell-maturation factor comprises at least one growth factor from the EGF family. The disclosure contemplates the use of any growth factor from the EGF family that is capable of inducing the differentiation of NKX6-1-positive pancreatic progenitor cells in a population into insulin-positive endocrine cells (e.g., alone, or in combination with any of a TGF-β signaling pathway inhibitor and/or a thyroid hormone signaling pathway activator). In some embodiments, the at least one growth factor from the EGF family comprises betacellulin. In some embodiments, at least one growth factor from the EGF family comprises EGF.

In some embodiments, the at least one additional β cell-maturation factor comprises a low concentration of a retinoic acid (RA) signaling pathway activator. The disclosure contemplates the use of any RA signaling pathway activator that induces the differentiation of NKX6-1-positive pancreatic progenitor cells to differentiate into insulin-positive endocrine cells (e.g., alone, or in combination with any of a TGF-β signaling pathway inhibitor and/or a thyroid hormone signaling pathway activator). In some embodiments, the RA signaling pathway activator comprises RA.

In some embodiments, the at least one additional β cell-maturation factor comprises a sonic hedgehog (SHH) pathway inhibitor. The disclosure contemplates the use of any SHH pathway inhibitor that induces the differentiation of NKX6-1-positive pancreatic progenitor cells to differentiate into insulin-positive endocrine cells (e.g., alone, or in combination with any of a TGF-β signaling pathway inhibitor and/or a thyroid hormone signaling pathway activator). In some embodiments, the SHH pathway inhibitor comprises Sant1.

In some embodiments, the population of cells (e.g., NKX6-1-positive pancreatic progenitor cells) is exposed to glucose.

In some embodiments, the population of cells is optionally contacted with a protein kinase inhibitor. In some embodiments, the population of cells is not contacted with the protein kinase inhibitor. In some embodiments, the population of cells is contacted with the protein kinase inhibitor. The disclosure contemplate the use of any protein kinase inhibitor that is capable of inducing the differentiation of NKX6-1-positive pancreatic progenitor cells in a population into insulin-positive endocrine cells (e.g., alone, or in combination with any of a TGF-β signaling pathway inhibitor and/or a thyroid hormone signaling pathway activator). In some embodiments, the protein kinase inhibitor comprises staurosporine.

In some embodiments, the insulin-positive endocrine cells are obtained by contacting Pdx1-positive, NKX6-1-positive pancreatic progenitor cells with i) at least one SHH pathway inhibitor, ii) a RA signaling pathway activator, iii) a γ-secretase inhibitor, iv) a TGF-β) signaling pathway inhibitor, v) a TH signaling pathway activator, and vi) at least one growth factor from the epidermal growth factor (EGF) family, to induce the differentiation of at least some of the Pdx1-positive, NKX6-1-positive pancreatic progenitor cells into Pdx1-positive, NKX6-1, insulin-positive endocrine cells, wherein the Pdx1-positive, NKX6-1, insulin-positive endocrine cells express Pdx1, NKX6-1, NKX2-2, Math, glis3, Sur1, Kir6.2, Znt8, SLC2A1, SLC2A3 and/or insulin.

The skilled artisan will appreciate that the concentrations of agents (e.g., growth factors) employed may vary.

In some embodiments, the NKX6-1-positive pancreatic progenitor cells are contacted with the at least one TGF-β signaling pathway inhibitor at a concentration of between 100 nM-100 μM. In some embodiments, the NKX6-1-positive pancreatic progenitor cells are contacted with the at least one TGF-β signaling pathway inhibitor at a concentration of 10 μM. In some embodiments, the NKX6-1-positive pancreatic progenitor cells are contacted with the at least one TGF-β signaling pathway inhibitor at a concentration of 100 nM, 200 nM, 300 nM, 400 nM, 500 nM, 600 nM, 700 nM, 800 nM, or 900 nM. In some embodiments, the NKX6-1-positive pancreatic progenitor cells are contacted with the at least one TGF-β signaling pathway inhibitor at a concentration of 2 μM, 3 μM, 4 μM, 5 μM, 6 μM, 7 μM, 8 μM, or 9 μM. In some embodiments, the NKX6-1-positive pancreatic progenitor cells are contacted with the at least one TGF-β signaling pathway inhibitor at a concentration of 9.1 μM, 9.2 μM, 9.3 μM, 9.4 μM, 9.5 μM, 9.6 μM, 9.7 μM, 9.8 μM or 9.9 μM. In some embodiments, the NKX6-1-positive pancreatic progenitor cells are contacted with the at least one TGF-β signaling pathway inhibitor at a concentration of 11 μM, 12 μM, 13 μM, 14 μM, 15 μM, 16 μM, 17 μM, 18 μM, or 19 μM. In some embodiments, the NKX6-1-positive pancreatic progenitor cells are contacted with the at least one TGF-β signaling pathway inhibitor at a concentration of 10.1 μM, 10.2 μM, 10.3 μM, 10.4 μM, 10.5 μM, 10.6 μM, 10.7 μM, 10.8 μM or 10.9 μM.

In some embodiments, the NKX6-1-positive pancreatic progenitor cells are contacted with the thyroid hormone signaling pathway activator at a concentration of between 0.1 μM-10 μM. In some embodiments, the NKX6-1-positive pancreatic progenitor cells are contacted with the thyroid hormone signaling pathway activator at a concentration of 1 μM. In some embodiments, the NKX6-1-positive pancreatic progenitor cells are contacted with the thyroid hormone signaling pathway activator at a concentration of 0.2 μM, 0.3 μM, 0.4 μM, 0.5 μM, 0.6 μM, 0.7 μM, 0.8 μM, or 0.9 μM. In some embodiments, the NKX6-1-positive pancreatic progenitor cells are contacted with the γ thyroid hormone signaling pathway activator at a concentration of 1.1 μM, 1.2 μM, 1.3 μM, 1.4 μM, 1.5 μM, 1.6 μM, 1.7 μM, 1.8 μM or 1.9 μM. In some embodiments, the NKX6-1-positive pancreatic progenitor cells are contacted with the thyroid hormone signaling pathway activator at a concentration of 2 μM, 3 μM, 4 μM, 5 μM, 6 μM, 7 μM, 8 μM, or 9 μM.

In some embodiments, the NKX6-1-positive pancreatic progenitor cells are contacted with the γ-secretase inhibitor at a concentration of between 0.1 μM-10 μM. In some embodiments, the NKX6-1-positive pancreatic progenitor cells are contacted with the γ-secretase inhibitor at a concentration of 1 μM. In some embodiments, the NKX6-1-positive pancreatic progenitor cells are contacted with the γ-secretase inhibitor at a concentration of 0.2 μM, 0.3 μM, 0.4 μM, 0.5 μM, 0.6 μM, 0.7 μM, 0.8 μM, or 0.9 μM. In some embodiments, the NKX6-1-positive pancreatic progenitor cells are contacted with the γ-secretase inhibitor at a concentration of 1.1 μM, 1.2 μM, 1.3 μM, 1.4 μM, 1.5 μM, 1.6 μM, 1.7 μM, 1.8 μM or 1.9 μM. In some embodiments, the NKX6-1-positive pancreatic progenitor cells are contacted with the γ-secretase inhibitor at a concentration of 2 μM, 3 μM, 4 μM, 5 μM, 6 μM, 7 μM, 8 μM, or 9 μM.

In some embodiments, the NKX6-1-positive pancreatic progenitor cells are contacted with the at least one growth factor from the EGF family at a concentration of between 2 ng/mL-200 ng/mL. In some embodiments, the NKX6-1-positive pancreatic progenitor cells are contacted with the at least one growth factor from the EGF family at a concentration of 3 ng/mL, 4 ng/mL, 5 ng/mL, 6 ng/mL, 7 ng/mL, 8 ng/mL, 9 ng/mL, 10 ng/mL, 11 ng/mL, 12 ng/mL, 13 ng/mL, 14 ng/mL, 15 ng/mL, 16 ng/mL, 17 ng/mL, 18 ng/mL, or 19 ng/mL. In some embodiments, the NKX6-1-positive pancreatic progenitor cells are contacted with the at least one growth factor from the EGF family at a concentration of 30 ng/mL, 35 ng/mL, 40 ng/mL, 45 ng/mL, 50 ng/mL, 55 ng/mL, 60 ng/mL, 65 ng/mL, 70 ng/mL, 75 ng/mL, 80 ng/mL, 85 ng/mL, 90 ng/mL, 95 ng/mL, or 100 ng/mL. In some embodiments, the NKX6-1-positive pancreatic progenitor cells are contacted with the at least one growth factor from the EGF family at a concentration of 21 ng/mL, 22 ng/mL, 23 ng/mL, 24 ng/mL, 25 ng/mL, 26 ng/mL, 27 ng/mL, 28 ng/mL or 29 ng/mL. In some embodiments, the NKX6-1-positive pancreatic progenitor cells are contacted with the at least one growth factor from the EGF family at a concentration of 20 ng/mL.

In some embodiments, the NKX6-1-positive pancreatic progenitor cells are contacted with the RA signaling pathway activator at a concentration of between 0.01 μM-1.0 μM. In some embodiments, the NKX6-1-positive pancreatic progenitor cells are contacted with the RA signaling pathway activator at a concentration of 0.02 μM, 0.03 μM, 0.04 μM, 0.05 μM, 0.06 μM, 0.07 μM, 0.08 μM, or 0.09 μM. In some embodiments, the NKX6-1-positive pancreatic progenitor cells are contacted with the RA signaling pathway activator at a concentration of 0.20 μM, 0.30 μM, 0.40 μM, 0.05 μM, 0.60 μM, 0.70 μM, 0.80 μM, or 0.90 μM. In some embodiments, the NKX6-1-positive pancreatic progenitor cells are contacted with the RA signaling pathway activator at a concentration of 0.1 μM.

In some embodiments, the NKX6-1-positive pancreatic progenitor cells are contacted with a low concentration of a RA signaling pathway activator at a concentration of between 0.01 μM-1.0 μM. In some embodiments, the NKX6-1-positive pancreatic progenitor cells are contacted with a low concentration of the RA signaling pathway activator at a concentration of 0.02 μM, 0.03 μM, 0.04 μM, 0.05 μM, 0.06 μM, 0.07 μM, 0.08 μM, or 0.09 μM. In some embodiments, the NKX6-1-positive pancreatic progenitor cells are contacted with the low concentration of a RA signaling pathway activator at a concentration of 0.20 μM, 0.30 μM, 0.40 μM, 0.05 μM, 0.60 μM, 0.70 μM, 0.80 μM, or 0.90 μM. In some embodiments, the NKX6-1-positive pancreatic progenitor cells are contacted with a low concentration of the RA signaling pathway activator at a concentration of 0.1 μM.

In some embodiments, the NKX6-1-positive pancreatic progenitor cells are contacted with the at least one SHH pathway inhibitor at a concentration of between 0.1 μM and 0.5 μM. In some embodiments, the NKX6-1-positive pancreatic progenitor cells are contacted with the at least one SHH pathway inhibitor at a concentration of 0.11 μM, 0.12 μM, 0.13 μM, 0.14 μM, 0.15 μM, 0.16 μM, 0.17 μM, 0.18 μM, 0.19 μM, 0.2 μM, 0.21 μM, 0.22 μM, 0.23 μM, or 0.24 μM. In some embodiments, the NKX6-1-positive pancreatic progenitor cells are contacted with the at least one SHH pathway inhibitor at a concentration of 0.26 μM, 0.27 μM, 0.28 μM, 0.29 μM, 0.30 μM, 0.31 μM, 0.32 μM, 0.33 μM, 0.34 μM, 0.35 μM, 0.36 μM, 0.37 μM, 0.38 μM, 0.39 μM, 0.40 μM, 0.41 μM, 0.42 μM, 0.43 μM, 0.44 μM, 0.45 μM, 0.46 μM, 0.47 μM, 0.48 μM, 0.49 μM. In some embodiments, the NKX6-1-positive pancreatic progenitor cells are contacted with the at least one SHH pathway inhibitor at a concentration of 0.25 μM.

In some embodiments, the NKX6-1-positive pancreatic progenitor cells are contacted with the protein kinase inhibitor at a concentration of between 10 nM-1 μM. In some embodiments, the NKX6-1-positive pancreatic progenitor cells are contacted with the protein kinase inhibitor at a concentration of 100 nM. In some embodiments, the NKX6-1-positive pancreatic progenitor cells are contacted with the protein kinase inhibitor at a concentration of 20 nM, 30 nM, 40 nM, 50 nM, 60 nM, 70 nM, 80 nM, or 90 nM. In some embodiments, the NKX6-1-positive pancreatic progenitor cells are contacted with the protein kinase inhibitor at a concentration of 110 nM, 120 nM, 130 nM, 140 nM, 150 nM, 160 nM, 170 nM, 180 nM or 190 nM. In some embodiments, the NKX6-1-positive pancreatic progenitor cells are contacted with the protein kinase inhibitor at a concentration of 200 nM, 300 nM, 400 nM, 500 nM, 600 nM, 700 nM, 800 nM, or 900 nM.

In some embodiments, the NKX6-1-positive pancreatic progenitor cells are contacted with glucose at a concentration of between 1 mM-50 mM. In some embodiments, the NKX6-1-positive pancreatic progenitor cells are contacted with glucose at a concentration of between 25 mM.

In some embodiments, the insulin-positive endocrine cells can be obtained by differentiating at least some of the Pdx1-positive, NKX6-1-positive pancreatic progenitor cells into Pdx1-positive, NKX6-1-positive, insulin-positive endocrine cells by a process of contacting the Pdx1-positive, NKX6-1-positive pancreatic progenitor cells under conditions that promote cell clustering with i) a TGF-β signaling pathway inhibitor, b) a TH signaling pathway activator, and optionally c) at least one SHH pathway inhibitor, ii) a RA signaling pathway activator, iii) a γ-secretase inhibitor, and vi) at least one growth factor from the epidermal growth factor (EGF) family, every other day for a period of between five and seven days to induce the differentiation of at least some of the Pdx1-positive, NKX6-1-positive pancreatic progenitor cells into Pdx1-positive, NKX6-1, insulin-positive endocrine cells, wherein the Pdx1-positive, NKX6-1, insulin-positive endocrine cells express Pdx1, NKX6-1, NKX2-2, Math, glis3, Sur1, Kir6.2, Znt8, SLC2A1, SLC2A3 and/or insulin.

In some embodiments, the insulin-positive endocrine cells can be obtained by differentiating at least some of the Pdx1-positive, NKX6-1-positive pancreatic progenitor cells in a population into Pdx1-positive, NKX6-1-positive, insulin-positive endocrine cells, e.g., by contacting the Pdx1-positive, NKX6-1-positive pancreatic progenitor cells with i) at least one SHH pathway inhibitor, ii) a RA signaling pathway activator, iii) a γ-secretase inhibitor, iv) a TGF-β) signaling pathway inhibitor, v) a TH signaling pathway activator, and vi) at least one growth factor from the epidermal growth factor (EGF) family, to induce the differentiation of at least some of the Pdx1-positive, NKX6-1-positive pancreatic progenitor cells into Pdx1-positive, NKX6-1, insulin-positive endocrine cells, wherein the Pdx1-positive, NKX6-1, insulin-positive endocrine cells express Pdx1, NKX6-1, NKX2-2, Mafb, glis3, Sur1, Kir6.2, Znt8, SLC2A1, SLC2A3 and/or insulin.

Generally, the population of cells is maintained in a suitable culture medium for a period of time sufficient to induce the differentiation of at least one of the NKX6-1-positive pancreatic progenitor cells in the population into an insulin-positive endocrine cell. An exemplary culture medium is shown in Table 4.

TABLE 4

| Agent | Concentration |
| --- | --- |
| MCDB131 | 1 L |
| Glucose | 3.6 g |
| NaHCO3 | 1.754 g |
| FAF-BSA | 20 g |
| ITS-X | 5 mL |
| GlutaMAX ™ | 10 mL |
| Vitamin C | 0.044 g |
| Heparin | 10 mg |
| P/S | 10 mL |

In some embodiments, BE5 media can be used as a suitable culture medium for differentiating NKX6-1-positive pancreatic progenitor cells into insulin-positive endocrine cells. In some embodiments, a suitable culture medium is shown in Table 5.

In some embodiments, conditions that promote cell clustering comprise a suspension culture. In some embodiments, the period of time comprises a period of time sufficient to maximize the number of cells co-expressing C-peptide and Nkx6-1. In some embodiments, the period of time is at least 5 days. In some embodiments, the period of time is between 5 days and 7 days. In some embodiments, the period of time is at least 7 days. In some embodiments, the suspension culture is replenished every day (e.g., with β cell-maturation factors). In some embodiments, a period of time of between 5 days and 7 days maximizes the number of cells co-expressing C-peptide and Nkx6-1.

In some embodiments, at least 15% of the NKX6-1-positive pancreatic progenitor cells in the population are induced to differentiate into insulin-positive endocrine cells.

In some embodiments, at least 99% of the NKX6-1-positive pancreatic progenitor cells in the population are induced to differentiate into insulin-positive endocrine cells.

Inducing the Maturation of Insulin+ Endocrine Cells into SC-β Cells

Aspects of the disclosure involve SC-β cells. SC-β cells of use herein can be derived from any source or generated in accordance with any suitable protocol. In some aspects, insulin-positive endocrine cells are induced to mature into to SC-β cells.

In some aspects, the disclosure provides a method for generating mature, glucose responsive β cells from insulin-positive endocrine cells, the method comprising contacting a population of cells (e.g., under conditions that promote cell clustering) comprising insulin-positive endocrine cells with at least two β cell maturation factors comprising a) a transforming growth factor-β (TGF-β) signaling pathway inhibitor, b) a thyroid hormone (TH) signaling pathway activator, to induce the in vitro maturation of at least one insulin-positive endocrine cell in the population into a SC-β cell.

Aspects of the disclosure involve generating SC-β cells which resemble endogenous mature β cells in form and function, but nevertheless are distinct from native β cells. The SC-β cells can exhibit a response to at least one glucose challenge. In some embodiments, the SC-β cells exhibit a response to at least two sequential glucose challenges. In some embodiments, the SC-β cells exhibit a response to at least three sequential glucose challenges. In some embodiments, the SC-β cell exhibits a response to multiple (e.g., sequential) glucose challenges that resembles the response of endogenous human islets to multiple glucose challenges. In some embodiments, the SC-β cells are capable of releasing or secreting insulin in response to two consecutive glucose challenges. In some embodiments, the SC-β cells are capable of releasing or secreting insulin in response to three consecutive glucose challenges. In some embodiments, the SC-β cells are capable of releasing or secreting insulin in response to four consecutive glucose challenges. In some embodiments, the SC-β cells are capable of releasing or secreting insulin in response to five consecutive glucose challenges. In some embodiments, the SC-β cells release or secrete insulin in response to perpetual consecutive glucose challenges. In some embodiments, cells can be assayed to determine whether they respond to sequential glucose challenges by determining whether they repeatedly increase intracellular $Ca^{2+}$, as described in the examples herein.

In some embodiments, the morphology of the SC-β cells resembles the morphology of endogenous β cells. In some embodiments, the SC-β cell exhibits a glucose stimulated insulin secretion (GSIS) response in vitro. In some embodiments, the SC-β cell exhibits a GSIS response in vivo. In some embodiments, the SC-β cell exhibits in vitro and in vivo GSIS responses. In some embodiments, the in vitro and/or in vitro GSIS response resembles the GSIS responses of endogenous mature β cells. In some embodiments, the SC-β cell exhibits an in vitro (GSIS) response that resembles the GSIS response of endogenous β cells. In some embodiments, the SC-β cell exhibits an in vivo GSIS response that resembles the GSIS response of endogenous β cells. The GSIS response may be observed immediately upon transplantation into a human or animal subject. In some embodiments, the GSIS response is observed within two weeks of transplantation of the SC-β cell into a human or animal subject. In some embodiments, the GSIS response is observed within two weeks of transplantation of the SC-β cell into a human or animal subject. In some embodiments, the GSIS response of the SC-β cell is observed up to three weeks, four weeks, five weeks, six weeks, seven weeks, eight weeks, nine weeks, ten weeks, 11 weeks, 12 weeks, 13 weeks, 14 weeks, 15 weeks, 16 weeks, 17 weeks, 18 weeks, 6 months, 7 months, 8 months, 9 months, 10 months, 11 months, or up to 1 year or more after transplantation of the SC-β cell into a human or animal subject.

In some embodiments, the SC-β cells display at least one marker of mature endogenous pancreatic β cells. Exemplary markers include, without limitation, Pdx1, HNF6, Ptf1a, Sox9, FoxA2, Nkx2.2, Ngn3, and NKX6-1. In some embodiments, the expression of a marker selected from the group consisting of, HNF6, Ptf1a, Sox9, FoxA2, Nkx2.2, Ngn3, and NKX6-1 is upregulated by a statistically significant amount in the SC-β cells relative to the pluripotent stem cells (e.g., embryonic stem cell or induced pluripotent cell) from which the SC-β cells are derived.

The disclosure contemplates the use of any TGF-β signaling pathway inhibitor that induces insulin-positive endocrine cells to differentiate and/or mature into SC-β cells (e.g., alone, or with any combination of at least one thyroid hormone (TH) signaling pathway activator, or optionally a protein kinase inhibitor). In some embodiments, the TGF-β signaling pathway comprises TGF-β receptor type I kinase signaling. In some embodiments, the TGF-β signaling pathway inhibitor comprises Alk5 inhibitor II.

The disclosure contemplates the use of any thyroid hormone signaling pathway activator that induces insulin-positive endocrine cells to differentiate and/or mature into SC-β cells (e.g., alone, or with any combination of at least one TGF-β signaling pathway inhibitor, or optionally a protein kinase inhibitor). In some embodiments, the thyroid hormone signaling pathway activator comprises T3.

In some embodiments, the Pdx1-positive, NKX6-1-positive, insulin-positive cells are optionally contacted with a protein kinase inhibitor. In some embodiments, the Pdx1-positive, NKX6-1-positive, insulin-positive endocrine cells are not contacted with the protein kinase inhibitor. In some embodiments, the Pdx1-positive, NKX6-1-positive, insulin-positive endocrine cells are contacted with the protein kinase inhibitor. The disclosure contemplates the use of any protein kinase inhibitor that induces insulin-positive endocrine cells to differentiate and/or mature into SC-β cells (e.g., alone, or with any combination of at least one TGF-β signaling pathway inhibitor, and/or thyroid hormone signaling pathway activator). In some embodiments, the protein kinase inhibitor comprises staurosporine.

In some embodiments, the method comprises contacting the population of cells (e.g., insulin-positive endocrine cells) with at least one additional β cell-maturation factor.

In some embodiments, the at least one additional β cell-maturation factor comprises a cystic fibrosis transmembrane conductance regulator (CFTR) inhibitor. In some embodiments, the method comprises contacting the Pdx1-positive, NKX6-1-positive, insulin-positive endocrine cells with a CFTR inhibitor. The disclosure contemplates the use of any CFTR inhibitor that induces insulin-positive endocrine cells to differentiate and/or mature into SC-β cells (e.g., alone, or with any combination of at least one TGF-β signaling pathway inhibitor, and/or a thyroid hormone signaling pathway activator, and optionally protein kinase inhibitor). In some embodiments, the CFTR inhibitor comprises Gly-H101.

In some embodiments, the at least one additional β cell-maturation factor comprises a O-GlcNAcase inhibitor. In some embodiments, the method comprises contacting the Pdx1-positive, NKX6-1-positive, insulin-positive endocrine cells with a O-GlcNAcase inhibitor. The disclosure contemplates the use of any O-GlcNAcase inhibitor that induces insulin-positive endocrine cells to differentiate and/or mature into SC-β cells (e.g., alone, or with any combination of at least one TGF-β signaling pathway inhibitor, and/or thyroid hormone signaling pathway activator, and optionally a protein kinase inhibitor). In some embodiments, the inhibitor of O-GlcNAcase comprises Thiamet G.

The skilled artisan will appreciate that the concentrations of agents (e.g., growth factors) employed may vary. In some embodiments, the insulin-positive endocrine cells are contacted with the at least one TGF-β signaling pathway inhibitor at a concentration of between 100 nM-100 μM. In some embodiments, the insulin-positive endocrine cells are contacted with the at least one TGF-β signaling pathway inhibitor at a concentration of 10 μM. In some embodiments, the insulin-positive endocrine cells are contacted with the at least one TGF-β signaling pathway inhibitor at a concentration of 200 nM, 300 nM, 400 nM, 500 nM, 600 nM, 700 nM, 800 nM, or 900 nM. In some embodiments, the insulin-positive endocrine cells are contacted with the at least one TGF-β signaling pathway inhibitor at a concentration of 2 μM, 3 μM, 4 μM, 5 μM, 6 μM, 7 μM, 8 μM, or 9 μM. In some embodiments, the insulin-positive endocrine cells are contacted with the at least one TGF-β signaling pathway inhibitor at a concentration of 9.1 μM, 9.2 μM, 9.3 μM, 9.4 μM, 9.5 μM, 9.6 μM, 9.7 μM, 9.8 μM or 9.9 μM. In some embodiments, the insulin-positive endocrine cells are contacted with the at least one TGF-β signaling pathway inhibitor at a concentration of 11 μM, 12 μM, 13 μM, 14 μM, 15 μM, 16 μM, 17 μM, 18 μM, or 19 μM. In some embodiments, the insulin-positive endocrine cells are contacted with the at least one TGF-β signaling pathway inhibitor at a concentration of 10.1 μM, 10.2 μM, 10.3 μM, 10.4 μM, 10.5 μM, 10.6 μM, 10.7 μM, 10.8 μM or 10.9 μM.

In some embodiments, the insulin-positive endocrine cells are contacted with the thyroid hormone signaling pathway activator at a concentration of between 0.1 μM-10 μM. In some embodiments, the insulin-positive endocrine cells are contacted with the thyroid hormone signaling pathway activator at a concentration of 1 μM. In some embodiments, the insulin-positive endocrine cells are contacted with the thyroid hormone signaling pathway activator at a concentration of 0.2 μM, 0.3 μM, 0.4 μM, 0.5 μM, 0.6 μM, 0.7 μM, 0.8 μM, or 0.9 μM. In some embodiments, the insulin-positive endocrine cells are contacted with the γ thyroid hormone signaling pathway activator at a concentration of 1.1 μM, 1.2 μM, 1.3 μM, 1.4 μM, 1.5 μM, 1.6 μM, 1.7 μM, 1.8 μM or 1.9 μM. In some embodiments, the insulin-positive endocrine cells are contacted with the thyroid hormone signaling pathway activator at a concentration of 2 μM, 3 μM, 4 μM, 5 μM, 6 μM, 7 μM, 8 μM, or 9 μM.

In some embodiments, the insulin-positive endocrine cells are contacted with the protein kinase inhibitor at a concentration of between 10 nM-1 μM. In some embodiments, the insulin-positive endocrine cells are contacted with the protein kinase inhibitor at a concentration of 100 nM. In some embodiments, the insulin-positive endocrine cells are contacted with the protein kinase inhibitor at a concentration of 20 nM, 30 nM, 40 nM, 50 nM, 60 nM, 70 nM, 80 nM, or 90 nM. In some embodiments, the insulin-positive endocrine cells are contacted with the protein kinase inhibitor at a concentration of 110 nM, 120 nM, 130 nM, 140 nM, 150 nM, 160 nM, 170 nM, 180 nM or 190 nM. In some embodiments, the insulin-positive endocrine cells are contacted with the protein kinase inhibitor at a concentration of 200 nM, 300 nM, 400 nM, 500 nM, 600 nM, 700 nM, 800 nM, or 900 nM.

In some embodiments, the Pdx1-positive, NKX6-1-positive, insulin-positive endocrine cells are contacted with the CFTR inhibitor at a concentration of between 100 nM-100 μM. In some embodiments, the Pdx1-positive, NKX6-1-positive, insulin-positive endocrine cells are contacted with the CFTR inhibitor at a concentration of between 10 nM-10 μM.

In some embodiments, the Pdx1-positive, NKX6-1-positive, insulin-positive endocrine cells are contacted with the O-GlcNAcase inhibitor at a concentration of between 100 nM-100 μM. In some embodiments, the Pdx1-positive, NKX6-1-positive, insulin-positive endocrine cells are contacted with the O-GlcNAcase inhibitor at a concentration of 10 nM-10 μM.

In some embodiments, a SC-β cell can be obtained by differentiating at least some of the Pdx1-positive, NKX6-1-positive, insulin-positive endocrine cells into SC-β cells by a process of contacting the Pdx1-positive, NKX6-1-positive, insulin-positive endocrine cells under conditions that promote cell clustering with i) a transforming growth factor β (TGF-β) signaling pathway inhibitor, ii) a thyroid hormone signaling pathway activator, and optionally iii) a protein kinase inhibitor, every other day for a period of between seven and 14 days to induce the in vitro maturation of at least some of the Pdx1-positive, NKX6-1-positive, insulin-positive endocrine cells into SC-β cells, wherein the SC-β cells exhibit a GSIS response both in vitro and/or in vivo. In some embodiments, the GSIS response resembles the GSIS response of an endogenous β cell.

In some embodiments, a SC-β cell can be obtained by differentiating at least some Pdx1-positive, NKX6-1-positive, insulin-positive endocrine cells in a population into SC-β cells, e.g., by contacting the Pdx1-positive, NKX6-1-positive, insulin-positive endocrine cells with i) a transforming growth factor β (TGF-β) signaling pathway inhibitor, ii) a thyroid hormone signaling pathway activator, and optionally iii) a protein kinase inhibitor, to induce the in vitro maturation of at least some of the Pdx1-positive, NKX6-1-positive, insulin-producing endocrine cells into SC-β cells, wherein the SC-β cells exhibit a GSIS response both in vitro and/or in vivo that resemble the GSIS response of an endogenous β cell.

In some aspects, the disclosure provides a method of generating SC-β cells, the method comprising: contacting Pdx1-positive, NKX6-1-positive, insulin-positive endocrine cells under conditions that promote cell clustering with i) a transforming growth factor β (TGF-β) signaling pathway inhibitor, ii) a thyroid hormone signaling pathway activator, and optionally iii) a protein kinase inhibitor, to induce the in vitro maturation of at least some of the Pdx1-positive, NKX6-1-positive, insulin-positive endocrine cells into SC-β cells, wherein the SC-β cells exhibit a GSIS response both in vitro and/or in vivo. In some embodiments, the GSIS response resembles the GSIS response of an endogenous β cell.

In some aspects, the disclosure provides a method of generating SC-β cells from pluripotent cells, the method comprising: a) differentiating pluripotent stem cells in a population into Pdx1-positive pancreatic progenitor cells; b) differentiating at least some of the Pdx1-positive pancreatic progenitor cells into Pdx1-positive, NKX6-1-positive pancreatic progenitor cells by a process of contacting the Pdx1-positive pancreatic progenitor cells under conditions that promote cell clustering with i) at least one growth factor from the FGF family, ii) at least one SHH pathway inhibitor, and optionally iii) a RA signaling pathway activator, every other day for a period of five days to induce the differentiation of at least some of the Pdx1-positive pancreatic progenitor cells in the population into NKX6-1-positive pancreatic progenitor cells, wherein the NKX6-1-positive pancreatic progenitor cells expresses Pdx1 and NKX6-1; c) differentiating at least some of the Pdx1-positive, NKX6-1-positive pancreatic progenitor cells into Pdx1-positive, NKX6-1-positive, insulin-positive endocrine cells by a process of contacting the Pdx1-positive, NKX6-1-positive pancreatic progenitor cells under conditions that promote cell clustering with i) a TGF-β signaling pathway inhibitor, b) a TH signaling pathway activator, and optionally c) at least one SHH pathway inhibitor, ii) a RA signaling pathway activator, iii) a γ-secretase inhibitor, and vi) at least one growth factor from the epidermal growth factor (EGF) family, every other day for a period of between five and seven days to induce the differentiation of at least some of the Pdx1-positive, NKX6-1-positive pancreatic progenitor cells into Pdx1-positive, NKX6-1, insulin-positive endocrine cells, wherein the Pdx1-positive, NKX6-1, insulin-positive endocrine cells express Pdx1, NKX6-1, NKX2-2, Math, glis3, Sur1, Kir6.2, Znt8, SLC2A1, SLC2A3 and/or insulin; and d) differentiating at least some of the Pdx1-positive, NKX6-1-positive, insulin-positive endocrine cells into SC-β cells by a process of contacting the Pdx1-positive, NKX6-1-positive, insulin-positive endocrine cells under conditions that promote cell clustering with i) a transforming growth factor β (TGF-β) signaling pathway inhibitor, ii) a thyroid hormone signaling pathway activator, and optionally iii) a protein kinase inhibitor, every other day for a period of between seven and 14 days to induce the in vitro maturation of at least some of the Pdx1-positive, NKX6-1-positive, insulin-positive endocrine cells into SC-β cells, wherein the SC-β cells exhibit a GSIS response in vitro and/or in vivo. In some embodiments, the GSIS response resembles the GSIS response of an endogenous mature β cells.

In some aspects, the disclosure provides a method of generating SC-β cells from pluripotent cells, the method comprising: a) differentiating at least some pluripotent cells in a population into Pdx1-positive pancreatic progenitor cells; b) differentiating at least some of the Pdx1-positive pancreatic progenitor cells into Pdx1-positive, NKX6-1-positive pancreatic progenitor cells by a process of contacting the Pdx1-positive pancreatic progenitor cells under conditions that promote cell clustering with i) KGF, ii) Sant1, and optionally iii) low concentrations of RA, every other day for a period of five days to induce the differentiation of at least one Pdx1-positive pancreatic progenitor cell in the population into NKX6-1-positive pancreatic progenitor cells, wherein the NKX6-1-positive pancreatic progenitor cells expresses Pdx1 and NKX6-1; c) differentiating at least some of the Pdx1-positive, NKX6-1-positive pancreatic progenitor cells into Pdx1-positive, NKX6-1-positive, insulin-positive endocrine cells by a process of contacting the Pdx1-positive, NKX6-1-positive pancreatic progenitor cells with i) Alk5 Inhibitor II, ii) T3, and optionally iii) Sant1, iv) RA, v) XXI, and vi) betacellulin, every other day for a period of between five and seven days to induce the differentiation of at least some of the Pdx1-positive, NKX6-1-positive pancreatic progenitor cells into Pdx1-positive, NKX6-1, insulin-positive endocrine cells, wherein the Pdx1-positive, NKX6-1, insulin-positive endocrine cells express Pdx1, NKX6-1, NKX2-2, Math, glis3, Sur1, Kir6.2, Znt8, SLC2A1, SLC2A3 and/or insulin; and d) differentiating at least some of the Pdx1-positive, NKX6-1-positive, insulin-positive endocrine cells into SC-β cells by a process of contacting the Pdx1-positive, NKX6-1-positive, insulin-positive endocrine cells under conditions that promote cell clustering with i) Alk5 inhibitor II, ii) T3, and optionally iii) staurosporine, every other day for a period of between seven and 14 days to induce the in vitro maturation of at least some of the Pdx1-positive, NKX6-1-positive, insulin-producing endocrine cells into SC-β cells, wherein the SC-β cells exhibit a GSIS response in vitro and in vivo that resemble the GSIS response of an endogenous β cell.

Generally, the Pdx1-positive, NKX6-1-positive, insulin-positive endocrine cells are maintained in a suitable culture medium for a period of time sufficient to induce the in vitro maturation of at least some of the Pdx1-positive, NKX6-1-positive, insulin-positive endocrine cells into SC-β cells. Exemplary suitable culture media are shown above in Table 4 and below in Table 5.

TABLE 5

| CMRL Islet Media ("CMRLS") |
| --- |
| CMRL 1066 Supplemented cat#99-603-CV Mediatech We supplement with 10% Hyclone FBS |

In some embodiments, the suitable culture medium comprises Connought Medical Research Laboratories 1066 supplemented islet media (CMRLS). In some embodiments, the suitable culture medium comprises a component of CMRLS (e.g., supplemental zinc). In some embodiments, the suitable culture medium is shown in Table 3. In some embodiments, the CMRLS is supplemented with serum (e.g., human). In some embodiments, the CMRLS is supplemented with serum replacements (e.g., KOSR). In some embodiments, the CMRLS is supplemented with fetal bovine serum. In some embodiments, the CMRLS is supplemented with 10% fetal bovine serum. In some embodiments, a suitable culture medium for differentiating insulin-positive endocrine cells into SC-β cells comprises S3 media. In some embodiments, conditions that promote cell clustering comprise a suspension culture. In some embodiments, the period of time comprises at least 7 days. In some embodiments, the period of time comprises between 7 days and 21 days. In some embodiments, the period of time comprises between 7 and 14 days. In some embodiments, the period of time comprises between 10 and 14 days. In some embodiments, the period of time comprises 14 days. In some embodiments, the suspension culture is replenished every other day (e.g., with the β cell-maturation factors).

In some embodiments, at least 1%, at least 2%, at least 3%, at least 4%, at least 5%, at least 6%, at least 7%, at least 8%, at least 9%, at least 10%, at least 20%, at least 30%, at least 40%, at least 50% of the Pdx1-positive, NKX6-1-positive, insulin-positive endocrine cells are induced to mature into SC-β cells. In some embodiments, at least at least 60%, at least 70%, at least 80%, at least 90%, at least 99% of the Pdx1-positive, NKX6-1-positive, insulin-positive endocrine cells are induced to mature into SC-β cells. In some embodiments, at least 30% of the cells generated comprise SC-β cells. In some embodiments, the SC-β cells express C-peptide, insulin, NKX6-1, Pdx1, and co-express NKX6-1 and C-peptide.

In some embodiments, the SC-β cells comprise human cells. In some embodiments, generation of the SC-β cells in vitro is scalable.

Isolated Populations of Cells

Aspects of the disclosure relate to isolated populations of cells produced according to a method described herein. In some embodiments, a population of SC-β cells are produced by contacting at least one insulin-positive endocrine cell or precursor thereof with at least one β cell maturation factors described herein. In some embodiments, a population of SC-β cells are produced by contacting at least one insulin-positive endocrine cell or precursor thereof with at least two β cell maturation factors described herein. In some embodiments, a population of SC-β cells are produced by contacting at least one insulin-positive endocrine cell or precursor thereof with at least three β cell maturation factors described herein. In some embodiments, a population of SC-β cells are produced by contacting at least one insulin-positive endocrine cell or precursor thereof with at least four β cell maturation factors described herein. In some embodiments, a population of SC-β cells are produced by contacting at least one insulin-positive endocrine cell or precursor thereof with at least five β cell maturation factors described herein. In some embodiments, a population of SC-β cells are produced by contacting at least one insulin-positive endocrine cell or precursor thereof with at least six, at least seven, at least eight, at least nine, or at least ten β cell maturation factors described herein.

In some aspects, the disclosure provides an isolated population of definitive endoderm cells. An isolated population of definitive endoderm cells can be obtained by differentiating at least some pluripotent cells in a population into definitive endoderm cells, e.g., by a process of contacting a population of pluripotent cells with i) at least one growth factor from the TGF-β superfamily, and ii) a Wnt signaling pathway activator, to induce the differentiation of at least some of the pluripotent cells in the population into definitive endoderm cells, wherein the definitive endoderm cells express at least one marker characteristic of definitive endoderm.

In some aspects, the disclosure provides an isolated population of primitive gut tube cells. An isolated population of primitive gut tube cells can be obtained by differentiating at least some definitive endoderm cells in a population into primitive gut tube cells, e.g., by a process of contacting the definitive endoderm cells with at least one growth factor from the fibroblast growth factor (FGF) family, to induce the differentiation of at least some of the definitive endoderm cells into primitive gut tube cells, wherein the primitive gut tube cells express at least one marker characteristic of definitive endoderm.

In some aspects, the disclosure provides an isolated population of Pdx1-positive pancreatic progenitor cells. An isolated population of Pdx1-positive pancreatic progenitor cells can be obtained by differentiating at least some primitive gut tube cells in a population into Pdx1-positive pancreatic progenitor cells, e.g., by a process of contacting the primitive gut tube cells with i) at least one bone morphogenic protein (BMP) signaling pathway inhibitor, ii) at least one growth factor from the FGF family, iii) at least one SHH pathway inhibitor, iv) at least one retinoic acid (RA) signaling pathway activator; and v) at least one protein kinase C activator, to induce the differentiation of at least some of the primitive gut tube cells into Pdx1-positive pancreatic progenitor cells, wherein the Pdx1-positive pancreatic progenitor cells express Pdx1.

In some aspects, the disclosure provides an isolated population of NKX6-1-positive pancreatic progenitor cells. An isolated population of NKX6-1-positive pancreatic progenitor cells can be obtained by differentiating at least some Pdx1-positive pancreatic progenitor cells in a population into Pdx1-positive, NKX6-1-positive pancreatic progenitor cells, e.g., by a process of contacting the Pdx1-positive pancreatic progenitor cells with i) at least one growth factor from the FGF family, ii) at least one SHH pathway inhibitor, and optionally iii) a RA signaling pathway activator, to induce the differentiation of at least one Pdx1-positive pancreatic progenitor cell in the population into NKX6-1-positive pancreatic progenitor cells, wherein the NKX6-1-positive pancreatic progenitor cells expresses Pdx1 and NKX6-1.

In some aspects, the disclosure provides an isolated population of insulin-positive endocrine cells. An isolated population of insulin-positive endocrine cells can be obtained by differentiating at least some Pdx1-positive, NKX6-1-positive pancreatic progenitor cells in a population into Pdx1-positive, NKX6-1-positive, insulin-positive endocrine cells, e.g., by a process of contacting the Pdx1-positive, NKX6-1-positive pancreatic progenitor cells with i) a TGF-β) signaling pathway inhibitor, ii) a TH signaling pathway activator, and optionally at least one additional β cell-maturation factor selected from the group consisting of i) at least one SHH pathway inhibitor, ii) a RA signaling pathway activator, iii) a γ-secretase inhibitor, iv) and vi) at least one growth factor from the epidermal growth factor (EGF) family, to induce the differentiation of at least some of the Pdx1-positive, NKX6-1-positive pancreatic progenitor cells into Pdx1-positive, NKX6-1, insulin-positive endocrine cells, wherein the Pdx1-positive, NKX6-1, insulin-positive endocrine cells express Pdx1, NKX6-1, NKX2-2, Math, glis3, Sur1, Kir6.2, Znt8, SLC2A1, SLC2A3 and/or insulin.

In some aspects, the disclosure provides an isolated population of SC-β cells. An isolated population of SC-β cells can be obtained by differentiating at least some Pdx1-positive, NKX6-1-positive, insulin-positive endocrine cells in a population into SC-β cells, e.g., by a process of contacting the Pdx1-positive, NKX6-1-positive, insulin-positive endocrine cells with i) a transforming growth factor β (TGF-β) signaling pathway inhibitor, ii) a thyroid hormone signaling pathway activator, and optionally iii) a protein kinase inhibitor, to induce the in vitro maturation of at least some of the Pdx1-positive, NKX6-1-positive, insulin-positive endocrine cells into SC-β cells, wherein the SC-β cells exhibit a GSIS response in vitro and/or in vivo. In some embodiments, the GSIS response resembles the GSIS response of an endogenous β cell.

Aspects of the disclosure involve microcapsules comprising isolated populations of cells described herein (e.g., SC-β cells). Microcapsules are well known in the art. Suitable examples of microcapsules are described in the literature (e.g., Jahansouz et al., "Evolution of β-Cell Replacement Therapy in Diabetes Mellitus: Islet Cell Transplantation" *Journal of Transplantation* 2011; Volume 2011, Article ID 247959; Orive et al., "Application of cell encapsulation for controlled delivery of biological therapeutics", *Advanced Drug Delivery Reviews* (2013), available on the worldwide web at subdomain dx.doi.org/10.1016/jaddr.2013.07.009; Hernandez et al., "Microcapsules and microcarriers for in situ cell delivery", *Advanced Drug Delivery Reviews* 2010; 62:711-730; Murua et al., "Cell microencapsulation technology: Towards clinical application", *Journal of Controlled Release* 2008; 132:76-83; and Zanin et al., "The development of encapsulated cell technologies as therapies for neurological and sensory diseases", *Journal of Controlled Release* 2012; 160:3-13). Microcapsules can be formulated in a variety of ways. Exemplary microcapsules comprise an alginate core surrounded by a polycation layer covered by an outer alginate membrane. The polycation membrane forms a semipermeable membrane, which imparts stability and biocompatibility. Examples of polycations include, without limitation, poly-L-lysine, poly-L-ornithine, chitosan, lactose modified chitosan, and photopolymerized biomaterials. In some embodiments, the alginate core is modified, for example, to produce a scaffold comprising an alginate core having covalently conjugated oligopeptides with an RGD sequence (arginine, glycine, aspartic acid). In some embodiments, the alginate core is modified, for example, to produce a covalently reinforced microcapsule having a chemoenzymatically engineered alginate of enhanced stability. In some embodiments, the alginate core is modified, for example, to produce membrane-mimetic films assembled by in-situ polymerization of acrylate functionalized phospholipids. In some embodiments, microcapsules are composed of enzymatically modified alginates using epimerases. In some embodiments, microcapsules comprise covalent links between adjacent layers of the microcapsule membrane. In some embodiment, the microcapsule comprises a subsieve-size capsule comprising aliginate coupled with phenol moieties. In some embodiments, the microcapsule comprises a scaffold comprising alginate-agarose. In some embodiments, the SC-β cell is modified with PEG before being encapsulated within alginate. In some embodiments, the isolated populations of cells, e.g., SC-β cells are encapsulated in photoreactive liposomes and alginate. It should be appreciate that the alginate employed in the microcapsules can be replaced with other suitable biomaterials, including, without limitation, PEG, chitosan, PES hollow fibers, collagen, hyaluronic acid, dextran with RGD, EHD and PEGDA, PMBV and PVA, PGSAS, agarose, agarose with gelatin, PLGA, and multilayer embodiments of these.

In some embodiments, compositions comprising populations of cells produced according to the methods described herein can also be used as the functional component in a mechanical device designed to produce one or more of the endocrine polypeptides of pancreatic islet cells. In its simplest form, the device contains a population of pancreatic beta cells (e.g., produced from populations of insulin-positive endocrine cells or precursors thereof) behind a semipermeable membrane that prevents passage of the cell population, retaining them in the device, but permits passage of insulin, glucagon, or somatostatin secreted by the cell population. This includes populations of pancreatic beta cells that are microencapsulated, typically in the form of cell clusters to permit the cell interaction that inhibits dedifferentiation. For example, U.S. Pat. No. 4,391,909 describe islet cells encapsulated in a spheroid semipermeable membrane made up of polysaccharide polymers >3,000 mol. wt. that are cross-linked so that it is permeable to proteins the size of insulin, but impermeable to molecules over 100,000 mol. wt. U.S. Pat. No. 6,023,009 describes islet cells encapsulated in a semipermeable membrane made of agarose and agaropectin. Microcapsules of this nature are adapted for administration into the body cavity of a diabetic patient, and are thought to have certain advantages in reducing histocompatibility problems or susceptibility to bacteria.

More elaborate devices are also contemplated for use to comprise a population of pancreatic beta cells produced from insulin-positive endocrine cells or precursors thereof according to the methods described herein, either for implantation into diabetic patients, or for extracorporeal therapy. U.S. Pat. No. 4,378,016 describes an artificial endocrine gland containing an extracorporeal segment, a subcutaneous segment, and a replaceable envelope containing the hormone-producing cells. U.S. Pat. No. 5,674,289 describes a bioartificial pancreas having an islet chamber, separated by a semipermeable membrane to one or more vascularizing chambers open to surrounding tissue. Useful devices typically have a chamber adapted to contain the islet cells, and a chamber separated from the islet cells by a semipermeable membrane which collects the secreted proteins from the islet cells, and which may also permit signaling back to the islet cells, for example, of the circulating glucose level.

Aspects of the disclosure involve assays comprising isolated populations of cells described herein (e.g., SC-β cells). In some embodiments, the assays can be used for identifying one or more candidate agents which promote or inhibit a β cell fate selected from the group consisting of β cell proliferation, β cell replication, and β cell death, β cell function, β cell susceptibility to immune attack, or β cell susceptibility to dedifferentiation or differentiation. In some embodiments, the assays can be used for identifying one or more candidate agents which promote the differentiation of at least one insulin-positive endocrine cell or a precursor thereof into SC-β cells. In some embodiments, the assays can be used for identifying one or more candidate agents which stimulate β cells to produce insulin or increase production or secretion of insulin.

The disclosure contemplates methods in which SC-β cells are generated according to the methods described herein from iPS cells derived from cells extracted or isolated from individuals suffering from a disease (e.g., diabetes, obesity, or a β cell-related disorder), and those SC-β cells are compared to normal β cells from healthy individuals not having the disease to identify differences between the SC-β cells and normal β cells which could be useful as markers for disease (e.g., epigenetic and/or genetic). In some embodiments, β cells are obtained from a diabetic individual and compared to normal β cells, and then the β cells are reprogrammed to iPS cells and the iPS cells are analyzed for genetic and/or epigenetic markers which are present in the β cells obtained from the diabetic individual but not present in the normal β cells, to identify markers (e.g., pre-diabetic). In some embodiments, the iPS cells and/or SC-β derived from diabetic patients are used to screen for agents (e.g., agents which are able to modulate genes contributing to a diabetic phenotype).

Methods of Differentiation of Insulin-Positive Endocrine Cells to SC-β Cells

Generating SC-β cells by conversion of at least one insulin-positive endocrine cell or a precursor thereof using the methods of the disclosure has a number of advantages. First, the methods of the disclosure allow one to generate autologous SC-β cells, which are cells specific to and genetically matched with an individual. In general, autologous cells are less likely than non-autologous cells to be subject to immunological rejection. The cells are derived from at least one insulin-positive endocrine cell or a precursor thereof, e.g., a pancreatic progenitor obtained by reprogramming a somatic cell (e.g., a fibroblast) from the individual to an induced pluripotent state, and then culturing the pluripotent cells to differentiate at least some of the pluripotent cells to at least one insulin-positive endocrine cell or a precursor thereof, followed by transplantation of the at least one insulin-positive endocrine cell or precursor thereof into the individual such that the at least one insulin-positive endocrine cell or precursor thereof matures in vivo into a SC-β cell, or induced maturation in vitro of the at least one insulin-positive endocrine cell into a SC-β cell.

In some embodiments, a subject from which at least one insulin-positive endocrine cell or precursor thereof are obtained is a mammalian subject, such as a human subject. In some embodiments, the subject is suffering from a β cell disorder. In some embodiments, the subject is suffering from diabetes. In some embodiments, the subject is suffering from prediabetes. In such embodiments, the at least one insulin-positive endocrine cell or precursor thereof can be differentiated into a SC-β cell ex vivo by the methods as described herein and then administered to the subject from which the cells were harvested in a method to treat the subject for the β cell disorder (e.g., diabetes).

In some embodiments, at least one insulin-positive endocrine cell or a precursor thereof is located within a subject (in vivo) and is converted to become a SC-β cell by the methods as disclosed herein in vivo. In some embodiments, conversion of at least one insulin-positive endocrine cell or a precursor thereof to a SC-β cell in vivo can be achieved by administering to a subject a composition comprising at least one, at least two, at least three, at least four, at least five, or at least six, or more β cell maturation factors as described herein. In some embodiments, conversion of at least one insulin-positive endocrine cell or a precursor thereof to a SC-β cell in vivo can be achieved by administering to a subject a composition comprising at least one, at least two, at least three, at least four, at least five, or at least six β cell maturation factors as described herein.

In some embodiments, contacting may be performed by maintaining the at least one insulin-positive endocrine cell or a precursor thereof in culture medium comprising the one or more β cell maturation factors. In some embodiments at least one insulin-positive endocrine cell or a precursor thereof can be genetically engineered. In some embodiments, at least one insulin-positive endocrine cell or a precursor thereof can be genetically engineered to express one or more β cell markers as disclosed herein, for example express at least one a polypeptide selected from pancreatic and duodenal homeobox 1 (PDX-1) polypeptide, insulin, c-peptide, amylin, E-cadherin, Hnf3β, PCI/3, B2, Nkx2.2, NKX6-1, GLUT2, PC2, ZnT-8, or an amino acid sequences substantially homologous thereof, or functional fragments or functional variants thereof.

Where the at least one insulin-positive endocrine cell or a precursor thereof is maintained under in vitro conditions, conventional tissue culture conditions and methods can be used, and are known to those of skill in the art. Isolation and culture methods for various cells are well within the abilities of one skilled in the art.

In the methods of the disclosure at least one insulin-positive endocrine cell or a precursor thereof can, in general, be cultured under standard conditions of temperature, pH, and other environmental conditions, e.g., as adherent cells in tissue culture plates at 37° C. in an atmosphere containing 5-10% CO2. The cells and/or the culture medium are appropriately modified to achieve conversion to SC-β cells as described herein. In certain embodiments, at least one insulin-positive endocrine cell or a precursor thereof, e.g., a pancreatic progenitor can be cultured on or in the presence of a material that mimics one or more features of the extracellular matrix or comprises one or more extracellular matrix or basement membrane components. In some embodiments MATRIGEL™ is used. Other materials include proteins or mixtures thereof such as gelatin, collagen, fibronectin, etc. In certain embodiments of the invention, at least one insulin-positive endocrine cell or a precursor thereof can be cultured in the presence of a feeder layer of cells. Such cells may, for example, be of murine or human origin. They can also be irradiated, chemically inactivated by treatment with a chemical inactivator such as mitomycin c, or otherwise treated to inhibit their proliferation if desired. In other embodiments at least one insulin-positive endocrine cell or a precursor thereof are cultured without feeder cells. In some embodiments, the insulin-positive endocrine cells or precursors thereof are cultured in conditions that promote cell clustering. As used herein, "conditions that promote cell clustering" refers to any condition which stimulates the clustering of cells during differentiation of the cells toward SC-β cells. In some embodiments, conditions that promote cell clustering comprise a suspension culture. Boretti and Gooch (Tissue Eng. 2006 April; 12(4):939-48) report that culture in least adherent conditions (low-serum medium, low-adherent substrate) stimulated cell clustering in the transdifferentiation of adult pancreatic ductal epithelial cells to beta cells in vitro. Accordingly, without wishing to be bound by theory, in some embodiments, conditions that promote cell clustering comprise minimally adherent conditions, e.g., low-serum medium, low-adherent substrate.

In certain examples, the β cell maturation factors can be used to induce the differentiation of at least one insulin-positive endocrine cell or precursor thereof by exposing or contacting at least one insulin-positive endocrine cell or precursor thereof with an effective amount of a β cell maturation factor described herein to differentiate the at least one insulin-positive endocrine cell or precursor thereof into at least one SC-β cell (e.g., a mature pancreatic β cell).

Accordingly, included herein are cells and compositions made by the methods described herein. The exact amount and type of β cell maturation factor can vary depending on the number of insulin-positive endocrine cells or precursors thereof, the desired differentiation stage and the number of prior differentiation stages that have been performed.

In certain examples, a β cell maturation factor is present in an effective amount. As used herein, "effective amount" refers to the amount of the compound that should be present for the differentiation of at least 10% or at least 20% or at least 30% of the cells in a population of insulin-positive endocrine cells or precursors thereof into SC-β cells.

In additional examples, β cell maturation factors can be present in the culture medium of the at least one insulin-positive endocrine cell or precursor thereof, or alternatively, the β cell maturation factors may be added to the at least one insulin-positive endocrine cell or precursor thereof during some stage of growth.

Confirmation of the Presence and the Identification of Cells SC-β Cells

One can use any means common to one of ordinary skill in the art to confirm the presence of a SC-β cell, e.g. a mature pancreatic β cell produced the induction of the differentiation of at least one insulin-positive endocrine cell or precursor thereof by exposure to at least one β cell maturation factor as described herein.

In some embodiments, the presence of β cell markers, e.g. chemically induced SC-β cells, can be done by detecting the presence or absence of one or more markers indicative of an endogenous β cell. In some embodiments, the method can include detecting the positive expression (e.g. the presence) of a marker for mature β cells. In some embodiments, the marker can be detected using a reagent, e.g., a reagent for the detection of NKX6-1 and C-peptide. In particular, SC-β cells herein express NKX6-1 and C-peptide, and do not express significant levels of other markers which would be indicative of immature β cells (e.g., MafB). A reagent for a marker can be, for example, an antibody against the marker or primers for a RT-PCR or PCR reaction, e.g., a semi-quantitative or quantitative RT-PCR or PCR reaction. Such markers can be used to evaluate whether a SC-β cell has been produced. The antibody or other detection reagent can be linked to a label, e.g., a radiological, fluorescent (e.g., GFP) or colorimetric label for use in detection. If the detection reagent is a primer, it can be supplied in dry preparation, e.g., lyophilized, or in a solution.

The progression of at least one insulin-positive endocrine cell or precursor thereof to a SC-β cell can be monitored by determining the expression of markers characteristic of mature β cells. In some processes, the expression of certain markers is determined by detecting the presence or absence of the marker. Alternatively, the expression of certain markers can be determined by measuring the level at which the marker is present in the cells of the cell culture or cell population. In certain processes, the expression of markers characteristic of SC-β cells as well as the lack of significant expression of markers characteristic of the insulin-positive endocrine cells or precursors thereof, e.g., pluripotent stem cell or pancreatic progenitor cell from which it was derived is determined.

As described in connection with monitoring the production of a SC-β cell (e.g., a mature pancreatic β cell) from an insulin-positive endocrine cell, qualitative or semi-quantitative techniques, such as blot transfer methods and immunocytochemistry, can be used to measure marker expression, using methods commonly known to persons of ordinary skill in the art. Alternatively, marker expression can be accurately quantitated through the use of technique such as quantitative-PCR by methods ordinarily known in the art. Additionally, it will be appreciated that at the polypeptide level, many of the markers of pancreatic islet hormone-expressing cells are secreted proteins. As such, techniques for measuring extracellular marker content, such as ELISA, may be utilized.

SC-β cells can also be characterized by the down-regulation of markers characteristic of the pluripotent stem from which the SC-β cell is induced from. For example, SC-β cells derived from pluripotent stem cell may be characterized by a statistically significant down-regulation of the pluripotent stem cell markers alkaline phosphatase (AP), NANOG, OCT-4, SOX-2, SSEA4, TRA-1-60 or TRA-1-81 in the mature relative to the expression in the pluripotent stem cell from which it was derived. Other markers expressed by pluripotent cell markers, include but are not limited to alkaline phosphatase (AP); ABCG2; stage specific embryonic antigen-1 (SSEA-1); SSEA-3; SSEA-4; TRA-1-60; TRA-1-81; Tra-2-49/6E; ERas/ECATS, E-cadherin; βIII-tubulin; α-smooth muscle actin (α-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPAS/ECAT2; ECAT3; ECAT6; ECAT7; ECAT8; ECAT9; ECAT10; ECAT15-1; ECAT15-2; Fth117; Sa114; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tcl1); DPPA3/Stella; DPPA4; Dnmt3L; Sox15; Stat3; Grb2; SV40 Large T Antigen; HPV16 E6; HPV16 E7, β-catenin, and Bmi1 and other general markers for pluripotency, etc, and at least one or more of these are down regulated by a statistically significant amount in a mature as compared to the pluripotent stem cell from which they were derived.

It is understood that the present invention is not limited to those markers listed as mature β cell markers herein, and the present invention also encompasses markers such as cell surface markers, antigens, and other gene products including ESTs, RNA (including microRNAs and antisense RNA), DNA (including genes and cDNAs), and portions thereof.

Enrichment, Isolation and Purification of a SC-β Cell

Another aspect of the present invention relates to the isolation of a population of SC-β cells from a heterogeneous population of cells, such a mixed population of cells comprising SC-β cells and insulin-positive endocrine cells or precursors thereof from which the SC-β cells were derived. A population of SC-β cells produced by any of the above-described processes can be enriched, isolated and/or purified by using any cell surface marker present on the SC-β cells which is not present on the insulin-positive endocrine cell or precursor thereof from which it was derived. Such cell surface markers are also referred to as an affinity tag which is specific for a SC-β cell. Examples of affinity tags specific for SC-β cells are antibodies, ligands or other binding agents that are specific to a marker molecule, such as a polypeptide, that is present on the cell surface of a SC-β cells but which is not substantially present on other cell types (e.g. insulin-positive endocrine cells or precursors thereof). In some processes, an antibody which binds to a cell surface antigen on a SC-β cell (e.g. a human SC-β cell) is used as an affinity tag for the enrichment, isolation or purification of chemically induced (e.g. by contacting with at least one β cell maturation factor as described herein) SC-β cells produced by the methods described herein. Such antibodies are known and commercially available.

The skilled artisan will readily appreciate the processes for using antibodies for the enrichment, isolation and/or purification of SC-β cell. For example, in some embodiments, the reagent, such as an antibody, is incubated with a cell population comprising SC-β cells, wherein the cell population has been treated to reduce intercellular and substrate adhesion. The cell population are then washed, centrifuged and resuspended. In some embodiments, if the antibody is not already labeled with a label, the cell suspension is then incubated with a secondary antibody, such as an FITC-conjugated antibody that is capable of binding to the primary antibody. The SC-β cells are then washed, centrifuged and resuspended in buffer. The SC-β cell suspension is then analyzed and sorted using a fluorescence activated cell sorter (FACS). Antibody-bound, fluorescent reprogrammed cells are collected separately from non-bound, non-fluorescent cells (e.g. immature, insulin-producing cells), thereby resulting in the isolation of SC-β cells from other cells present in the cell suspension, e.g. insulin-positive endocrine cells or precursors thereof, or immature, insulin-producing cell (e.g. other differentiated cell types).

In another embodiment of the processes described herein, the isolated cell composition comprising SC-β cells can be further purified by using an alternate affinity-based method or by additional rounds of sorting using the same or different markers that are specific for SC-β cells. For example, in some embodiments, FACS sorting is used to first isolate a SC-β cell which expresses NKX6-1, either alone or with the expression of C-peptide, or alternatively with a β cell marker disclosed herein from cells that do not express one of those markers (e.g. negative cells) in the cell population. A second FAC sorting, e.g. sorting the positive cells again using FACS to isolate cells that are positive for a different marker than the first sort enriches the cell population for reprogrammed cells.

In an alternative embodiment, FACS sorting is used to separate cells by negatively sorting for a marker that is present on most insulin-positive endocrine cells or precursors thereof but is not present on SC-β cells.

In some embodiments of the processes described herein, SC-β cells are fluorescently labeled without the use of an antibody then isolated from non-labeled cells by using a fluorescence activated cell sorter (FACS). In such embodiments, a nucleic acid encoding GFP, YFP or another nucleic acid encoding an expressible fluorescent marker gene, such as the gene encoding luciferase, is used to label reprogrammed cells using the methods described above. For example, in some embodiments, at least one copy of a nucleic acid encoding GFP or a biologically active fragment thereof is introduced into at least one insulin-positive endocrine cell which is first chemically induced into a SC-β cell, where a downstream of a promoter expressed in SC-β cell, such as the insulin promoter, such that the expression of the GFP gene product or biologically active fragment thereof is under control of the insulin promoter.

In addition to the procedures just described, chemically induced SC-β cells may also be isolated by other techniques for cell isolation. Additionally, SC-β cells may also be enriched or isolated by methods of serial subculture in growth conditions which promote the selective survival or selective expansion of the SC-β cells. Such methods are known by persons of ordinary skill in the art, and may include the use of agents such as, for example, insulin, members of the TGF-beta family, including Activin A, TGF-beta1, 2, and 3, bone morphogenic proteins (BMP-2, -3, -4, -5, -6, -7, -11, -12, and -13), fibroblast growth factors-1 and -2, platelet-derived growth factor-AA, and -BB, platelet rich plasma, insulin-like growth factors (IGF-I, II) growth differentiation factor (GDF-5, -6, -7, -8, -10, -11, -15), vascular endothelial cell-derived growth factor (VEGF), Hepatocyte growth factor (HGF), pleiotrophin, endothelin, Epidermal growth factor (EGF), beta-cellulin, among others. Other pharmaceutical compounds can include, for example, nicotinamide, glucagon like peptide-I (GLP-1) and II, GLP-1 and 2 mimetibody, Exendin-4, retinoic acid, parathyroid hormone.

Using the methods described herein, enriched, isolated and/or purified populations of SC-β cells can be produced in vitro from insulin-positive endocrine cells or precursors thereof (which were differentiated from pluripotent stem cells by the methods described herein). In some embodiments, preferred enrichment, isolation and/or purification methods relate to the in vitro production of human SC-β cell from human insulin-positive endocrine cells or precursors thereof, which were differentiated from human pluripotent stem cells, or from human induced pluripotent stem (iPS) cells. In such an embodiment, where SC-β cells are differentiated from insulin-positive endocrine cells, which were previously derived from definitive endoderm cells, which were previously derived from iPS cells, the SC-β cell can be autologous to the subject from whom the cells were obtained to generate the iPS cells.

Using the methods described herein, isolated cell populations of SC-β cells are enriched in SC-β cell content by at least about 2- to about 1000-fold as compared to a population of cells before the chemical induction of the insulin-positive endocrine cell or precursor population. In some embodiments, SC-β cells can be enriched by at least about 5- to about 500-fold as compared to a population before the chemical induction of an insulin-positive endocrine cell or precursor population. In other embodiments, SC-β cells can be enriched from at least about 10- to about 200-fold as compared to a population before the chemical induction of insulin-positive endocrine cell or precursor population. In still other embodiments, SC-β cell can be enriched from at least about 20- to about 100-fold as compared to a population before the chemical induction of insulin-positive endocrine cell or precursor population. In yet other embodiments, SC-β cell can be enriched from at least about 40- to about 80-fold as compared to a population before the chemical induction of insulin-positive endocrine cell or precursor population. In certain embodiments, SC-β cell can be enriched from at least about 2- to about 20-fold as compared to a population before the chemical induction of insulin-positive endocrine cell or precursor population.

Compositions Comprising SC-β Cells

Some embodiments of the present invention relate to cell compositions, such as cell cultures or cell populations, comprising SC-β cells, wherein the SC-β cells have been derived from at least one insulin-positive endocrine cell or a precursor thereof. In some embodiments, the cell compositions comprise insulin-positive endocrine cells. In some embodiments, the cell compositions comprise NKX6-1-pancreatic progenitor cells. In some embodiments, the cell compositions comprise Pdx1-pancreatic progenitor cells. In some embodiments, the cell compositions comprise primitive gut tube cells. In some embodiments, the cell compositions comprise definitive endoderm cells.

In accordance with certain embodiments, the chemically induced SC-β cells are mammalian cells, and in a preferred embodiment, such SC-β cells are human SC-β cells. In some embodiments, the insulin-positive endocrine cells have been derived from definitive endoderm cells e.g. human definitive endoderm stem cells. In accordance with certain embodiments, the chemically induced Pdx1-positive pancreatic progenitors are mammalian cells, and in a preferred embodiment, such Pdx1-positive pancreatic progenitors are human Pdx1-positive pancreatic progenitors.

Other embodiments of the present invention relate to compositions, such as an isolated cell population or cell culture, comprising SC-β cells produced by the methods as disclosed herein. In some embodiments of the present invention relate to compositions, such as isolated cell populations or cell cultures, comprising chemically-induced SC-β cells produced by the methods as disclosed herein. In such embodiments, the SC-β cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the SC-β cells population. In some embodiments, the composition comprises a population of SC-β cells which make up more than about 90% of the total cells in the cell population, for example about at least 95%, or at least 96%, or at least 97%, or at least 98% or at least about 99%, or about at least 100% of the total cells in the cell population are SC-β cells.

Certain other embodiments of the present invention relate to compositions, such as an isolated cell population or cell cultures, comprise a combination of SC-β cells and insulin-positive endocrine cells or precursors thereof from which the SC-β cells were derived. In some embodiments, the insulin-positive endocrine cells from which the SC-β cells are derived comprise less than about 25%, less than about 20%, less than about 15%, less than about 10%, less than about 5%, less than about 4%, less than about 3%, less than about 2% or less than about 1% of the total cells in the isolated cell population or culture.

Additional embodiments of the present invention relate to compositions, such as isolated cell populations or cell cultures, produced by the processes described herein and which comprise chemically induced SC-β cells as the majority cell type. In some embodiments, the methods and processes described herein produces an isolated cell culture and/or cell populations comprising at least about 99%, at least about 98%, at least about 97%, at least about 96%, at least about 95%, at least about 94%, at least about 93%, at least about 92%, at least about 91%, at least about 90%, at least about 89%, at least about 88%, at least about 87%, at least about 86%, at least about 85%, at least about 84%, at least about 83%, at least about 82%, at least about 81%, at least about 80%, at least about 79%, at least about 78%, at least about 77%, at least about 76%, at least about 75%, at least about 74%, at least about 73%, at least about 72%, at least about 71%, at least about 70%, at least about 69%, at least about 68%, at least about 67%, at least about 66%, at least about 65%, at least about 64%, at least about 63%, at least about 62%, at least about 61%, at least about 60%, at least about 59%, at least about 58%, at least about 57%, at least about 56%, at least about 55%, at least about 54%, at least about 53%, at least about 52%, at least about 51% or at least about 50% SC-β cells.

In another embodiment, isolated cell populations or compositions of cells (or cell cultures) comprise human SC-β cells. In other embodiments, the methods and processes as described herein can produce isolated cell populations comprising at least about 50%, at least about 45%, at least about 40%, at least about 35%, at least about 30%, at least about 25%, at least about 24%, at least about 23%, at least about 22%, at least about 21%, at least about 20%, at least about 19%, at least about 18%, at least about 17%, at least about 16%, at least about 15%, at least about 14%, at least about 13%, at least about 12%, at least about 11%, at least about 10%, at least about 9%, at least about 8%, at least about 7%, at least about 6%, at least about 5%, at least about 4%, at least about 3%, at least about 2% or at least about 1% SC-β cells. In preferred embodiments, isolated cell populations can comprise human SC-β cells. In some embodiments, the percentage of SC-β cells in the cell cultures or populations is calculated without regard to the feeder cells remaining in the culture.

Still other embodiments of the present invention relate to compositions, such as isolated cell populations or cell cultures, comprising mixtures of SC-β cells and insulin-positive endocrine cells or precursors thereof from which they were differentiated from. For example, cell cultures or cell populations comprising at least about 5 SC-β cells for about every 95 insulin-positive endocrine cells or precursors thereof can be produced. In other embodiments, cell cultures or cell populations comprising at least about 95 SC-β cells for about every 5 insulin-positive endocrine cells or precursors thereof can be produced. Additionally, cell cultures or cell populations comprising other ratios of SC-β cells to insulin-positive endocrine cells or precursors thereof are contemplated. For example, compositions comprising at least about 1 SC-β cell for about every 1,000,000, or at least 100,000 cells, or a least 10,000 cells, or at least 1000 cells or 500, or at least 250 or at least 100 or at least 10 insulin-positive endocrine cells or precursors thereof can be produced.

Further embodiments of the present invention relate to compositions, such as cell cultures or cell populations, comprising human cells, including human SC-β cell which displays at least one characteristic of an endogenous β cell.

In preferred embodiments of the present invention, cell cultures and/or cell populations of SC-β cells comprise human SC-β cells that are non-recombinant cells. In such embodiments, the cell cultures and/or cell populations are devoid of or substantially free of recombinant human SC-β cells.

β Cell Maturation Factors

Aspects of the disclosure involve contacting insulin-positive endocrine cells or precursors thereof with β cell maturation factors, for example, to induce the maturation of the insulin-positive endocrine cells or differentiation of the precursors thereof into SC-β cells (e.g., mature pancreatic β cells). The term "β cell maturation factor" refers to an agent that promotes or contributes to conversion of at least one insulin-positive endocrine cell or a precursor thereof to a SC-β cell. In some embodiments, the β cell maturation factor induces the differentiation of pluripotent cells (e.g., iPSCs or hESCs) into definitive endoderm cells, e.g., in accordance with a method described herein. In some embodiments, the β cell maturation factor induces the differentiation of definitive endoderm cells into primitive gut tube cells, e.g., in accordance with a method described herein. In some embodiments, the β cell maturation factor induces the differentiation of primitive gut tube cells into Pdx1-positive pancreatic progenitor cells, e.g., in accordance with a method described herein. In some embodiments, the β cell maturation factor induces the differentiation of Pdx1-positive pancreatic progenitor cells into NKX6-1-positive pancreatic progenitor cells, e.g., in accordance with a method described herein. In some embodiments, the β cell maturation factor induces the differentiation of NKX6-1-positive pancreatic progenitor cells into insulin-positive endocrine cells, e.g., in accordance with a method described herein. In some embodiments, the β cell maturation factor induces the maturation of insulin-positive endocrine cells into SC-β cells, e.g., in accordance with a method described herein.

Generally, at least one β cell maturation factor described herein can be used alone, or in combination with other β cell maturation factors, to generate SC-β cells according to the methods as disclosed herein. In some embodiments, at least two, at least three, at least four, at least five, at least six, at least seven, at least eight, at least nine, or at least ten β cell maturation factors described herein are used in the methods of generating SC-β cells.

Transforming Growth Factor-β (TGF-β) Superfamily

Aspects of the disclosure relate to the use of growth factors from the transforming growth factor-β (TGF-β) superfamily as β cell maturation factors. The "TGF-β superfamily" means proteins having structural and functional characteristics of known TGFβ family members. The TGFβ family of proteins is well characterized, both from structural and functional aspects. It includes the TGFβ series of proteins, the Inhibins (including Inhibin A and Inhibin B), the Activins (including Activin A, Activin B, and Activin AB), MIS (Müllerian inhibiting substance), BMP (bone morphogenetic proteins), dpp (decapentaplegic), Vg-1, MNSF (monoclonal nonspecific suppressor factor), and others. Activity of this family of proteins is based on specific binding to certain receptors on various cell types. Members of this family share regions of sequence identity, particularly at the C-terminus, that correlate to their function. The TGFβ family includes more than one hundred distinct proteins, all sharing at least one region of amino acid sequence identity. Members of the family include, but are not limited to, the following proteins, as identified by their GenBank accession numbers: P07995, P18331, P08476, Q04998, P03970, P43032, P55102, P27092, P42917, P09529, P27093, P04088, Q04999, P17491, P55104, Q9WUK5, P55103, O88959, O08717, P58166, 061643, P35621, P09534, P48970, Q9NR23, P25703, P30884, P12643, P49001, P21274, O46564, O19006, P22004, P20722, Q04906, Q07104, P30886, P18075, P23359, P22003, P34821, P49003, Q90751, P21275, Q06826, P30885, P34820, Q29607, P12644, Q90752, 046576, P27539, P48969, Q26974, P07713, P91706, P91699, P27091, O42222, Q24735, P20863, O18828, P55106, Q9PTQ2, O14793, O08689, O42221, O18830, O18831, O18836, O35312, O42220, P43026, P43027, P43029, O95390, Q9R229, O93449, Q9Z1W4, Q9BDW8, P43028, Q7Z4P5, P50414, P17246, P54831, P04202, P01137, P09533, P18341, O19011, Q9Z1Y6, P07200, Q9Z217, O95393, P55105, P30371, Q9MZE2, Q07258, Q96S42, P97737, AAA97415.1, NP-776788.1, NP-058824.1, EAL24001.1, 1S4Y, NP-001009856.1, NP-032406.1, NP-999193.1, XP-519063.1, AAG17260.1, CAA40806.1, NP-001009458.1, AAQ55808.1, AAK40341.1, AAP33019.1, AAK21265.1, AAC59738.1, CAI46003.1, B40905, AAQ55811.1, AAK40342.1, XP-540364.1, P55102, AAQ55810.1, NP-990727.1, CAA51163.1, AAD50448.1, JC4862, PN0504, BAB17600.1, AAH56742.1, BAB17596.1, CAG06183.1, CAG05339.1, BAB17601.1, CAB43091.1, A36192, AAA49162.1, AAT42200.1, NP-789822.1, AAA59451.1, AAA59169.1, XP-541000.1, NP-990537.1, NP-002184.1, AAC14187.1, AAP83319.1, AAA59170.1, BAB16973.1, AAM66766.1, WFPGBB, 1201278C, AAH30029.1, CAA49326.1, XP-344131.1, AAH48845.1, XP-148966.3, 148235, B41398, AAH77857.1, AAB26863.1, 1706327A, BAA83804.1, NP-571143.1, CAG00858.1, BAB17599.1, BAB17602.1, AAB61468.1, PN0505, PN0506, CAB43092.1, BAB17598.1, BAA22570.1, BAB16972.1, BAC81672.1, BAA12694.1, BAA08494.1, B36192, C36192, BAB16971.1, NP-034695.1, AAA49160.1, CAA62347.1, AAA49161.1, AAD30132.1, CAA58290.1, NP-005529.1, XP-522443.1, AAM27448.1, XP-538247.1, AAD30133.1, AAC36741.1, AAH10404.1, NP-032408.1, AAN03682.1, XP-509161.1, AAC32311.1, NP-651942.2, AAL51005.1, AAC39083.1, AAH85547.1, NP-571023.1, CAF94113.1, EAL29247.1, AAW30007.1, AAH90232.1, A29619, NP-001007905.1, AAH73508.1, AAD02201.1, NP-999793.1, NP-990542.1, AAF19841.1, AAC97488.1, AAC60038.1, NP 989197.1, NP-571434.1, EAL41229.1, AAT07302.1, CAI19472.1, NP-031582.1, AAA40548.1, XP-535880.1, NP-037239.1, AAT72007.1, XP-418956.1, CAA41634.1, BAC30864.1, CAA38850.1, CAB81657.2, CAA45018.1, CAA45019.1, BAC28247.1, NP-031581.1, NP-990479.1, NP-999820.1, AAB27335.1, 545355, CAB82007.1, XP-534351.1, NP-058874.1, NP-031579.1, 1REW, AAB96785.1, AAB46367.1, CAA05033.1, BAA89012.1, 1ES7, AAP20870.1, BAC24087.1, AAG09784.1, BAC06352.1, AAQ89234.1, AAM27000.1, AAH30959.1, CAG01491.1, NP-571435.1, 1REU, AAC60286.1, BAA24406.1, A36193, AAH55959.1, AAH54647.1, AAH90689.1, CAG09422.1, BAD16743.1, NP-032134.1, XP-532179.1, AAB24876.1, AAH57702.1, AAA82616.1, CAA40222.1, CAB90273.2, XP-342592.1, XP-534896.1, XP-534462.1, 1LXI, XP-417496.1, AAF34179.1, AAL73188.1, CAF96266.1, AAB34226.1, AAB33846.1, AAT12415.1, AAO33819.1, AAT72008.1, AAD38402.1, BAB68396.1, CAA45021.1, AAB27337.1, AAP69917.1, AAT12416.1, NP-571396.1, CAA53513.1, AAO33820.1, AAA48568.1, BAC02605.1, BAC02604.1, BAC02603.1, BAC02602.1, BAC02601.1, BAC02599.1, BAC02598.1, BAC02597.1, BAC02595.1, BAC02593.1, BAC02592.1, BAC02590.1, AAD28039.1, AAP74560.1, AAB94786.1, NP-001483.2, XP-528195.1, NP-571417.1, NP-001001557.1, AAH43222.1, AAM33143.1, CAG10381.1, BAA31132.1, EAL39680.1, EAA12482.2, P34820, AAP88972.1, AAP74559.1, CAI16418.1, AAD30538.1, XP-345502.1, NP-038554.1, CAG04089.1, CAD60936.2, NP-031584.1, B55452, AAC60285.1, BAA06410.1, AAH52846.1, NP-031580.1, NP-036959.1, CAA45836.1, CAA45020.1, Q29607, AAB27336.1, XP-547817.1, AAT12414.1, AAM54049.1, AAH78901.1, AAO25745.1, NP-570912.1, XP-392194.1, AAD20829.1, AAC97113.1, AAC61694.1, AAH60340.1, AAR97906.1, BAA32227.1, BAB68395.1, BAC02895.1, AAW51451.1, AAF82188.1, XP-544189.1, NP-990568.1, BAC80211.1, AAW82620.1, AAF99597.1, NP-571062.1, CAC44179.1, AAB97467.1, AAT99303.1, AAD28038.1, AAH52168.1, NP-001004122.1, CAA72733.1, NP-032133.2, XP-394252.1, XP-224733.2, JH0801, AAP97721.1, NP-989669.1, 543296, P43029, A55452, AAH32495.1, XP-542974.1, NP-032135.1, AAK30842.1, AAK27794.1, BAC30847.1, EAA12064.2, AAP97720.1, XP-525704.1, AAT07301.1, BAD07014.1, CAF94356.1, AAR27581.1, AAG13400.1, AAC60127.1, CAF92055.1, XP-540103.1, AAO20895.1, CAF97447.1, AAS01764.1, BAD08319.1, CAA10268.1, NP-998140.1, AAR03824.1, AAS48405.1, AAS48403.1, AAK53545.1, AAK84666.1, XP-395420.1, AAK56941.1, AAC47555.1, AAR88255.1, EAL33036.1, AAW47740.1, AAW29442.1, NP-722813.1, AAR08901.1, AAO15420.2, CAC59700.1, AAL26886.1, AAK71708.1, AAK71707.1, CAC51427.2, AAK67984.1, AAK67983.1, AAK28706.1, P07713, P91706, P91699, CAG02450.1, AAC47552.1, NP-005802.1, XP-343149.1, AW34055.1, XP-538221.1, AAR27580.1, XP-125935.3, AAF21633.1, AAF21630.1, AAD05267.1, Q9Z1W4, NP-031585.2, NP-571094.1, CAD43439.1, CAF99217.1, CAB63584.1, NP-722840.1, CAE46407.1, XP-417667.1, BAC53989.1, BAB19659.1, AAM46922.1, AAA81169.1, AAK28707.1, AAL05943.1, AAB17573.1, CAH25443.1, CAG10269.1, BAD16731.1, EAA00276.2, AAT07320.1, AAT07300.1, AAN15037.1, CAH25442.1, AAK08152.2, 2009388A, AAR12161.1, CAG01961.1, CAB63656.1, CAD67714.1, CAF94162.1, NP-477340.1, EAL24792.1, NP-001009428.1, AAB86686.1, AAT40572.1, AAT40571.1, AAT40569.1, NP-033886.1, AAB49985.1, AAG39266.1, Q26974, AAC77461.1, AAC47262.1, BAC05509.1, NP-055297.1, XP-546146.1, XP-525772.1, NP-060525.2, AAH33585.1, AAH69080.1, CAG12751.1, AAH74757.2, NP-034964.1, NP-038639.1, 042221, AAF02773.1, NP-062024.1, AAR18244.1, AAR14343.1, XP-228285.2, AAT40573.1, AAT94456.1, AAL35278.1, AAL35277.1, AAL17640.1, AAC08035.1, AAB86692.1, CAB40844.1, BAC38637.1, BAB16046.1, AAN63522.1, NP-571041.1, AAB04986.2, AAC26791.1, AAB95254.1, BAA11835.1, AAR18246.1, XP-538528.1, BAA31853.1, AAK18000.1, XP-420540.1, AAL35276.1, AAQ98602.1, CAE71944.1, AAW50585.1, AAV63982.1, AAW29941.1, AAN87890.1, AAT40568.1, CAD57730.1, AAB81508.1, AAS00534.1, AAC59736.1, BAB79498.1, AAA97392.1, AAP85526.1, NP-999600.2, NP-878293.1, BAC82629.1, CAC60268.1, CAG04919.1, AAN10123.1, CAA07707.1 AAK20912.1, AAR88254.1, CAC34629.1, AAL35275.1, AAD46997.1, AAN03842.1, NP-571951.2, CAC50881.1, AAL99367.1, AAL49502.1, AAB71839.1, AAB65415.1, NP-624359.1, NP-990153.1, AAF78069.1, AAK49790.1, NP-919367.2, NP-001192.1, XP-544948.1, AAQ18013.1, AAV38739.1, NP-851298.1, CAA67685.1, AAT67171.1, AAT37502.1, AAD27804.1, AAN76665.1, BAC11909.1, XP-421648.1, CAB63704.1, NP-037306.1, A55706, AAF02780.1, CAG09623.1, NP-067589.1, NP-035707.1, AAV30547.1, AAP49817.1, BAC77407.1, AAL87199.1, CAG07172.1, B36193, CAA33024.1, NP-001009400.1, AAP36538.1, XP-512687.1, XP-510080.1, AAH05513.1, 1KTZ, AAH14690.1, AAA31526.1.

It is contemplated that any growth factor from the TGF-β superfamily that is capable, either alone or in combination with one or more other β cell maturation factors, of inducing the differentiation of at least one insulin-producing, endocrine cell or precursor thereof into a SC-β cell can be used in the methods, compositions, and kits described herein.

The growth factor from the TGF-β can be naturally obtained or recombinant. In some embodiments, the growth factor from the TGF-β superfamily comprises Activin A. The term "Activin A" includes fragments and derivatives of Activin A. The sequence of an exemplary Activin A is disclosed as SEQ ID NO: 1 in U.S. Pub. No. 2009/0155218 (the '218 publication'). Other non-limiting examples of Activin A are provided in SEQ ID NO: 2-16 of the '218 publication, and non-limiting examples of nucleic acids encoding Activin A are provided in SEQ ID NO:33-34 of the '218 publication. In some embodiments, the growth factor from the TGF-β superfamily comprises a polypeptide having an amino acid sequence at least 30%, at least 40%, at least 50%, at least 60%, at least 70%, at least 80%, at least 90%, at least 95%, or at least 99%, or greater identical to SEQ ID NO: 1 of the '218 publication.

In some embodiments, the growth factor from the TGF-β superfamily comprises growth differentiation factor 8 (GDF8). The term "GDF8" includes fragments and derivatives of GDF8. The sequences of GDF8 polypeptides are available to the skilled artisan. In some embodiments, the growth factor from the TGF-β superfamily comprises a polypeptide having an amino acid sequence at least 30%, at least 40%, at least 50%, at least 60%, at least 70%, at least 80%, at least 90%, at least 95%, or at least 99%, or greater identical to the human GDF8 polypeptide sequence (GenBank Accession EAX10880).

In some embodiments, the growth factor from the TGF-β superfamily comprises a growth factor that is closely related to GDF8, e.g., growth differentiation factor 11 (GDF11). The polypeptide sequences of GDF11 are available to the skilled artisan. In some embodiments, the growth factor from the TGF-β superfamily comprises a polypeptide having an amino acid sequence at least 30%, at least 40%, at least 50%, at least 60%, at least 70%, at least 80%, at least 90%, at least 95%, or at least 99%, or greater identical to the human GDF11 polypeptide sequence (GenBank Accession AAF21630).

In certain embodiments, the methods, compositions, and kits disclosed herein exclude at least one growth factor from the TGF-β superfamily.

In some embodiments, the at least one growth factor from the TGF-β superfamily can be replaced with an agent mimics the at least one growth factor from the TGF-β superfamily Exemplary agents that mimic the at least one growth factor from the TGF-β superfamily, include, without limitation, IDE1 and IDE2

TGF-β Signaling Pathway Inhibitors

Aspects of the disclosure relate to the use of TGF-β signaling pathway inhibitors as β cell maturation factors. It is contemplated that any TGF-β signaling pathway inhibitor that is capable, either alone or in combination with one or more other β cell maturation factors, of inducing the differentiation of at least one insulin-producing, endocrine cell or precursor thereof into a SC-β cell can be used in the methods, compositions, and kits described herein. In certain embodiments, the methods, compositions, and kits disclosed herein exclude a TGF-β signaling pathway inhibitor.

In some embodiments, the TGF-β signaling pathway comprises TGF-β receptor type I kinase (TGF-β RI) signaling. In some embodiments, the TGF-β signaling pathway inhibitor comprises ALK5 inhibitor II (CAS 446859-33-2, an ATP-competitive inhibitor of TGF-β RI kinase, also known as RepSox, IUPAC Name: 2-[5-(6-methylpyridin-2-yl)-1H-pyrazol-4-yl]-1,5-naphthyridine. In some embodiments, the TGF-β signaling pathway inhibitor is an analog or derivative of ALK5 inhibitor II.

In some embodiments, the analog or derivative of ALK5 inhibitor II is a compound of Formula I as described in U.S. Patent Publication No. 2012/0021519, incorporated by reference herein in its entirety.

In some embodiments, the TGF-β signaling pathway inhibitor is a TGF-β receptor inhibitor described in U.S. Patent Publication No. 2010/0267731. In some embodiments, the TGF-β signaling pathway inhibitor comprises an ALK5 inhibitor described in U.S. Patent Publication Nos. 2009/0186076 and 2007/0142376.

In some embodiments, the TGF-β signaling pathway inhibitor is A 83-01. In some embodiments, the TGF-β signaling pathway inhibitor is not A 83-01. In some embodiments, the compositions and methods described herein exclude A 83-01.

In some embodiments, the TGF-β signaling pathway inhibitor is SB 431542. In some embodiments, the TGF-β signaling pathway inhibitor is not SB 431542. In some embodiments, the compositions and methods described herein exclude SB 431542.

In some embodiments, the TGF-β signaling pathway inhibitor is D 4476. In some embodiments, the TGF-β signaling pathway inhibitor is not D 4476. In some embodiments, the compositions and methods described herein exclude D 4476.

In some embodiments, the TGF-β signaling pathway inhibitor is GW 788388. In some embodiments, the TGF-β signaling pathway inhibitor is not GW 788388. In some embodiments, the compositions and methods described herein exclude GW 788388.

In some embodiments, the TGF-β signaling pathway inhibitor is LY 364947. In some embodiments, the TGF-β signaling pathway inhibitor is not LY 364947. In some embodiments, the compositions and methods described herein exclude LY 364947.

In some embodiments, the TGF-β signaling pathway inhibitor is LY 580276. In some embodiments, the TGF-β signaling pathway inhibitor is not LY 580276. In some embodiments, the compositions and methods described herein exclude LY 580276.

In some embodiments, the TGF-β signaling pathway inhibitor is SB 525334. In some embodiments, the TGF-β signaling pathway inhibitor is not SB 525334. In some embodiments, the compositions and methods described herein exclude SB 525334.

In some embodiments, the TGF-β signaling pathway inhibitor is SB 505124. In some embodiments, the TGF-β signaling pathway inhibitor is not SB 505124. In some embodiments, the compositions and methods described herein exclude SB 505124.

In some embodiments, the TGF-β signaling pathway inhibitor is SD 208. In some embodiments, the TGF-β signaling pathway inhibitor is not SD 208. In some embodiments, the compositions and methods described herein exclude SD 208.

In some embodiments, the TGF-β signaling pathway inhibitor is GW 6604. In some embodiments, the TGF-β signaling pathway inhibitor is not GW 6604. In some embodiments, the compositions and methods described herein exclude GW 6604.

In some embodiments, the TGF-β signaling pathway inhibitor is GW 788388. In some embodiments, the TGF-β signaling pathway inhibitor is not GW 788388. In some embodiments, the compositions and methods described herein exclude GW 788388.

From the collection of compounds described above, the following can be obtained from various sources: LY-364947, SB-525334, SD-208, and SB-505124 available from Sigma, P.O. Box 14508, St. Louis, Mo., 63178-9916; 616452 and 616453 available from Calbiochem (EMD Chemicals, Inc.), 480 S. Democrat Road, Gibbstown, N. J., 08027; GW788388 and GW6604 available from GlaxoSmithKline, 980 Great West Road, Brentford, Middlesex, TW8 9GS, United Kingdom; LY580276 available from Lilly Research, Indianapolis, Ind. 46285; and SM16 available from Biogen Idec, P.O. Box 14627, 5000 Davis Drive, Research Triangle Park, N.C., 27709-4627.

WNT Signaling Pathway

Aspects of the disclosure relate to the use of activators of the WNT signaling pathway as β cell maturation factors. It is contemplated that any WNT signaling pathway activator that is capable, either alone or in combination with one or more other β cell maturation factors, of inducing the differentiation of at least one insulin-producing, endocrine cell or precursor thereof into a SC-β cell can be used in the methods, compositions, and kits described herein.

In some embodiments, the WNT signaling pathway activator comprises CHIR99021. In some embodiments, the WNT signaling pathway activator comprises a derivative of CHIR99021, e.g., a salt of CHIR99021, e.g., trihydrochloride, a hydrochloride salt of CHIR99021. In some embodiments, the WNT signaling pathway activator comprises Wnt3a recombinant protein. In some embodiments, the WNT signaling pathway activator comprises a glycogen synthase kinase 3 (GSK3) inhibitor. Exemplary GSK3 inhibitors include, without limitation, 3F8, A 1070722, AR-A 014418, BIO, BIO-acetoxime, FRATide, 10Z-Hymenialdisine, Indirubin-3'oxime, kenpaullone, L803, L803-mts, lithium carbonate, NSC 693868, SB 216763, SB 415286, TC-G 24, TCS 2002, TCS 21311, TWS 119, and analogs or derivatives of any of these. In certain embodiments, the methods, compositions, and kits disclosed herein exclude a WNT signaling pathway activator.

Fibroblast Growth Factor (FGF) Family

Aspects of the disclosure relate to the use of growth factors from the FGF family as β cell maturation factors. It is contemplated that any growth factor from the FGF family that is capable, either alone or in combination with one or more other β cell maturation factors, of inducing the differentiation of at least one insulin-producing, endocrine cell or precursor thereof into a SC-β cell can be used in the methods, compositions, and kits described herein. In certain embodiments, the methods, compositions, and kits disclosed herein exclude a growth factor from the FGF family.

In some embodiments, the at least one growth factor from the FGF family comprises keratinocyte growth factor (KGF). The polypeptide sequences of KGF are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human KGF polypeptide sequence (GenBank Accession AAB21431).

In some embodiments, the at least one growth factor from the FGF family comprises FGF2. The polypeptide sequences of FGF2 are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human FGF2 polypeptide sequence (GenBank Accession NP_001997).

In some embodiments, the at least one growth factor from the FGF family comprises FGF8B. The polypeptide sequences of FGF8B are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human FGF8B polypeptide sequence (GenBank Accession AAB40954).

In some embodiments, the at least one growth factor from the FGF family comprises FGF10. The polypeptide sequences of FGF10 are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human FGF10 polypeptide sequence (GenBank Accession CAG46489).

In some embodiments, the at least one growth factor from the FGF family comprises FGF21. The polypeptide sequences of FGF21 are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human FGF21 polypeptide sequence (GenBank Accession AAQ89444.1).

Bone Morphogenic Protein (BMP) Signaling Pathway Inhibitors

Aspects of the disclosure relate to the use of BMP signaling pathway inhibitors as β cell maturation factors. The BMP signaling family is a diverse subset of the TGF-β superfamily (Sebald et al. Biol. Chem. 385:697-710, 2004). Over twenty known BMP ligands are recognized by three distinct type II (BMPRII, ActRIIa, and ActRIIb) and at least three type I (ALK2, ALK3, and ALK6) receptors. Dimeric ligands facilitate assembly of receptor heteromers, allowing the constitutively-active type II receptor serine/threonine kinases to phosphorylate type I receptor serine/threonine kinases. Activated type I receptors phosphorylate BMP-responsive (BR-) SMAD effectors (SMADs 1, 5, and 8) to facilitate nuclear translocation in complex with SMAD4, a co-SMAD that also facilitates TGF signaling. In addition, BMP signals can activate intracellular effectors such as MAPK p38 in a SMAD-independent manner (Nohe et al. Cell Signal 16:291-299, 2004). Soluble BMP antagonists such as noggin, chordin, gremlin, and follistatin limit BMP signaling by ligand sequestration.

It is contemplated that any BMP signaling pathway inhibitor that is capable, either alone or in combination with one or more other β cell maturation factors, of inducing the differentiation of at least one insulin-producing, endocrine cell or precursor thereof into a SC-β cell can be used in the methods, compositions, and kits described herein. In certain embodiments of any aspect described herein, the methods, compositions, and kits disclosed herein exclude a BMP signaling pathway inhibitor.

In some embodiments, the BMP signaling pathway inhibitor comprises LDN 193189 (also known as LDN193189, 1062368-24-4, LDN-193189, DM 3189, DM-3189, IUPAC Name: 4-[6-(4-piperazin-1-ylphenyl)pyrazolo[1,5-a]pyrimidin-3-yl]quinolone).

In some embodiments, the BMP signaling pathway inhibitor comprise an analog or derivative of LDN 193189, e.g., a salt, hydrate, solvent, ester, or prodrug of LDN 193189. In some embodiments, a derivative (e.g., salt) of LDN 193189 comprises LDN193189 hydrochloride.

In some embodiments, the BMP signaling pathway inhibitor comprises a compound of Formula I from U.S. Patent Publication No. 2011/0053930.

Sonic Hedgehog (SHH) Signaling Pathway

Aspects of the disclosure relate to the use of SHH signaling pathway inhibitors as β cell maturation factors. It is contemplated that any SHH signaling pathway inhibitor that is capable, either alone or in combination with one or more other β cell maturation factors, of inducing the differentiation of at least one insulin-producing, endocrine cell or precursor thereof into a SC-β cell can be used in the methods, compositions, and kits described herein.

In some embodiments, the SHH signaling pathway inhibitor comprises Sant1. In some embodiments, the SHH signaling pathway inhibitor comprises SANT2. In some embodiments, the SHH signaling pathway inhibitor comprises SANT3. In some embodiments, the SHH signaling pathway inhibitor comprises SANT4. In some embodiments, the SHH signaling pathway inhibitor comprises Cur61414. In some embodiments, the SHH signaling pathway inhibitor comprises forskolin. In some embodiments, the SHH signaling pathway inhibitor comprises tomatidine. In some embodiments, the SHH signaling pathway inhibitor comprises AY9944. In some embodiments, the SHH signaling pathway inhibitor comprises triparanol. In some embodiments, the SHH signaling pathway inhibitor comprises compound A or compound B (as disclosed in U.S. Pub. No. 2004/0060568). In some embodiments, the SHH signaling pathway inhibitor comprises a steroidal alkaloid that antagonizes hedgehog signaling (e.g., cyclopamine or a derivative thereof) as disclosed in U.S. Pub. No. 2006/0276391. In certain embodiments, the methods, compositions, and kits disclosed herein exclude a SHH signaling pathway inhibitor.

Retinoic Acid Signaling Pathway

Aspects of the disclosure relate to the use of modulators of retinoic acid signaling as β cell maturation factors. It is contemplated that any modulator of retinoic acid signaling that is capable, either alone or in combination with one or more other β cell maturation factors, of inducing the differentiation of at least one insulin-producing, endocrine cell or precursor thereof into a SC-β cell can be used in the methods, compositions, and kits described herein.

In some embodiments, the modulator of retinoic acid signaling comprises an activator of retinoic acid signaling. In some embodiments, the RA signaling pathway activator comprises retinoic acid. In some embodiments, the RA signaling pathway activator comprises a retinoic acid receptor agonist. Exemplary retinoic acid receptor agonists include, without limitation, CD 1530, AM 580, TTNPB, CD 437, Ch 55, BMS 961, AC 261066, AC 55649, AM 80, BMS 753, tazarotene, adapalene, and CD 2314.

In some embodiments, the modulator of retinoic acid signaling comprises an inhibitor of retinoic acid signaling. In some embodiments, the retinoic acid signaling pathway inhibitor comprises DEAB (IUPAC Name: 2-[2-(diethylamino)ethoxy]-3-prop-2-enylbenzaldehyde). In some embodiments, the retinoic acid signaling pathway inhibitor comprises an analog or derivative of DEAB.

In some embodiments, the retinoic acid signaling pathway inhibitor comprises a retinoic acid receptor antagonist. In some embodiments, the retinoic acid receptor antagonist comprises (E)-4-[2-(5,6-dihydro-5,5-dimethyl-8-phenyl-2-naphthalenyl)ethenyl]benzoic acid, (E)-4-[[(5,6-dihydro-5,5-dimethyl-8-phenylethynyl)-2-naphthalenyl]ethenyl]benzoic acid, (E)-4-[2-[5,6-dihydro-5,5-dimethyl-8-(2-naphthalenyl)-2-naphthalenyl]ethenyl]-benzoic acid, and (E)-4-[2-[5,6-dihydro-5,5-dimethyl-8-(4-methoxyphenyl)-2-naphthalenyl]ethenyl]benzoic acid. In some embodiments, the retinoic acid receptor antagonist comprises BMS 195614 (CAS #253310-42-8), ER 50891 (CAS #187400-85-7), BMS 493 (CAS #170355-78-9), CD 2665 (CAS #170355-78-9), LE 135 (CAS #155877-83-1), BMS 453 (CAS #166977-43-1), or MM 11253 (CAS #345952-44-5).

In certain embodiments, the methods, compositions, and kits disclosed herein exclude a modulator of retinoic acid signaling. In certain embodiments, the methods, compositions, and kits disclosed herein exclude a retinoic acid signaling pathway activator. In certain embodiments, the methods, compositions, and kits disclosed herein exclude a retinoic acid signaling pathway inhibitor.

Protein Kinase C

Aspects of the disclosure relate to the use of protein kinase C activators as β cell maturation factors. Protein kinase C is one of the largest families of protein kinase enzymes and is composed of a variety of isoforms. Conventional isoforms include a, βI, βII, γ; novel isoforms include δ, ε, η, Θ; and atypical isoforms include ξ, and ι/λ. PKC enzymes are primarily cytosolic but translocate to the membrane when activated. In the cytoplasm, PKC is phosphorylated by other kinases or autophosphorylates. In order to be activated, some PKC isoforms (e.g., PKC-ε) require a molecule to bind to the diacylglycerol ("DAG") binding site or the phosphatidylserine ("PS") binding site. Others are able to be activated without any secondary binding messengers at all. PKC activators that bind to the DAG site include, but are not limited to, bryostatin, picologues, phorbol esters, aplysiatoxin, and gnidimacrin. PKC activators that bind to the PS site include, but are not limited to, polyunsaturated fatty acids and their derivatives. It is contemplated that any protein kinase C activator that is capable, either alone or in combination with one or more other β cell maturation factors, of inducing the differentiation of at least one insulin-producing, endocrine cell or precursor thereof into a SC-β cell can be used in the methods, compositions, and kits described herein.

In some embodiments, the PKC activator comprises PdbU. In some embodiments, the PKC activator comprises TPB. In some embodiments, the PKC activator comprises cyclopropanated polyunsaturated fatty acids, cyclopropanated monounsaturated fatty acids, cyclopropanated polyunsaturated fatty alcohols, cyclopropanated monounsaturated fatty alcohols, cyclopropanated polyunsaturated fatty acid esters, cyclopropanated monounsaturated fatty acid esters, cyclopropanated polyunsaturated fatty acid sulfates, cyclopropanated monounsaturated fatty acid sulfates, cyclopropanated polyunsaturated fatty acid phosphates, cyclopropanated monounsaturated fatty acid phosphates, macrocyclic lactones, DAG derivatives, isoprenoids, octylindolactam V, gnidimacrin, iripallidal, ingenol, napthalenesulfonamides, diacylglycerol kinase inhibitors, fibroblast growth factor 18 (FGF-18), insulin growth factor, hormones, and growth factor activators, as described in WIPO Pub. No. WO/2013/071282. In some embodiments, the bryostain comprises bryostatin-1, bryostatin-2, bryostatin-3, bryostatin-4, bryostatin-5, bryostatin-6, bryostatin-7, bryostatin-8, bryostatin-9, bryostatin-10, bryostatin-11, bryostatin-12, bryostatin-13, bryostatin-14, bryostatin-15, bryostatin-16, bryostatin-17, or bryostatin-18. In certain embodiments, the methods, compositions, and kits disclosed herein exclude a protein kinase C activator.

γ-Secretase Inhibitors

Aspects of the disclosure relate to the use of γ-secretase inhibitors as β cell maturation factors. It is contemplated that any γ-secretase inhibitor that is capable, either alone or in combination with one or more other β cell maturation factors, of inducing the differentiation of at least one insulin-producing, endocrine cell or precursor thereof into a SC-β cell can be used in the methods, compositions, and kits described herein. Numerous γ-secretase inhibitors are known. In some embodiments, the γ-secretase inhibitor comprises XXI. In some embodiments, the γ-secretase inhibitor comprises DAPT. Additional exemplary γ-secretase inhibitors include, without limitation, the γ-secretase inhibitors described in U.S. Pat. Nos. 7,049,296, 8,481,499, 8,501,813, and WIPO Pub. No. WO/2013/052700. In certain embodiments, the methods, compositions, and kits disclosed herein exclude a γ-secretase inhibitor.

Thyroid Hormone Signaling Pathway Activators

Aspects of the disclosure relate to the use of thyroid hormone signaling pathway activators as β cell maturation factors. It is contemplated that any thyroid hormone signaling pathway activator that is capable, either alone or in combination with one or more other β cell maturation factors, of inducing the differentiation of at least one insulin-positive endocrine cell or precursor thereof into a SC-β cell can be used in the methods, compositions, and kits described herein. In certain embodiments of any aspect described herein, the methods, compositions, and kits disclosed herein exclude a thyroid hormone signaling pathway activator. In certain embodiments of any aspect described herein, the methods, compositions, and kits disclosed herein exclude T3 or an analog of T3 described herein.

In some embodiments, the thyroid hormone signaling pathway activator comprises triiodothyronine (T3). In some embodiments, the thyroid hormone signaling pathway activator comprises an analog or derivative of T3. Exemplary analogs of T3 include, but are not limited to, selective and non-selective thyromimetics, TRβ selective agonist-GC-1, GC-24,4-Hydroxy-PCB 106, MB07811, MB07344, 3,5-diiodothyropropionic acid (DITPA); the selective TR-β agonist GC-1; 3-Iodothyronamine (T(1)AM) and 3,3',5-triiodothyroacetic acid (Triac) (bioactive metabolites of the hormone thyroxine (T(4)); KB-2115 and KB-141; thyronamines; SKF L-94901; DIBIT; 3'-AC-T2; tetraiodothyroacetic acid (Tetrac) and triiodothyroacetic acid (Triac) (via oxidative deamination and decarboxylation of thyroxine [T4] and triiodothyronine [T3] alanine chain), 3,3',5'-triiodothyronine (rT3) (via T4 and T3 deiodination), 3,3'-diiodothyronine (3,3'-T2) and 3,5-diiodothyronine (T2) (via T4, T3, and rT3 deiodination), and 3-iodothyronamine (T1AM) and thyronamine (T0AM) (via T4 and T3 deiodination and amino acid decarboxylation), as well as for TH structural analogs, such as 3,5,3'-triiodothyropropionic acid (Triprop), 3,5-dibromo-3-pyridazinone-1-thyronine (L-940901), N-[3,5-dimethyl-4-(4'-hydroxy-3'-isopropylphenoxy)-phenyl]-oxamic acid (CGS 23425), 3,5-dimethyl-4-[(4'-hydroxy-3'-isopropylbenzyl)-phenoxy]acetic acid (GC-1), 3,5-dichloro-4-[(4-hydroxy-3-isopropylphenoxy)phenyl]acetic acid (KB-141), and 3,5-diiodothyropropionic acid (DITPA).

In some embodiments, the thyroid hormone signaling pathway activator comprises a prodrug or prohormone of T3, such as T4 thyroid hormone (e.g., thyroxine or L-3,5,3',5'-tetraiodothyronine).

In some embodiments, the thyroid hormone signaling pathway activator is an iodothyronine composition described in U.S. Pat. No. 7,163,918.

Epidermal Growth Factor (EGF) Family

Aspects of the disclosure relate to the use of growth factors from the EGF family as β cell maturation factors. It is contemplated that any growth factor from the EGF family that is capable, either alone or in combination with one or more other β cell maturation factors, of inducing the differentiation of at least one insulin-producing, endocrine cell or precursor thereof into a SC-β cell can be used in the methods, compositions, and kits described herein. In some embodiments, the at least one growth factor from the EGF family comprises betacellulin. In some embodiments, at least one growth factor from the EGF family comprises EGF. Epidermal growth factor (EGF) is a 53 amino acid cytokine which is proteolytically cleaved from a large integral membrane protein precursor. In some embodiments, the growth factor from the EGF family comprises a variant EGF polypeptide, for example an isolated epidermal growth factor polypeptide having at least 90% amino acid identity to the human wild-type EGF polypeptide sequence, as disclosed in U.S. Pat. No. 7,084,246. In some embodiments, the growth factor from the EGF family comprises an engineered EGF mutant that binds to and agonizes the EGF receptor, as is disclosed in U.S. Pat. No. 8,247,531. In some embodiments, the at least one growth factor from the EGF family is replaced with an agent that activates a signaling pathway in the EGF family. In some embodiments, the growth factor from the EGF family comprises a compound that mimics EGF. In certain embodiments, the methods, compositions, and kits disclosed herein exclude a growth factor from the EGF family.

Protein Kinase Inhibitors

Aspects of the disclosure relate to the use of protein kinase inhibitors as β cell maturation factors. It is contemplated that any protein kinase inhibitor that is capable, either alone or in combination with other β cell maturation factors, of inducing the differentiation of at least one insulin-producing, endocrine cell or precursor thereof into a SC-β cell can be used in the methods, compositions, and kits described herein.

In some embodiments, the protein kinase inhibitor comprises staurosporine. In some embodiments, the protein kinase inhibitor comprises an analog of staurosporine. Exemplary analogs of staurosporine include, without limitation, Ro-31-8220, a bisindolylmaleimide (Bis) compound, 10'-{5"-[(methoxycarbonyl)amino]-2"-methyl}-phenylaminocarbonylstaurosporine, a staralog (see, e.g., Lopez et al., "Staurosporine-derived inhibitors broaden the scope of analog-sensitive kinase technology", *J. Am. Chem. Soc.* 2013; 135(48):18153-18159), and, cgp41251.

In some embodiments, the protein kinase inhibitor is an inhibitor of PKCβ. In some embodiments, the protein kinase inhibitor is an inhibitor of PKCβ with the following structure or a derivative, analogue or variant of the compound as follows:

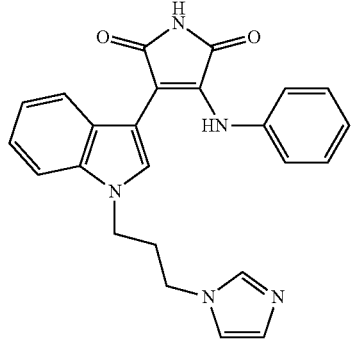 [SMILES: O=C1NC(=O)C(c2cn(CCCn3ccnc3)c3ccccc23)=C1Nc1ccccc1]

In some embodiments, the inhibitor of PKCβ is a GSK-2 compound with the following structure or a derivative, analogue or variant of the compound as follows:

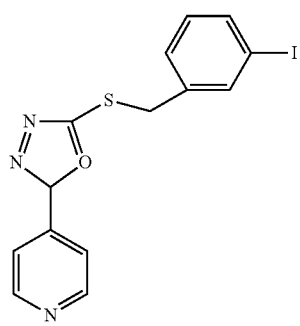

In some embodiments, the inhibitor of PKC is a bisindolylmaleimide. Exemplary bisindolylmaleimides include, without limitation, bisindolylmaleimide I, bisindolylmaleimide II, bisindolylmaleimide III, hydrochloride, or a derivative, analogue or variant. In some embodiments, a derivative or variant or analogue thereof is selected from a derivative or variant of analogue of a compound selected from the compounds selected from:

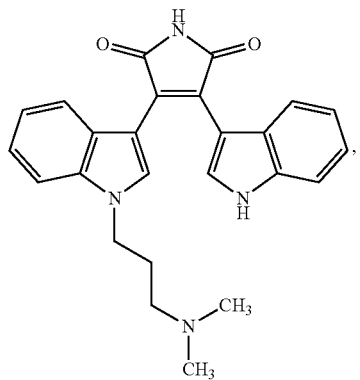

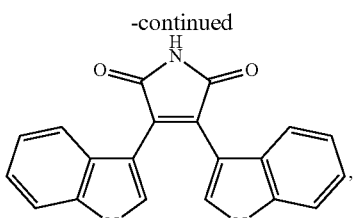

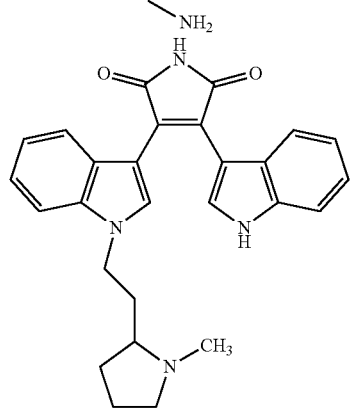

In some embodiments, the PKC inhibitor is a pseudohypericin, or a derivative, analogue or variant of the compound as follows:

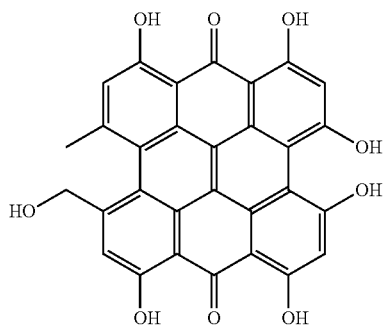 [SMILES: Cc1cc(O)c2c(=O)c3c(O)cc(O)c4c5c(O)cc(O)c6c(=O)c7c(O)cc(CO)c8c1c2c(c34)c(c65)c78]

In some embodiments, the PKC inhibitor is indorublin-3-monoxime, 5-Iodo or a derivative, analogue or variant of the following compound:

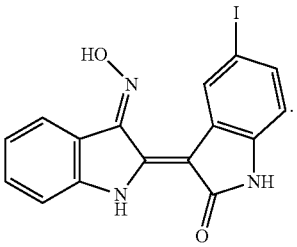 [SMILES: O=C1Nc2ccc(I)cc2/C1=C1/Nc2ccccc2/C1=N\O]

In certain embodiments, the methods, compositions, and kits disclosed herein exclude a protein kinase inhibitor.
Cystic Fibrosis Transmembrane Conductance Regulator (CFTR) Inhibitor Aspects of the disclosure relate to the use of CFTR inhibitors as β cell maturation factors. It is contemplated that any CFTR inhibitor that is capable, either alone or in combination with one or more other β cell maturation factors, of inducing the differentiation of at least one insulin-producing, endocrine cell or precursor thereof into a SC-β cell can be used in the methods, compositions, and kits described herein.

Numerous CFTR inhibitors of use herein are available to the skilled artisan. Exemplary CFTR inhibitors include, without limitation, LPA2 receptor agonist inhibitors of CFTR disclosed in U.S. Pub. No. 2007/0078111, hydrazide-containing CFTR inhibitors disclosed in U.S. Pat. No. 7,888,332, and CFTR inhibitors disclosed in WIPO Pub. No. WO/2008/121877, a CFTR inhibitor compound disclosed in U.S. Pub. No. 2008/0269206. In some embodiments, the CFTR inhibitor comprises a glycine hydrazide pore-occluding CFTR inhibitor. In some embodiments, the CFTR inhibitor comprises Gly-H101. In some embodiments, the CFTR inhibitor comprises a Gly-H101 derivative or analog (see, e.g., Muanprasat et al., "Discovery of Glyciine Hydrazide Pore-occluding CFTR Inhibitors", *J. Gen. PHysiol* 2004; 124(2):125-137). In certain embodiments, the methods, compositions, and kits disclosed herein exclude a CFTR inhibitor.

O-GlcNAcase Inhibitor

Aspects of the disclosure relate to the use of O-GlcNAcase inhibitors as β cell maturation factors. It is contemplated that any O-GlcNAcase inhibitor that is capable, either alone or in combination with one or more other β cell maturation factors, of inducing the differentiation of at least one insulin-producing, endocrine cell or precursor thereof into a SC-β cell can be used in the methods, compositions, and kits described herein. Numerous O-GlcNAcase inhibitors of use herein are available to the skilled artisan. Exemplary O-GlcNAcase inhibitors include, without limitation, permeable glycosidase inhibitors (see, e.g., WIPO Pub. No. WO/2013/169576 and WO/2013/166654), and selective glycosidase inhibitors (see, e.g., WIPO Pub. No. WO/2013/000084 and WO/2013/000085). In some embodiments, the O-GlcNAcase inhibitor comprises Thiamet G. In certain embodiments, the methods, compositions, and kits disclosed herein exclude a O-GlcNAcase inhibitor.

Admixture Compositions

Another aspect of the present invention relates to an admixture of insulin-positive endocrine cells or precursor thereof, and at least one β cell maturation factor, for example, for inducing the differentiation of at least one insulin-positive endocrine cell or precursor thereof to become SC-β cells.

In another aspect of the present invention relates to composition, such as a reaction admixture comprising at least one insulin-positive endocrine cell or precursor thereof (e.g. a population of insulin-positive endocrine cells or precursors thereof for differentiating into SC-β cells) and at least one β cell maturation factor. Alternatively, the present invention relates to a reaction admixture comprising (i) a population of SC-β cells produced by chemical induction of differentiation of a population of insulin-positive endocrine cells or precursors thereof to a SC-β cell, and (ii) at least one β cell maturation factor.

In some embodiments, the concentrations of the at least one β cell maturation factor added to the reaction mixture is a sufficient dose for inducing at least one insulin-positive endocrine cells or precursors thereof to differentiate to a SC-β cell, as described herein.

In some embodiments, the composition comprises a concentration of at least one β cell maturation factor of about between 25 nM to 10 μM, or between about 25 nM to 50 nM, or about 50 nM to 100 nM, or about 100 nM to 200 nM, or about 200 nM to about 500 nM or about 500 nM to about 1 μM, or about 11 μM to 2 μm, or about 2 μM to 5 μm, or about 5 μM to 10 μM.

In some embodiments, a composition or admixture comprises a concentration of at least one β cell maturation factor of at least about 5 nM, at least about 7 nM, at least about 10 nM, at least about 12 nM, at least about 15 nM, at least about 17 nM, at least about 20 nM, at least about 25 nM, at least about 30 nM, at least about 35 nM, at least about 40 nM, at least about 45 nM, at least about 50 nM, at least about 100 nM or at least about 200 nM, or at least about 300 nM or at least about 400 nM or at least about 500 nM or more than 500 nM, or any integer between 10-500 nM or any integer between 5-50 nM, or any integer between 50-100 nM, or any integer between 100 nM-200 nM or any integer between 200 nM-500 nM. In some embodiments, a composition or admixture comprises a concentration of at least one β cell maturation factor of at least about 0.1 μM, or at least about 0.2 μM, or at least about 0.3 μM, or at least about 0.4 μM, or at least about 0.5 μM, or at least about 1 μM, at least about 1.5 μM, at least about 2 μM, at least about 2.5 μM, at least about 3 μM, at least about 3.5 μM, at least about 4 μM, at least about 4.5 μM, at least about 5 μM, at least about 6 μM, at least about 7 μM, at least about 8 μM, at least about 9 μM, or at least about 10 μM, or more than 10 μM, or any integer between 0.1-0.5 μM or any integer between about 0.5-10 μM or any integer between 0.1-10 μM, or any integer between 0.5-5 μM, or any integer between 5 μM-10 μM.

Compositions and Kits

Described herein are compositions which comprise a cell described herein (e.g., a SC-β cell or mature pancreatic β cell). In some embodiments, the composition also includes a β cell maturation factor described herein and/or cell culture media. Described herein are also compositions comprising the compounds described herein (e.g. cell culture media comprising one or more of the compounds described herein). Described herein are kits.

Another aspect of the present invention relates to kits for practicing methods disclosed herein and for making SC-β cells or mature pancreatic β cells disclosed herein. In one aspect, a kit includes at least one insulin-positive endocrine cell or precursor thereof and at least one β cell maturation factor as described herein, and optionally, the kit can further comprise instructions for converting at least one insulin-positive endocrine cell or precursor thereof to a population of SC-β cells using a method described herein. In some embodiments, the kit comprises at least two β cell maturation factors. In some embodiments, the kit comprises at least three β cell maturation factors. In some embodiments, the kit comprises at least four β cell maturation factors. In some embodiments, the kit comprises at least five β cell maturation factors. In some embodiments, the kit comprises at least six β cell maturation factors. In some embodiments, the kit comprises at least seven β cell maturation factors. In some embodiments, the kit comprises at least eight β cell maturation factors. In some embodiments, the kit comprises at least nine β cell maturation factors. In some embodiments, the kit comprises at least ten β cell maturation factors. In some embodiments, the kit comprises β cell maturation factors for differentiating pluripotent cells to definitive endoderm cells. In some embodiments, the kit comprises β cell maturation factors for differentiating definitive endoderm cells to primitive gut tube cells. In some embodiments, the kit comprises β cell maturation factors for differentiating primitive gut tube cells to Pdx1-positive pancreatic progenitor cells. In some embodiments, the kit comprises β cell maturation factors for differentiating NKX6-1-positive pancreatic progenitor cells to insulin-positive endocrine cells. In some embodiments, the kit comprises β cell maturation factors for differentiating insulin-positive endocrine cells to SC-β cells.

In some embodiments, the kit comprises any combination of β cell maturation factors, e.g., for differentiating pluripotent cells to definitive endoderm cells, differentiating definitive endoderm cells to primitive gut tube cells, differentiating primitive gut tube cells to Pdx1-positive pancreatic progenitor cells, differentiating NKX6-1-positive pancreatic progenitor cells to insulin-positive endocrine cells, and differentiating insulin-positive endocrine cells to SC-β cells.

In one embodiment, the kit can comprise a pluripotent stem cell for the purposes of being used as a positive control, for example to assess or monitor the effectiveness or ability of a compound of formula (I) to chemically induce the pluripotent stem cell to differentiate into at least one insulin-positive endocrine cell or precursors thereof, and subsequently into a SC-β cell. Accordingly, the kit can comprise sufficient amount of at least one β cell maturation factor for inducing the differentiation of a control pluripotent stem cell population (positive control) as well as inducing the differentiation of a population of pluripotent stem cells of interest (e.g. the users preferred pluripotent stem cell e.g. an iPS cell) into at least one insulin-positive endocrine cell or precursors thereof, or into a SC-β cell.

In some embodiment, the compound in the kit can be provided in a watertight or gas tight container which in some embodiments is substantially free of other components of the kit. The compound can be supplied in more than one container, e.g., it can be supplied in a container having sufficient reagent for a predetermined number of reactions e.g., 1, 2, 3 or greater number of separate reactions to induce pluripotent stem cells to definitive endoderm cells, and subsequently into insulin-positive endocrine cells or precursors thereof, and subsequently into SC-β cells. A β cell maturation factor can be provided in any form, e.g., liquid, dried or lyophilized form. It is preferred that a compound(s) (e.g., β cell maturation factors) described herein be substantially pure and/or sterile. When a compound(s) described herein is provided in a liquid solution, the liquid solution preferably is an aqueous solution, with a sterile aqueous solution being preferred. When a compound(s) described herein is provided as a dried form, reconstitution generally is by the addition of a suitable solvent. The solvent, e.g., sterile water or buffer, can optionally be provided in the kit.

In some embodiments, the kit further optionally comprises information material. The informational material can be descriptive, instructional, marketing or other material that relates to the methods described herein and/or the use of a compound(s) described herein for the methods described herein.

The informational material of the kits is not limited in its instruction or informative material. In one embodiment, the informational material can include information about production of the compound, molecular weight of the compound, concentration, date of expiration, batch or production site information, and so forth. In one embodiment, the informational material relates to methods for administering the compound. Additionally, the informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In one embodiment, the informational material can include instructions to administer a compound(s) (e.g., a β cell maturation factor) as described herein in a suitable manner to perform the methods described herein, e.g., in a suitable dose, dosage form, or mode of administration (e.g., a dose, dosage form, or mode of administration described herein) (e.g., to a cell in vitro or a cell in vivo). In another embodiment, the informational material can include instructions to administer a compound(s) described herein to a suitable subject, e.g., a human, e.g., a human having or at risk for a disorder described herein or to a cell in vitro.

In addition to a compound(s) described herein, the composition of the kit can include other ingredients, such as a solvent or buffer, a stabilizer, a preservative, a flavoring agent (e.g., a bitter antagonist or a sweetener), a fragrance or other cosmetic ingredient, and/or an additional agent, e.g., for inducing pluripotent stem cells (e.g., in vitro) or for treating a condition or disorder described herein. Alternatively, the other ingredients can be included in the kit, but in different compositions or containers than a compound described herein. In such embodiments, the kit can include instructions for admixing a compound(s) described herein and the other ingredients, or for using a compound(s) described herein together with the other ingredients, e.g., instructions on combining the two agents prior to administration.

A β cell maturation factor as described herein can be provided in any form, e.g., liquid, dried or lyophilized form. It is preferred that a compound(s) described herein be substantially pure and/or sterile. When a compound(s) described herein is provided in a liquid solution, the liquid solution preferably is an aqueous solution, with a sterile aqueous solution being preferred. When a compound(s) described herein is provided as a dried form, reconstitution generally is by the addition of a suitable solvent. The solvent, e.g., sterile water or buffer, can optionally be provided in the kit.

The kit can include one or more containers for the composition containing at least one β cell maturation factor as described herein. In some embodiments, the kit contains separate containers (e.g., two separate containers for the two agents), dividers or compartments for the composition(s) and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a compound described herein. The containers of the kits can be air tight, waterproof (e.g., impermeable to changes in moisture or evaporation), and/or light-tight.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In a preferred embodiment, the device is a medical implant device, e.g., packaged for surgical insertion.

The kit can also include a component for the detection of a marker for SC-β cells, e.g., for a marker described herein, e.g., a reagent for the detection of positive SC-β cells. Or in some embodiments, the kit can also comprise reagents for the detection of negative markers of SC-β cells for the purposes of negative selection of SC-β cells or for identification of cells which do not express these negative markers (e.g., SC-β cells). The reagents can be, for example, an antibody against the marker or primers for a RT-PCR or PCR reaction, e.g., a semi-quantitative or quantitative RT-PCR or PCR reaction. Such markers can be used to evaluate whether an iPS cell has been produced. If the detection reagent is an antibody, it can be supplied in dry preparation, e.g., lyophilized, or in a solution. The antibody or other detection reagent can be linked to a label, e.g., a radiological, fluorescent (e.g., GFP) or colorimetric label for use in detection. If the detection reagent is a primer, it can be supplied in dry preparation, e.g., lyophilized, or in a solution.

It may be desirable to perform an analysis of the karyotype of the SC-β cells. Accordingly, the kit can include a component for karyotyping, e.g., a probe, a dye, a substrate, an enzyme, an antibody or other useful reagents for preparing a karyotype from a cell.

The kit can include SC-β cells, e.g., mature pancreatic β cells derived from the same type of insulin-positive endocrine cell or precursor thereof, for example for the use as a positive cell type control.

The kit can also include informational materials, e.g., instructions, for use of two or more of the components included in the kit.

The informational material can be descriptive, instructional, marketing or other material that relates to the methods described herein and/or the use of a compound(s) described herein for differentiating a pluripotent stem cell according to the methods described herein. In one embodiment, the informational material can include information about production of the compound, molecular weight of the compound, concentration, date of expiration, batch or production site information, and so forth. In one embodiment, the informational material relates to methods for culturing a population of insulin-positive endocrine cells in the presence of at least one β cell maturation factor described herein.

Methods of Administering a Cell

In one embodiment, the cells described herein, e.g. a population of SC-β cells are transplantable, e.g., a population of SC-β cells can be administered to a subject. In some embodiment, the subject who is administered a population of SC-β cells is the same subject from whom a pluripotent stem cell used to differentiate into a SC-β cell was obtained (e.g. for autologous cell therapy). In some embodiments, the subject is a different subject. In some embodiments, a subject suffering from diabetes such as type I diabetes, or is a normal subject. For example, the cells for transplantation (e.g. a composition comprising a population of SC-β cells) can be a form suitable for transplantation, e.g., organ transplantation.

The method can further include administering the cells to a subject in need thereof, e.g., a mammalian subject, e.g., a human subject. The source of the cells can be a mammal, preferably a human. The source or recipient of the cells can also be a non-human subject, e.g., an animal model. The term "mammal" includes organisms, which include mice, rats, cows, sheep, pigs, rabbits, goats, horses, monkeys, dogs, cats, and preferably humans. Likewise, transplantable cells can be obtained from any of these organisms, including a non-human transgenic organism. In one embodiment, the transplantable cells are genetically engineered, e.g., the cells include an exogenous gene or have been genetically engineered to inactivate or alter an endogenous gene.

A composition comprising a population of SC-β cells can be administered to a subject using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6):563 (2001). Timed-release technology involving alternate delivery methods can also be used in this invention. For example, timed-release formulations based on polymer technologies, sustained-release techniques and encapsulation techniques (e.g., polymeric, liposomal) can also be used for delivery of the compounds and compositions delineated herein.

Pharmaceutical Compositions Comprising a Population of Insulin-Producing, Glucose Responsive Cells For administration to a subject, a cell population produced by the methods as disclosed herein, e.g. a population of SC-β cells (produced by contacting at least one insulin-positive endocrine cell with at least one β cell maturation factor (e.g., any one, two, three, four, five, or more β cell maturation factors as described herein) can be administered to a subject, for example in pharmaceutically acceptable compositions. These pharmaceutically acceptable compositions comprise a therapeutically-effective amount a population of SC-β cells as described above, formulated together with one or more pharmaceutically acceptable carriers (additives) and/or diluents.

As described in detail below, the pharmaceutical compositions of the present invention can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The phrase "therapeutically-effective amount" as used herein in respect to a population of cells means that amount of relevant cells in a population of cells, e.g., SC-β cells or mature pancreatic β cells, or composition comprising SC-β cells of the present invention which is effective for producing some desired therapeutic effect in at least a sub-population of cells in an animal at a reasonable benefit/risk ratio applicable to any medical treatment. For example, an amount of a population of SC-β cells administered to a subject that is sufficient to produce a statistically significant, measurable change in at least one symptom of Type 1, Type 1.5 or Type 2 diabetes, such as glycosylated hemoglobin level, fasting blood glucose level, hypoinsulinemia, etc. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, the symptoms of a disease or disorder are alleviated by at least 5%, at least 10%, at least 20%, at least 30%, at least 40%, or at least 50%.

Treatment of Diabetes is determined by standard medical methods. A goal of Diabetes treatment is to bring sugar levels down to as close to normal as is safely possible. Commonly set goals are 80-120 milligrams per deciliter (mg/dl) before meals and 100-140 mg/dl at bedtime. A particular physician may set different targets for the patent, depending on other factors, such as how often the patient has low blood sugar reactions. Useful medical tests include tests on the patient's blood and urine to determine blood sugar level, tests for glycosylated hemoglobin level (HbA1c; a measure of average blood glucose levels over the past 2-3 months, normal range being 4-6%), tests for cholesterol and fat levels, and tests for urine protein level. Such tests are standard tests known to those of skill in the art (see, for example, American Diabetes Association, 1998). A successful treatment program can also be determined by having fewer patients in the program with complications relating to Diabetes, such as diseases of the eye, kidney disease, or nerve disease.

Delaying the onset of diabetes in a subject refers to delay of onset of at least one symptom of diabetes, e.g., hyperglycemia, hypoinsulinemia, diabetic retinopathy, diabetic nephropathy, blindness, memory loss, renal failure, cardiovascular disease (including coronary artery disease, peripheral artery disease, cerebrovascular disease, atherosclerosis, and hypertension), neuropathy, autonomic dysfunction, hyperglycemic hyperosmolar coma, or combinations thereof, for at least 1 week, at least 2 weeks, at least 1 month, at least 2 months, at least 6 months, at least 1 year, at least 2 years, at least 5 years, at least 10 years, at least 20 years, at least 30 years, at least 40 years or more, and can include the entire lifespan of the subject.

In certain embodiments, the subject is a mammal, e.g., a primate, e.g., a human. The terms, "patient" and "subject" are used interchangeably herein. Preferably, the subject is a mammal. The mammal can be a human, non-human primate, mouse, rat, dog, cat, horse, or cow, but are not limited to these examples. Mammals other than humans can be advantageously used as subjects that represent animal models of Type 1 diabetes, Type 2 Diabetes Mellitus, or pre-diabetic conditions. In addition, the methods described herein can be used to treat domesticated animals and/or pets. A subject can be male or female. A subject can be one who has been previously diagnosed with or identified as suffering from or having Diabetes (e.g., Type 1 or Type 2), one or more complications related to Diabetes, or a pre-diabetic condition, and optionally, but need not have already undergone treatment for the Diabetes, the one or more complications related to Diabetes, or the pre-diabetic condition. A subject can also be one who is not suffering from Diabetes or a pre-diabetic condition. A subject can also be one who has been diagnosed with or identified as suffering from Diabetes, one or more complications related to Diabetes, or a pre-diabetic condition, but who show improvements in known Diabetes risk factors as a result of receiving one or more treatments for Diabetes, one or more complications related to Diabetes, or the pre-diabetic condition. Alternatively, a subject can also be one who has not been previously diagnosed as having Diabetes, one or more complications related to Diabetes, or a pre-diabetic condition. For example, a subject can be one who exhibits one or more risk factors for Diabetes, complications related to Diabetes, or a pre-diabetic condition, or a subject who does not exhibit Diabetes risk factors, or a subject who is asymptomatic for Diabetes, one or more Diabetes-related complications, or a pre-diabetic condition. A subject can also be one who is suffering from or at risk of developing Diabetes or a pre-diabetic condition. A subject can also be one who has been diagnosed with or identified as having one or more complications related to Diabetes or a pre-diabetic condition as defined herein, or alternatively, a subject can be one who has not been previously diagnosed with or identified as having one or more complications related to Diabetes or a pre-diabetic condition.

As used herein, the phrase "subject in need of SC-β cells" refers to a subject who is diagnosed with or identified as suffering from, having or at risk for developing diabetes (e.g., Type 1, Type 1.5 or Type 2), one or more complications related to diabetes, or a pre-diabetic condition.

A subject in need of a population of SC-β cells can be identified using any method used for diagnosis of diabetes. For example, Type 1 diabetes can be diagnosed using a glycosylated hemoglobin (A1C) test, a random blood glucose test and/or a fasting blood glucose test. Parameters for diagnosis of diabetes are known in the art and available to skilled artisan without much effort.

In some embodiments, the methods of the invention further comprise selecting a subject identified as being in need of additional SC-β cells. A subject in need a population of SC-β cells can be selected based on the symptoms presented, such as symptoms of type 1, type 1.5 or type 2 diabetes. Exemplary symptoms of diabetes include, but are not limited to, excessive thirst (polydipsia), frequent urination (polyuria), extreme hunger (polyphagia), extreme fatigue, weight loss, hyperglycemia, low levels of insulin, high blood sugar (e.g., sugar levels over 250 mg, over 300 mg), presence of ketones present in urine, fatigue, dry and/or itchy skin, blurred vision, slow healing cuts or sores, more infections than usual, numbness and tingling in feet, diabetic retinopathy, diabetic nephropathy, blindness, memory loss, renal failure, cardiovascular disease (including coronary artery disease, peripheral artery disease, cerebrovascular disease, atherosclerosis, and hypertension), neuropathy, autonomic dysfunction, hyperglycemic hyperosmolar coma, and combinations thereof.

In some embodiments, a composition comprising a population of SC-β cells for administration to a subject can further comprise a pharmaceutically active agent, such as those agents known in the art for treatment of diabetes and or for having anti-hyperglycemic activities, for example, inhibitors of dipeptidyl peptidase 4 (DPP-4) (e.g., Alogliptin, Linagliptin, Saxagliptin, Sitagliptin, Vildagliptin, and Berberine), biguanides (e.g., Metformin, Buformin and Phenformin), peroxisome proliferator-activated receptor (PPAR) modulators such as thiazolidinediones (TZDs) (e.g., Pioglitazone, Rivoglitazone, Rosiglitazone and Troglitazone), dual PPAR agonists (e.g., Aleglitazar, Muraglitazar and Tesaglitazar), sulfonylureas (e.g., Acetohexamide, Carbutamide, Chlorpropamide, Gliclazide, Tolbutamide, Tolazamide, Glibenclamide (Glyburide), Glipizide, Gliquidone, Glyclopyramide, and Glimepiride), meglitinides ("glinides") (e.g., Nateglinide, Repaglinide and Mitiglinide), glucagon-like peptide-1 (GLP-1) and analogs (e.g., Exendin-4, Exenatide, Liraglutide, Albiglutide), insulin and insulin analogs (e.g., Insulin lispro, Insulin aspart, Insluin glulisine, Insulin glargine, Insulin detemir, Exubera and NPH insulin), alpha-glucosidase inhibitors (e.g., Acarbose, Miglitol and Voglibose), amylin analogs (e.g. Pramlintide), Sodium-dependent glucose cotransporter T2 (SGLT T2) inhibitors (e.g., Dapagliflozin, Remogliflozin and Sergliflozin) and others (e.g. Benfluorex and Tolrestat).

In type 1 diabetes, β cells are undesirably destroyed by continued autoimmune response. Thus, this autoimmune response can be attenuated by use of compounds that inhibit or block such an autoimmune response. In some embodiments, a composition comprising a population of SC-β cells for administration to a subject can further comprise a pharmaceutically active agent which is a immune response modulator. As used herein, the term "immune response modulator" refers to compound (e.g., a small-molecule, antibody, peptide, nucleic acid, or gene therapy reagent) that inhibits autoimmune response in a subject. Without wishing to be bound by theory, an immune response modulator inhibits the autoimmune response by inhibiting the activity, activation, or expression of inflammatory cytokines (e.g., IL-12, IL-23 or IL-27), or STAT-4. Exemplary immune response modulators include, but are not limited to, members of the group consisting of Lisofylline (LSF) and the LSF analogs and derivatives described in U.S. Pat. No. 6,774,130, contents of which are herein incorporated by reference in their entirety.

A composition comprising SC-β cells can be administrated to the subject in the same time, of different times as the administration of a pharmaceutically active agent or composition comprising the same. When administrated at different times, the compositions comprising a population of SC-β cells and/or pharmaceutically active agent for administration to a subject can be administered within 5 minutes, 10 minutes, 20 minutes, 60 minutes, 2 hours, 3 hours, 4, hours, 8 hours, 12 hours, 24 hours of administration of the other. When a compositions comprising a population of SC-β cells and a composition comprising a pharmaceutically active agent are administered in different pharmaceutical compositions, routes of administration can be different. In some embodiments, a subject is administered a composition comprising SC-β cells. In other embodiments, a subject is administered a composition comprising a pharmaceutically active agent. In another embodiment, a subject is administered a compositions comprising a population of SC-β cells mixed with a pharmaceutically active agent. In another embodiment, a subject is administered a composition comprising a population of SC-β cells and a composition comprising a pharmaceutically active agent, where administration is substantially at the same time, or subsequent to each other.

Toxicity and therapeutic efficacy of administration of a compositions comprising a population of SC-β cells can be determined by standard pharmaceutical procedures in cell cultures or experimental animals, e.g., for determining the LD50 (the dose lethal to 50% of the population) and the ED50 (the dose therapeutically effective in 50% of the population). Compositions comprising a population of SC-β cells that exhibit large therapeutic indices, are preferred.

The amount of a composition comprising a population of SC-β cells can be tested using several well-established animal models.

The non-obese diabetic (NOD) mouse carries a genetic defect that results in insulitis showing at several weeks of age (Yoshida et al., Rev. Immunogenet. 2:140, 2000). 60-90% of the females develop overt diabetes by 20-30 weeks. The immune-related pathology appears to be similar to that in human Type I diabetes. Other models of Type I diabetes are mice with transgene and knockout mutations (Wong et al., Immunol. Rev. 169:93, 1999). A rat model for spontaneous Type I diabetes was recently reported by Lenzen et al. (Diabetologia 44:1189, 2001). Hyperglycemia can also be induced in mice (>500 mg glucose/dL) by way of a single intraperitoneal injection of streptozotocin (Soria et al., Diabetes 49:157, 2000), or by sequential low doses of streptozotocin (Ito et al., Environ. Toxicol. Pharmacol. 9:71, 2001). To test the efficacy of implanted islet cells, the mice are monitored for return of glucose to normal levels (<200 mg/dL).

Larger animals provide a good model for following the sequelae of chronic hyperglycemia. Dogs can be rendered insulin-dependent by removing the pancreas (J. Endocrinol. 158:49, 2001), or by feeding galactose (Kador et al., Arch. Opthalmol. 113:352, 1995). There is also an inherited model for Type I diabetes in keeshond dogs (Am. J. Pathol. 105:194, 1981). Early work with a dog model (Banting et al., Can. Med. Assoc. J. 22:141, 1922) resulted in a couple of Canadians making a long ocean journey to Stockholm in February of 1925.

By way of illustration, a pilot study can be conducted by implanting a population of SC-β cells into the following animals: a) non-diabetic nude (T-cell deficient) mice; b) nude mice rendered diabetic by streptozotocin treatment; and c) nude mice in the process of regenerating islets following partial pancreatectomy. The number of cells transplanted is equivalent to ~1000-2000 normal human β cells implanted under the kidney capsule, in the liver, or in the pancreas. For non-diabetic mice, the endpoints of can be assessment of graft survival (histological examination) and determination of insulin production by biochemical analysis, RIA, ELISA, and immunohistochemistry. Streptozotocin treated and partially pancreatectomized animals can also be evaluated for survival, metabolic control (blood glucose) and weight gain.

In some embodiments, data obtained from the cell culture assays and in animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose of a composition comprising a population of SC-β cells can also be estimated initially from cell culture assays. A dose may be formulated in animal models in vivo to achieve a secretion of insulin at a concentration which is appropriate in response to circulating glucose in the plasma. Alternatively, the effects of any particular dosage can be monitored by a suitable bioassay.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

In another aspect of the invention, the methods provide use of an isolated population of SC-β cells as disclosed herein. In one embodiment of the invention, an isolated population of SC-β cells as disclosed herein may be used for the production of a pharmaceutical composition, for the use in transplantation into subjects in need of treatment, e.g. a subject that has, or is at risk of developing diabetes, for example but not limited to subjects with congenital and acquired diabetes. In one embodiment, an isolated population of SC-β cells may be genetically modified. In another aspect, the subject may have or be at risk of diabetes and/or metabolic disorder. In some embodiments, an isolated population of SC-β cells as disclosed herein may be autologous and/or allogeneic. In some embodiments, the subject is a mammal, and in other embodiments the mammal is a human.

The use of an isolated population of SC-β cells as disclosed herein provides advantages over existing methods because the population of SC-β cells can be differentiated from insulin-positive endocrine cells or precursors thereof derived from stem cells, e.g. iPS cells obtained or harvested from the subject administered an isolated population of SC-β cells. This is highly advantageous as it provides a renewable source of SC-β cells with can be differentiated from stem cells to insulin-positive endocrine cells by methods commonly known by one of ordinary skill in the art, and then further differentiated by the methods described herein to pancreatic β-like cells or cells with pancreatic β cell characteristics, for transplantation into a subject, in particular a substantially pure population of mature pancreatic β-like cells that do not have the risks and limitations of cells derived from other systems.

In another embodiment, an isolated population of SC-β cells (e.g., mature pancreatic β cells or β-like cells can be used as models for studying properties for the differentiation into insulin-producing cells, e.g. to pancreatic β cells or pancreatic β-like cells, or pathways of development of cells of endoderm origin into pancreatic β cells.

In some embodiments, the insulin-positive endocrine cells or SC-β cells may be genetically engineered to comprise markers operatively linked to promoters that are expressed when a marker is expressed or secreted, for example, a marker can be operatively linked to an insulin promoter, so that the marker is expressed when the insulin-positive endocrine cells or precursors thereof differentiation into SC-β cells which express and secrete insulin. In some embodiments, a population of SC-β cells can be used as a model for studying the differentiation pathway of cells which differentiate into islet β cells or pancreatic β-like cells.

In other embodiments, the insulin-producing, glucose responsive cells can be used as models for studying the role of islet β cells in the pancreas and in the development of diabetes and metabolic disorders. In some embodiments, the SC-β cells can be from a normal subject, or from a subject which carries a mutation and/or polymorphism (e.g. in the gene Pdx1 which leads to early-onset insulin-dependent diabetes mellitus (NIDDM), as well as maturity onset diabetes of the young type 4 (MODY4), which can be used to identify small molecules and other therapeutic agents that can be used to treat subjects with diabetes with a mutation or polymorphism in Pdx1. In some embodiments, the SC-β cells may be genetically engineered to correct the polymorphism in the Pdx1 gene prior to being administered to a subject in the therapeutic treatment of a subject with diabetes. In some embodiments, the SC-β cells may be genetically engineered to carry a mutation and/or polymorphism.

In one embodiment of the invention relates to a method of treating diabetes or a metabolic disorder in a subject comprising administering an effective amount of a composition comprising a population of SC-β cells as disclosed herein to a subject with diabetes and/or a metabolic disorder. In a further embodiment, the invention provides a method for treating diabetes, comprising administering a composition comprising a population of SC-β cells as disclosed herein to a subject that has, or has increased risk of developing diabetes in an effective amount sufficient to produce insulin in response to increased blood glucose levels.

In one embodiment of the above methods, the subject is a human and a population of SC-β cells as disclosed herein are human cells. In some embodiments, the invention contemplates that a population of SC-β cells as disclosed herein are administered directly to the pancreas of a subject, or is administered systemically. In some embodiments, a population of SC-β cells as disclosed herein can be administered to any suitable location in the subject, for example in a capsule in the blood vessel or the liver or any suitable site where administered the population of SC-β cells can secrete insulin in response to increased glucose levels in the subject.

The present invention is also directed to a method of treating a subject with diabetes or a metabolic disorder which occurs as a consequence of genetic defect, physical injury, environmental insult or conditioning, bad health, obesity and other diabetes risk factors commonly known by a person of ordinary skill in the art. Efficacy of treatment of a subject administered a composition comprising a population of SC-β cells can be monitored by clinically accepted criteria and tests, which include for example, (i) Glycated hemoglobin (A1C) test, which indicates a subjects average blood sugar level for the past two to three months, by measuring the percentage of blood sugar attached to hemoglobin, the oxygen-carrying protein in red blood cells. The higher your blood sugar levels, the more hemoglobin has sugar attached. An A1C level of 6.5 percent or higher on two separate tests indicates the subject has diabetes. A test value of 6-6.5% suggest the subject has prediabetes. (ii) Random blood sugar test. A blood sample will be taken from the subject at a random time, and a random blood sugar level of 200 milligrams per deciliter (mg/dL)-11.1 millimoles per liter (mmol/L), or higher indicated the subject has diabetes. (iii) Fasting blood sugar test. A blood sample is taken from the subject after an overnight fast. A fasting blood sugar level between 70 and 99 mg/dL (3.9 and 5.5 mmol/L) is normal. If the subjects fasting blood sugar levels is 126 mg/dL (7 mmol/L) or higher on two separate tests, the subject has diabetes. A blood sugar level from 100 to 125 mg/dL (5.6 to 6.9 mmol/L) indicates the subject has prediabetes. (iv) Oral glucose tolerance test. A blood sample will be taken after the subject has fasted for at least eight hours or overnight and then ingested a sugary solution, and the blood sugar level will be measured two hours later. A blood sugar level less than 140 mg/dL (7.8 mmol/L) is normal. A blood sugar level from 140 to 199 mg/dL (7.8 to 11 mmol/L) is considered prediabetes. This is sometimes referred to as impaired glucose tolerance (IGT). A blood sugar level of 200 mg/dL (11.1 mmol/L) or higher may indicate diabetes.

In some embodiments, the effects of administration of a population of SC-β cells as disclosed herein to a subject in need thereof is associated with improved exercise tolerance or other quality of life measures, and decreased mortality. The effects of cellular therapy with a population of SC-β cells can be evident over the course of days to weeks after the procedure. However, beneficial effects may be observed as early as several hours after the procedure, and may persist for several years. In some embodiments, the effects of cellular therapy with a population of SC-β cells occurs within two weeks after the procedure.

In some embodiments, a population of SC-β cells as disclosed herein may be used for tissue reconstitution or regeneration in a human patient or other subject in need of such treatment. In some embodiments compositions of populations of SC-β cells can be administered in a manner that permits them to graft or migrate to the intended tissue site and reconstitute or regenerate the functionally deficient area. Special devices are available that are adapted for administering cells capable of reconstituting a population of β cells in the pancreas or at an alternative desired location. Accordingly, the SC-β cells may be administered to a recipient subject's pancreas by injection, or administered by intramuscular injection.

In some embodiments, compositions comprising a population of SC-β cells as disclosed herein have a variety of uses in clinical therapy, research, development, and commercial purposes. For therapeutic purposes, for example, a population of SC-β cells as disclosed herein may be administered to enhance insulin production in response to increase in blood glucose level for any perceived need, such as an inborn error in metabolic function, the effect of a disease condition (e.g. diabetes), or the result of significant trauma (i.e. damage to the pancreas or loss or damage to islet β cells). In some embodiments, a population of SC-β cells as disclosed herein are administered to the subject not only help restore function to damaged or otherwise unhealthy tissues, but also facilitate remodeling of the damaged tissues.

To determine the suitability of cell compositions for therapeutic administration, the population of SC-β cells can first be tested in a suitable animal model. At one level, cells are assessed for their ability to survive and maintain their phenotype in vivo. Cell compositions comprising SC-β cells can be administered to immunodeficient animals (such as nude mice, or animals rendered immunodeficient chemically or by irradiation). Tissues are harvested after a period of regrowth, and assessed as to whether the administered cells or progeny thereof are still present.

This can be performed by administering cells that express a detectable label (such as green fluorescent protein, or β-galactosidase); that have been prelabeled (for example, with BrdU or [3H] thymidine), or by subsequent detection of a constitutive cell marker (for example, using human-specific antibody). The presence and phenotype of the administered population of SC-β cells can be assessed by immunohistochemistry or ELISA using human-specific antibody, or by RT-PCR analysis using primers and hybridization conditions that cause amplification to be specific for human polynucleotides, according to published sequence data.

A number of animal models for testing diabetes are available for such testing, and are commonly known in the art, for example as disclosed in U.S. Pat. No. 6,187,991 which is incorporated herein by reference, as well as rodent models; NOD (non-obese mouse), BB_DB mice, KDP rat and TCR mice, and other animal models of diabetes as described in Rees et al, Diabet Med. 2005 April; 22(4):359-70; Srinivasan K, et al., Indian J Med. Res. 2007 March; 125(3):451-7; Chatzigeorgiou A, et al., In Vivo. 2009 March-April; 23(2):245-58, which are incorporated herein by reference.

In some embodiments, a population of SC-β cells as disclosed herein may be administered in any physiologically acceptable excipient, where the SC-β cells may find an appropriate site for replication, proliferation, and/or engraftment. In some embodiments, a population of SC-β cells as disclosed herein can be introduced by injection, catheter, or the like. In some embodiments, a population of SC-β cells as disclosed herein can be frozen at liquid nitrogen temperatures and stored for long periods of time, being capable of use on thawing. If frozen, a population of SC-β cells will usually be stored in a 10% DMSO, 50% FCS, 40% RPMI 1640 medium. Once thawed, the cells may be expanded by use of growth factors and/or feeder cells associated with culturing SC-β cells as disclosed herein.

In some embodiments, a population of SC-β cells as disclosed herein can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition comprising a population of SC-β cells as disclosed herein will be adapted in accordance with the route and device used for administration. In some embodiments, a composition comprising a population of SC-β cells can also comprise or be accompanied with one or more other ingredients that facilitate the engraftment or functional mobilization of the SC-β cells. Suitable ingredients include matrix proteins that support or promote adhesion of the SC-β cells, or complementary cell types, especially endothelial cells. In another embodiment, the composition may comprise resorbable or biodegradable matrix scaffolds.

In some embodiments, a population of SC-β cells as disclosed herein may be genetically altered in order to introduce genes useful in insulin-producing cells such as pancreatic β cells, e.g. repair of a genetic defect in an individual, selectable marker, etc., or genes useful in selection against non-insulin-producing cells differentiated from at least one insulin-positive endocrine or precursor thereof or for the selective suicide of implanted SC-β cells. In some embodiments, a population of SC-β cells can also be genetically modified to enhance survival, control proliferation, and the like. In some embodiments a population of SC-β cells as disclosed herein can be genetically altering by transfection or transduction with a suitable vector, homologous recombination, or other appropriate technique, so that they express a gene of interest. In one embodiment, a population of SC-β cells is transfected with genes encoding a telomerase catalytic component (TERT), typically under a heterologous promoter that increases telomerase expression beyond what occurs under the endogenous promoter, (see International Patent Application WO 98/14592, which is incorporated herein by reference). In other embodiments, a selectable marker is introduced, to provide for greater purity of the population of SC-β cells. In some embodiments, a population of SC-β cells may be genetically altered using vector containing supernatants over a 8-16 h period, and then exchanged into growth medium for 1-2 days. Genetically altered SC-β cells can be selected using a drug selection agent such as puromycin, G418, or blasticidin, and then recultured.

Gene therapy can be used to either modify a cell to replace a gene product, to facilitate regeneration of tissue, to treat disease, or to improve survival of the cells following implantation into a subject (i.e. prevent rejection).

In an alternative embodiment, a population of SC-β cells as disclosed herein can also be genetically altered in order to enhance their ability to be involved in tissue regeneration, or to deliver a therapeutic gene to a site of administration. A vector is designed using the known encoding sequence for the desired gene, operatively linked to a promoter that is either pan-specific or specifically active in the differentiated cell type. Of particular interest are cells that are genetically altered to express one or more growth factors of various types, such as somatostatin, glucagon, and other factors.

Many vectors useful for transferring exogenous genes into target SC-β cells as disclosed herein are available. The vectors may be episomal, e.g. plasmids, virus derived vectors such as cytomegalovirus, adenovirus, etc., or may be integrated into the target cell genome, through homologous recombination or random integration, e.g. retrovirus derived vectors such MMLV, HIV-1, ALV, etc. In some embodiments, combinations of retroviruses and an appropriate packaging cell line may also find use, where the capsid proteins will be functional for infecting the SC-β cells as disclosed herein. Usually, SC-β cells and virus will be incubated for at least about 24 hours in the culture medium. In some embodiments, the SC-β cells are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line.

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) Mol. Cell. Biol. 5:431-437); PA317 (Miller et al. (1986) Mol. Cell. Biol. 6:2895-2902) GRIP (Danos et al. (1988) PNAS 85:6460-6464). Retroviruses packaged with xenotropic envelope protein, e.g. AKR env, are capable of infecting most mammalian cell types, except murine cells. In some embodiments, the vectors may include genes that must later be removed, e.g. using a recombinase system such as Cre/Lox, or the cells that express them destroyed, e.g. by including genes that allow selective toxicity such as herpesvirus TK, Bcl-Xs, etc.

Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in different cell types.

In one aspect of the present invention, a population of SC-β cells as disclosed herein are suitable for administering systemically or to a target anatomical site. A population of SC-β cells can be grafted into or nearby a subject's pancreas, for example, or may be administered systemically, such as, but not limited to, intraarterial or intravenous administration. In alternative embodiments, a population of SC-β cells of the present invention can be administered in various ways as would be appropriate to implant in the pancreatic or secretory system, including but not limited to parenteral, including intravenous and intraarterial administration, intrathecal administration, intraventricular administration, intraparenchymal, intracranial, intracisternal, intrastriatal, and intranigral administration. Optionally, a population of SC-β cells are administered in conjunction with an immunosuppressive agent.

In some embodiments, a population of SC-β cells can be administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement, including but not limited to improved survival rate or more rapid recovery, or improvement or elimination of symptoms and other indicators as are selected as appropriate measures by those skilled in the art. A population of SC-β cells can be administered to a subject the following locations: clinic, clinical office, emergency department, hospital ward, intensive care unit, operating room, catheterization suites, and radiologic suites.

In other embodiments, a population of SC-β cells is stored for later implantation/infusion. A population of SC-β cells may be divided into more than one aliquot or unit such that part of a population of SC-β cells is retained for later application while part is applied immediately to the subject. Moderate to long-term storage of all or part of the cells in a cell bank is also within the scope of this invention, as disclosed in U.S. Patent Application Serial No. 20030054331 and Patent Application No. WO03024215, and is incorporated by reference in their entireties. At the end of processing, the concentrated cells may be loaded into a delivery device, such as a syringe, for placement into the recipient by any means known to one of ordinary skill in the art.

In some embodiments a population of SC-β cells can be applied alone or in combination with other cells, tissue, tissue fragments, growth factors such as VEGF and other known angiogenic or arteriogenic growth factors, biologically active or inert compounds, resorbable plastic scaffolds, or other additive intended to enhance the delivery, efficacy, tolerability, or function of the population. In some embodiments, a population of SC-β cells may also be modified by insertion of DNA or by placement in cell culture in such a way as to change, enhance, or supplement the function of the cells for derivation of a structural or therapeutic purpose. For example, gene transfer techniques for stem cells are known by persons of ordinary skill in the art, as disclosed in (Morizono et al., 2003; Mosca et al., 2000), and may include viral transfection techniques, and more specifically, adeno-associated virus gene transfer techniques, as disclosed in (Walther and Stein, 2000) and (Athanasopoulos et al., 2000). Non-viral based techniques may also be performed as disclosed in (Murarnatsu et al., 1998).

In another aspect, in some embodiments, a population of SC-β cells could be combined with a gene encoding pro-angiogenic growth factor(s). Genes encoding anti-apoptotic factors or agents could also be applied. Addition of the gene (or combination of genes) could be by any technology known in the art including but not limited to adenoviral transduction, "gene guns," liposome-mediated transduction, and retrovirus or lentivirus-mediated transduction, plasmid adeno-associated virus. Cells could be implanted along with a carrier material bearing gene delivery vehicle capable of releasing and/or presenting genes to the cells over time such that transduction can continue or be initiated. Particularly when the cells and/or tissue containing the cells are administered to a patient other than the patient from whom the cells and/or tissue were obtained, one or more immunosuppressive agents may be administered to the patient receiving the cells and/or tissue to reduce, and preferably prevent, rejection of the transplant. As used herein, the term "immunosuppressive drug or agent" is intended to include pharmaceutical agents which inhibit or interfere with normal immune function. Examples of immunosuppressive agents suitable with the methods disclosed herein include agents that inhibit T-cell/B-cell costimulation pathways, such as agents that interfere with the coupling of T-cells and B-cells via the CTLA4 and B7 pathways, as disclosed in U.S. Patent Pub. No 2002/0182211, which is incorporated herein by reference. In one embodiment, a immunosuppressive agent is cyclosporine A. Other examples include myophenylate mofetil, rapamicin, and anti-thymocyte globulin. In one embodiment, the immunosuppressive drug is administered with at least one other therapeutic agent. The immunosuppressive drug is administered in a formulation which is compatible with the route of administration and is administered to a subject at a dosage sufficient to achieve the desired therapeutic effect. In another embodiment, the immunosuppressive drug is administered transiently for a sufficient time to induce tolerance to the cardiovascular stem cells of the invention.

Pharmaceutical compositions comprising effective amounts of a population of SC-β cells are also contemplated by the present invention. These compositions comprise an effective number of SC-β cells, optionally, in combination with a pharmaceutically acceptable carrier, additive or excipient. In certain aspects of the present invention, a population of SC-β cells are administered to the subject in need of a transplant in sterile saline. In other aspects of the present invention, a population of SC-β cells are administered in Hanks Balanced Salt Solution (HBSS) or Isolyte S, pH 7.4. Other approaches may also be used, including the use of serum free cellular media. In one embodiment, a population of SC-β cells are administered in plasma or fetal bovine serum, and DMSO. Systemic administration of a population of SC-β cells to the subject may be preferred in certain indications, whereas direct administration at the site of or in proximity to the diseased and/or damaged tissue may be preferred in other indications.

In some embodiments, a population of SC-β cells can optionally be packaged in a suitable container with written instructions for a desired purpose, such as the reconstitution or thawing (if frozen) of a population of SC-β cells prior to administration to a subject.

In one embodiment, an isolated population of SC-β cells as disclosed herein are administered with a differentiation agent. In one embodiment, the SC-β cells are combined with the differentiation agent to administration into the subject. In another embodiment, the cells are administered separately to the subject from the differentiation agent. Optionally, if the cells are administered separately from the differentiation agent, there is a temporal separation in the administration of the cells and the differentiation agent. The temporal separation may range from about less than a minute in time, to about hours or days in time. The determination of the optimal timing and order of administration is readily and routinely determined by one of ordinary skill in the art.

Diagnosis of Diabetes

Type 1 diabetes is an autoimmune disease that results in destruction of insulin-producing β cells of the pancreas. Lack of insulin causes an increase of fasting blood glucose (around 70-120 mg/dL in nondiabetic people) that begins to appear in the urine above the renal threshold (about 190-200 mg/dl in most people). The World Health Organization defines the diagnostic value of fasting plasma glucose concentration to 7.0 mmol/l (126 mg/dl) and above for Diabetes Mellitus (whole blood 6.1 mmol/or 110 mg/dl), or 2-hour glucose level of 11.1 mmol/L or higher (200 mg/dL or higher).

Type 1 diabetes can be diagnosed using a variety of diagnostic tests that include, but are not limited to, the following: (1) glycated hemoglobin (A1C) test, (2) random blood glucose test and/or (3) fasting blood glucose test.

The Glycated hemoglobin (A1C) test is a blood test that reflects the average blood glucose level of a subject over the preceding two to three months. The test measures the percentage of blood glucose attached to hemoglobin, which correlates with blood glucose levels (e.g., the higher the blood glucose levels, the more hemoglobin is glycosylated). An A1C level of 6.5 percent or higher on two separate tests is indicative of diabetes. A result between 6 and 6.5 percent is considered prediabetic, which indicates a high risk of developing diabetes.

The Random Blood Glucose Test comprises obtaining a blood sample at a random time point from a subject suspected of having diabetes. Blood glucose values can be expressed in milligrams per deciliter (mg/dL) or millimoles per liter (mmol/L). A random blood glucose level of 200 mg/dL (11.1 mmol/L) or higher indicates the subject likely has diabetes, especially when coupled with any of the signs and symptoms of diabetes, such as frequent urination and extreme thirst.

For the fasting blood glucose test, a blood sample is obtained after an overnight fast. A fasting blood glucose level less than 100 mg/dL (5.6 mmol/L) is considered normal. A fasting blood glucose level from 100 to 125 mg/dL (5.6 to 6.9 mmol/L) is considered prediabetic, while a level of 126 mg/dL (7 mmol/L) or higher on two separate tests is indicative of diabetes.

Type 1 diabetes can also be distinguished from type 2 diabetes using a C-peptide assay, which is a measure of endogenous insulin production. The presence of anti-islet antibodies (to Glutamic Acid Decarboxylase, Insulinoma Associated Peptide-2 or insulin), or lack of insulin resistance, determined by a glucose tolerance test, is also indicative of type 1, as many type 2 diabetics continue to produce insulin internally, and all have some degree of insulin resistance.

Testing for GAD 65 antibodies has been proposed as an improved test for differentiating between type 1 and type 2 diabetes as it appears that the immune system is involved in Type 1 diabetes etiology.

In some embodiments, the present invention provides compositions for the use of populations of SC-β cells produced by the methods as disclosed herein to restore islet function in a subject in need of such therapy. Any condition relating to inadequate production of a pancreatic endocrine (insulin, glucagon, or somatostatin), or the inability to properly regulate secretion may be considered for treatment with cells (e.g. populations of SC-β cells) prepared according to this invention, as appropriate. Of especial interest is the treatment of Type I (insulin-dependent) diabetes mellitus.

Subjects in need thereof can be selected for treatment based on confirmed long-term dependence on administration of exogenous insulin, and acceptable risk profile. The subject receives approximately 10,000 SC-β cells or cell equivalents per kg body weight. If the cells are not autologous, in order to overcome an allotype mismatch, the subject can be treated before surgery with an immunosuppressive agent such as FK506 and rapamycin (orally) and daclizumab (intravenously). A composition comprising a population of SC-β cells can be infused through a catheter in the portal vein. The subject can then be subjected to abdominal ultrasound and blood tests to determine liver function. Daily insulin requirement is tracked, and the subject is given a second transplant if required. Follow-up monitoring includes frequent blood tests for drug levels, immune function, general health status, and whether the patient remains insulin independent.

General approaches to the management of the diabetic patient are provided in standard textbooks, such as the Textbook of Internal Medicine, 3rd Edition, by W. N. Kelley ed., Lippincott-Raven, 1997; and in specialized references such as Diabetes Mellitus: A Fundamental and Clinical Text 2nd Edition, by D. Leroith ed., Lippincott Williams & Wilkins 2000; Diabetes (Atlas of Clinical Endocrinology Vol. 2) by C. R. Kahn et al. eds., Blackwell Science 1999; and Medical Management of Type 1 Diabetes 3rd Edition, McGraw Hill 1998. Use of islet cells for the treatment of Type I diabetes is discussed at length in Cellular Inter-Relationships in the Pancreas: Implications for Islet Transplantation, by L. Rosenberg et al., Chapman & Hall 1999; and Fetal Islet Transplantation, by C. M. Peterson et al. eds., Kluwer 1995.

As always, the ultimate responsibility for subject selection, the mode of administration, and dosage of a population of SC-β cells is the responsibility of the managing clinician. For purposes of commercial distribution, populations of SC-β cells as disclosed herein are typically supplied in the form of a pharmaceutical composition, comprising an isotonic excipient prepared under sufficiently sterile conditions for human administration. This invention also includes sets of populations of SC-β cells that exist at any time during their manufacture, distribution, or use. The sets of populations of SC-β cells comprise any combination of two or more cell populations described in this disclosure, exemplified but not limited to the differentiation of definitive endoderm cells to become pdx1-positive pancreatic progenitor cells, and their subsequent differentiation e.g. into insulin-producing cells such as mature pancreatic β cells or mature pancreatic β-like cells as the term is defined herein. In some embodiments, the cell compositions comprising populations of SC-β cells can be administered (e.g. implanted into a subject) in combination with other cell types e.g. other differentiated cell types, sometimes sharing the same genome. Each cell type in the set may be packaged together, or in separate containers in the same facility, or at different locations, under control of the same entity or different entities sharing a business relationship.

For general principles in medicinal formulation of cell compositions, the reader is referred to Cell Therapy: Stem Cell Transplantation, Gene Therapy, and Cellular Immunotherapy, by G. Morstyn & W. Sheridan eds, Cambridge University Press, 1996. The composition is optionally packaged in a suitable container with written instructions for a desired purpose, such as the treatment of diabetes.

In some embodiments, compositions comprising populations of SC-β cells can also be used as the functional component in a mechanical device designed to produce one or more of the endocrine polypeptides of pancreatic islet cells. In its simplest form, the device contains a population of SC-β cells behind a semipermeable membrane that prevents passage of the cell population, retaining them in the device, but permits passage of insulin, glucagon, or somatostatin secreted by the cell population. This includes populations of SC-β cells that are microencapsulated, typically in the form of cell clusters to permit the cell interaction that inhibits dedifferentiation. For example, U.S. Pat. No. 4,391,909 describe islet cells encapsulated in a spheroid semipermeable membrane made up of polysaccharide polymers >3,000 mol. wt. that are cross-linked so that it is permeable to proteins the size of insulin, but impermeable to molecules over 100,000 mol. wt. U.S. Pat. No. 6,023,009 describes islet cells encapsulated in a semipermeable membrane made of agarose and agaropectin. Microcapsules of this nature are adapted for administration into the body cavity of a diabetic patient, and are thought to have certain advantages in reducing histocompatibility problems or susceptibility to bacteria.

More elaborate devices are also contemplated for use to comprise a population of SC-β cells, either for implantation into diabetic patients, or for extracorporeal therapy. U.S. Pat. No. 4,378,016 describes an artificial endocrine gland containing an extracorporeal segment, a subcutaneous segment, and a replaceable envelope containing the hormone-producing cells. U.S. Pat. No. 5,674,289 describes a bioartificial pancreas having an islet chamber, separated by a semipermeable membrane to one or more vascularizing chambers open to surrounding tissue. Useful devices typically have a chamber adapted to contain the islet cells, and a chamber separated from the islet cells by a semipermeable membrane which collects the secreted proteins from the islet cells, and which may also permit signaling back to the islet cells, for example, of the circulating glucose level.

Methods of Identifying β Cell Maturation Factors that Increase the Production of SC-β Cells or Pancreatic β Cells Described herein is a method of identifying a β cell maturation factor or agent that increases the production of SC-β cells (e.g., mature pancreatic β cells). In certain examples, a high content and/or high throughput screening method is provided. The method includes exposing at least one insulin-positive endocrine cell or a precursor thereof to at least one compound (e.g., a library compound or a compound described herein) and determining if the compound increases the production of SC-β cells, e.g., mature pancreatic β cells from the at least one insulin-positive endocrine cell or the precursor thereof. A cell can be identified as a SC-β cell (e.g., a mature pancreatic β cell) using one or more of the markers described herein. In some examples, the at least one insulin-positive endocrine cell or the precursor thereof may be differentiated prior to exposure to the library. In other examples, two or more compounds may be used, either individually or together, in the screening assay. In additional examples, the at least one insulin-positive endocrine cell or the precursor thereof may be placed in a multi-well plate, and a library of compounds may be screened by placing the various members of the library in different wells of the multi-well plate. Such screening of libraries can rapidly identify compounds that are capable of generating SC-β cells, e.g., mature pancreatic β cells, from the at least one insulin-positive endocrine cell or precursor thereof.

In some embodiments, the method further comprises isolating a population of the SC-β cells, e.g., pancreatic β cells (e.g., wherein at least 5%, 10%, 15%, 20%, 25%, 30%, 35%, 50%, 75% or greater of the subject cell type).

In some embodiments, the method further comprises implanting the SC-β cells produced by the methods as disclosed herein into a subject (e.g., a subject having diabetes, e.g., type I, type II or Type 1.5 diabetes). In some embodiments, the SC-β cell is derived from a stem cell obtained from a subject. In some embodiments, the SC-β cell is derived from a stem cell from a donor different than the subject, e.g., a relative of the subject.

In one aspect, the invention features a SC-β cell, e.g., a mature pancreatic β cell made by a method described herein. In another aspect, the invention features a composition comprising a SC-β cell made by a method described herein.

In another aspect, the invention features a kit comprising: insulin-positive endocrine cells or precursors thereof; at least one β cell maturation factor described herein; and instructions for using the insulin-positive endocrine cells or precursors thereof and the at least one β cell maturation factor to produce a SC-β cell (e.g., mature pancreatic β cell). In some embodiments, the kit further comprises: a component for the detection of a marker for a mature β cell, e.g., for a marker described herein, e.g., a reagent for the detection of a marker of β cell maturity, e.g., an antibody against the marker; and a mature pancreatic β cell, e.g., for use as a control.

In some embodiments, the kit further comprises: a component to differentiate an endodermal cell, e.g., a definitive endodermal cell to a cell of a second cell type, e.g., at least one insulin-positive endocrine cell or precursors thereof; and instructions for using the endodermal cell (e.g., the definitive endodermal cell) described herein and the component to produce the cell of a second type, e.g., at least one insulin-positive endocrine cell or precursors thereof. In some embodiments, the kit further comprises: a component for the detection of a marker for the cell of the second cell type, e.g., for a marker described herein, e.g., a reagent for the detection of Pdx1, e.g., an antibody against the marker; and a cell or the second cell type, e.g., at least one insulin-positive endocrine cell or precursors thereof, e.g., for use as a control.

In one aspect, the invention features a method of facilitating differentiation of insulin-positive endocrine cells or precursors thereof to SC-β cells comprising providing at least one insulin-positive pancreatic endocrine cell or precursor thereof, and providing at least one β cell maturation factor (e.g., 1, 2, 3, 4, 5, 6, 7, 8, 9, 10 or more β cell maturation factors described herein) to differentiate the at least one insulin-positive endocrine cell or precursor thereof to a SC-β cell (e.g., a mature pancreatic β cell), upon exposure of the stem cell to the at least one β cell maturation factor. In some embodiments, the at least one insulin-positive endocrine cell or precursor thereof is from a mammal. In some embodiments, the at least one insulin-positive endocrine cell or precursor thereof is from mouse or human. In some embodiments, the at least one insulin-positive endocrine cell or precursor thereof derived from culturing an embryonic stem cell (e.g., a mammalian embryonic stem cell such as a mouse or human embryonic stem cell). In some embodiments, the at least one insulin-positive endocrine cell or precursor thereof derived from culturing an induced pluripotent stem cell (e.g., a mammalian iPs cell such as a mouse or human iPs cell).

In some embodiments, a plurality of insulin-positive endocrine cells or precursors thereof are differentiated into a plurality of mature pancreatic β cells or SC-β cells, for example, by contacting the plurality of insulin-positive endocrine cells or precursors thereof with at least one, at least two, at least three, or more of the β cell maturation factors as described herein.

In some embodiments, the a plurality of insulin-positive endocrine cells or precursors thereof are exposed to the β cell maturation factors, for about 1, 2, 4, 6, 8, 10, 12, 14, 16, or more days. In some embodiments, the plurality of insulin-positive endocrine cells or precursors thereof are exposed to the β cell maturation factors at a concentration of about 25 nM, 50 nM, 100 nM, 150 nM, 200 nM, 250 nM, 400 nM, 500 nM, 600 nM, 700 nM, 800 nM, 1 µM, 2 µM, 3 µM, 4 µM, 5 µM or 10 µM. In some embodiments, the plurality of insulin-positive endocrine cells or precursors thereof are exposed to the β cell maturation factors at a concentration of about 250 nM, 400 nM, 500 nM, 600 nM, 700 nM, or 800 nM. In some embodiments, greater than about 20%, 30%, 40%, 50%, 60%, 70%, 80%, or 90% of the insulin-positive endocrine cells or precursors thereof are differentiated into the mature pancreatic β cells or SC-β cells.

In some aspects, the disclosure provides artificial islets constructed using the SC-β cells described herein. In some aspects, an artificial islet comprises one or more SC-β cells differentiated in vitro from pluripotent stem cells, e.g., according to a method described herein.

In some aspects, the disclosure provides an artificial pancreas comprising SC-β cells differentiated in vitro from pluripotent stem cells.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the disclosure. Further, all patents, patent applications, and publications identified are expressly incorporated herein by reference for the purpose of describing and disclosing, for example, the methodologies described in such publications that might be used in connection with the disclosure. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

Example 1—Generation of Functional Pancreatic β Cells In Vitro

Summary

The generation of insulin-producing pancreatic β cells from stem cells in vitro would provide an unprecedented cell source for drug discovery and cell transplantation therapy in diabetes. However, insulin-producing cells previously generated from human pluripotent stem cells (hPSC) lack many characteristics of bona fide β cells including function in vitro and/or in vivo. The work described herein demonstrates an exemplary scalable differentiation protocol that generates SC-β cells from hPSC in vitro. Surprisingly, and unexpectedly, these SC-β cells secrete amounts of insulin comparable to adult β cells in response to multiple sequential glucose challenges, flux Ca2+, express markers found in β cells, and package insulin into secretary granules. As a proof of concept, SC-β cells also respond to known diabetes drugs and proliferative cues in vitro. Furthermore, the SC-β cells secrete high levels of human insulin in the serum of mice immediately after transplantation, and transplantation of these cells immediately ameliorates hyperglycemia in diabetic mice. The work described herein represents a major advance in the use of stem cell-derived β cells (i.e., SC-β cells) for the treatment of diabetes and for in vitro β cell study and drug screening.

The following work demonstrates several advantages of the SC-β cells produced according to the methods described herein, for example, the SC-β cells perform glucose stimulated insulin secretion in vitro, resemble human islet β cells by gene expression and ultrastructure, secrete human insulin and ameliorate hyperglycemia when transplanted into mice, provide a new platform for cell therapy (e.g., transplantation into a subject in need of additional and/or functional β cells), drug screening (e.g., for insulin production/secretion, survival, dedifferentiation, etc.), research (e.g., determining the differences in function between normal and diabetic β cells), and tissue engineering (e.g., using the SC-β cells as the first cell type in reconstructing an islet).

Introduction

The discovery of human pluripotent stem cells (hPSC) opened the door to the possibility that replacement cells and tissues could one day be generated for disease treatment or drug screening. Research in the past decade has moved the field closer to that goal through development of strategies to generate cells that would otherwise be difficult to obtain, like neurons or cardiomyocytes (Kriks et al., 2011; Shiba et al., 2012). These cells have also been transplanted into animal models and are able to engraft into the host, in some cases with a beneficial effect like suppression of arrhythmias with stem cell-derived cardiomyocytes (Shiba et al., 2012), restoration of locomotion after spinal injury with oligodendrocyte progenitor cells (Keirstead et al., 2005), or improved vision after transplantation of retinal epithelial cells into rodent models of blindness (Lu et al., 2009).

One of the most rapidly growing diseases that may be treatable by stem cell derived tissues is diabetes, affecting more than 300 million people worldwide according to the International Diabetes Federation. Type 1 diabetes results from the autoimmune destruction of β cells in the pancreatic islet whereas the more common type 2 diabetes results from peripheral tissue insulin resistance and β cell dysfunction. These patients, particularly those suffering from type 1 diabetes, could potentially be cured through transplantation of new, functional β cells. Transplantation of cadaveric human islets has demonstrated that patients can be made insulin independent for five year or longer via this strategy, but this approach is very limited because of the scarcity of donor human islets (Bellin et al., 2012). The generation of an unlimited supply of human β cells from stem cells could extend this therapy to millions of new patients. β cells are an ideal test case for regenerative medicine as only a single cell type needs to be generated and those cells can be placed anywhere in the body within an immunoprotective device (e.g., a microcapsule as described herein) as or material with access to the vasculature.

Pharmaceutical screening to identify new drugs that can improve β cell function or proliferation is also hindered by limited supplies of cadaveric islets and their high variability due to variation in cause of death, donor genetic background, and other factors in their isolation. Thus a consistent, uniform supply of SC-β cells could provide a unique and valuable drug discovery platform for diabetes.

Research to date has made considerable progress towards generating the β cell lineage in vitro from hPSC. Definitive endoderm and subsequent pancreatic progenitors can now be differentiated with high efficiencies (Kroon et al., 2008; D'Amour et al., 2006; D'Amour et al., 2005; Rezania et al., 2012). Importantly these cells can further differentiate into functional β cells within three to four months after transplantation into rodents (Kroon et al., 2008; Rezania et al., 2012), indicating that they contain the developmental potential to develop into β cells if provided enough time and appropriate cues. Unfortunately, the months-long process the cells undergo in vivo remains a black box, and it is unclear if this process would work in human patients. Other work has focused on generating insulin-producing cells from human pancreatic progenitors in vitro. However, the cells generated to date are not bona fide β cells. These cells either fail to perform glucose stimulated insulin secretion in vitro, fail to express appropriate β cell markers like NKX6-1 or PDX1, abnormally co-express other hormones like glucagon, fail to function after transplantation in vivo, or display a combination of these abnormal features (D'Amour et al., 2006; Cheng et al., 2012; Narayanan et al., 2013; Xie et al., 2013; Nostro et al., 2011).

The work described herein provides a strategy for virtually unlimited, large-scale production of functional human β cells from hPSC in vitro. By using sequential modulation of signaling pathways in combination in a 3-dimensional cell culture system, monohormonal insulin-producing cells (SC-β cells) that co-express key β cell markers and display β cell ultrastructural features can be generated. Furthermore, these cells mimic the function of human islets both in vitro and in vivo. Finally, the cells demonstrate proof of concept of their utility for the dual aims of in vitro drug screening and in vivo transplantation therapy for diabetes.

Results
Generation of Glucose Sensing Insulin Secreting β Cells from hPSC In Vitro An exemplary method for generating functional β cells from hPSC in vitro is outlined in FIG. 1A. To produce large numbers of β cells, a scalable suspension-based culture system that can generate >$10^8$ hPSC and later differentiated cell types was utilized (Schulz et al., 2012). Clusters of HUES8 human embryonic stem cells, approximately 100-200 µm in diameter, were induced into highly pure definitive endoderm (>95% Sox17+) and subsequently early pancreatic progenitors (>90% PDX1+) using protocols adapted from previous publications (FIG. 1B) (Schulz et al., 2012; Rezania et al., 2012). Next, a method using extended time in culture with FGF family member KGF, hedgehog inhibitor Sant1, and a low concentration of retinoic acid to generate high levels of NKX6-1+/PDX1+ co-expressing pancreatic progenitor clusters (>60% NKX6-1+/PDX1+ cells) was identified (FIG. 1A.) Transplantation of these pancreatic progenitors into mice has been reported to give rise to functional β cells in vivo after 3-4 months (Rezania et al., 2012). This was used as a starting point for developing the protocol to recapitulate this generation of functional β cells in vitro.

The NKX6-1+/PDX1+ pancreatic progenitor cells were then differentiated into C-peptide-expressing endocrine cells using either a previously published protocol (control differentiation) or a newly developed protocol (new differentiation). The control differentiation protocol produced cells over the course of several months that were monohormonal INS+ and INS+/GCG+ or INS+/SST+ polyhormonal (PH) cells. The nomenclature PH was used to refer to this cell population. The new differentiation protocol, on the other hand, involved 2-3 weeks of a unique series of culture steps involving hedgehog signaling inhibition, retinoic acid signaling, gamma-secretase inhibition, TGFβ signaling inhibition, EGF signaling, thyroid hormone signaling and the islet media CMRL 1066 (Nostro et al., 2011; Rezania et al., 2012; Thowfeequ et al., 2007; Aguayo-Mazzucato et al., 2013; D'Amour et al., 2006). It was hypothesized that the C-peptide+ cells generated with this new differentiation protocol were similar to primary adult β (1° β) cells and, as such, are referred to stem cell-β (SC-β) cells (i.e., SC-β cells).

The key functional feature of a β cell is its ability to repeatedly perform glucose stimulated insulin secretion (GSIS). Nearly all existing directed differentiation protocols generate insulin-expressing cells from hPSC that fail to perform GSIS in vitro (D'Amour et al., 2006). One protocol has been reported using endodermal progenitor lines as a starting population that can make cells that could secrete some insulin in response to a single glucose challenge (Cheng et al., 2012). Conversely, the SC-β cells generated utilizing the methods described herein can respond to at least three sequential high glucose challenges. These cells secreted high levels of insulin in a pattern similar to primary adult β cells, while PH cells from the control protocol failed to respond to glucose (FIGS. 2A-2C and FIGS. 3A-2C). The stimulation index, as calculated by the ratio of insulin secreted in high glucose (20 mM) to low glucose (2 mM), was similar for SC-β cells compared to primary adult β cells, 2.3±0.9 and 2.3±1.4 respectively. Additionally, there was a small percentage of high glucose challenges for which both SC-β cells and primary adult β cells both did not respond. Furthermore, the amount of insulin secreted per cell in response to 20 mM glucose by SC-β cells was indistinguishable from that secreted by primary adult β cells, 2.6±1.6 and 2.5±1.2 µIU/$10^3$ cells, respectively. Taken together, this data suggests that the in vitro function of SC-β cells generated using the new differentiation protocol is very similar to their bona fide primary adult β cell counterparts.

The in vitro functionality of SC-β cells generated using the new differentiation protocol was later confirmed by measuring changes in intracellular $Ca^{2+}$. β cells sense changing glucose levels through calcium signaling; increasing glucose levels leads to membrane depolarization causing an influx of calcium ions which is responsible for triggering insulin release (Mohammed et al., 2009). Thus calcium influx in cellular clusters stained with Fluo-4 AM, a fluorescent calcium indicator dye, in real-time using fluorescent microscopy was monitored (FIG. 4A). This method allowed analysis of calcium flux on both a population and single cell level, and showed that both SC-β cells and primary adult β cells responded to sequential glucose challenges by repeatedly increasing intracellular $Ca^{2+}$ in similar manners, consistent with normal GSIS, while PH cells generated with the control differentiation protocol displayed an abnormal calcium response, consistent with their abnormal GSIS (FIG. 4B). When single cell analysis was performed, most individual SC-β cells and primary adult β cells responded to 2-3 sequential glucose challenges by fluxing calcium while most PH cells responded to 0 challenges (FIG. 4C-4E). Unlike rodent β cells, human β cells are known to display a degree of dyssynchrony in response to high glucose (Rutter and Hodson, 2013). These data show that both the entire population and individual cells within the SC-β cell clusters function similarly to β cells within isolated islets and further support the conclusion that the SC-β cells generated using the new differentiation protocol function in vitro.

Stem Cell-Derived β Cells From hPSC Resemble Primary Human β Cells

Figures 5A, 5B, 5C, 5D, 5E, 5F:
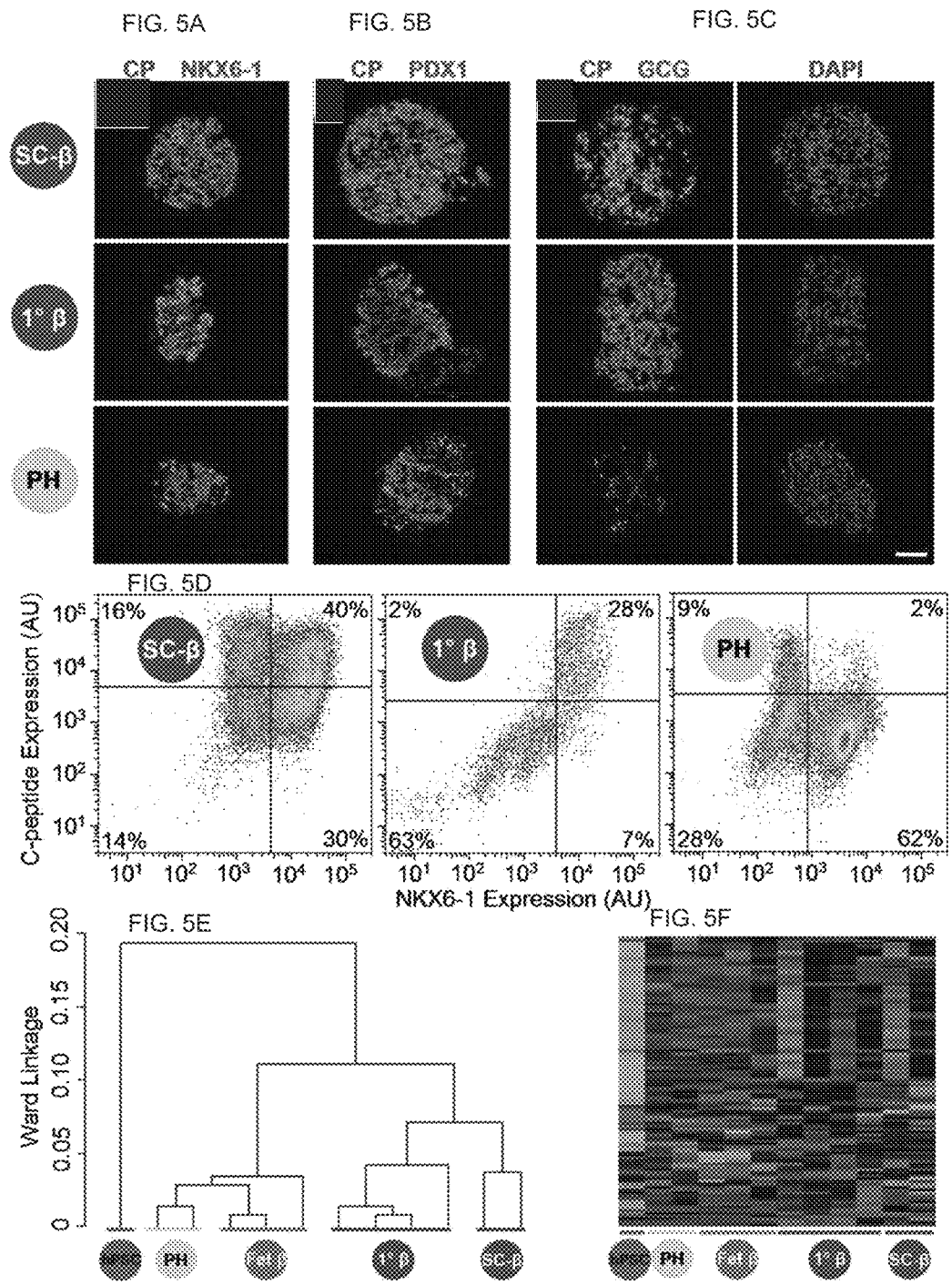
FIGS. 5A, 5B, 5C, 5D, 5E and 5F demonstrate that SC-β express human β cell markers at protein and gene expression level.
Figure 6:
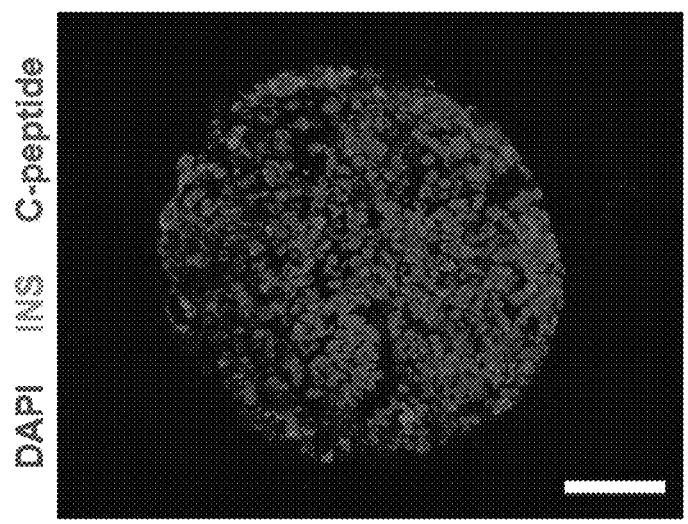
FIG. 6 illustrates the histology of a SC-β cell cluster stained for DAPI (blue), insulin (green), C-peptide (red). Scale bar=100 μm.
Figure 7A:
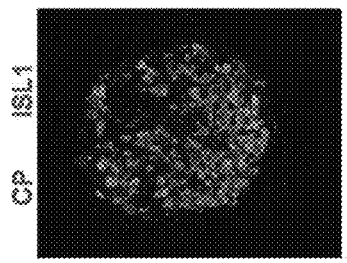
FIGS. 7A, 7B, and 7C demonstrate additional histological staining of SC-β cells.
Figure 7B:
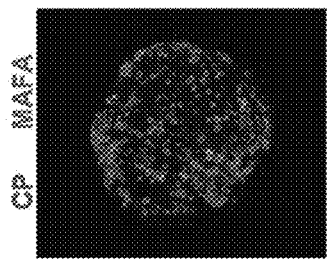
Figure 7C:
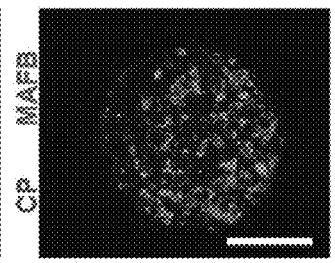
Figures 8A, 8B, 8C:
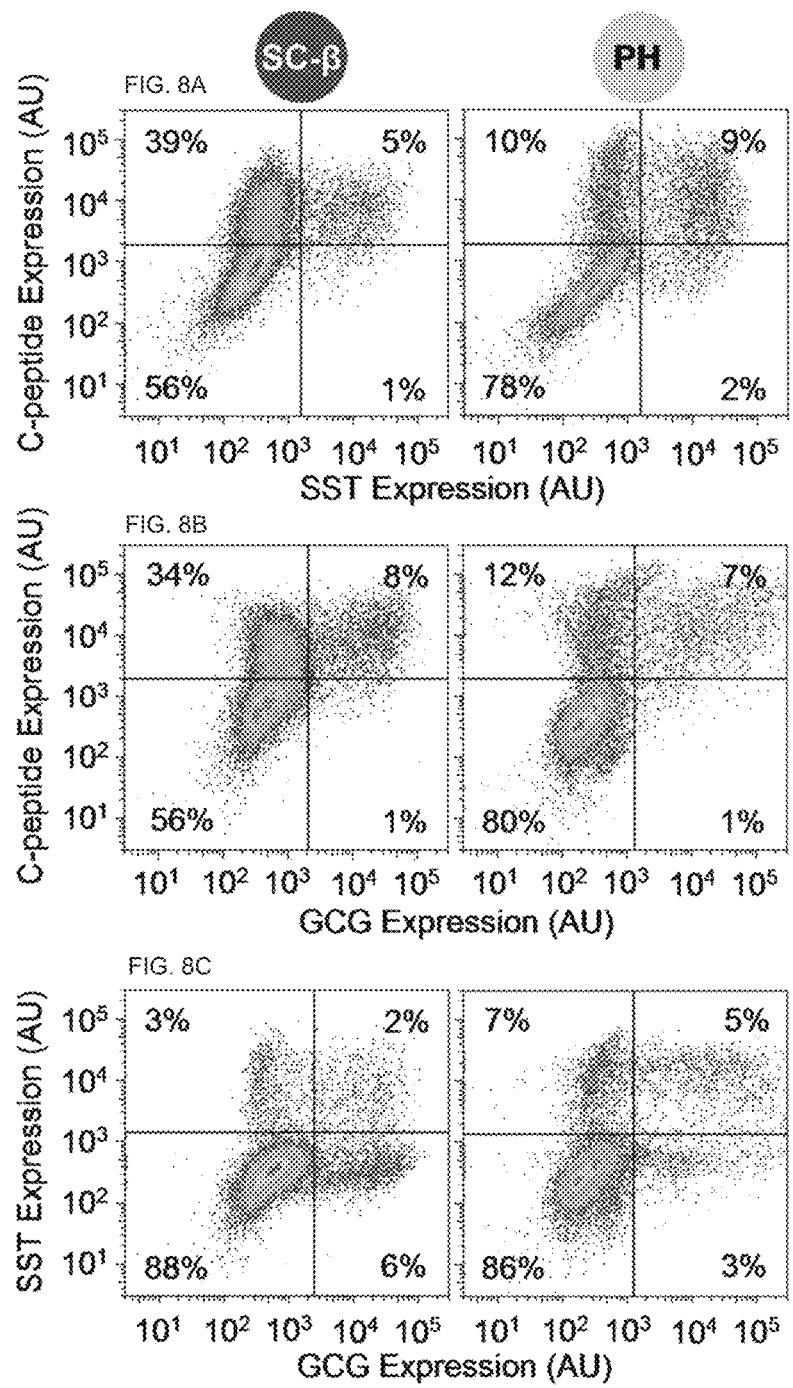
FIGS. 8A, 8B and 8C show representative flow cytometry dot plots and population percentages of SC-β cells and PH cells stained for C-peptide and SST (FIG. 8A), C-peptide and GCG (FIG. 8B), and SST and GCG (FIG. 8C).

After observing that SC-β cells function like primary adult β cells in vitro, the two cell populations were then analyzed by protein expression, gene expression, and ultrastructure. Unlike most previously reported hPSC-derived insulin-producing cells, these SC-β cells express both normal β cell markers PDX1 and NKX6-1 (FIGS. 5A and 5B). Rare non-β cell hormones are observed but do not co-localize with NKX6-1/C-peptide co-positive cells (FIG. 5C). SC-β cells stain positive for both insulin and C-peptide, a stoichiometric byproduct of proinsulin processing, indicating that the insulin staining comes from cell-endogenous insulin production (FIG. 6) and stain for ISL1, MAFA, and MAFB (FIG. 7A-7C). Flow cytometry quantification reveals that the methods described herein can produce 40% NKX6-1/C-peptide, similar to the percentage found in cadaveric human islets (FIG. 5D). Furthermore, only 8% of total C-peptide+ cells co-express glucagon and 4% co-express somatostatin (FIG. 8A-8C.) Although largely monohormonal cells have been previously reported in one study, those cells were not shown to express key β cell identity marker NKX6-1 or to function in vivo (Cheng 2012.) Recent work has shown that directed differentiation protocols that generate higher levels of NKX6-1 lead to better transplantation outcomes for the pancreatic progenitor transplants (Rezania et al., 2013). Additionally, conditional knock-out studies have shown that NKX6-1 expression is necessary for β cell function in adult mouse islets, suggesting that co-expression of these factors in our cells may help explain their functional abilities (Taylor et al., 2013).

The improved protein expression of several key β cell markers indicated that the transcriptional network of these cells better matched that of human islet β cells. Recent work has demonstrated that INS+PH cells generated by previous protocols do not resemble adult islet INS+β cells (Hrvatin et al., 2014; Xie et al., 2013). Microarray analysis of sorted INS+ cells generated by previously published protocols showed that they clustered with fetal β cells rather than with functional adult human β cells sorted via the same method.

To compare the SC-β cells of the disclosure to adult human islets, INS+/NKX6-1+ cells were sorted using the same method and performed global gene expression analysis by microarray. Unlike the previously published stem cell-derived INS+PH cells, the SC-β cells described herein clustered more closely with human adult β cells than fetal β cells or INS+PH cells (FIG. 5E). In addition, these data showed that the expression of canonical β cells genes, like PDX1, MNX1, and NKX2-2 were more similar between SC-β cells and adult human β cells than previous INS+PH cells. An analysis of the top 100 most differentially expressed genes in the data set also showed that SC-β cells and adult human β cells were more similar to one another than previous PH or fetal β cells (FIG. 5F). There remain differences between SC-β cells and human adult β cells that could be improved with additional minor changes to the culture media composition during late stages of differentiation.

Since the gene and protein expression patterns of SC-β cells resemble those of primary human β cells, it was hypothesized that SC-β cells should also package their insulin protein into appropriate secretory granules like bona fide β cells do. β cells package insulin into secretory granules that are initially pale grey with a halo and further mature into dark crystallized polygonal granules with a light halo (FIG. 9A). Previous studies of INS+ cells generated from stem cells revealed that these cells have only polyhormonal and alpha-like granules, which are distinct round granules with a dark halo (D'Amour et al., 2006; Kroon et al., 2008). These results were recapitulated with the control protocol that produced INS+ cells that had only abnormal polyhormonal and alpha-like granules and few, if any, β cell granules (FIG. 9A). On the other hand, the methods described herein generated SC-β cells that packaged and crystallized insulin protein into prototypical β cell granules (FIG. 9A). Both developing insulin granules and mature, crystallized insulin granules were observed in both primary human β cells and SC-β cells (FIG. 9B). To confirm the protein content of these granules, immunogold labeling was performed with particles against insulin and glucagon. Whereas the PH cell granules abnormally contained both insulin and glucagon protein, the primary human β cell and SC-β cells granules contained only insulin (FIG. 9C). Thus the ultrastructure of SC-β cells mirrors that of adult human β cells.

Generation of Glucose Sensing Insulin Secreting β Cells from hiPSC In Vitro

The new differential protocol used to develop the functional β Cells from hPSC as discussed above was further used to generate functional β cells from hiPSC lines in vitro. The hiPSC lines were generated at the Harvard iPSC Core with skin fibroblasts grown out from either non-diabetic or type 1 diabetic patients. In contrast to the hPSC line which was generated from embryos, the hiPSC line was generated from human tissue, showing that the functional β cells can be developed directly from diseased patients, i.e., patients with type 1 diabetes.

Figure 10A:
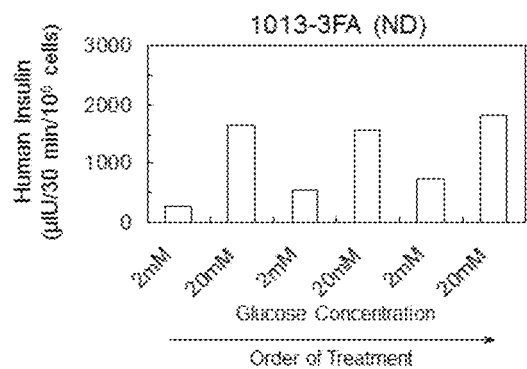
FIGS. 10A and 10B demonstrate that stem cell-derived β (SC-β) cells generated from hiPSC in vitro secrete insulin in response to multiple sequential high glucose challenges like primary human β cells.
Figure 10B:
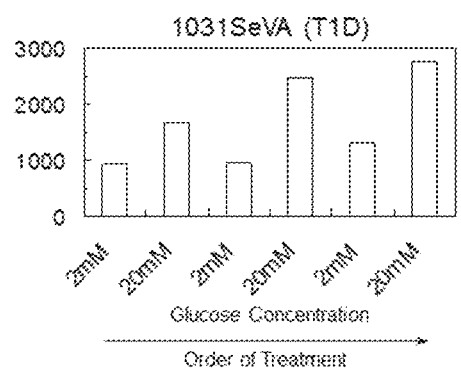

The resulting β cells were subjected to glucose challenges to determine their ability to repeatedly perform glucose stimulated insulin secretion (GSIS). It was found that multiple β cells generated utilizing the methods described herein can respond to at least three sequential high glucose challenges (FIGS. 10A-10B). In this particular experiment, hiPSC-β cells derived from a non-diabetic cell line (1013-3FA) were compared to hiPSC-β cells derived from a type 1 diabetic cell line (1031SeVA). The stimulation index, as calculated by the ratio of insulin secreted in high glucose (20 mM) to low glucose (2 mM), was greater for the β cells derived from the non-diabetic cell line compared to the β cells derived from the type 1 diabetic cell line. Furthermore, the amount of insulin secreted per cell in response to either a 2 mM or 20 mM glucose challenge was greater for the β cells derived from the type 1 diabetic cell line than for the β cells derived from the non-diabetic cell line. Taken together, these data suggest that the in vitro function of hiPSC-β cells derived from a type 1 diabetic cell line is similar to the non-diabetic cell counterparts.

After observing that hiPSC-β cells are responsive to glucose in vitro, the inventors next analyzed how similar the non-diabetic and type 1 diabetic cell populations were by protein expression, gene expression, and ultrastructure. Three different non-diabetic cell lines and three different type 1 diabetic cell lines were used to determine expression of NKX6-1/C-peptide. As was the case with the hPSC, these hiPSC-β cells expressed both normal β cell markers PDX1 and NKX6-1 (FIGS. 11A-11F). Flow cytometry quantification reveals that the methods described herein can produce about 40% NKX6-1/C-peptide, similar to the percentage found in cadaveric human islets (FIG. 5D).

Stem Cell-Derived β Cells Function In Vivo after Transplantation

The data described thus far are consistent with the generation of functional human β cells in vitro. To further test their capacity to function in vivo, these cells were transplanted under the kidney capsule of immunocompromised mice (FIGS. 12A-12D and Table S1).

12A). As a control, we also transplanted PH cells generated using previously published protocols and found that these cells did not secrete significant levels of insulin in response to glucose in vivo (FIG. 12A). Moreover, it was also confirmed that the pancreatic progenitors generated failed to produce appreciable insulin in vivo within two weeks, as has been previously published (FIG. 12C).

Some insulin producing cells that are not bona fide β cells can secrete insulin in an unregulated manner into the bloodstream of animal, functioning like an insulin pellet rather than a responsive β cell. To test whether SC-β cells not only secrete high levels of insulin but also do so in a functionally responsive manner the amount of human insulin in the bloodstream of the mice both before and after an acute glucose challenge was measured. For both human islet transplants and SC-β cells transplants, 9 out of 12 mice tested showed functional glucose stimulated insulin secretion in vivo two weeks post-transplant (FIG. 12A).

TABLE S1

ELISA measurements of human insulin from the serum of mice transplanted with SC-β cells, primary β cells, and PH cells

| Cell Type | ms# | Human Insulin (μIU/mL) 0' | Human Insulin (μIU/mL) 30' | Cell Type | ms# | Human Insulin (μIU/mL) 0' | Human Insulin (μIU/mL) 30' | Cell Type | ms# | Human Insulin (μIU/mL) 0' | Human Insulin (μIU/mL) 30' |
|---|---|---|---|---|---|---|---|---|---|---|---|
| SC-β cells | 1 | 2.2 | 1.1 | 1° β cells | 1 | 1.1 | 2.8 | PH cells | 1 | nd | 0.4 |
|  | 2 | 5.1 | 2.5 |  | 2 | 1.4 | 2.0 |  | 2 | nd | 0.1 |
|  | 3 | 1.8 | 4.0 |  | 3 | 0.5 | 2.4 |  | 3 | nd | 0.1 |
|  | 4 | 1.3 | 3.2 |  | 4 | 0.7 | 1.4 |  | 4 | nd | 0.4 |
|  | 5 | 2.1 | 2.4 |  | 5 | 1.1 | 1.7 |  | 5 | nd | 0.4 |
|  | 6 | nd | 8.5 |  | 6 | −0.4 | −0.1 |  | 6 | 0.1 | 0.1 |
|  | 7 | nd | 7.5 |  | 7 | 1.4 | 3.9 |  | 7 | 0.2 | 0.2 |
|  | 8 | nd | 5.9 |  | 8 | nd | 5.1 * |  | 8 | 0.0 | 0.3 |
|  | 9 | nd | 5.9 |  | 9 | nd | 13.0 * |  | 9 | 0.0 | −0.2 |
|  | 10 | nd | 2.9 |  | 10 | nd | 5.1 * |  | 10 | 0.5 | 1.2 |
|  | 11 | 1.4 | 5.3 |  | 11 | nd | 1.5 * |  | 11 | nd | 0.7 |
|  | 12 | 1.7 | 2.6 |  | 12 | nd | 4.4 |  | 12 | nd | 1.0 |
|  | 13 | 2.3 | 4.3 |  | 13 | nd | 7.0 |  | 13 | nd | 1.6 |
|  | 14 | 0.9 | 1.4 |  | 14 | nd | 2.2 |  | 14 | nd | 1.1 |
|  | 15 | nd | 3.3 |  | 15 | nd | 3.2 |  | 15 | 0.3 | 0.6 |
|  | 16 | nd | 3.5 |  | 16 | nd | 3.9 |  | 16 | 0.1 | 0.2 |
|  | 17 | nd | 4.3 |  | 17 | 1.0 | 0.6 |  | 17 | 2.6 | 0.1 |
|  | 18 | nd | 3.2 |  | 18 | 0.9 | 1.7 |  |  |  |  |
|  | 19 | nd | 45.0 # |  | 19 | 5.9 | 2.6 |  |  |  |  |
|  | 20 | nd | 36.1 # |  | 20 | 1.6 | 2.3 |  |  |  |  |
|  | 21 | nd | 14.8 # |  | 21 | 1.0 | 1.7 |  |  |  |  |
|  | 22 | nd | 67.5 # |  |  |  |  |  |  |  |  |
|  | 23 | nd | 57.7 # |  |  |  |  |  |  |  |  |
|  | 24 | nd | 3.0 |  |  |  |  |  |  |  |  |
|  | 25 | nd | 2.8 |  |  |  |  |  |  |  |  |
|  | 26 | nd | 5.6 |  |  |  |  |  |  |  |  |
|  | 27 | nd | 7.5 |  |  |  |  |  |  |  |  |
|  | 28 | nd | 7.8 |  |  |  |  |  |  |  |  |
|  | 29 | nd | 6.4 |  |  |  |  |  |  |  |  |
|  | 30 | 5.0 | 11.4 |  |  |  |  |  |  |  |  |
|  | 31 | 4.3 | 5.1 |  |  |  |  |  |  |  |  |
|  | 32 | 3.8 | 2.5 |  |  |  |  |  |  |  |  | nd = not determined
cultured 2 wk in vitro during final step; all other SC-β cells cultured 1 wk When adult human islets are transplanted, human insulin is detectable in the serum of these mice within two weeks. Conversely, when previously published pancreatic progenitors were transplanted into mice no insulin is detected at two weeks post-transplant (Kroon et al., 2008; Schulz et al., 2012; Rezania et al., 2012). Instead the cells require a 3-4 month long, poorly understood maturation phase in vivo. On the other hand, SC-β cells, like human islets, secrete high levels of insulin into the host bloodstream in response to a glucose challenge within two weeks of transplant (FIG.

After the terminal in vivo GSIS challenge was performed, these animals were sacrificed and the engrafted kidneys removed for analysis. Histological sections of these kidneys revealed the presence of large grafts of human cells under the kidney capsule Immunofluorescence staining of these grafts showed that both SC-β cells and human islet grafts contained high levels of insulin expressing cells (FIG. 12B). Those INS+ cells also co-expressed the canonical β cell transcription factor PDX1 as expected for functional β cells. Analysis of insulin and glucagon staining further revealed that the SC-β cells remained monohormonal after transplantation (FIGS. 13A-13B). A minor population of GCG+ a cells are also generated in this protocol as observed by immunofluorescence and flow cytometry analyses (FIG. 7 and FIG. 10) and those cells are also observed in vivo post-transplantation (FIG. 13).

It was further observed that insulin secretion in vitro increased over time when media, particularly supplemented CMRL media containing Alk5 inhibitor and T3 hormone, was used in the last differentiation step. Thus SC-β cells were cultured in vitro for an additional week (two weeks instead of one week in this last step media) and were observed to see whether they would also secrete more insulin in vivo. After transplanting these aged cells, ten fold higher levels of insulin were unexpectedly observed than the same number of transplanted younger SC-β cells (FIG. 12D). Thus the levels of insulin function achievable in vivo with human SC-β cells was similar to that achieved by transplantation of human islets. Taken together these transplantation data suggest that SC-β cells can provide an alternative clinical option for cell transplantation that does not rely on variable and limited supplies of donated cadaveric islets or on a poorly understood and poorly controllable in vivo maturation period from transplanted stem cell derived pancreatic progenitors.

Culture Media

Figure 14A:
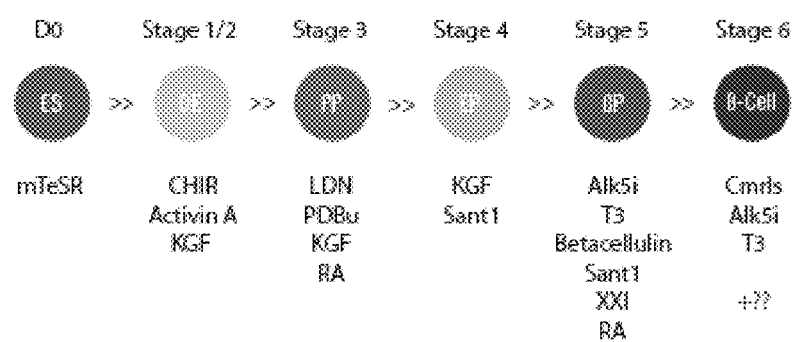
FIGS. 14A, 14B and 14C demonstrate the use of media at the last step of differentiation to allow SC-β cells to secrete more insulin in vivo.
Figures 14B, 14C:
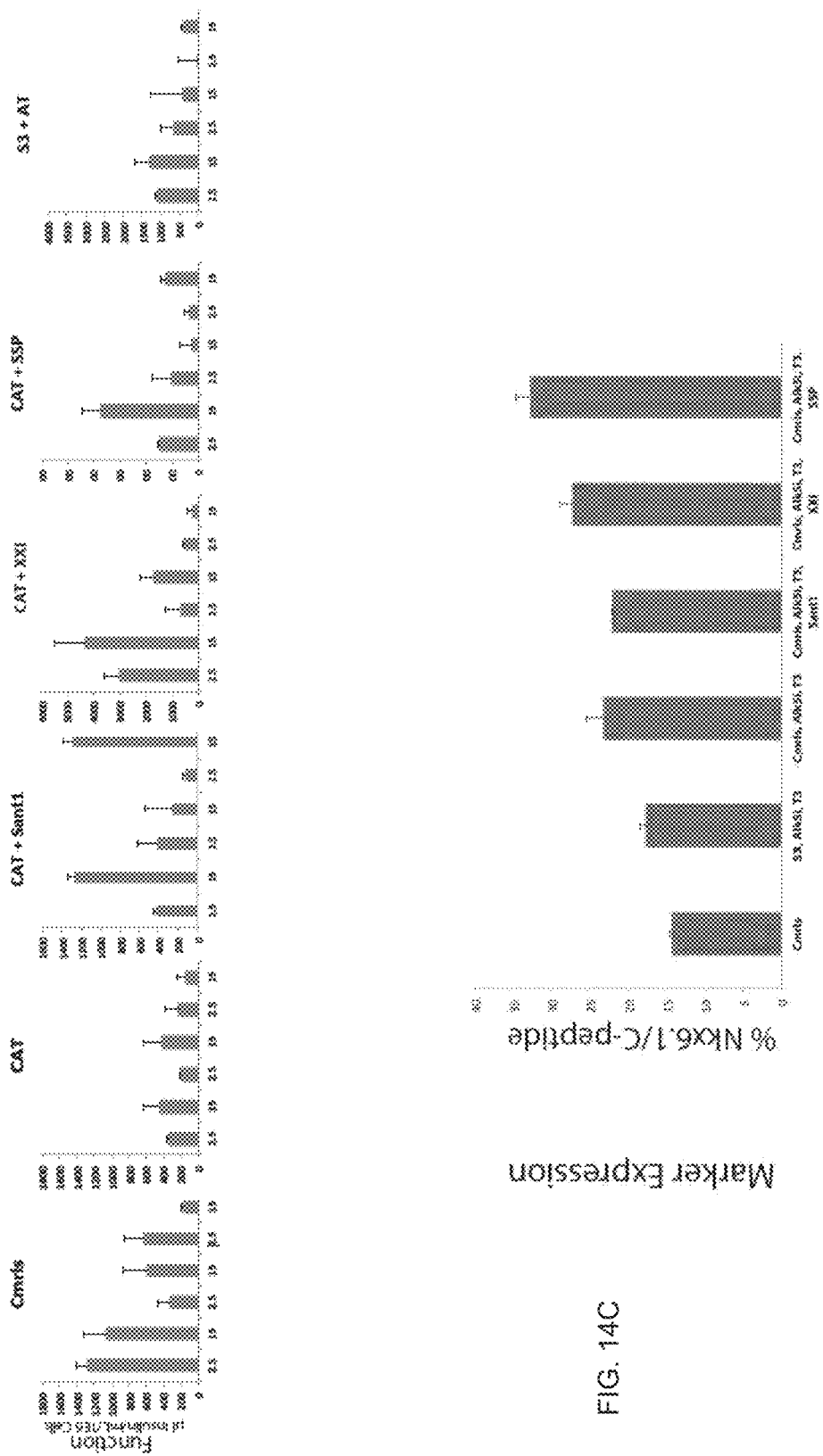

To induce the in vitro maturation of at least some of the Pdx1-positive, NKX6-1-positive, insulin-positive endocrine cells into SC-β cells, the Pdx1-positive, NKX6-1-positive, insulin-positive endocrine cells are maintained in a suitable culture medium for a sufficient period of time. In the present invention, as mentioned above, it was found that using CMRL media containing Alk5 inhibitor and T3 hormone allowed SC-β cells cultured in vitro to secrete more insulin in vivo. Adding additional factors to the CMRL media at the last step of differentiation (Stage 6) (FIG. 14A), however, was also found to generate a better glucose stimulated insulin secretion (GSIS) response by SC-β cells as measured by either stimulation index between high and low glucose challenges or by the amount of insulin released. Such additional factors may include, but are not limited to, Sant1, XXI, and SSP. The stimulation index, as calculated by the ratio of insulin secreted in high glucose (15 mM) to low glucose (2.5 mM), was greater for the SC-β cells maintained in a CMRL media containing Alk5 inhibitor, T3 hormone and either Sant1, XXI or SSP than those SC-β cells maintained in only CMRL media, CMRL media containing Alk5 inhibitor and T3 hormone, or S3 media containing Alk5 inhibitor and T3 hormone (FIG. 14B). Furthermore, the amount of insulin secreted was greater for the SC-β cells maintained in a CMRL media containing Alk5 inhibitor, T3 hormone and either Sant1, XXI or SSP than those SC-β cells maintained in only CMRL media, CMRL media containing Alk5 inhibitor and T3 hormone, or S3 media containing Alk5 inhibitor and T3 hormone (FIG. 14C). Taken together, these data suggest that not only is maintaining SC-β cells in CMRL media important in the final differentiation step to induce maturation of at least some of the Pdx1-positive, NKX6-1-positive, insulin-positive endocrine cells into SC-β cells, but the further addition of certain factors such as Sant1, XXI, or SSP to the CMRL media will enhance glucose stimulated insulin secretion (GSIS) of the cells.

Enhancing Survival and Function of Cells

One challenge for the stem cell field has been generating a sufficient quantity of SC-β cells that can be useful for drug screening, disease modeling, or therapeutic use. For example, hES cells are technically difficult to culture, are vulnerable to apoptosis upon cellular detachment and dissociation, undergo massive cell death particularly after complete dissociation, and have low cloning efficiency. (Watanabe, K. et al., Nature Biotechnology 25, 681-686 (2007)). As a result, the quantity of viable SC-β cells yielded may be low. By modify the protocol between Steps 3 and 6 in the manner shown in FIG. 15A, more pure NKX6.1+ endocrine clusters can be generated (FIG. 15B) leading to more SC-β cells that can be therapeutically useful.

In Steps 3-5, for instance, cell survival can be improved by adding a rho-associated protein kinase inhibitor, or a Rock inhibitor. It is believed that the addition of a Rock inhibitor enhances survival of ES cells by preventing dissociation-induced apoptosis thus increasing their cloning efficiency. (Watanabe et al.) Examples of Rock inhibitors include, but are not limited to, Y-27632, Fasudil/HA1077, and H-1152. In the present invention, treating the cells with a Rock inhibitor has been shown to improve cell survival (FIG. 15C).

Figure 15D:
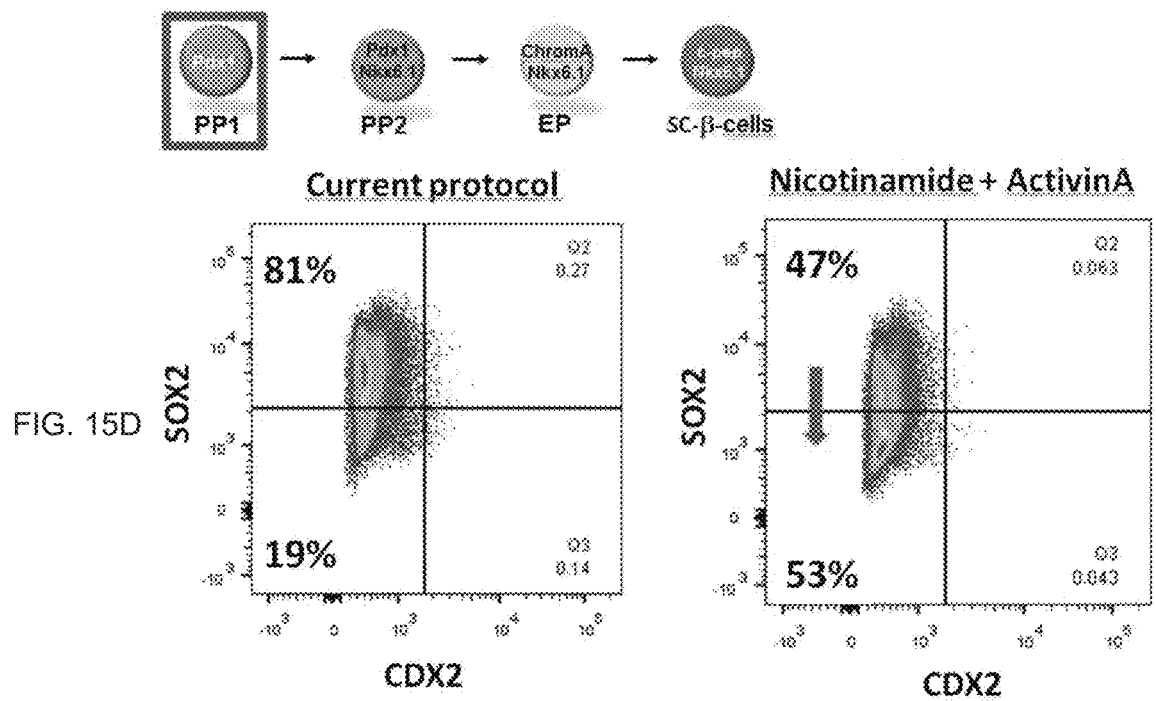
Figure 15E:
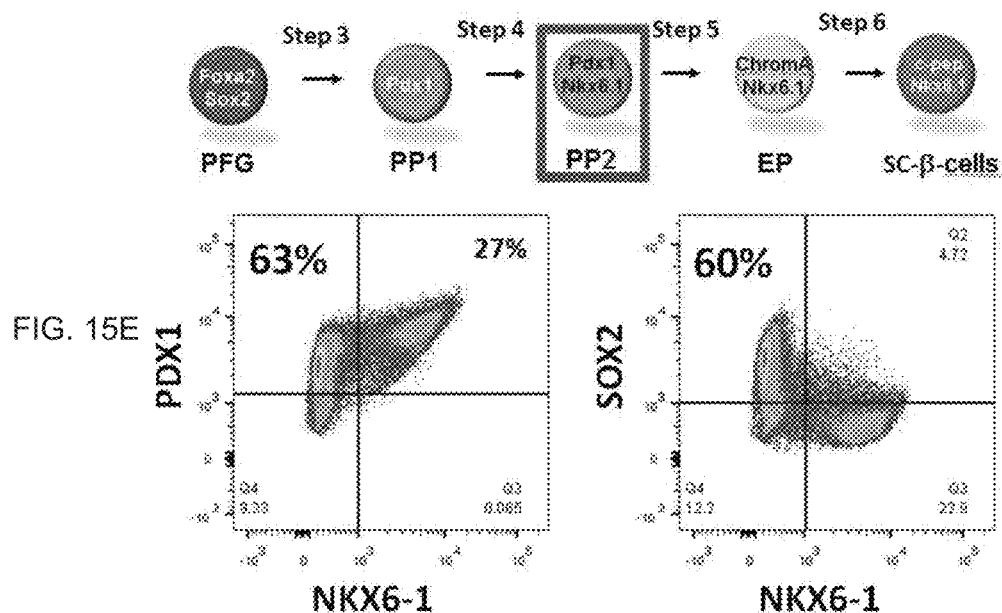

In addition to treating the cells with a Rocki inhibitor, the cells in Steps 3-4 can be treated with ActivinA alone or in combination with Nicotinamide. Activin A and Nicotinamide have both been shown to improve cell survival. One way in which they improve cell survival is by down-regulating SOX2, a marker for a pluripotent stem cell, from about 81% to about 47% (FIG. 15D). Since SOX2 and NKX6-1 are mutually exclusive (FIG. 15E), down-regulation of SOX2 results in the up-regulation of NKX6-1, a marker for a mature pancreatic β cell.

In Steps 5-6, cell survival can further be enhanced by treating cells with staurosporine. Staurosporine is known to be an activator of neuronal, glial, and stem cell-like neurosphere differentiation and is also thought to induce apoptosis. (Schumacher, et al., Mol. Cell. Neurosci. 2003; 23(4): 669-680). In the present invention, the addition of staurosporine resulted in a near pure endocrine population by increasing the percentage of Chromogranin A, a pancreatic endocrine cell marker, (FIG. 15F) and increasing the percentage of NKX6-1.C-peptide+ cells (FIG. 15G).

Finally, cell survival can further be enhanced by treating cells with a culture medium containing Alk5i, T3 in combination with XXI, a γ-secretase inhibitor that improves β cell maturation. As shown in FIGS. 15H and 15I, the addition of XXI to the medium at Steps 5 and 6 can increase the NeuroD1+ population.

Taken together, these data suggest that adding certain compounds to the cells at various stages throughout the process is important in improving cell survival and also enriching the population of cells that can differentiate into therapeutically useful SC-β cells.

Utility of SC-β Cells for Translational Biology

A major challenge for the stem cell field has been generating differentiated cell types that are close enough to their normally developed counterparts to be useful for drug screening, disease modeling, or therapeutic use. SC-β cells generated using the new differentiation protocol as discussed herein appear to function both in vitro and in vivo in a similar manner to primary human β cells. It was therefore hypothesized that these cells could be useful for translational medicine (FIG. 16A).

One of the most common therapeutic strategies for treating Type 2 diabetes is the administration of oral anti-diabetic medications. Many of these pharmaceutical agents act directly on the β cell to increase insulin secretion. For example, sulfonylurea drugs increase secretion of endogenous insulin through blocking potassium channels (Modi, 2007). Current drug screening on β cells is restricted to rodent islets, transformed cell lines or highly variable and limited supplies of cadaveric human islets. Given that rodent metabolism only partially mimics human metabolism, a reliable, consistent supply of human β cells for analysis would be very valuable. Here the inventors examined whether SC-β cells could be used for therapeutic screening in vitro.

The inventors first tested whether SC-β cells could respond to existing anti-diabetic drugs from several different classes (FIG. 16B). LY2608204 is glucokinase activator in clinical trials while liraglutide, tolbutamide, and nateglinide are examples of GLP-1 agonists and secretagogues (sulfonylureas and meglitinides), respectively, that have been used clinically (Matschinsky, 2009; Modi, 2007; Vetere et al., 2014). Indeed SC-β cells showed a trend toward responding to treatment with these drugs by increasing insulin secretion in vitro following a glucose challenge (FIG. 16C). These data provide initial proof of concept that SC-β cells could provide a novel platform for future drug screening.

Next the inventors tested whether SC-β cells could model β cell replication. Increasing a patient's β cell mass may improve glycemic control by producing more insulin in total without needing to increase the amount of insulin produced per β cell. To date, few if any drugs that have promoted β cell replication in rodent or cell line models have been translated to human β cells. Hormonal control of β cell replication has been suggested through studies of islet mass in human pregnancy and rodent studies using prolactin treatment (Parsons et al., 1992; Labriola et al., 2007; Brelje et al., 2004). The inventors tested whether treatment with prolactin could increase β cell replication in a SC-β cell population. After culturing SC-β cells with prolactin, cells were stained and fixed for C-peptide and the proliferation marker Ki67 (FIGS. 16D and 16E). Like primary human β cells, the baseline number of Ki67+ proliferating SC-β cells was very low (0.20±0.08% Ki67+/C-peptide+) (FIG. 16F). Quantification of untreated and prolactin-treated cells revealed a trend toward increased proliferation downstream of prolactin (0.39±0.08% Ki67+/C-peptide+), suggesting that SC-β cells may be able to respond to proliferation cues in replication screens (FIG. 16F).

Finally, the inventors examined whether SC-β cells could be directly useful as a cell therapy for treating diabetes. Unlike type 2 diabetes, increasing β cell function or β cell replication via new pharmaceuticals is likely to have little therapeutic benefit to patients with Type 1 diabetes where the pancreatic β cells are destroyed by autoimmune attack. These patients can be effectively treated by replacing lost β cells with donor allogeneic islets through the Edmonton transplantation protocol (Shapiro et al., 2006).

Figure 17:
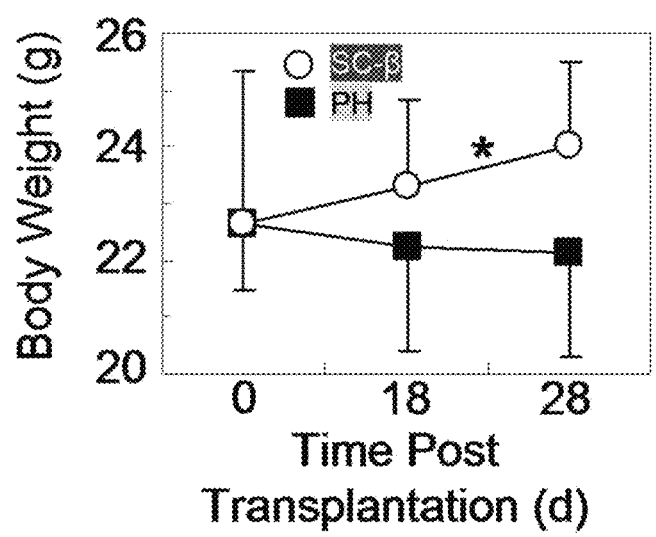
FIG. 17 is a graph illustrating the body weight of Akita mice transplanted with SC-β cells (n=6) or PH cells (n=6). *$p<0.05$ comparing the two cell groups at the 18 and 28 d time point.

One useful model of this kind of severe diabetes is the Akita mouse. Akita mice harbor a mutation in the insulin gene that leads to protein misfolding, complete and irreversible β cell failure, and progressively more severe hyperglycemia. Akita mice can be restored to normoglycemia via mouse or human islet transplantation into the kidney capsule (Pearson et al., 2008). Therefore SC-β cells generated according to the methods described herein were tested to see if they could also function to control diabetic hyperglycemia. The results showed that transplantation of SC-β cells, but not PH INS+ cells of previous protocols, into young Akita mice rapidly reversed the progressively worsening hyperglycemia observed in these animals (FIG. 16G). Fasting blood glucose measurements of mice transplanted with SC-β cells were on average less than 200 mg/dl whereas those transplanted with control PH cells showed progressively higher blood glucose levels above 400 mg/dl, as has been observed for non-transplanted Akita mice (FIG. 16G) (Pearson et al., 2008). As expected, human insulin levels were high in SC-β cell transplanted animals and barely detectable in PH cell transplanted control animals (FIG. 16H). The mice transplanted with SC-β cells also showed better weight maintenance than control mice, indicative of normalized insulin function (FIG. 17). Thus SC-β cells are capable secreting insulin and halting and reversing progressive hyperglycemia in a diabetic mouse model almost immediately following transplantation.

Discussion

The work described herein demonstrates that functional human β cells can be directly generated from hPSC and hiPSC in vitro. Collectively, the data described herein demonstrate that these cells (i.e., SC-β cells) function similarly to primary human β cells both in vitro and in vivo post-transplantation. SC-β cells generated according to the methods described herein present several new opportunities for β cell study and therapy. Limited supplies of donated cadaveric islets, high variability between samples due to patient characteristics or isolation and the trivially small amount of human β cell replication in vitro has severely limited human β cell supply to-date. This limitation has restricted transplantation options for patients as well as high throughput drug screening and disease modeling. A single 68 kg (150 1b) patient requires roughly 340-748 million transplanted islet cells to effectively resolve type 1 diabetes via islet transplantation (McCall and Shapiro, 2012). The strategy described herein is both efficient and highly scalable making it practical for a single laboratory to grow hundreds of millions to billions of SC-β cells at a time. A major clinical advantage of SC-β cells compared to previously described stem cell derived therapies for diabetes is that these cells provide the first opportunity for a cell therapy that does not require a potentially unpredictable "black box" period of further differentiation in vivo.

Unlike primary human β cells, SC-β cells can also be generated from cells of any desired genetic background. iPS cells from patients with diabetes or other metabolic syndromes can now be derived and differentiated into SC-β cells for disease modeling and study of β cell function or susceptibility to stress or immune attack. Technologies like TALEN and CRISPR enable genome editing of ES or iPS cells to incorporate and test variants identified by genetic analyses like genome wide association studies (GWAS). Similarly, β cell drug responses could now be compared between genetically matched pairs of mutant and non-mutant β cells (Ding et al., 2013). Identification and testing of novel biomarkers for β cell function or pharmacogenetics is also enabled by the combination of these technologies. Thus SC-β cells provide a novel, human-specific platform for in vitro drug discovery and characterization in metabolism and diabetes.

The generation of SC-β cells also represents a potentially useful step towards the future generation of islets and pancreatic organs. Incorporating pancreatic niche cells, like mesenchymal or endothelial cells into cultures of stem cell derived pancreatic cells may be beneficial (Sneddon et al., 2012; Lammert et al., 2001). Other evidence suggests that the presence of alpha and delta cells may be important for precise tuning of normal β cell function (Rodriguez-Diaz et al., 2011). Furthermore, tissue engineering of a pancreatic organ will require incorporation of functional exocrine and ductal tissue, potentially in carefully specified architecture. The generation of SC-β cells represents a step forward towards making a clinical impact through harnessing stem cell biology.

Experimental Procedures
Cell Culture hPSC lines were maintained undifferentiated in mTESR1 (StemCell Technologies Inc.; 05850) in 500 ml stir flasks (Corning, VWR; 89089-814) placed on a 9-Position stir plate set at rotation rate of 70 rpm in a 37° C. incubator, 5% $CO_2$, and 100% humidity. The line HUES8 was the primary line utilized. Cells were dispersed with Accutase and were seeded as single cells at 0.5 million/ml in mTESR with 10 µM Y27632 (Abcam; ab120129). mTESR1 media was changed (w/o Y27632) 48 hours later. Cultures were split 24 hours after that media change to keep cluster diameter size <300 µm. Cultures were regularly tested for pathogens, karyotype and for maintenance of pluripotency markers.

Exemplary media used for directed differentiation were as follows:

S1 media: MCDB131 (Cellgro; 15-100-CV)+8 mM D-(+)-Glucose (Sigma; G7528)+2.46 g/L $NaHCO_3$ (Sigma; 53817)+2% FAF-BSA (Proliant; 68700)+ITS-X (Invitrogen; 51500056) 1:50.000+2 mM GlutaMAX™ (Invitrogen; 35050079)+0.25 mM Vitamin C (Sigma Aldrich; A4544)+1% Pen/Strep (Cellgro; 30-002-CI).

S2 media: MCDB131+8 mM D-Glucose+1.23 g/L $NaHCO_3$+2% FAF-BSA+ITS-X 1:50.000+2 mMl GlutaMAX™+0.25 mM Vitamin C+1% Pen/Strep.

S3 media: MCDB131+8 mM D-Glucose+1.23 g/L $NaHCO_3$+2% FAF-BSA+ITS-X 1:200+2 mMl GlutaMAX™+0.25 mM Vitamin C+1% Pen/Strep BE5 media: MCDB131+20 mM D-Glucose+1.754 g/L $NaHCO_3$+2% FAF-BSA+ITS-X 1:200+2 mM GlutaMAX™+0.25 mM Vitamin C+1% Pen/Strep+Heparin 10 µg/ml (Sigma; H3149).

CMRLS: CMRL 1066 Supplemented (Mediatech; 99-603-CV)+10% FBS (HyClone™, VWR; 16777)+1% Pen/Strep.

All media were filter sterilized through a 0.22 µm bottle top filter (Corning). For all following media changes, small molecules and growth factors were added to the base media immediately before media change in a low-light hood.

For initiation of SC-β cell differentiation, cells were seeded at 0.5 million/ml and differentiation was started 48 hours later. Media changes were as follows—

Day1: S1+100 ng/ml Activin A (R&D Systems; 338-AC)+3 µM Chir99021 (Stemgent; 04-0004-10)).

Day2: S1+100 ng/ml Activin A. Days 4, 6: S2+50 ng/ml KGF (Peprotech; AF-100-19)).

Days 7, 8: S3+50 ng/ml KGF+0.25 µM Sant1 (Sigma; S4572)+2 µM Retinoic acid (RA) (Sigma; R2625)+200 nM LDN193189 (only Day7) (Sigma; SML0559)+500 nM PdBU (EMD Millipore; 524390)).

Days 9, 11, 13: S3+50 ng/ml KGF+0.25 µM Sant1+100 nM RA.

Days 14, 16: BE5+0.25 µM Sant1+50 nM RA+1 µM XXI (EMD Millipore; 565790)+10 µM Alk5i II (Axxora; ALX-270-445)+1 µM L-3,3',5-Triiodothyronine (T3) (EMD Millipore; 64245)+20 ng/ml Betacellulin (Thermo Fisher Scientific; 50932345)).

Days 18, 20: BE5+25 nM RA+1 µM XXI+10 µM Alk5i II+1 µM T3+20 ng/ml Betacellulin.

Days 21-35 (media change every second day): CMRLS+10 µM Alk5i II+1 µM T3. Cells were tested by in vitro assays after between days 28 and 32. Cells were transplanted on day 28, unless otherwise noted.

Alternatively, Days 21-35: CMRLS+10 µM Alk5i II+1 µM T3+Sant1.

Alternatively, Days 21-35: CMRLS+10 µM Alk5i II+1 µM T3+XXI.

Alternatively, Days 21-35: CMRLS+10 µM Alk5i II+1 µM T3+SSP.

For generation of PH protocol cells to mimic previous publications, the same differentiation protocol was used until day 14. On days 14 and 16, cells were fed with S3+1 µM Alk5i II, 200 nM LDN193189, and 100 nM RA (Rezania et al., 2012). On days 18 and onward, cells were fed every other day with S3+100 nM RA. Cells were maintained in this media until experimental analysis. Cells were maintained in culture and tested after the same number of days in differentiation media as the SC-β cells to control for the impact of time.

Flow Cytometry

Cells were dispersed into single-cell suspension by incubation in TrypLE Express at 37° C. for 10-30 min in a 15 ml falcon tube. Starting at stage 5, clusters take longer to dissociate into single cells. Clusters should be incubated with TrypLE Express until they dissociate to single cells upon mixing by pipetting gently up and down with a P1000. The TrypLE Express was quenched with 3-4 times media and cells were spun down for 5 min at 1000 rpm. Cells were washed twice in PBS and transferred to a 1.7 ml Safe seal microcentrifuge tube (Bioscience Inc.; 11510). Make sure having 1-10 mio cells/tube and use 0.5-1 ml volumes in the following. Cells were resuspended in 4% paraformaldehyde (PFA) (Electron Microscopy Science Nm; 15710) and incubated on ice for 30 min. Cells were then washed 3 times in PBS followed by incubation in blocking buffer (PBS+0.1% TritonX100 (VWR; EM-9400)+5% donkey serum (Jackson Immunoresearch; 017-000-121)) on ice for 1 hour. After fixation cells are more resistant to centrifugation, so after fixation all centrifugations were done at 3000 g for 3 min. Cells were then resuspended in blocking buffer with primary antibodies and incubated at 4° C. overnight.

Primary antibodies were used 1:300 unless otherwise noted: Goat anti-human PDX-1/IPF1 (R&D Systems; AF2419), mouse anti-NKX6-1 (University of Iowa, Developmental Hybridoma Bank; F55A12-supernatant) (1:100), rabbit anti-Chromogranin A (Abcam; ab15160), rat anti-insulin (pro-)/C-peptide (Developmental Studies Hybridoma Bank at the University of Iowa; GN-ID4) (need to add glucagon and somatostatin). Cells were washed 2 times in blocking buffer and then incubated in blocking buffer with secondary antibodies on ice for 2 hours (protected from light). Secondary antibodies conjugated to Alexa Fluor 488, 647 (Life Technologies) or PE (Thermo Fisher Scientific; NC9774252) were used to visualize primary antibodies. Cells were then washed 3 times in sorting buffer (PBS+0.5% BSA (Sigma; A8412)) and finally resuspended in 500-7000 sorting buffer, filtered through a 40 µm nylon mash into FACS tubes (BD Falcon; 352235), and analyzed using the LSR-II FACS machine (BD Biosciences) with at least 30,000 events being recorded. Analysis of the results was done using FlowJo software.

Immunofluorescence

Cells were dispersed and plated onto 96 well plates. After one day of culture, cells were washed in PBS and fixed in 4% PFA for 20 min at RT. Following 3 washes with PBS, cells were blocked for 1 hour at RT in PBS+0.1% Triton X-100+5% donkey serum. All primary antibody incubations were done overnight at 4° C. in blocking solution at a 1:500 dilution: Goat anti-human PDX-1/IPF1, mouse anti-NKX6-1, rabbit anti-Chromogranin A, rat anti-insulin (pro-)/C- peptide, Ki67. Cells were washed 2 times in PBS the next day, followed by secondary antibody incubation for 1 hour at RT at a 1:500 dilution (protected from light). Secondary antibodies conjugated to Alexa Fluor 488, 594 or 647 (Life Technologies) were used to visualize primary antibodies. Following 3 washes with PBS, all nuclei were visualized by staining with DAPI (Invitrogen; D1306). Representative images were taken using an Olympus IX51 Microscope or Zeiss LSC 700 confocal microscope. The percentage of target cell-types was quantified using the Array Scan Cellomics high-content screening system. Here 30 images were acquired per well and quantified. Cells labeled by antibody staining and total cell number (based on DAPI nuclei staining) were quantified to obtain percentages of target cell types.

Immunohistochemistry

Cell clusters or islets were fixed by immersion in 4% PFA for 1 hour at RT. Samples were then washed 3 times with PBS, embedded in Histogel™, and sectioned for histological analysis. 10 µm sections were then subjected to deparaffinization using Histoclear (Thermoscientific; C78-2-G) and rehydrated. For antigen retrieval slides were emerged in 0.1M EDTA (Ambion; AM9261) and placed in a pressure cooker (Proteogenix; 2100 Retriever) for two hours. Slides were then blocked with PBS+0.1% Triton X-100+5% donkey serum for 1 hour at RT, followed by incubation in blocking solution with primary antibodies overnight at 4° C. The following primary antibodies were used 1:100 unless otherwise noted: Goat anti-human PDX-1/IPF1, mouse anti-NKX6-1, rabbit anti-Chromogranin A, rat anti-insulin (pro-)/C-peptide, glucagon, somatostatin. Cells were washed 2 times in PBS the next day, followed by secondary antibody incubation for 2 hour at RT (protected from light). Secondary antibodies conjugated to Alexa Fluor 488 or 594 were used to visualize primary antibodies. Following washes with PBS, the histology slides were mounted in Vectashield mounting medium with DAPI (Vector Laboratories; H-1200), covered with coverslips and sealed with nail polish. Representative images were taken using an Olympus IX51 Microscope or Zeiss LSM 510 or 710 confocal microscope.

Glucose Stimulated Insulin Secretion

Krebs buffer (Krb): Di $H_2O$ with 128 mM NaCl, 5 mM KCl, 2.7 mM $CaCl_2$, 1.2 mM $MgCl_2$, 1 mM $Na_2HPO_4$, 1.2 mM $KH_2PO_4$, 5 mM $NaHCO_3$, 10 mM HEPES (Life Technologies; 15630080), 0.1% BSA (Proliant; 68700). Solutions were equilibrated to 37° C. in incubator and 1 ml volumes were used in the following protocol. Approximately 0.5 million cells as clusters were transferred to autoclaved 1.7 ml Safe seal microcentrifuge tubes and washed 2 times in Krb. Clusters were then pre-incubated in Krb with 2 mM glucose for 2 hours in incubator to remove residual insulin. It is worth noting that for all incubations tube lids were left open and covered by a lid that allowed for air exchange. Clusters were washed 2 times in Krb and then incubated in Krb containing 2 mM Glucose for exactly 30 min and 200 ul of the supernatant collected after incubation (low glucose sample). Clusters were washed 2 times in Krb and then incubated in Krb with 20 mM Glucose for exactly 30 min and 200 ul of supernatant was collected after incubation (high glucose sample). Challenging with low and high glucose was repeated two additional times (3 paired challenges in total). Finally, clusters were washed 2 times in Krb and then incubated in Krb with 2 mM Glucose+30 mM KCl for exactly 30 min and 200 ul of supernatant was collected after incubation (KCl polarization challenge sample). After the KCl challenge, clusters were dispersed using Tryple and counted by Viacell (manufacturer) to normalize insulin secretion amounts by cell number.

Supernatant samples containing secreted insulin were then processed using the Human Ultrasensitive Insulin ELISA (ALPCO Diagnostics; 80-INSHUU-E01.1) and samples were measured by a FLUOstar optima spectrophotometer (BMG lantech) at 450 nm. If the ELISA was not performed on the same day, samples were stored at −80° C. In order to get insulin concentrations within the range of the ELISA, diluting the samples between 1:100 and 1:200 in PBS was usually sufficient.

Electron Microscopy

Cell clusters were fixed with a mixture containing 1.25% PFA, 2.5% glutaraldehyde, and 0.03% picric acid in 0.1 M sodium cocodylate buffer (pH 7.4) for at least 2 hours at RT. Cell clusters were then washed in 0.1M cacodylate buffer and post-fixed with a mixture of 1% Osmium tetroxide (OsO4) and 1.5% Potassium ferrocyanide (KFeCN6) for at least 2 hours at RT, washed in 0.1M cacodylate buffer and post-fixed with 1% Osmiumtetroxide (OsO4)/1.5% Potassiumferrocyanide (KFeCN6) for 1 hour, washed in water 3× and stained in 1% aqueous uranyl acetate for 1 hour followed by 2 washes in water and subsequent dehydration in grades of alcohol (10 min each; 50%, 70%, 90%, 2×10 min 100%). The samples were then incubated in propyleneoxide for 1 hour and infiltrated ON in a 1:1 mixture of propyleneoxide and TAAB Epon (Marivac Canada Inc. St. Laurent, Canada). The following day the samples were embedded in TAAB Epon and polymerized at 60° C. for 48 hours. Ultrathin sections (about 60 nm) were cut on a Reichert Ultracut-S microtome, picked up on to copper grids, stained with 0.2% lead citrate and examined in a JEOL 1200EX Transmission electron microscope or a TecnaiG$^2$ Spirit BioTWIN. Images were recorded with an AMT 2 k CCD camera and analyzed using ImageJ software.

SCID-Beige Transplantation Studies 5 million hPSC derived cells as clusters were resuspended in RPMI1640 media (Life technologies; 11875-093), aliquoted into PCR tube with the volume of 200 uL, and kept on ice for 5 to 10 minutes before the loading into the catheter. For the preparation of cell loading, each catheter, infusion set 23G×¾" (Terumo; SB*S23BL) connected to 1 mL syringe, was rinsed with 1 ml of 5% FBS serum (Corning; 35-011-CV) added RPMI media then loaded with 0.6 ml of no serum added RPMI media. Clusters were loaded through the tip of the catheter needle and placed vertically to settle on the bottom of the catheter tubing and near the top of the needle by gravity for 5 minutes in room temperature. During the cell preparation step, immunodeficient (SCID/Beige) mice (what age?) were anesthetized with avertin 1.25% (250 mg/kg; 0.5 ml/25 g 1.25% Avertin/body weight), and left ventricle surgical site was shaved and disinfected with betadine and alcohol. Incision of about 1 cm was made to expose the kidney and clusters were injected under the kidney capsule by inserting catheter needle under the kidney capsule and injecting about 100 ul volume containing 5 million equivalent cells of clusters. Abdominal cavity was closed with PDS absorbable sutures (POLYDOX; 2016-06)) and skin with surgical clips (Kent Scientific Corp; INS750346-2). Mice were placed on a microtemp circulating pump and blanket (~37° C.) during the surgery/recovery period to aid in the rapid recovery of mice following anesthesia and given a dose of 5 mg/mkg carprofen right after the surgery and 24 hours after the initial dose. The average time for transplantation is approximately 3 minutes per mouse. Wound clips were removed 14 days after surgery and the mice were monitored twice a week.

After two weeks of recovery from surgery, the presence of human insulin and the glucose-responsiveness of the transplanted cells were assessed by performing glucose tolerance test (GTT). After fasting the mice for 16 hours overnight, GTT was performed by IP injection of 2 g D-(+)-glucose/1 kg body weight and blood collection of pre and/or post injection through facial vein puncture using lancet (Feather; 2017-01). Human insulin was subsequently quantified using the human insulin ELISA kit (ALPCO Diagnostics; 80-IN-SHUU-E01.1). Grafts were dissected from the SCID mice, fixed in 4% PFA (Electron Microscopy Science Nm; 15710), embedded in paraffin, and sectioned for histological analysis.

Calcium Imaging

About 10 to 20 hPSC derived clusters were plated on 96 well plate coated with MATRIGEL™ and allowed to adhere for 24 hours in a 37° C. incubator, 5% $CO_2$, and 100% humidity. Clusters were washed with prewarmed (37° C.) Krebs buffer added with 2.5 mM glucose then incubated with 50 µM $Ca^{2+}$-sensitive fluorescent probe Fluo4-AM (Life Technologies; F14217) in 2.5 mM glucose Krb buffer for 45 minutes in 37° C. incubator. Clusters were washed with 2.5 mM glucose Krb buffer then incubated further in 37° C. incubator for additional 15 minutes. Clusters were then right away staged in the AxioZoom V16 microscope (Carl Zeiss) for acquirement of high resolution time series imaging of multiple batches of clusters in different wells. Fluo-4 was excited at 488 nm and its emission was recorded between 490 and 560 nm. Time series images were acquired at single cell resolution of 80× magnification in every 17 seconds and up to 10 wells were imaged in one imaging. Progression of glucose challenges and time of the stimulation during imaging was as follows. Imaging started with 5 minute stimulation of 2 mM glucose in Krb followed by 5 minute stimulation of 20 mM glucose in Krb buffer. These low then high glucose stimulations were repeated two more times, then imaging ended with 5 minute stimulation of 30 mM KCl in Krb buffer and with the total imaging time of 35 minutes. Between the stimulations, imaging was stopped and clusters were washed with 2 mM glucose Krb buffer and then added with the next glucose Krb buffer. Fluorescence intensity changes during 35 minutes of imaging were analyzed in the single cell resolution using Imagej/Fiji by applying StackReg to correct for the movement of the clusters over the course of the imaging, and ROI manager to measure the fluorescence intensity of the cells throughout the imaging. All 7 stimulations of 5 minute clips were made into one movie using VirtualDub and published in youtube for data sharing.

Intracellular Flow Cytometry and Gene Expression Analysis

MARIS was carried out as described in Hrvatin et al., 2014. Cells were harvested in single cell suspension, fixed in 4% PFA on ice, incubated with primary antibody and then secondary antibodies in buffer containing RNasin. Cells were then sorted by FACS to obtain at least 100,000 cells per sample. Samples were subsequently incubated in digestion Buffer at 50° C. for 3 hours, prior to RNA isolation. RNA concentration was quantified using Nanodrop 1000. Double-stranded cDNA was generated by reverse transcription from at least 100 ng of total RNA. Amplified mRNA (cRNA) was then generated by In vitro transcription overnight with biotin-labeled nucleotides and concentrated by vacuum centrifugation at 30° C. At least 750 ng cRNA per sample was hybridized to Human HT-12 Expression BeadChips (Illumina) using the Whole-Genome Expression Direct Hybridization kit (Illumina). Chips were scanned on the Illumina Beadstation 500. Raw data was adjusted by background subtraction and rank-invariant normalization. Before calculating fold change, an offset of 20 was added to all probe set means to eliminate negative signals. The p-values for differences between mean signals were calculated in GenomeStudio by t-test and corrected for multiple hypotheses testing by the Benjamini-Hochberg method in combination with the Illumina custom false discovery rate (FDR) model.

REFERENCES

Aguayo-Mazzucato, C., Zavacki, A. M., Marinelarena, A., Hollister-Lock, J., Khattabi, I. E., Marsili, A., Weir, G. C., Sharma, A., Larsen, P. R., and Bonner-Weir, S. (2013). Thyroid Hormone Promotes Postnatal Rat Pancreatic β-Cell Development and Glucose-Responsive Insulin Secretion Through MAFA. Diabetes 62, 1569-580.

Bellin, M. D., Barton, F. B., Heitman, A., Harmon, J., Balamurugan, A. N., Kandaswamy, R., Sutherland, D. E., Alejandro, R., and Hering, B. J. (2012). Potent Induction Immunotherapy Promotes Long-Term Insulin Independence After Islet Transplantation in Type 1 Diabetes. American Journal of Transplantation 12, 1576-583.

Brelje, T. C., Stout, L. E., Bhagroo, N. V., and Sorenson, R. L. (2004). Distinctive roles for prolactin and growth hormone in the activation of signal transducer and activator of transcription 5 in pancreatic islets of langerhans. Endocrinology 145, 4162-175.

Cheng, X., Ying, L., Lu, L., Galva®, A. M., Mills, J. A., Lin, H. C., Kotton, D. N., Shen, S. S., Nostro, M. C., et al. (2012). Self-renewing endodermal progenitor lines generated from human pluripotent stem cells. Cell Stem Cell 10, 371-384.

D'Amour, K. A., Agulnick, A. D., Eliazer, S., Kelly, O. G., Kroon, E., and Baetge, E. E. (2005). Efficient differentiation of human embryonic stem cells to definitive endoderm. Nat Biotechnol 23, 1534-541.

D'Amour, K. A., Bang, A. G., Eliazer, S., Kelly, O. G., Agulnick, A. D., Smart, N. G., Moorman, M. A., Kroon, E., Carpenter, M. K., and Baetge, E. E. (2006). Production of pancreatic hormone-expressing endocrine cells from human embryonic stem cells. Nat Biotechnol 24, 1392-1401.

Ding, Q., Lee, Y.-K., Schaefer, E. K., Peters, D., Veres, A., Kim, K., Kuperwasser, N., Motola, D., Meissner, T., et al. (2013). A TALEN Genome-Editing System for Generating Human Stem Cell-Based Disease Models. Cell Stem Cell 12, 238-251.

Hrvatin, S., O'Donnell, C. W., Deng, F., Millman, J. R., Pagliuca, F. W., Dilorio, P., Rezania, A., Gifford, D. K., and Melton, D. A. (2014). Differentiated human stem cells resemble fetal, not adult, β cells. Proc Natl Acad Sci USA, 201400709.

Keirstead, H. S., Nistor, G., Bernal, G., Totoiu, M., Cloutier, F., Sharp, K., and Steward, O. (2005). Human embryonic stem cell-derived oligodendrocyte progenitor cell transplants remyelinate and restore locomotion after spinal cord injury. The Journal of neuroscience 25, 4694-4705.

Kriks, S., Shim, J.-W., Piao, J., Ganat, Y. M., Wakeman, D. R., Xie, Z., Carrillo-Reid, L., Auyeung, G., Antonacci, C., and Buch, A. (2011). Dopamine neurons derived from human ES cells efficiently engraft in animal models of Parkinson's disease. Nature 480, 547-551.

Kroon, E., Martinson, L. A., Kadoya, K., Bang, A. G., Kelly, O. G., Eliazer, S., Young, H., Richardson, M., Smart, N. G., et al. (2008). Pancreatic endoderm derived from human embryonic stem cells generates glucose-responsive insulin-secreting cells in vivo. Nat Biotechnol 26, 443-452.

Labriola, L., Montor, W. R., Krogh, K., Lojudice, F. H., Genzini, T., Goldberg, A. C., Eliaschewitz, F. G., and Sogayar, M. C. (2007). Beneficial effects of prolactin and laminin on human pancreatic islet-cell cultures. Mol Cell Endocrinol 263, 120-133.

Lammert, E., Cleaver, O., and Melton, D. (2001). Induction of pancreatic differentiation by signals from blood vessels. Science 294, 564-67.

Lu, B., Malcuit, C., Wang, S., Girman, S., Francis, P., Lemieux, L., Lanza, R., and Lund, R. (2009). Long-term safety and function of RPE from human embryonic stem cells in preclinical models of macular degeneration. Stem Cells 27, 2126-135.

Matschinsky, F. M. (2009). Assessing the potential of glucokinase activators in diabetes therapy. Nature Reviews Drug Discovery 8, 399-416.

McCall, M., and Shapiro, A. M. J. (2012). Update on Islet Transplantation. Cold Spring Harb Perspect Med 2, a007823.

Modi, P. (2007). Diabetes beyond insulin: review of new drugs for treatment of diabetes mellitus. Curr Drug Discov Technol 4, 39-47.

Mohammed, J. S., Wang, Y., Harvat, T. A., Oberholzer, J., and Eddington, D. T. (2009). Microfluidic device for multimodal characterization of pancreatic islets. Lab Chip 9, 97-106.

Narayanan, K., Lim, V. Y., Shen, J., Tan, Z. W., Rajendran, D., Luo, S. C., Gao, S., Wan, C. A., and Ying, J. (2013). Extracellular matrix-mediated differentiation of human embryonic stem cells: Differentiation to insulin-secreting beta cells. Tissue Eng Part A 20, 424-433.

Nostro, M. C., Sarangi, F., Ogawa, S., Holtzinger, A., Corneo, B., Li, X., Micallef, S. J., Park, I. H., Basford, C., et al. (2011). Stage-specific signaling through TGF{beta} family members and WNT regulates patterning and pancreatic specification of human pluripotent stem cells. Development 138, 861-871.

Parsons, J. A., Brelje, T. C., and Sorenson, R. L. (1992). Adaptation of islets of Langerhans to pregnancy: increased islet cell proliferation and insulin secretion correlates with the onset of placental lactogen secretion. Endocrinology 130, 1459-466.

Pearson, T., Greiner, D. L., and Shultz, L. D. (2008). Creation of "humanized" mice to study human immunity. Curr Protoc Immunol Chapter 15, Unit 15.21.

Rezania, A., Bruin, J. E., Riedel, M. J., Mojibian, M., Asadi, A., Xu, J., Gauvin, R., Narayan, K., Karanu, F., et al. (2012). Maturation of Human Embryonic Stem Cell-Derived Pancreatic Progenitors Into Functional Islets Capable of Treating Pre-existing Diabetes in Mice. Diabetes 61, 2016-029.

Rezania, A., Bruin, J. E., Xu, J., Narayan, K., Fox, J. K., O'Neil, J. J., and Kieffer, T. J. (2013). Enrichment of human embryonic stem cell-derived NKX6-1-expressing pancreatic progenitor cells accelerates the maturation of insulin-secreting cells in vivo. Stem Cells 31, 2432-442.

Rodriguez-Diaz, R., Dando, R., Jacques-Silva, M. C., Fachado, A., Molina, J., Abdulreda, M. H., Ricordi, C., Roper, S. D., Berggren, P. O., and Caicedo, A. (2011). Alpha cells secrete acetylcholine as a non-neuronal paracrine signal priming beta cell function in humans. Nat Med 17, 888-892.

Rutter, G. A., and Hodson, D. J. (2013). Minireview: Intraislet Regulation of Insulin Secretion in Humans. Molecular Endocrinology 27, 1984-995.

Schulz, T. C., Lynn, F. C., Young, H. Y., Agulnick, A. D., Babin, M. J., Baetge, E. E., Bang, A. G., Bhoumik, A., Cepa, I., et al. (2012). A Scalable System for Production of Functional Pancreatic Progenitors from Human Embryonic Stem Cells. PLoS ONE 7, e37004.

Shapiro, A. M., Ricordi, C., Hering, B. J., Auchincloss, H., Lindblad, R., Robertson, R. P., Secchi, A., Brendel, M. D., Berney, T., et al. (2006). International trial of the Edmonton protocol for islet transplantation. N Engl J Med 355, 1318-330.

Shiba, Y., Fernandes, S., Zhu, W. Z., Filice, D., Muskheli, V., Kim, J., Palpant, N. J., Gantz, J., Moyes, K. W., and Reinecke, H. (2012). Human ES-cell-derived cardiomyocytes electrically couple and suppress arrhythmias in injured hearts. Nature 489, 322-25.

Sneddon, J. B., Borowiak, M., and Melton, D. A. (2012). Self-renewal of embryonic-stem-cell-derived progenitors by organ-matched mesenchyme. Nature 491, 765-68.

Taylor, B. L., Liu, F. F., and Sander, M. (2013). NKX6-1 Is Essential for Maintaining the Functional State of Pancreatic Beta Cells. Cell Rep 4, 1262-275.

Thowfeequ, S., Ralphs, K. L., Yu, W., Slack, J. M. W., and Tosh, D. (2007). Betacellulin inhibits amylase and glucagon production and promotes beta cell differentiation in mouse embryonic pancreas. Diabetologia 50, 1688-697.

Vetere, A., Choudhary, A., Burns, S. M., and Wagner, B. K. (2014). Targeting the pancreatic β-cell to treat diabetes. Nature Reviews Drug Discovery Xie, R., Everett, L. J., Lim, H. W., Patel, N. A., Schug, J., Kroon, E., Kelly, O. G., Wang, A., D'Amour, K. A., et al. (2013). Dynamic Chromatin Remodeling Mediated by Polycomb Proteins Orchestrates Pancreatic Differentiation of Human Embryonic Stem Cells. Cell Stem Cell 12, 224-237.

What is claimed is:

1. A method of administering a composition to a subject with Type 1 Diabetes, comprising the step of administering to the subject a composition comprising one or more cell clusters; wherein the one or more cell clusters comprise a plurality of cells that express glucagon and/or somatostatin; and wherein at least 20% of the cells in the one or more cell clusters are non-native pancreatic β-cells that:
    (a) express chromogranin A, ISL1, PDX1, and C-peptide and one or more of the following genes: ZNT8, MNX1, or ABCC8;
    (b) exhibit an in vitro glucose-stimulated insulin secretion response when subjected to a glucose challenge; and
    (c) do not express somatostatin or glucagon.

2. The method of claim 1, wherein the plurality of non-native pancreatic β-cells exhibit an in vitro glucose-stimulated insulin secretion response when subjected to a first glucose challenge, a second glucose challenge, and a third glucose challenge, when the first glucose challenge, the second glucose challenge and the third glucose challenge are applied sequentially.

3. The method of claim 1, wherein the plurality of non-native pancreatic β-cells are generated from stem cells in vitro.

4. The method of claim 3, wherein the stem cells are human embryonic stem cells.

5. The method of claim 3, wherein the stem cells are human induced pluripotent stem cells.

6. The method of claim 1, wherein the plurality of non-native pancreatic β-cells exhibit a glucose-stimulated calcium flux in vitro.

7. The method of claim 1, wherein the plurality of non-native pancreatic β-cells express ZNT8.

8. The method of claim 1, wherein the plurality of non-native pancreatic β-cells express PC2.

9. The method of claim 1, wherein the plurality of non-native pancreatic β-cells express MNX1.

10. The method of claim 1, wherein the plurality of non-native pancreatic β-cells express ABCC8.

11. The method of claim 1, wherein the plurality of non-native pancreatic β-cells express MAFA.

12. The method of claim 1, wherein the plurality of non-native pancreatic β-cells express MAFB.

13. The method of claim 1, wherein the plurality of the non-native pancreatic β-cells exhibit an in vitro glucose-stimulated insulin secretion response when subjected to a first glucose challenge at a first glucose concentration and to a second glucose challenge at a second glucose concentration, when the first glucose challenge and the second glucose challenge are applied sequentially, wherein the first glucose concentration is higher than the second glucose concentration, and wherein the plurality of non-native pancreatic β-cells exhibit a stimulation index of at least 1.1, wherein the stimulation index equals a ratio of insulin secreted in response to a first glucose concentration compared to a second glucose concentration.

14. The method of claim 1, wherein the insulin secreted by the plurality of non-native pancreatic β-cells is at least 0.5 μIU per 1000 cells per 30 minute incubation when the plurality of non-native pancreatic β-cells is exposed to at least 20 mM of glucose.

15. The method of claim 1, comprising administering the composition via the portal vein.

16. The method of claim 1, wherein the plurality of non-native pancreatic β-cells are genetically modified.

17. The method of claim 1, wherein 20-70% of the cells in the one or more cell clusters are the plurality of non-native pancreatic β-cells.

18. The method of claim 1, wherein 30-60% of the cells in the one or more cell clusters are the plurality of non-native pancreatic β-cells.

19. The method of claim 18, wherein the composition comprises a plurality of cell clusters.

20. The method of claim 1, wherein the one or more cell clusters comprise one of the following: a) a C-peptide-negative/glucagon-positive cell; b) a C-peptide-negative/somatostatin-positive cell; c) a glucagon-positive/somatostatin-negative cell; d) a glucagon-negative/somatostatin-positive cell; or e) any combination thereof.

21. The method of claim 1, wherein the one or more cell clusters have a diameter <300 μm.

22. The method of claim 1, wherein the composition comprises a plurality of cell clusters; and wherein the plurality of non-native pancreatic β-cells are generated from human stem cells in vitro.

23. The method of claim 22, wherein the plurality of non-native pancreatic β-cells express MAFB.

24. The method of claim 22, wherein the plurality of non-native pancreatic β-cells express MAFA.

25. The method of claim 22, wherein the plurality of non-native pancreatic β-cells exhibit an in vitro glucose-stimulated insulin secretion response when subjected to a first glucose challenge, a second glucose challenge, and a third glucose challenge, when the first glucose challenge, the second glucose challenge and the third glucose challenge are applied sequentially.

26. The method of claim 22, wherein the one or more cell clusters have a diameter <300 μm.

27. The method of claim 22, wherein the plurality of non-native pancreatic β-cells are genetically modified.

28. The method of claim 22, wherein the plurality of non-native pancreatic β-cells express PC2 and ABCC8.

29. The method of claim 22, comprising administering the composition via the portal vein.

30. The method of claim 1, wherein the composition is in a device, and wherein the method comprises implanting the device into the subject.

* * * * *